(12) United States Patent
Konkel et al.

(10) Patent No.: US 9,047,864 B2
(45) Date of Patent: Jun. 2, 2015

(54) **ANTIGEN COMPOSITIONS AND METHODS OF INHIBITING *CAMPYLOBACTER JEJUNI* BACTERIAL INFECTION AND USES OF THE ANTIGEN COMPOSITIONS**

(75) Inventors: Michael Konkel, Pullman, WA (US); Tri Duong, College Station, TX (US); Charlie Larson, Hamilton, MT (US); Jason Neal-McKinney, Pullman, WA (US)

(73) Assignee: Washington State University, Pullman, WA (US)

( * ) Notice: Subject to any disclaimer, the term of this patent is extended or adjusted under 35 U.S.C. 154(b) by 70 days.

(21) Appl. No.: 13/384,073

(22) PCT Filed: Jul. 16, 2010

(86) PCT No.: PCT/US2010/042262
§ 371 (c)(1),
(2), (4) Date: Mar. 22, 2012

(87) PCT Pub. No.: WO2011/009042
PCT Pub. Date: Jan. 20, 2011

(65) Prior Publication Data
US 2012/0183570 A1 Jul. 19, 2012

Related U.S. Application Data

(60) Provisional application No. 61/226,256, filed on Jul. 16, 2009.

(51) Int. Cl.
*A61K 39/02* (2006.01)
*A61P 31/04* (2006.01)
*C12N 15/85* (2006.01)
*C12N 15/31* (2006.01)
*C07K 14/205* (2006.01)
*C07K 5/107* (2006.01)
*G10L 13/04* (2013.01)
*A61K 39/00* (2006.01)
*C07K 14/195* (2006.01)
*C12N 15/74* (2006.01)

(52) U.S. Cl.
CPC ............ *G10L 13/043* (2013.01); *A61K 35/747* (2013.01); *A61K 39/00* (2013.01); *A61K 39/0225* (2013.01); *A61K 39/025* (2013.01); *A61K 2039/521* (2013.01); *A61K 2039/523* (2013.01); *A61K 2039/542* (2013.01); *C07K 14/195* (2013.01); *C12N 15/746* (2013.01)

(58) Field of Classification Search
CPC .................. A61K 2039/542; A61K 2039/523; A61K 39/025; A61K 35/747; C07K 14/23531; C12N 15/746
See application file for complete search history.

(56) References Cited

U.S. PATENT DOCUMENTS

| 6,156,546 A | 12/2000 | Konkel et al. |
| 2007/0249553 A1 | 10/2007 | Newell et al. |
| 2008/0131453 A1 | 6/2008 | Thompson |

FOREIGN PATENT DOCUMENTS

WO 2005-049641 6/2005

OTHER PUBLICATIONS

Greenspan et al. (Nature Biotechnology 7: 936-937, 1999).*
Bowie et al (Science, 1990, 257:1306-1310).*
Flanagan et al. (Infection and Immunity vol. 77, No. 6, pp. 2399 to 2407).*

* cited by examiner

*Primary Examiner* — Robert A Zeman
(74) *Attorney, Agent, or Firm* — Whitham, Curtis, Christofferson & Cook, P.C.

(57) ABSTRACT

Methods and compositions for reducing the incidence of *C. jejuni* bacteria infections in poultry and in humans and other animals are formulated to include *C. jejuni* antigens, and particularly CadF, FlpA and FlaA. The antigens may be provided in the form of polypeptides or by hosts that produce the antigens. Fibronectin binding proteins of *C. jejuni* may also be used to deliver substances of interest to humans and other animals.

2 Claims, 40 Drawing Sheets

Figure 2

| Band | Est. Size (kDa) | S3B OMPs | | | | | | | | | 81-176 OMPs | | | | | | | | |
|---|---|---|---|---|---|---|---|---|---|---|---|---|---|---|---|---|---|---|---|
| | | 121 | 123 | 129 | 132 | 135 | 139 | 140 | 144 | 147 | 121 | 123 | 129 | 132 | 135 | 139 | 140 | 144 | 147 |
| 1 | 90 | X[b] | X | X | O[c] | X | X | X | X | X | | X | | O | X | X | X | X | X |
| 2 | 83 | X | X | X | | X | X | X | X | X | | | | | | | | | |
| 3 | 65 | X | X | X | X | X | X | X | X | X | | X | X | X | X | X | X | X | X |
| 4 | 60 | X | X | X | X | X | X | X | X | X | X | X | X | X | X | O | X | X | X |
| 5 | 56 | X | X | X | O | X | X | X | X | X | X | O | X | X | X | X | X | X | X |
| 6 | 54 | X | | O | O | | | O | | | | | | | | | | | |
| 7 | 50 | | | | | | | | | | | | | | | | | | |
| 8 | 45 | X | X | X | X | X | X | X | X | X | X | X | X | X | X | X | X | X | X |
| 9 | 42 | | | | | | | | | | | | | | | | | | |
| 10 | 40 | X | X | X | X | X | X | X | X | X | X | X | X | X | X | X | X | X | X |
| 11 | 37 | X | X | X | O | X | X | X | X | X | | | | | | | | | |
| 12 | 32 | X | X | X | X | X | X | X | X | X | | | | | X | | | | X |
| 13 | 28 | X | | X | O | X | X | X | X | | | | | | | | | | |
| 14 | 26 | | | | | | | | | | | X | X | X | X | X | | | |
| 15 | 23 | | X | X | X | X | X | X | X | X | | X | X | X | X | X | | | |
| 16 | 20 | O | X | X | X | X | X | X | X | X | | | | | | | O | O | |
| 17 | 16 | | | | | | | | | | | | | | | | | X | X | X |

[a] Proteins reactive with one or more of the sera were identified and given numerical values; 1-16.
[b] Detection of a strong reactive band = X
[c] Detection of a faint reactive band = O

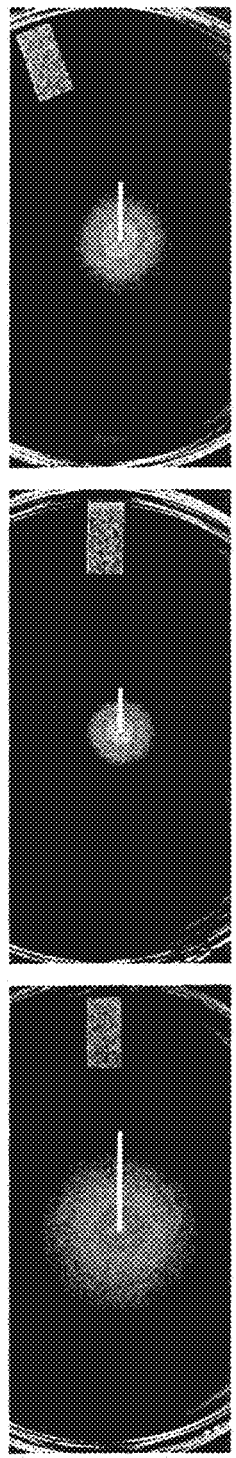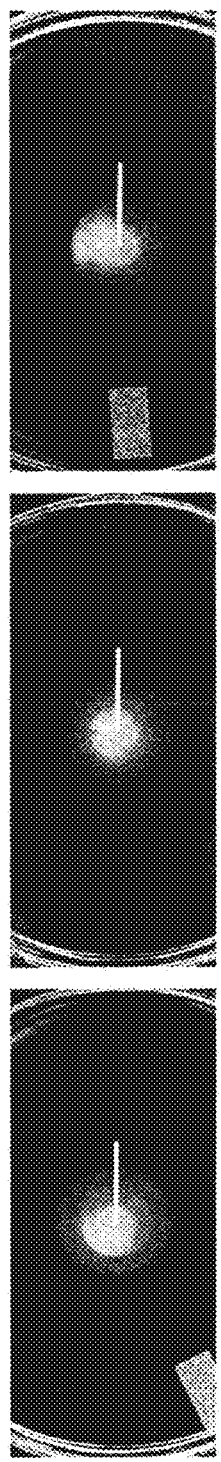

| Gene name | Gene no. (CJJ81176_) | Mass (kDa) | Protein identification | Total score[a] | % coverage[b] | Subcellular location (PSORTb)[c] |
|---|---|---|---|---|---|---|
| FlaA | 1339 | 59.7 | Flagellin | 136.25 | 75.17 | Extracellular |
| PorA | 1275 | 45.7 | Major outer membrane protein | 112.41 | 70.05 | Outer membrane |
| FlgE | 0025 | 89.4 | Flagellar hook protein | 79.40 | 57.76 | Outer membrane |
|  | 1185 | 52.6 | Hypothetical protein | 29.27 | 40.13 | Outer membrane |
|  | 0641 | 19.5 | Nonheme iron-containing ferritin | 23.55 | 64.07 | Cytoplasm |
| chuA | 1601 | 80.0 | TonB-dependent heme receptor | 22.63 | 20.51 | Outer membrane |
| FlaB | 1338 | 59.5 | Flagellin | 104.45 | 68.06 | Extracellular |
|  | 1519 | 17.4 | Bacterioferritin, putative | 16.09 | 69.13 | Unknown |
|  | 1295 | 46.1 | Fibronectin type III domain protein | 15.19 | 22.68 | Unknown |
| cadF | 1471 | 36.1 | Fibronectin-binding protein | 14.87 | 31.35 | Outer membrane/SP |
|  | 0471 | 79.3 | TonB-dependent receptor, putative, degenerate | 14.83 | 13.64 | Outer membrane |
| pepB | 0936 | 54.1 | Leucyl aminopeptidase | 14.07 | 18.01 | Cytoplasm |
|  | 0126 | 22.5 | Lipoprotein, putative | 12.87 | 35.75 | Unknown |
| omp85 | 0164 | 83.2 | Outer membrane protein | 12.41 | 12.04 | Outer membrane |
|  | 0127 | 49.3 | Hypothetical protein | 12.35 | 19.55 | Cytoplasm |
| glnA | 0722 | 53.9 | Glutamine synthetase, type I | 12.33 | 20.59 | Cytoplasm |
| cmeC | 0388 | 55.4 | RND efflux system, outer membrane lipoprotein | 12.02 | 17.07 | Outer membrane/SP |
| bisC | 0291 | 93.8 | Biotin sulfoxide reductase | 11.58 | 9.67 | Periplasm |
| kpsD | 1438 | 60.9 | Capsular polysaccharide ABC transporter | 10.54 | 9.06 | Periplasm |
| betA | 0439 | 64.1 | Oxidoreductase, putative | 9.73 | 8.73 | Unknown |
| ggaC | 0757 | 27.8 | ABC-type amino acid transport, solute binding protein | 9.09 | 18.73 | Periplasm/SP |
| ilvC | 0660 | 37.1 | Ketol-acid reductoisomerase | 8.63 | 13.24 | Unknown |
| eno | 1668 | 45.3 | Phosphopyruvate hydratase | 8.48 | 10.63 | Cytoplasm |
| PEB3 | 0315 | 27.5 | Major antigenic peptide PEB3 | 8.02 | 22.00 | Outer membrane |
|  | 0894 | 81.9 | Flagellin family protein | 8.01 | 8.67 | Outer membrane |
| tuf | 0499 | 80.1 | Elongation factor Tu | 8.00 | 13.78 | Cytoplasm |
|  | 0356 | 22.0 | Putative peroxiredoxin, AhpC/Tsa family | 6.36 | 16.67 | Cytoplasm |
| PEB2 | 0799 | 27.4 | Major antigenic peptide PEB2 | 6.15 | 15.45 | Unknown/SP |

[a] The score derived from Protein predict searches of LC/MALDI/TOF-TOF data compared to C. jejuni 81-176 proteins.
[b] The percentage of the protein sequence covered by the peptides from LC/MALDI-TOF.
[c] The predicted subcellular location of the protein (as defined by PSORT2.0), SP - signal peptide present.

*Figure 4A*

| Gene name | Gene no. (CJJ81176_) | Mass (kDa) | Protein identification | Total score[a] | % coverage[b] | Subcellular location (PSORTb)[c] |
|---|---|---|---|---|---|---|
| FlgK | 1459 | 67.1 | Flagellar hook-associated protein | 6.04 | 9.70 | Outer membrane |
|  | 0586 | 35.0 | Hypothetical protein | 6.00 | 11.33 | Outer membrane |
|  | 0125 | 14.1 | Lipoprotein, putative | 5.00 | 9.02 | Unknown |
|  | 0019 | 24.3 | Hypothetical protein | 4.97 | 9.81 | Unknown/SP |
| groEL | 1234 | 58.0 | Chaperone | 4.67 | 5.50 | Cytoplasm |
|  | 0128 | 43.5 | Hypothetical protein | 4.42 | 5.25 | Outer membrane |
| metX | 0023 | 46.9 | Homoserine O-acetyltransferase | 4.19 | 8.27 | Cytoplasm |
|  | 0974 | 16.3 | Hypothetical protein | 4.19 | 13.89 | Unknown/SP |
| ilvE | 0296 | 34.0 | Branched-chain amino acid aminotransferase | 4.02 | 7.57 | Unknown |
|  | 1016 | 20.6 | Hypothetical protein, putative | 4.01 | 11.58 | Unknown/SP |
|  | 0419 | 37.5 | Lipoprotein, putative | 4.00 | 7.23 | Unknown |
| mapA | 1048 | 24.4 | Outer membrane lipoprotein | 4.00 | 16.36 | Outer membrane |
| gjaA | 1001 | 31.1 | ABC-type amino acid transport/signal transduction | 3.45 | 9.32 | Periplasm/SP |
|  | 0124 | 51.5 | Lipoprotein, putative | 3.06 | 4.64 | Unknown |
| omp18 | 0148 | 18.0 | Peptidoglycan-associated lipoprotein | 2.74 | 6.06 | Outer membrane |
| uvrA | 0366 | 105.5 | Excinuclease ABC subunit A | 2.65 | 0.85 | Cytoplasm |
| fusA | 0513 | 76.7 | Elongation factor G | 2.62 | 1.30 | Cytoplasm |
| rpoC | 0510 | 158.9 | DNA-directed RNA polymerase, beta' subunit | 2.48 | 0.79 | Cytoplasm |
| rplB | 1701 | 30.5 | 50S ribosomal protein L2 | 2.30 | 5.07 | Cytoplasm |
| cmeA | 0390 | 40.0 | RND efflux system, membrane fusion protein | 2.21 | 4.63 | Inner membrane/SP |
| ggt | 0067 | 60.3 | Gamma-glutamyltransferase | 2.15 | 1.98 | Periplasm/SP |
|  | 1050 | 48.9 | Conserved hypothetical protein, authentic frameshift | 2.09 | 3.54 | Outer membrane |
| metK | 1114 | 44.7 | S-adenosylmethionine synthetase | 2.08 | 3.72 | Cytoplasm |
|  | 1418 | 30.4 | Putative methyltransferase | 2.04 | 5.79 | Unknown |
| atpA | 0140 | 54.8 | F0F1 ATP synthase subunit alpha | 2.00 | 2.59 | Cytoplasm |
|  | 0438 | 27.0 | Hypothetical protein | 2.00 | 3.72 | Cytoplasm |
|  | 1045 | 18.6 | Lipoprotein, putative | 2.00 | 8.77 | Unknown/SP |
| hemB | 1013 | 36.8 | Delta-aminolevulinic acid dehydratase | 2.00 | 3.06 | Cytoplasm |

[a] The score derived from Protein predict searches of LC/MALDI/TOF-TOF data compared to *C. jejuni* 81-176 proteins.
[b] The percentage of the protein sequence covered by the peptides from LC/MALDI/TOF-TOF.
[c] The predicted subcellular location of the protein (as defined by PSORT2.0), SP - signal peptide present.

*Figure 4B*

| Gene name | Gene no. (CJJ81176_) | Mass (kDa) | Protein identification | Total score[a] | % coverage[b] | Subcellular location (PSORTb)[c] |
|---|---|---|---|---|---|---|
| cdtC | 0114 | 21.4 | Cytolethal distending toxin, subunit C | 2.00 | 6.35 | Unknown/SP |
| hup | 1731 | 10.3 | DNA-binding protein HU | 2.00 | 15.31 | Cytoplasm |
| tpx | 0800 | 18.8 | Thiol peroxidase | 2.00 | 9.14 | Unknown |
|  | 0447 | 13.2 | Hypothetical protein | 2.00 | 13.64 | Cytoplasm |

[a] The score derived from Protein predict searches of LC/MALDI/TOF-TOF data compared to *C. jejuni* 81-176 proteins.
[b] The percentage of the protein sequence covered by the peptides from LC/MALDI/TOF-TOF.
[c] The predicted subcellular location of the protein (as defined by PSORT2.0). SP - signal peptide present.

*Figure 4C*

| Band | Molecular Mass (kDa) | Protein | Protein ID | MASCOT[a] | Percent sequence coverage (%)[b] | No. peptides matched[c] |
|---|---|---|---|---|---|---|
| 1 | 89.4 | FlgE2 | Flagellar hook protein | 3515 | 41 | 127 |
| 2 | 89.4 | FlgE2 | Flagellar hook protein | 1016 | 22 | 30 |
| 3 | 83.1 | CJJ81176_0164 | Outer membrane protein, OMP 85 family | 133 | 13 | 7 |
|  | 59.7/59.5 | FlaA/FlaB | Flagellar filament | ND[d] | ND | ND |
| 4 | 59.5 | FlaB | Flagellar filament | 2832 | 48 | 97 |
|  | 59.7 | FlaA | Flagellar filament | 1716 | 31 | 57 |
| 5 | 55.4 | CmeC | Outer membrane channel protein, RND efflux pump | 137 | 11 | 4 |
|  | 59.5 | FlaB | Flagellar filament | 2832 | 43 | 97 |
|  | 59.7 | FlaA | Flagellar filament | 1716 | 31 | 57 |
| 6 | 52.6 | CJJ81176_1185 | Hypothetical outer membrane protein | 1662 | 34 | 56 |
|  | 55.4 | CmeC | Outer membrane channel protein, RND efflux pump | 137 | 11 | 4 |
| 7 | 59.5 | FlaB | Flagellar filament | 429 | 21 | 14 |
|  | 59.7 | FlaA | Flagellar filament | 301 | 17 | 10 |
|  | 46.1 | CJJ81176_1295 | Fibronectin type III domain protein | 65 | 12 | 3 |
| 8 | 59.5 | FlaB | Flagellar filament | 631 | 27 | 19 |
|  | 59.7 | FlaA | Flagellar filament | 521 | 21 | 16 |
|  | 43.5 | CJJ81176_0128 | Hypothetical periplasmic protein | 137 | 13 | 4 |
| 9 | 40.0 | CmeA | Membrane fusion protein, RND efflux system pump | 363 | 24 | 13 |
| 10 | 59.5 | FlaB | Flagellar filament | 876 | 36 | 32 |
|  | 59.7 | FlaA | Flagellar filament | 738 | 29 | 25 |
| 11 | 36.1 | CadF | Outer membrane fibronectin-binding protein | ND[e] | ND | ND |
| 12 | 31.1 | CjaA | Putative solute-binding protein (surface antigen) | 302 | 24 | 9 |
|  | 36.5 | SdhB | Succinate dehydrogenase, iron-sulfur protein | 168 | 16 | 4 | a The score derived from MASCOT searches of nano-LC/MS/MS data against the C. jejuni 81-176 strain.
b Percentage of the sequence covered by the sequenced peptides from nano-LC/MS/MS.
c Refers to the number of sequenced peptides from nano-LC/MS/MS.
d Not determined, identification was performed through immunoblots using anti-FlaAB antibodies raised in rabbits (Fig. 3).
e Not determined, identification was performed through immunoblots using anti-CadF antibodies raised in goats (Fig 2A).
f Not determined, lipooligosaccharide (LOS) is a common antigen found below 19 kDa and is characterized by a large diffuse band (33).

*Figure 5A*

| Band | Molecular Mass (kDa) | Protein | Protein ID | MASCOT[a] | Percent sequence coverage (%)[b] | No. peptides matched[c] |
|---|---|---|---|---|---|---|
| 13 | 35.0 | CJJ81176_0586 | Hypothetical protein, outer membrane protein | 520 | 25 | 14 |
|  | 27.8 | CjaC | Solute binding outer membrane protein | 511 | 22 | 16 |
| 14 | 27.5 | PEB3 | Major antigenic peptide, PEB3 | 544 | 27 | 24 |
|  | 27.4 | PEB2 | Major antigenic peptide, PEB2 | 259 | 27 | 15 |
|  | 29.9 | CJJ81176_1525 | Tungstate ABC transporter protein | 206 | 23 | 5 |
|  | 27.8 | CjaC | Solute binding outer membrane protein | 32 | 5 | 1 |
| 15 | 59.5 | FlaB | Flagellar filament | 1268 | 16 | 54 |
|  | 59.7 | FlaA | Flagellar filament | 932 | 15 | 35 |
|  | 45.7 | PorA | Major outer membrane protein | 177 | 18 | 5 |
| 16 | 22.5 | CJJ81176_0126 | Putative lipoprotein | 625 | 49 | 25 |
|  | 24.3 | MapA | Outer membrane lipoprotein | 233 | 19 | 8 |
| 17 |  | LOS | Lipooligosaccharide | ND[f] | ND | ND |

[a] The score derived from MASCOT searches of nano-LC/MS/MS data against the *C. jejuni* 81-176 strain.
[b] Percentage of the sequence covered by the sequenced peptides from nano-LC/MS/MS.
[c] Refers to the number of sequenced peptides from nano-LC/MS/MS.
[d] Not determined, identification was performed through immunoblots using anti-FlaAB antibodies raised in rabbits (Fig. 3).
[e] Not determined, identification was performed through immunoblots using anti-CadF antibodies raised in goats (Fig 2A).
[f] Not determined, lipooligosaccharide (LOS) is a common antigen found below 19 kDa and is characterized by a large diffuse band (33).

*Figure 5B*

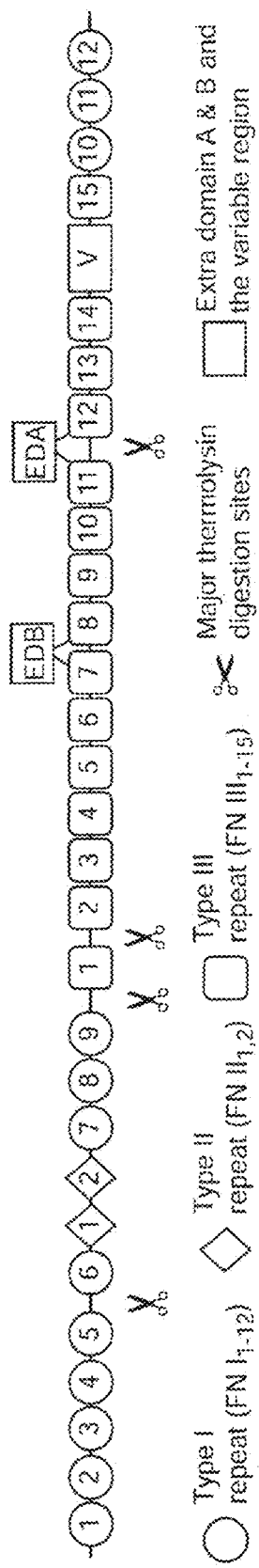
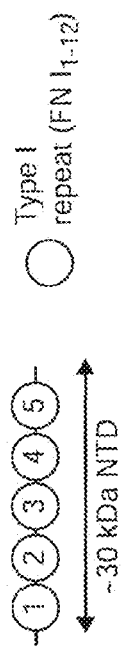
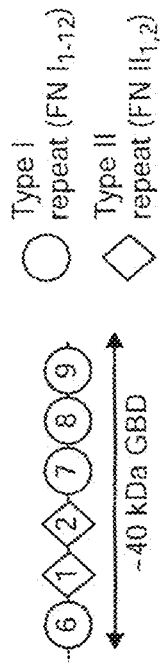
Figure 16A
Figure 16B
Figure 16C

```
FlpA 135-224    RLEAVP-EVQAVTNLPNRIKLIWR-PHPDFRVDSYIIERTKGDDKEFKKIAEVKNRLNAE 58
FN3-1           SSGPVEVFITETPSQPNSHPIQWNAPQPSH-ISKYILRWRPKNSVGRWKEATIPGHLN-S 58
                  *   *.  : . ..  **   :  * .*:*  :..:**:.    :     : ;**

FlpA 135-224    YIDSDLKPNENSSYRIIAVSFNGIKSGSSQVVSS 92
FN3-1           YTIKGLKPGVVYEGQLISIQQYGHQ--------- 83
                *   .***.   .   : ::::  .    *  :
```

*Figure 21*

```
81-176 FlaA      MGFRINTNVAALNAKANADLNAKSLDASLNAKSLDASLSRLSSGLRINSAADDASGMAIADSLRSQANTLGQAISNGND  70
8116 FlaA        MGFRINTNVAALNAKANSDLNAKSLDASLSRLSSGLRINSAADDASGMAIADSLRSQANTLGQAISNGND  70
F38011 FlaA      MGFRINTNVAALNAKANSDLNAKSLDASLSRLSSGLRINSAADDASGMAIADTLRSQANTLGQAISNGND  70
jejuni 84-25 FlaA MGFRINTNVAALNAKANADLNAKSLDSSLARLSSGLRINSAADDASGMAIADSLRSQANTLGQAISNGND  70
jejuni 260.94 FlaA MGFRINTNVAALNAKANADLNSKSLDSSLARLSSGLRINSAADDASGMAIADSLRSQANTLGQAISNGND  70
jejuni CF93-6 FlaA MGFRINTNVAALNAKANADLNSKSLDASLSRLSSGLRINSAADDASGMAIADSLRSQANTLGQAISNGND  70
NCTC11168 FlaA   MGFRINTNVAALNAKANADLNSKSLDASLSRLSSGLRINSAADDASGMAIADSLRSQANTLGQAISNGND  70
Rm1221 FlaA      MGFRINTNVAALNAKANADLNSKSLDASLSRLSSGLRINSAADDASGMAIADSLRSQANTLGQAISNGND  70
                                    10        20        30        40        50        60        70

81-176 FlaA      ALGILQTADKAMDEQLKILDTIKTKATQAAQDGQSLKTRTMLQADINRLMEELDNIANTTSFNGKQLLSG  140
8116 FlaA        ALGILQTADKAMDEQLKILDTIKTKATQAAQDGQSLKTRTMLQADINKLMEELDNIANTTSFNGKQLLSG  140
F38011 FlaA      ALGILQTADKAMDEQLKILDTIKTKATQAAQDGQSLKTRTMLQADINKLMEELDNIANTTSFNGKQLLSG  140
jejuni 84-25 FlaA ALGILQTADKAMDEQLKILDTIKTKATQAAQDGQSLKTRTMLQADINKLMEELDNIANTTSFNGKQLLSG  140
jejuni 260.94 FlaA ALGILQTADKAMDEQLKILDTIKTKATQAAQDGQSLKTRTMLQADINKLMEELDNIANTTSFNGKQLLSG  140
jejuni CF93-6 FlaA ALGILQTADKAMDEQLKILDTIKTKATQAAQDGQSLKTRTMLQADINKLMEELDNIANTTSFNGKQLLSG  140
NCTC11168 FlaA   ALGILQTADKAMDEQLKILDTIKTKATQAAQDGQSLKTRTMLQADINKLMEELDNIANTTSFNGKQLLSG  140
Rm1221 FlaA      ALGILQTADKAMDEQLKILDTIKTKATQAAQDGQSLKTRTMLQADINRLMEELDNIANTTSFNGKQLLSG  140
                           80        90       100       110       120       130       140
```

*Figure 33A*

```
                 ▓                                                                          ▓
                 NFINQEFQIGASSNQTVKATIGATQSSKIGVTRFETGCQISTSGVVGLTIKNYNGIDDFQKVVISTSV
                         150       160       170       180       190       200       210
81-176 FlaA      NFTNQEFQIGASSNQTVKATIGATQSSKIGVTRFEFTGAQSFTSCVVGLTIKNYNGIEDFKFDNVVISTSV 210
81116 FlaA       NFTNQEFQIGASSNQTVKATIGATQSSKIGVTRFEFTGAQSFTSGVVGLTIKNYNGIEDFKFDNVVISTSV 210
F38011 FlaA      GFTNQEFQIGSSSNQTVKATIGATQSSKIGVTRFETGTGSVTSGVVGLTIKNYNGIEDFKFQDVVISTSV 210
jejuni 84-25 FlaA NFINQEFQIGASSNQTVKATIGATQSSKIGLRFETGCGRISTSGEVQFTLKNYNGIDDFKFDNVVISTSV 210
jejuni 260.94 FlaAGFTNQEFQIGSSSNQTVKATIGATQSSKIGVTRFETGSQFTSGVVGLTIKNYNGIEDFKFDNVVISTSV 210
jejuni CF93-6 FlaANFINQEFQIGASSNQTVKATIGATQSSKIGLTRFETGCGRISTSGEVQFTLKNYNGIDDFQFQKVVISTSV 210
NCTC11168 FlaA   NFINQEFQIGASSNQTVKATIGATQSSKIGVTRFETGCGRITSGGEVQFTLKNYNGIDDFQFQKVVISTSV 210
Rm1221 FlaA      NFINQEFQIGASSNQTVKATIGATQSSKIGVTRFETGCGRITSGGEVQFTLKNYNGIDDFQFQKVVISTSV 210

▓▓                                                ▓▓
                 GTGLGALADEINKNADKTGVRATFTVETRGIAAVKAGTTSDDFAINGVTIGKVDYKDGDGNGALVAAINA
                         220       230       240       250       260       270       280
81-176 FlaA      GTGLGALAEEINKSADKTGVRATYDVKTTGVYAIKEGTTSQEFAINGVTIGKIEYKDGDGNGSLISAINA 280
81116 FlaA       GTGLGALAEEINKSADKTGVRATYDVKTTGVYAIKEGTTSQDFAINGVTIGKIEYKDGDGNGSLISAINA 280
F38011 FlaA      GTGLGALAEEINKNADKTGVRASYDVRTGAYAIKAGSTSSDFAINGVTIGKVDYKDGDGNGSLVSAINA 280
jejuni 84-25 FlaA GTGLGALAEEINKNADKTGVRATFFVETRGIAAVRAGATSDTFAINGVKIGKVDYKDGDANCALVAAINS 280
jejuni 260.94 FlaAGTGLGALADEINKNADKTGVRATFTVETRGIAAVRAGATSDTFAINGVIIGKVDYKDGDNGSLISAINA 280
jejuni CF93-6 FlaAGTGLGALADEINKNADKTGVRATFTVETRGIAAVRACATSDTFAINGVKIGKVDYKDGDANCALVAAINS 280
NCTC11168 FlaA   GTGLGALADEINKNADKTGVRATFTVETRGIAAVRAGATSDTFAINGVKIGKVDYKDGDANCALVAAINS 280
Rm1221 FlaA      GTGLGALADEINKNADKTGVRATFTVETRGMAAVRAGTTSNDFAINGVTIGQVAYEBCDGNCALVAAINS 280
```

*Figure 33B*

```
              VKDTTCVEASIDANGQLVLTSADGRGIKIDGNIGGAGILADMKENYGRLSLVKNDCKDILSGTNLSAA
              290       300       310       320       330       340       350
81-176 FlaA   VKDTTGVQASKDENGKLVLTSADGRGIKITGDIGVGSGILANQKENYGRLSLVKNDCRDINISGTNLSAI 350
81116 FlaA    VKDTTGVQASKDENGKLVLTSADGRGIKITGDIGVGSGILANQKENYGRLSLVKNDCRDINISGTNLSAI 350
F38011 FlaA   VKDTIGVQASQDENGRIVLTSADGRGIKIEGNIGGAGILQ--KENYGRLSLVKNDGRDINSGTNLSAI 348
jejuni 84-25 FlaA VKDTTCVEASIDANGQLLTSREGRGIKIDGNIGGAFINADMKENYGRLSLVKNDCKDILISGSNLSSA 350
jejuni 260.94 FlaA VKDTTGVQASKDENGKLVLTSADGRGIKITGDIGVGSGILSAQKENYGRLSLVKNDGRDINVSGTCLSAI 350
jejuni CF93-6 FlaA VKDTTCVEASIDANGQLLTSREGRGIKIDGNIGGAFINADMKENYGRLSLVKNUGKDILISGSNLSSA 350
NCTC11168 FlaA VKDTTCVEASIDANGQLLTSREGRGIKIDGNIGGAFINADMKENYGRLSLVKNDCKDILSCSMLSSA 350
Rm1221 FlaA   VKDTTCVFASIDANGQLLTSREGRGIKIDGNICGAFINANMKENYGRLSLVKNDCKDILVSGTCLSFA 350

CFGATDFISQASVSLRESKGQIDANIADAMGFGSYNGG---VVLGGYSSVSAYMSSAGSCFSSSGFSV
              360       370       380       390       400       410       420
81-176 FlaA   GMGTTDMISQSSVSLRESKGQISATNADAMGFNSYKGGG-KFVFTQNVSSISAFMSAQGSCFSRGSGFSV 419
81116 FlaA    GMGTTDMISQSSVSLRESKGQISATNADAMGFNSYKCCG-KFVFTQNVSSISAFMSAQGSGFSRGSGFSV 419
F38011 FlaA   GMGAADIISQTSVSLRESKGQIDANTADAMGFNAYCGGGKQVIRNSISSVSCLMSAACSGFSSAACSGFSI 418
jejuni 84-25 FlaA GFGATQFISQASVSLRESKGQIDANIADAMGFGSANK----VVLGGYSSVSAYMSSAGSGFSSGSGYSV 416
jejuni 260.94 FlaA GMGAADMISQASVSIRESKGQISAANADAMGFNSYNGGAKQILQVOASSISAFMSQAGSGFSAGSGFSA 420
jejuni CF93-6 FlaA GFGATQFISQASVSLRESKGQIDANIADAMGFGSANKG---VVLGGYSSVSAYMSSABSGFSSGSGYSV 416
NCTC11168 FlaA GFGATQFISQASVSLRESKGQIDANIADAMGFGSANKG---VVLGCYSSVSAYMSSAGSGFSSSGSGYSV 416
Rm1221 FlaA   GFGANSFISQASISLRESKGQLDANIADAMGFGSVNKG---VVIGGFSTVSAYMSSEGSGFSAGSGYSI 416
```

*Figure 33C*

```
                GSGKNYSTGLA.NAIIIS--AAASLSTVYNVSAGSCFSSGSGLSQFATLKTTA---FGVKDETAGVTTLK
                    430        440        450        460        470        480       490

31-176  FlaA    CSGKNLSVGLSQCIQIIS--SAASMSNTYVVSAGSCFSSGSGNSQFAALKTTA---ANTTDETAGVTTLK 484
81116   FlaA    CSGKNLSVGLSQCIQIIS--SAASMSNTYVVSAGSCFSSGSGNSQFAALKTTA---ANTTDETAGVTTLK 484
RM1221  FlaA    CSGKNMSTMLDNSIIASSMTTANAMSAYNVSAGSGFSSGSGNSQFATLKTSAGNAVGAANETSGVTTLK 488
jejuni 84-25 FlaA  CSGKNYSTSHA-NAIAIS--AASQLSTVYNVSAGSGFSSGSGFSVGSGNSQFAALKTTA---FGVKDETAGVTTLK 480
jejuni 260.94 FlaA GSGKCYSTILSGSVQIVS--STASMSSTYVISAGSGFSVSAGSGFSSGSTLSQFAALKTST---VSAHEATAGVTTLK 485
jejuni CF93-6 FlaA CSGKNYSTGFA-NAIAIS--AASQLSTVYNVSAGSGFSSGSGSTLSQFATMKTTA---FCVKDETAGVTTLK 480
NCTC11168 FlaA  CSGKNYSTGFA-NAIAIS--AASQLSTVYNVSAGSGFSSGSGSTLSQFATMKTTA---FCVKDETAGVTTLK 480
Rm1221  FlaA    CSGKGYSATLTGNATFIS--TASAASRVYNVSSGSGFSTGSNLSQFATMKTSV---LGVKDETAGVTTLK 481

GAMAVMDIAETAITNLDQIRADIGSVQNQVTSTINNITVTQVNVKAAESQIRDVDFAAESANYSKANILA
                    500        510        520        530        540        550       560

31-176  FlaA    GAMAVMDIAETAITNLDQIRADIGSIQKQVTSTINNITVTQVNVKAAESQIRDVDFASESANYSKANILA 554
81116   FlaA    GAMAVMDIAETAITNLDQIRADIGSIQKQVTSTINNITVTQVNVKAAESQIRDVDFASESANYSKANILA 554
RM1221  FlaA    GAMAVMDIAETAINNLDQIRADIGSVQNQITSTINNITVTQVNVKAAFSTIRDVDFASESANYSKANILA 558
jejuni 84-25 FlaA  GAMAVMDIAETAITTNIDQIRADIGSVQNQVTSTINNITVTQVNVKAAESQIRDVDFAAESANYSKANILA 550
jejuni 260.94 FlaA GAMAVMDIAETAITNLDQIRADIGSVQNQVTSTINNITVTQVNVKSAESQIRDVDFAAESANYSKANILA 555
jejuni CF93-6 FlaA GAMAVMDIAETAITNLDQIRADIGSVQNQVTSTINNITVTQVNVKAAESQIRDVDFAAESANYSKANILA 550
NCTC11168 FlaA  GAMAVMDIAETAITNLDQIRADIGSVQNQVTSTINNITVTQVNVKAAESQIRDVDFAAESANYSKANILA 550
Rm1221  FlaA    GAMAVMDIAETAITNLDQIRADIGSVQNQVTSTINNITVTQVNVKAAESQIRDVDFAAESANYSKANILA 551
```

*Figure 33D*

| | | |
|---|---|---|
| 81-176 FlaA | QSGSYAMAQANSVQQNVLRLLQ | 576 |
| 81116 FlaA | QSGSYAMAQANSSQQNVLRLLQ | 576 |
| 38011 FlaA | QSGSYAMAQANSSQQNVLRLLQ | 580 |
| jejuni 84-25 FlaA | QSGSYAMAQANSSQQNVLRLLQ | 572 |
| jejuni 260.94 FlaA | QSGAQSGSYAMAQANSVQQNVLRLLQ | 577 |
| jejuni 260.94 FlaA | QSGSYAMAQANSVQQNVLRLLQ | 572 |
| NCTC11168 FlaA | QSGSYAMAQANSVQQNVLRLLQ | 572 |
| Rm1221 FlaA | QSGSYAMAQANSVQQNVLRLLQ | 573 |

*Figure 33E*

ANTIGEN COMPOSITIONS AND METHODS OF INHIBITING *CAMPYLOBACTER JEJUNI* BACTERIAL INFECTION AND USES OF THE ANTIGEN COMPOSITIONS

CROSS-REFERENCE TO RELATED APPLICATIONS

This application is a 371 of International Application Number PCT/US2010/042262 filed Jul. 16, 2010, which claims benefit of U.S. Provisional Patent Application Ser. No. 61/226,256 filed Jul. 16, 2009. and which are incorporated herein by reference.

The present disclosure relates to reducing the incidence of *C. jejuni* bacteria infections in poultry and in humans, and more particularly to novel antigenic compositions, vaccines, and methods for generating an immune response against *C. jejuni* bacteria in an animal.

BACKGROUND

The following includes information that may be useful in understanding the present inventions. It is not an admission that any of the information provided herein is prior art, or relevant, to the presently described or claimed inventions, or that any publication or document that is specifically or implicitly referenced is prior art.

The bacterial genus *Campylobacter* are gram-negative, spiral-shaped motile bacteria that include numerous species associated with many animals, both domestic and wild, commonly found in chickens, turkeys, cattle, sheep, horses and rodents. The bacteria can infect the host animal through various routes of transmission, including by food, water, and through contact with other animals. Contamination of meat in a slaughterhouse is also prevalent. Humans are frequently infected with *Campylobacter jejuni* by handling or consuming poultry products. *Campylobacter* infections in humans also surpass the number of *Salmonella* infections (Walker et al., Microbiological reviews, 50: 81-94 (1986)). *Campylobacter jejuni* is the most common *Campylobacter* species isolated in association with human diarrhea. *Campylobacter jejuni* is responsible for approximately 2 to 3 million cases of foodborne illness per year in the U.S. with an estimated cost of treatment and loss of productivity of $8 billion annually (Buzby, J. C. et al (1997), J. Infect. Dis. 176 Suppl 2:S192-197). Diarrhea caused by *Campylobacter jejuni* typically manifests for about 2-7 days and is self-limiting, but the infection in young children, elderly and immunocompromised individuals often requires antibiotic treatment. *Campylobacter* can cause enteric infections in humans, and are occasionally the cause of more severe diseases like meningitis, neurologic complications, appendicitis, urinary tract infection, and spontaneous abortions (Glaser et al., New Engl. J. Med., 305: 1444-1452 (1981), Butzler et al., Clinics in Gastroenterol., 8: 737-765 (1979), Schwerer et al., J. Endotox. Res. 2: 395-403 (1995) and Salloway et al., Infect. Immun. 64: 2945-2949 (1996). *Campylobacter jejuni* infections are also associated with Guillain-Barré syndrome (Allos, B. M. (2001), Clin. Infect. Dis. 32:1201-1206). Given the seriousness of the problems associated with this infectious agent, novel compositions and methods for inhibiting and preventing *Campylobacter jejuni* infections in birds, poultry, and in humans are very much needed. The inventions described herein satisfy this need.

BRIEF SUMMARY

An embodiments of the invention relates to *C. jejuni* antigens which can be used to elicit an immune response against *C. jejuni* bacteria in an animal. In some embodiments, the immune response is a protective immune response, and prevents (or substantially decreases) the ability of *C. jejuni* bacteria to colonize or establish an infection in an animal to whom the antigens have been administered. While animals of any age can benefit from administration of the antigenic compositions, young (juvenile), especially newborn animals, are frequently targeted for vaccination.

The CadF, FlpA and FlaA antigens have been identified as particularly effective antigens. Without being bound by theory, it is believed that these antigens, which are at least in part exposed on the surface of the *C. jejuni* bacteria, play a role in and may be necessary for mediating the attachment of *C. jejuni* bacteria to, and hence infection of, animal cells. Administration of these antigens to an animal (either the entire protein, or immunologically effective portions thereof) results in the production of antibodies to these antigens by the animal. When the animal is subsequently exposed to *C. jejuni*, the antibodies bind to these antigenic proteins on the bacteria's surface and prevent or block the bacteria from binding to and infecting the cell.

While CadF, FlpA and FlaA are particularly effective antigens for use against *C. jejuni* infection, either alone or in combination, the use of other antigens to which *C. jejuni* antibody responses are prevalent is also contemplated, including one or more of *C. jejuni* proteins/polypeptides CmeA, CmeC, CjaA, CjaC, CJJ81176_0126 or a CJJ81176_0126 homolog, CJJ81176_0128 or a CJJ81176_0128 homolog, CJJ81176_0164 or a CJJ81176_0164 homolog, CJJ81176_0164 or a CJJ81176_0164 homolog or a CJJ81176_0164, CJJ81176_0586 or a CJJ81176_0586 homolog, CJJ81176_1185 or a CJJ81176_1185 homolog, CJJ81176_1295 or a CJJ81176_1295 homolog, CJJ81176_1525 or a CJJ81176_1525 homolog, FlaB, FlgE2, PEB2, PEB3, PorA, MapA, and SdhB, or one or more antigenic fragments of any of these.

FlpA, in some embodiments, may be used to provide antigens, pharmaceuticals, drugs (e.g. anticancer drugs), toxins, etc. to human cells based on its binding to human cells and fibronectin. Other antigens of *C. jejuni* may be used similarly, e.g. in the form of a chimera or fusion product with the substance of interest.

The invention provides a method for preventing or treating *Campylobacter jejuni* colonization in an animal. The method comprises the step of providing to the animal 1) one or more *C. jejuni* polypeptides; or 2) a host genetically engineered to contain and express nucleic acid sequences encoding one or more *C. jejuni* polypeptides.

The invention also provides a host genetically engineered to contain and express nucleic acid sequences encoding one or more *C. jejuni* polypeptides.

Further embodiments of the invention provide a modified bacterial S-layer protein having an internal insertion of at least one heterologous polypeptide from a *C. jejuni* bacterium.

The invention also provides an antigenic composition for generating an immune response to *C. jejuni* in an animal. The antigenic composition comprises 1) at least a first polypeptide selected from the group consisting of *C. jejuni* CadF, FlaA, FlpA, and antigenic fragments thereof; and 2) at least a second *C. jejuni* polypeptide that is different from said first polypeptide.

The invention further provides a method for delivering a substance of interest to a subject. The method comprises the steps of: 1) providing the subject with a fusion product containing a fibronectin binding protein of *C. jejuni* and a substance of interest, wherein said fibronectin binding protein and said substance of interest are associated with one another; and 2) permitting said fusion product to bind fibronectin in cells or tissues of said subject.

BRIEF DESCRIPTION OF THE DRAWINGS

FIG. 2. Data representing the presence (X=strong reactivity, O=weak reactivity) or absence (blank) of bands that reacted with the maternal antibodies as determined from immunoblots of outer membrane protein (OMP) extracts of the *C. jejuni* homologous (S3B) and heterologous (81-176) strains probed with the Cj S3B-SPF sera., represented in tabular form.

FIG. 3 shows Cj S3B-SPF pooled sera contain antibodies that reduce the motility of *C. jejuni* S3B, but not of *C. jejuni* 81-176. Panels: A, Motility assays performed with the *C. jejuni* S3B strain; and B, Motility assays performed with the *C. jejuni* 81-176 strain. The horizontal lines (white) indicate the diameter of the spots (i.e., from the center to the edge of the bacterial zone).

FIG. 4 illustrates *C. jejuni* 81-176 outer membrane proteins identified by LC/MALDI/TOF-TOF.

FIG. 5 depicts predicted "best-fit" immunogenic membrane-associated *C. jejuni* proteins identified by nano-LC/MS/MS.

FIG. 16A-C. Schematic of Fn and Fn fragments used in this study: A, full-length fibronectin (Fn); B, the Fn N-terminal domain (NTD); C, the gelatin-binding domain (GBD). The NTD and GBD are produced by digestion of Fn with thermolysin.

FIG. 21. ClustalW sequence alignment. The amino acid sequence of FlpA-D2 (aa135-224) was compared to the sequences of the FN3 domains from Fn. FlpA-D2 was most similar to FN3[1] sharing 22.9% sequence identity, 15.7% conserved substitutions, and 21.7% semi-conserved substitutions.

FIG. 33A-E. Comparison of FlaA sequences from 8 different *C. jejuni* strains.

DETAILED DESCRIPTION

Figures 1A, 1B:
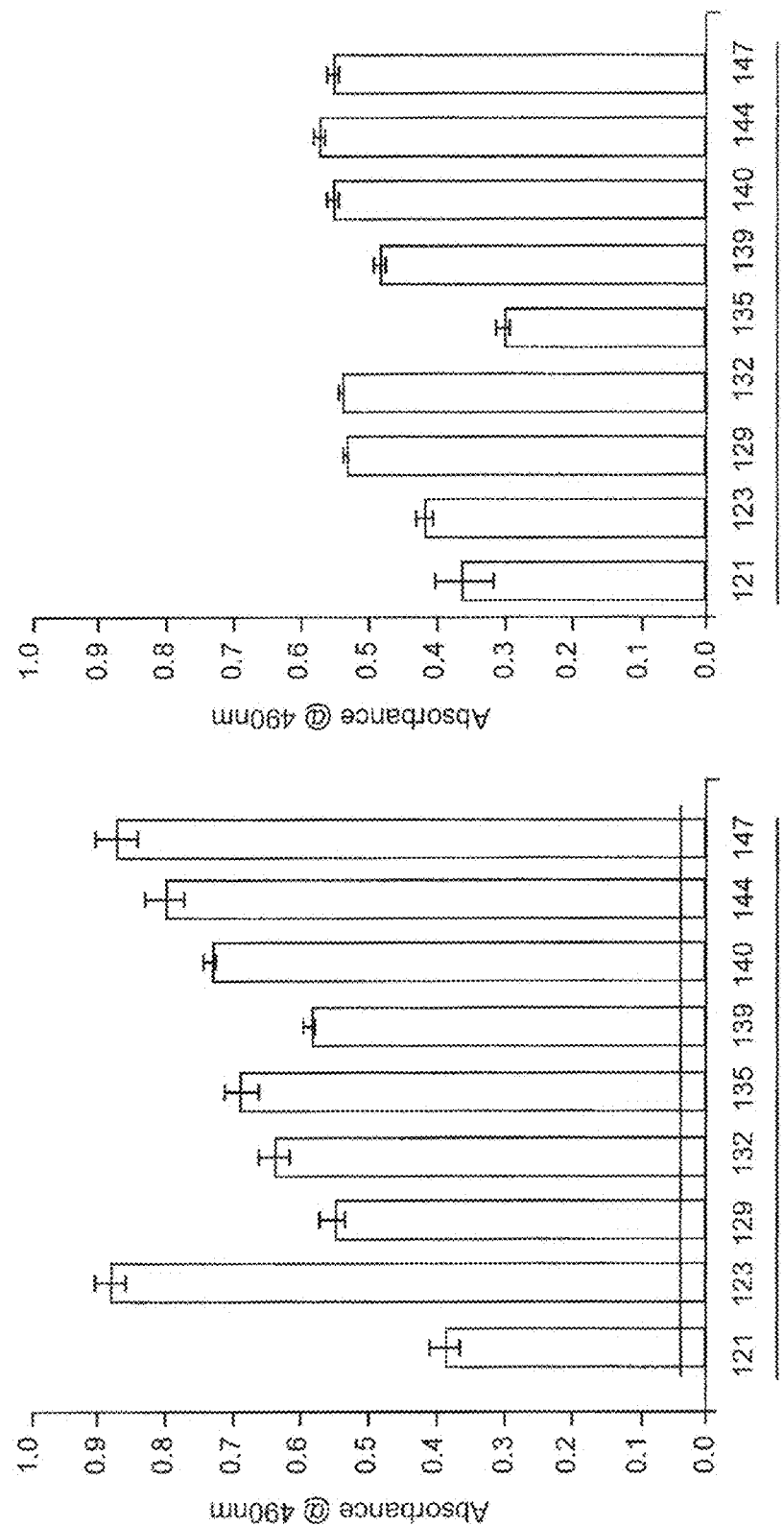
FIGS. 1A and B shows the reactivity of the Cj S3B-SPF sera against *C. jejuni* outer membrane proteins extracted from A, homologous (S3B) and B, heterologous (81-176) strains. Numbers on the x-axis indicate the identification numbers of the serum samples. Vertical bars represent the arithmetic mean and the error bars represent the standard deviation for triplicate samples. The horizontal lines represent the negative cutoff value determined from nine sera collected from control chickens not colonized with *C. jejuni*.

An embodiment of the invention provides immunogenic *C. jejuni* antigens that are immunogenic and which can be used to elicit an immune response against *C. jejuni* in an animal to whom the antigens are administered. Particular antigens of interest include CadF, FlaA and FlpA, as well as others described herein, e.g. in Table 1.

Results presented herein shows for the first time that CadF, a well-characterized 37 kDa fibronectin binding protein, is immunogenic in chickens. Noteworthy is that the CadF protein, which is necessary for *C. jejuni* colonization of chickens (Ziprin, R. L., et al. (1999), Avian Dis. 43:586-589), was detected in both the *C. jejuni* S3B and 81-176 strains. A preferred epitope of CadF identified and provided herein includes the 30-amino acid sequence HYGAGVKFRLSDSLALRLETRDQTNFNHAN (residues 127-156, SEQ ID NO:1) and fragments thereof that are capable of producing a desired immunological response, for example, the sequence FRLS (SEQ ID NO:2).

FlpA antigen, or immunogenic portions thereof, may also be used in the compositions and methods of the invention. In one embodiment, the immunogenic portion of FlpA is and residues 141-170 of FlpA: FVQAVTNLPNRIKLIWRPHPDFRVDSYIIE (SEQ ID NO: 3).

FlaA antigen, or immunogenic portions thereof, may also be used in the compositions and methods of the invention. In one embodiment, the immunogenic portion of FlaA is residues 278-307 of FlaA: INAVKDTTGVEASIDANGQLVLTSADGRGI (SEQ ID NO: 4).

Definitions

Terms that are not defined below or elsewhere in the specification shall have their art-recognized meaning.

Amino acids used in compounds provided herein (e.g., peptides and proteins) can be genetically encoded amino acids, naturally occurring non-genetically encoded amino acids, or synthetic amino acids. Both L- and D-enantiomers of any of the above can be utilized in the compounds. The following abbreviations may be used herein for the following genetically encoded amino acids (and residues thereof): alanine (Ala, A); arginine (Arg, R); asparagine (Asn, N); aspartic acid (Asp, D); cysteine (Cys, C); glycine (Gly, G); glutamic acid (Glu, E); glutamine (Gln, Q); histidine (His, H); isoleucine (Ile, I); leucine (Leu, L); lysine (Lys, K); methionine (Met, M); phenylalanine (Phe, F); proline (Pro, P); serine (Ser, S); threonine (Thr, T); tryptophan (Trp, W); tyrosine (Tyr, Y); and valine (Val, V).

The invention provides nucleic acid sequences (which may be genes) which encode the *C. jejuni* antigens described herein, as well as nucleotide sequences that are variants of or homologous to those sequences. Such polynucleotides typically have at least about 70% homology, and may exhibit at least about 75%, 80%, 85%, 90%, 95%, 96%, 97%, 98% or 99% homology with the relevant sequence, for example over a region of at least about 15, 20, 30, 40, 50, or 100 or more contiguous nucleotides. As used herein, the terms "homology and homologues" are also used to refer to corresponding polynucleotides or proteins from genetically related but not identical organisms (e.g., different strains of bacteria as identified by their strain numbers). These polynucleotides and polypeptides may be identical, or they may, for example, have sequence variations.

Homologous or variant sequences typically differ from the sequence disclosed herein by at least (or by no more than) about 1, 2, 5, 10, 15, 20 or more mutations (which may be substitutions, deletions or insertions). These mutations may be measured across any of the regions mentioned above in relation to calculating homology. The homologous sequence typically hybridizes selectively to the original sequence at a level significantly above background. Selective hybridization is typically achieved using conditions of medium to high stringency (for example 0.03M sodium chloride and 0.03M sodium citrate at from about 50° C. to about 60° C.).

Levels or degrees of homology may be calculated based on any method in the art. For example the UWGCG Package provides the BESTFIT program, which can be used to calculate homology (Devereux et al., Nucleic Acids Research 12, p 387-395 (1984)). The PILEUP and BLAST algorithms can be used to calculate homology or align sequences, for example as described in Altschul S. F.; *J Mol Evol* 36: 290-300 (1993); Altschul, S. F. et al.; *J Mol Biol* 215: 403-10 (1990). Software for performing BLAST analyses is publicly available through the National Center for Biotechnology Information.

The invention also includes nucleic acid sequences that are complementary to the sequences disclosed herein. Complementary sequences may be DNA, RNA or hybrids thereof. The term "complementary" generally refers to the natural binding of polynucleotides by base pairing, and may be complete or partial. "Hybridizable" and "complementary" are terms that are used to indicate a sufficient degree of complementarity such that binding, preferably stable binding sufficient to carry out an intended action, for example, occurs between the DNA or RNA target and the polynucleotide.

The term "stringent conditions" refers to conditions that permit hybridization between polynucleotides, as is understood by those of skill in the art. For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Stringent temperature conditions will ordinarily include temperatures of at least about 30° C., more preferably of at least about 37° C., and most preferably of at least about 42° C. Berger and Kimmel, Methods In Enzymology, Vol. 152: *Guide To Molecular Cloning Techniques*, San Diego (1987): Academic Press, Inc. and Sambrook et al., Molecular Cloning (1989): A Laboratory Manual, 2nd Ed., Vols. 1-3, Cold Spring Harbor Laboratory).

In general, the terms "protein", "polypeptide" and "peptide" refer to any polymer of two or more individual amino acids (whether or not naturally occurring) linked via peptide bonds, "protein", "polypeptide" and "peptide" may be used interchangeably herein. Similarly, protein fragments, analogs, derivatives, and variants are encompassed by these terms. The term "fragment" or "portion" of a protein refers to a polypeptide comprising fewer than all of the amino acid residues of the protein. A "domain" of a protein is also a fragment, and comprises the amino acid residues of the protein often required to confer activity, function, or structure. In some embodiments, polypeptides provided herein have conservative amino acid substitutions relative to a reference amino acid sequence. The present invention encompasses *C.* jejuni proteins (polypeptide, peptides) as described herein, as well as amino acid sequences variants having about at least about 75%, 80%, 85%, 90%, 95%, 96%, 97%, 98% or 99% or more sequence identity with the disclosed amino acid sequence. More typically, such variant sequences have between 1 and 5 (e.g., 1, 2, 3, 4, or 5) conservative amino acid substitutions relative to the amino acid sequences that are explicitly disclosed herein. An antigenic fragment (or epitope, antigenic determinant, etc.) includes any part of a polypeptide as long as it is capable of eliciting a desired immune response.

Identification of Camplyobacter jejuni Proteins Recognized by Chicken Maternal Antibodies A common aspect of the inventions relates to methods and compositions for reducing the number of C. jejuni that colonize animals by promoting an immune response to C. jejuni in animals. In some embodiments, the animals are birds such as chickens. This directly addresses human infections resulting from exposure of C. jejuni through poultry because a decrease in the number of C. jejuni exposed chickens is expected to result in lower exposure of humans to C. jejuni.

This problem was approached by first looking at chicken maternal antibodies. In chickens, the levels of antibodies against C. jejuni vary considerably through the lifecycle of the chicken. At the time of a chicks hatching, maternal antibodies against C. jejuni are at high levels. These maternal antibodies transferred from the mother to the chick remain high in the chick for 3-4 days, at which point they gradually decrease until they become undetectable at about 2-3 weeks of age. Importantly, the colonization of chicks by C. jejuni coincides with the decrease in these maternal antibodies. The mechanisms by which maternal antibodies protect chicks against C. jejuni infections are not clear. They may interfere with bacterial motility, promote clearance by agglutination, block ion/nutrient transport, decrease viability through complement-mediated killing, and/or block the interaction between bacterial adhesions and host cell intentional receptors. Stern, N. J. (1990), Avian Dis. 34:595-601). Antibodies against the bacteria start being generated after the chick has been colonized with C. jejuni. These antibodies may not be sufficient to clear an existing colonization, but once the chick's own antibody production sets in, a decrease in the number of C. jejuni organisms can be observed. Shoaf-Sweeney, K. D. et al. (2008), Appl. Environ. Microbiol. 74 (22) 6867-75.

Antigenic proteins recognized by chicken maternal antibodies believed to be useful for the design and preparation of vaccines are identified and described herein. The studies described in Example 1 identified C. jejuni membrane-associated proteins recognized by maternal antibodies, as the antibodies passed from hens to chicks are partially protective against Campylobacter colonization of chicks. The proteins identified were further characterized to evaluate their efficacy as C. jejuni vaccine candidates. While a total of 60 proteins were identified in the OMP extracts from C. jejuni 81-176, fewer proteins (i.e., ~20) were identified that reacted with the antibodies in the Cj S3B-SPF sera. The identified proteins include CadF, CmeA, CmeC, CjaA, CjaC, CJJ81176_0126, CJJ81176_0128, CJJ81176_0164, CJJ81176_0586 CJJ81176_1185, CJJ81176_1295, CJJ81176_1525, FlaA, FlaB, FlgE2, FlpA, PEB2, PEB3, PorA, MapA, and SdhB (see Table 1).

The Cj S3B-SPF sera contained antibodies that reacted with the flagellar hook protein (FlgE2) and the flagellar FlaA and FlaB filament proteins in C. jejuni S3B and 81-176. FlgE2 has a molecular mass of 89.4 kDa and is required for motility, flagellar assembly, and protein secretion in C. jejuni (Hendrixson, D. R., and V. J. DiRita (2003), Mol. Microbiol. 50:687-702; Konkel, M. E. et al. (2004), J. Bacteriol. 186: 3296-3303). Although the predicted molecular mass of these proteins is around 59 kDa, glycosylation has been shown to alter the mass of the proteins by up to 10% depending on the level of modification (Thibault, P. et al. (2001), J. Biol. Chem. 276:34862-34870). A band between 65 and 63 kDa was observed as judged by immunoblot analysis with an anti-C. jejuni flagellin specific serum. It is possible that this band represents glycosylated forms of the FlaA or FlaB proteins, whereas the proteins with apparent molecular masses of less than 60 kDa represent degradation products.

The Cj S3B-SPF sera contained antibodies that reacted against C. jejuni strain-specific proteins as well as proteins common amongst C. jejuni strains. For example, a 40 kDa immunoreactive protein, CmeA (band 9), was recognized in the OMP extracts of the C. jejuni S3B and 81-176 strains by all of the Cj S3B-SPF sera, whereas a 54 kDa protein, presumably CmeC, was primarily recognized in the OMP extracts of the C. jejuni S3B strain. Together the CmeA, B, and C proteins comprise a resistance-nodulation-division (RND) efflux pump that is involved in resistance to a broad range of antimicrobials and bile salts (Lin, J., L. O. Michel, and Q. Zhang. (2002), Antimicrob. Agents Chemother. 46:2124-2131; Lin, J. et al. (2003), Infect. Immun., 71:4250-4259). CmeB is the inner membrane efflux transporter, whereas CmeA is localized in the periplasmic space, and CmeC forms an outer membrane channel. CmeABC is widely distributed in C. jejuni isolates (Lin, J., L. O. Michel, and Q. Zhang. (2002), Antimicrob. Agents Chemother. 46:2124-2131), and comparison of the deduced amino acid of each protein from four C. jejuni strains (NCTC11168, RM1221, 81116, and 81-176) revealed that sequence of each protein was well conserved (>98% similarity) amongst these strains.

Two outer membrane substrate-binding proteins involved in amino acid transport, CjaA (band 12) and CjaC (band 13), were identified. CjaA has been characterized as an extracytoplasmic solute receptor in a putative ATP-binding cassette-type cysteine transporter (Muller, A. et al. (2005), Mol. Microbiol. 57:143-155), while CjaC has been shown to be required for histidine transport (Garvis, S. G., G. J. Puzon, and M. E. Konkel (1996), Infect. Immun. 64:3537-3543). It is possible that amino acid transport system proteins may serve as good vaccine components because C. jejuni is asaccharolytic and relies on exogenous sources of amino acids for energy production. The Cj S3B-SPF sera was found to contain antibodies that reacted against the CjaA and CjaC proteins in the C. jejuni S3B strain, but not in the 81-176 strain. Pawelec et al. ((2000), FEMS Microbiol. Lett. 185:43-49) demonstrated genetic diversity in both cjaA and cjaC among C. jejuni isolates, with as much as 16% variation noted at the nucleotide level. The relevant antigenic surfaces of CjaA and CjaC are cross-reactive with each other. Thus, slight variations in the amino acid sequences may account for the reduced or absent antibody response to CjaA and CjaC in the C. jejuni 81-176 strain.

The results presented in Example 1 shows for the first time that CadF, a well-characterized 37 kDa fibronectin binding protein, is immunogenic in chickens. Noteworthy is that the CadF protein, which is necessary for C. jejuni colonization of chickens (Ziprin, R. L., et al. (1999), Avian Dis. 43:586-589), was detected in both the C. jejuni S3B and 81-176 strains. A preferred epitope of CadF identified and provided herein includes the 30-amino acid sequence HYGAGVKFRLSD-SLALRLETRDQINFNHAN (residues 127-156, SEQ ID NO:1) and fragments thereof that are capable of producing a desired immunological response. Such fragments or portions of this sequence include, for example, fragments comprising at least 3, 4, 5, 6, 7, 8, 9, 10, 11, 12, 13, 14, 15, 16, 17, 18, 19, 20, 21, 22, 23, 24, 25, 26, 27, 28, or 29 contiguous amino acids membrane protein based on its amino acid sequence. *C. jejuni* antigens utilized in various embodiments of the invention are summarized in Table 1.

TABLE 1

Listing of *C. jejuni* antigens and corresponding Genbank Accession numbers.
NCTC11168 81-176

| NCTC11168 | | | 81-176 | | |
|---|---|---|---|---|---|
| Gene/locus | Protein | GeneID #* | Gene/locus | Protein | GeneID #* |
| cadF/Cj1478c | CadF | 905765 | cadF/CJJ81176__1471 | CadF | 4683585 |
| SEQ ID NO: 5 | SEQ ID NO: 6 | | SEQ ID NO: 7 | SEQ ID NO: 8 | |
| cmeA/Cj0367c | CmeA | 904690 | cmeA/CJJ81176__0390 | CmeA | 4683757 |
| SEQ ID NO: 9 | SEQ ID NO: 10 | | SEQ ID NO: 11 | SEQ ID NO: 12 | |
| cmeC/Cj0365c | CmeC | 904688 | cmeC/CJJ81176__0388 | CmeC | 4683000 |
| SEQ ID NO: 13 | SEQ ID NO: 14 | | SEQ ID NO: 15 | SEQ ID NO: 16 | |
| cjaA/Cj0982c | CjaA | 905273 | cjaA/CJJ81176__1001 | CjaA | 4682355 |
| SEQ ID NO: 17 | SEQ ID NO: 18 | | SEQ ID NO: 19 | SEQ ID NO: 20 | |
| hisJ/Cj0734c | HisJ | 905052 | cjaC/CJJ81176__0757 | CjaC | 4683779 |
| SEQ ID NO: 21 | SEQ ID NO: 22 | | SEQ ID NO: 23 | SEQ ID NO: 24 | |
| Cj0091 | SEQ ID NO: 26 | 904419 | CJJ81176__0126 | SEQ ID NO: 28 | 4683012 |
| SEQ ID NO: 25 | | | SEQ ID NO: 27 | | |
| Cj0093 | SEQ ID NO: 30 | 904421 | CJJ81176__0128 | SEQ ID NO: 32 | 4683182 |
| SEQ ID NO: 29 | | | SEQ ID NO: 31 | | |
| Cj0129c | SEQ ID NO: 34 | 904463 | CJJ81176__0164 | SEQ ID NO: 36 | 4682724 |
| SEQ ID NO: 33 | | | SEQ ID NO: 35 | | |
| Cj0561c | SEQ ID NO: 38 | 905206 | CJJ81176__0586 | SEQ ID NO: 40 | 4682256 |
| SEQ ID NO: 37 | | | SEQ ID NO: 39 | | |
| omp50/Cj1170c | Omp50 | 905460 | CJJ81176__1185 | SEQ ID NO: 44 | 4683343 |
| SEQ ID NO: 41 | SEQ ID NO: 42 | | SEQ ID NO: 43 | | |
| flpA/Cj1279c | FlpA | 905570 | CJJ81176__1295 | FlpA | 4683528 |
| SEQ ID NO: 45 | SEQ ID NO: 46 | | SEQ ID NO: 47 | SEQ ID NO: 48 | |
| Cj1540 | SEQ ID NO: 50 | 905822 | CJJ81176__1525 | SEQ ID NO: 52 | 4682905 |
| SEQ ID NO: 49 | | | SEQ ID NO: 51 | | |
| flaA/Cj1339c | FlaA | 905631 | flaA/CJJ81176__1339 | FlaA | 4682159 |
| SEQ ID NO: 53 | SEQ ID NO: 54 | | SEQ ID NO: 55 | SEQ ID NO: 56 | |
| flaB/Cj1338c | FlaB | 905630 | flaB/CJJ81176__1338v | FlaB | 4682956 |
| SEQ ID NO: 57 | SEQ ID NO: 58 | | SEQ ID NO: 59 | SEQ ID NO: 60 | |
| flgE*/cj1729c | FlgE** | 906004 | flgE/CJJ81176__0025 | FlgE | 4682758 |
| SEQ ID NO: 61 | SEQ ID NO: 62 | | SEQ ID NO: 63 | SEQ ID NO: 64 | |
| peb2/Cj0778 | PEB2 | 905087 | peb2/CJJ81176__0799 | PEB2 | 4682647 |
| SEQ ID NO: 65 | SEQ ID NO: 66 | | SEQ ID NO: 67 | SEQ ID NO: 68 | |
| peb3/Cj0289c | PEB3 | 904613 | peb3/CJJ81176__0315 | PEB3 | 4682380 |
| SEQ ID NO: 69 | SEQ ID NO: 70 | | SEQ ID NO: 71 | SEQ ID NO: 72 | |
| porA/Cj1259 | PorA | 905550 | porA/CJJ81176__1275 | PorA | 4683701 |
| SEQ ID NO: 73 | SEQ ID NO: 74 | | SEQ ID NO: 75 | SEQ ID NO: 76 | |
| mapA/Cj1029c | MapA | 905321 | mapA/CJJ81176__1048 | MapA | 4682391 |
| SEQ ID NO: 77 | SEQ ID NO: 78 | | SEQ ID NO: 79 | SEQ ID NO: 80 | |
| sdhB/Cj0438 | SdhB | 904763 | sdhB/CJJ81176__0464 | SdhB | 4683096 |
| SEQ ID NO: 81 | SEQ ID NO: 82 | | SEQ ID NO: 83 | SEQ ID NO: 84 | |

*GenBank Nucleotide Sequence GeneID #
**FlgE, aka FlgE2.

capable of producing a desired immunological response. In one embodiment, the fragment comprises at least 4 contiguous amino acids, for example, the sequence FRLS (SEQ ID NO:2). One desired immunological response of an antibody that binds to a CadF epitope is inhibiting CadF binding to fibronectin. Another desired immunological response is to sufficiently inhibit *Campylobacter* colonization of chickens, which may be caused by inhibiting CadF binding to fibronectin.

Several *C. jejuni* OMPs were also found to be immunogenic. These proteins included PEB3, MapA, and CJJ81176__0586. The function of PEB3 is not known (Pei, Z. H., et al. (1991), J. Biol. Chem. 266:16363-16369). MapA is an outer membrane lipoprotein that has been used as an identification tool to distinguish between *C. jejuni* and *C. coli* (Stucki, U. et al. (1995), J. Clin. Microbiol. 33:855-859), and to detect and diagnose individuals with *C. jejuni* infection (Campbell, L. K. et al. (2006), Mod. Pathol. 19:1042-1046). CJJ81176__0586 has been identified as a hypothetical outer Characterization of Adhesion Proteins and Identification of FlpA Colonization Factor Another aspect of the invention is the identification and characterization of bacterial adhesin proteins, and more particularly to identify and characterize adhesin proteins of *C. jejuni* useful for making vaccines against *C. jejuni*. Bacterial adherence to host epithelial cells is believed to be critical for chicken colonization, as cell attachment may prevent clearance of the bacteria via host mediated mechanical force. Studies were performed to assess the conservation of putative *C. jejuni* adhesin-encoding genes cadF, capA, jlpA, peb1A, porA, Cj1279c (flpA), and Cj1349c and additionally to identify the contribution of the corresponding proteins in *C. jejuni* host cell interactions. The results presented in Example 2 show that the cadF, jlpA, porA, peb1A, flpA, and Cj1349c genes were conserved amongst the isolates, whereas the presence of the capA gene was variable. The results further showed that the *C. jejuni* CadF, CapA, FlpA, and Cj1349c proteins contribute to the bacterium's in vitro adherence to chicken LMH hepatocellular carcinoma epithelial cells, while CadF, PEB1, and FlpA contribute to the bacterium's in vivo colonization of broiler chicks. Included in these finding is the first novel showing that FlpA promotes the binding of *C. jejuni* to host cells and plays a role in *C. jejuni* colonization of chickens.

Experiments were performed with *C. jejuni* isolates collected from human, poultry, bovine, porcine, ovine, and canine sources. These isolates were genetically diverse, as judged by MLST. The isolates were found to comprise 42 unique sequence types, four of which had not been identified previously. The clonal complexes identified amid the *C. jejuni* livestock (i.e., bovine, porcine and ovine) isolates included two complexes, CC42 and CC61, that were determined in previous studies to be associated significantly with bovine and ovine (Colles, F. M., et al. (2003), Microbial. 69:7409-7413; Kwan, P. S., et al. (2008), Microbiol. 74:5130-5138). Furthermore, the eleven clonal complexes identified in the 41 poultry isolates included several poultry-associated complexes [i.e., CC45, CC257 and CC354; (Dingle, K. E. et al., (2002) Emerg. Infect. Dis. 8:949-955)]. Additionally, the clonal complexes of the human isolates identified in this study were also found within the poultry and livestock isolates, and vice versa. Therefore, no predominant food animal source of human infection was identified in this study.

As discussed above, genetic analysis of the adhesin profiles amongst the strains via dot blot assays demonstrated conservation of the *C. jejuni* cadF, jlpA, porA, peb1A, flpA, and Cj1349c genes. While the dot-blot hybridization assay is stringent enough to detect the presence or absence of the well-conserved adhesin genes, it cannot detect strain-to-strain sequence variations. However, the amino-acid sequences of the putative adhesins CadF, JlpA, PEB1, Cj1279c, and Cj1349 are all greater than 95% identical between *C. jejuni* strains, and CapA is greater than 85% identical between *C. jejuni* strains. These studies further indicate that the capA gene was absent from 40% of the *C. jejuni* strains recovered from humans, and was absent from 39% of the *C. jejuni* strains recovered from animals.

This is the first time the functional role of the *C. jejuni* proteins examined has been compared by generating a mutation in these genes within a single genetic background. The *C. jejuni* CadF, CapA, FlpA and Cj1349c proteins were found to play a significant role in the bacterium's in vitro adherence to chicken epithelial cells, whereas JlpA and PEB1 did not appear to play a role in cell adherence. For example, it was found that insertional mutagenesis of jlpA did not result in a reduction in binding to chicken LMH cells. In agreement with the results from the in vitro binding assays, the jlpA mutant was able to colonize broiler chickens at a level comparable with that of a wild-type isolate.

While it was found that a *C. jejuni* peb1A mutant bound to chicken LMH cells at a level comparable to that of a wild-type isolate, the mutant did not colonize broiler chickens. The in vitro data indicates that PEB1 does not appear to act as an adhesin but rather plays a critical role in aspartate and glutamate transport. The CapA protein was identified as a putative autotransporter based on in silico analysis. Ashgar et al. (2007, J. Bacteriol. 189:1856-1865), reported that a capA knockout failed to colonize and persist in Rhode Island Red chickens. Studies described herein showed that the capA gene was not conserved amongst *C. jejuni* isolates. Indeed, 15 of the *C. jejuni* poultry isolates utilized in this study lacked the capA gene. It was also found that the *C. jejuni* capA mutant exhibited a 47% reduction in binding to chicken LMH epithelial cells when compared with the wild-type isolate, yet was able to colonize broiler chickens as efficiently as the wild-type isolate. The reason for the discrepancy in this data and that of Ashgar et al. is not known. However, based on these results, it is concluded that the CapA protein is an adhesion protein that is not required for the colonization of broiler chickens.

CadF is a highly conserved 37 kDa outer membrane protein that binds to the extracellular matrix component Fn (Konkel, M. E. et al. (2005), Mol. Microbiol. 57:1022-1035; Konkel, M. E. et al. (1997), Mol. Microbiol. 24:953-963; Konkel, M. E. et al. 1999, J. Clin. Microbiol. 37:510-517; Monteville, M. R., and M. E. Konkel (2002), Infect. Immun. 70:6665-6671). The results presented here show that the *C. jejuni* cadF mutant demonstrated a 41% reduction in binding to chicken LMH cells and was unable to efficiently colonize broiler chickens. Since the Fn-binding protein CadF is critical to *C. jejuni* host cell adherence, it is hypothesized that FlpA and Cj1349c may play a role in host cell attachment. Cj1349c has been annotated as a putative Fn/fibrinogen-binding protein. The Cj1349c mutant demonstrated a 14% reduction in binding to chicken LMH cells (P<0.05). However, reduced colonization of broiler chicks was not observed with a Cj1349c mutant when compared with the wild-type isolate. Based on the in vitro experiments, Cj1349c may act as an adhesin. However, the functional role of Cj1349c in vivo is not clear based on the chicken colonization experiments. FlpA contains Fn type III domains. Interestingly, the flpA mutant showed a 39% reduction in binding to chicken LMH epithelial cells relative to the wild-type isolate. In addition, the flpA mutant failed to efficiently colonize broiler chickens, as only two of ten broiler chicks were colonized. To address the concern that a mutation in flpA may have a polar effect, a mutation was generated in Cj1278c. The Cj1278c mutant did not show a significant reduction in binding to chicken LMH cells relative to the wild-type isolate. These data suggest that FlpA is a novel *C. jejuni* adhesin involved in *C. jejuni*-host cell adherence and chicken colonization.

In summary, the cadF, jlpA, peb1A, porA, flpA, and Cj1349c genes are conserved amongst *C. jejuni* isolates, whereas the presence of the capA gene is variable. CadF, CapA, FlpA, and Cj1349c proteins facilitate *C. jejuni* adherence to chicken LMH cells, which is consistent with the hypothesis that more than one protein contributes to the binding of *C. jejuni* to host epithelial cells. The results indicate that both the CadF and FlpA proteins play a significant role in *C. jejuni* colonization of chickens. Based on the in vivo assays, it is apparent that the CapA and Cj1349c proteins are not essential for *C. jejuni* to colonize chickens, but the possibility that they contribute to the process cannot be ruled out. Additionally, the PEB1 protein is required for *C. jejuni* to colonize chickens. This finding is likely due to that fact that it is involved in amino acid transport required for viability within the host. These results have led to the determination that FlpA (Cj1279c) is a novel *C. jejuni* adhesin.

In Example 3, the binding properties of FlpA were further characterized and FlpA was determined to be a member of the Microbial Surface Components Recognizing Adhesive Matrix Molecules (MSCRAMMs) family. Experimental evidence showed that *C. jejuni* FlpA is surface exposed, promotes the attachment of *C. jejuni* to host epithelial cells, and has fibronectin (Fn) binding activity. The identification of FlpA as a second MSCRAMM in *C. jejuni* highlights the importance of Fn binding in host colonization and disease.

In addition, in Example 4, the specific sites of FlpA and Fn adherence were determined. ELISAs using recombinant proteins encoding each of the three FlpA domains demonstrated that FlpA-D2 contained the Fn-binding domain. Using an array of synthetic peptides spanning the FlpA-D2 amino acid sequence, seven amino acids $^{158}$PHPDFRV$^{164}$ (SEQ ID NO: 51) were identified within FlpA-D$^2$ with maximal Fn-binding activity. Since FN3 repeats are involved in intramolecular interactions with the N-terminus of Fn, the ability FlpA to bind two thermolytic fragments generated form the N-terminus of Fn—the 30 kDa N-terminal domain (NTD) and the gelatin-binding domain (GBD) were determined. FlpA bound the Fn gelatin-binding domain (GBD), but not the NTD. Furthermore, the amounts of FlpA bound to the GBD and full-length Fn were similar, indicating the GBD is the primary site of FlpA adherence to Fn. Collectively, these data demonstrated that residues $^{158}$PHPDFRV$^{164}$ within FlpA-D2 mediate adherence to the GBD of Fn.

Vaccine Compositions

The invention provides vaccine or antigenic (immunogenic) compositions which comprise one or more *C. jejuni* antigens (e.g. proteins or polypeptides), or antigenic fragments thereof. The antigens may be chemically synthesized, prepared by recombinant technology (e.g. expressed by/from an organism that is genetically engineered to contain and express nucleic acids encoding the antigens), or isolated from cultures of *C. jejuni* bacteria. Preferred antigens are listed, for example, in Table 1. The SEQ ID NOS: for each of the sequences in Table 1 (both the amino acid sequence and the nucleotide sequence encoding the amino acid sequence) are provided in the Sequence Listing filed concurrently herewith. In some embodiments, the antigens are one or more of CadF, FlpA and FlaA, or one or more antigenic fragments thereof. The antigenic fragments include but are not limited to 30-mer antigenic epitopes as follows: residues 127-156 of CadF: HYGAGVKFRLSDSLALRLETRDQINFNHAN (SEQ ID NO: 1) or the 4-mer identified within this sequence, FRLS (SEQ ID NO:2); residues 141-170 of FlpA: FVQAVTNLP-NRIKLIWRPHPDFRVDSYIIE (SEQ ID NO: 3) and residues 278-307 of FlaA: INAVKDTTGVEASIDANGQLVLT-SADGRGI (SEQ ID NO: 4). Other antigenic fragments of these sequences may also be used, include, for example, fragments comprising at least 3, 4, 5, 6, 7, 8, 9, 10, 11, 12, 13, 14, 15, 16, 17, 18, 19, 20, 21, 22, 23, 24, 25, 26, 27, 28, or 29 contiguous amino acids capable of producing a desired immunological response. Sequence variants of these proteins and antigenic fragments, as described herein, may also be utilized in the compositions. The antigens may be present in a single polypeptide construct which contains multiple copies of the same antigen, or copies of different antigens, i.e. a chimeric construct. For example, a chimeric polypeptide may include at least two of CadF, FlpA and FlaA, or immunogenic fragments thereof, e.g. one or more copies of at least two of the three 30mers described above, and/or various other shorter sequences (e.g. FRLS (SEQ ID NO:2)). Chimeras may also include various spacer or linker sequences between the antigens in the construct.

In some embodiments, the *C. jejuni* proteinaceous antigens per se are present in a composition that is used to vaccinate an animal. However, the invention also encompasses hosts or vectors comprising nucleic acid sequence which encode the antigens, and in some embodiments, the compositions include such hosts. For example, various bacterial and viral hosts may be genetically engineered to contain and express sequences encoding the antigens, and then the genetically modified bacteria or viruses may be used to infect the animal and to express the antigens within the animal. Generally, the *C. jejuni* antigens are heterologous with respect to the host, i.e. the *C. jejuni* antigens are not naturally (in nature) found in the host organism. The host organisms may be attenuated so that they themselves do not cause any disease symptoms. Examples of suitable bacterial vectors include but are not limited to various plasmids that replicate in *Lactobacillus* (discussed in detail below), such as pAS3 and pLBS-GFP-EmR ((Bhowmik T, et al. (1993) J Bacteriol. 175:6341-4; Mota R M, et al. (2006) BMC Biotechnol. 5; 6:2)). Such vectors also generally include one or more promoters to insure active transcription of the genes encoding the antigens, and may also include various enhancer sequences, stop signals, etc., as appropriate to achieve adequate expression of the sequences.

In one embodiment of the invention, the antigens of the invention are expressed in a bacterial host as a chimera which also includes an export protein that causes the antigens to be transported to and/or presented on the surface of the host bacterium. The antigens are thus readily accessible to the immune system of a vaccine recipient, and the elication of an immune response is encouraged or facilitated. In one exemplary embodiment, the export sequence is the export signal and cell wall anchor sequence of the *Lactobacillus* S-protein (i.e. residues 1 to 32 of the LbsA S-layer protein from *L. crispatus* strain MH315 [complete LbsA S-layer protein amino acid and encoding nucleotide sequences are provided in SEQ ID NOS. 168 and 169, respectively], residues 320 to 422 of the LbsB S-layer protein from *L. crispatus* strain MH315 [complete LbsB S-layer protein amino acid and encoding nucleotide sequences are provided in SEQ ID NOS. 170 and 171, respectively]). Other export and anchoring sequences may be used in a similar manner, examples of which include but are not limited to *L. acidophilus* strain NCFM SlpA (the amino acid and encoding nucleotide sequences of which are provided in SEQ ID NOS: 172 and 173, respectively), and SlpB (the amino acid and encoding nucleotide sequences of which are provided in SEQ ID NOS: 174 and 175, respectively), and the *L. helveticus* strain CNRZ32 SlpA (the amino acid and encoding nucleotide sequences of which are provided in SEQ ID NOS: 176 and 177, respectively).

The antigens or hosts which produce the antigens are generally provided to a vaccine recipient in a suitable physiological compatible carrier, examples of which include but are not limited to normal saline solutions (e.g. buffered at pH 7.0-8.0) and water (see, for example, *Remingtons Pharmaceutical Sciences*, Mack Publishing Co., A. R. Gennaro edit. 1985). In order to facilitate delivery of the antigens, the formulation may include, as optional ingredients, other substances known in the art, e.g. diluents, solubilizing or emulsifying agents, salts, buffering agents, excipients, penetration enhancers, surfactants, antioxidants, stabilizers, preservatives, wetting agents, lipids, chelating agents, etc., so long as they do not interfere with the biological activities of the components of the compositions provided herein. The formulations are generally sterile, except that host organisms may be present. A preferred carrier for vaccines provided herein, especially bacterial vaccines, is water.

Methods of Vaccination

Another aspect of the invention is directed to methods of treating or preventing a *C. jejuni* bacteria colony formation in an animal by administering a therapeutically effective amount of the antigens described herein. Also, the *C. jejuni* antigens could be used in combination with other antigens (e.g. human infectants such as HIV, malaria, tuberculosis, etc.), e.g. in the form of a chimera or fusion product. A "therapeutically effective amount" is the amount of the antigen that will elicit a desired response, for example, an immune response in the vaccinated animal.

One desired immunological response may be the generation of antibodies that bind to the antigens described herein, when located in a live, potentially infective *C. jejuni* to which a vaccinated animal is exposed after vaccination, e.g. by binding to a CadF epitope and inhibiting CadF binding to fibronectin. Another desired immunological response is to sufficiently inhibit *Campylobacter* colonization of an animal chickens, which may be caused by inhibiting CadF binding to fibronectin.

In some embodiments, the animal is a bird, but this need not always be the case. Other species also harbor *C. jejuni* and may be vaccinated as descried herein, including but not limited to domestic pets, rodents, various wild animals, and especially animals that are used as food, e.g. cattle (especially calves), pigs, etc. The vaccine may be administered to birds, and these may be of any type (e.g. domesticated, wild, in protected areas such as zoos and wildlife preserves, etc.). However, the vaccine will be especially useful for inoculating birds that are raised for food, e.g. chickens, turkeys, geese, ducks, ostriches, etc., or those that are raised in proximity to humans (e.g. pets such as parrots, canaries, etc., or prize hens, roosters, etc.).

In some embodiments, the vaccine is administered to young or juvenile animals, or even to animals that are very young, e.g. newborn. For example, when the animal is a bird, administration may be to a bird that is less than one month old, e.g. to a bird that is between one day and three weeks in age, or to a bird that is between one day and two weeks in age. In some embodiments, the vaccine is administered within the window of time between when maternal antibodies are still active in the animal, and the time when maternal antibodies wane. The vaccine formulation may be administered only once, or may be repeatedly administered, e.g. for up to about 2, 3, 4, or 5 days or more.

The vaccine and immunogenic formulations provided herein are generally intended for use in immunizing birds, especially chickens, although this need not always be the case. Typical routes of administration include but are not limited to addition of the antigens and/or of hosts which produce the antigens to substances which are ingested by the animal, usually water, although addition to other food sources are not excluded. In other embodiments, the antigens and or hosts which produce the antigens are administered as an aerosol, e.g. a virus that is genetically engineered to contain and express the antigens may be introduced into the environment of the animal chicken e.g. as an aerosol, and enter via inhalation into the respiratory tract. In still other embodiments, and especially when individual domesticated animals (e.g. pets) are concerned, administration may be via injection, e.g. intramuscular, subcutanelously, etc.

When vaccines are given orally via a water system, it is preferred that sanitizers are absent when vaccines are being given. To neutralize the effects of chlorine and certain elements in the domestic water supply, a neutralizing agent such as skimmed milk may be added to the water (a rate of 500 ml of skimmed milk to 10 liters of water is suitable). For example, skimmed milk can be added about thirty minutes before the vaccine. In order to achieve a good vaccine administration, it is preferable to administer the vaccine such that all the animals drink the vaccine medicated water within 1-2 hours. This is preferred because after this time period the viability of a live vaccine can rapidly decline. In broilers (aka fryers) or birds less than 4 weeks of age, this may be achieved by withholding water for about 30 minutes before giving the vaccine to make the birds thirsty. In birds over 4 week of age, the water may be withheld from about 2 to 8 hours or overnight (about 6, 7, 8, 9, 10, 12, or more hours). For younger birds, water may be withheld for about 20 minutes, 45 minutes, one hour, 90 minutes, or up to a couple of hours. As birds drink when feeding, vaccination should be timed to coincide with food being present in the feed tracks. The water can be provided at a time when birds are likely to be drinking, such as morning time for broilers. Lighting can be used to influence the birds drinking, where turning the lights down is used to reduce drinking and turning the lights on is used to stimulate the birds to go to feeders and drinkers. Following vaccination clean water should be again made available to the birds.

The dose of antigen that is administered may vary from situation to situation, depending on, for example, the type of animal being vaccinated, the age or breed, the particular antigen that is used, the form of the antigen (e.g. antigen alone, or a host that manufactures the antigens), etc.

The data obtained from the cell culture assays and animal studies can be used in formulating a range of dosages for use. Guidance as to particular dosages and methods of delivery is provided in the literature and generally available to practitioners in the art. In general, dosage is sufficient to achieve, in the animal, a level of antigen that is from about 0.01 mg/kg to about 100 mg per kg of body weight. If a bacterial or viral host is administered, sufficient amounts to allow the host to colonize the gastrointestinal (GI) tract of the host, and/or to produce sufficient antigen to cause a significant immune response in the vaccine recipient are administered. A suitable amount will usually be at least about $10^5$ cfu, and preferably about $10^6$ cfu or more per dose. Larger dosages such as about $10^7$, $10^8$, $10^9$ and up to about $10^{10}$ cfu may be used. This allows a sufficient amount of bacteria or virus to pass into the intestine, if required. The above amounts of bacteria or virus may correspond, to for instance, about $10^6$ to about $10^8$ cfu per kg of body weight of the animal. The concentration of bacteria or virus in the vaccine are typically at least about $1\times10^6$/ml, such as at least about $5\times10^6$/ml, $1\times10^7$/ml, $1\times10^8$/ml, $1\times10^9$/ml, or $1\times10^{10}$/ml.

Several vaccines for use in preventing diseases in poultry have been reported (See, e.g., U.S. Pat. Nos. 5,294,441, 5,389,368, 5,468,485, 5,387,744, and 6,866,847, the complete contents of each of which are hereby incorporated by reference), and the information contained therein may be useful with respect to vaccine compositions and method of administration.

Probiotic Bacteria

Probiotics are live microorganisms which, when administrated in adequate amounts to a host, confer a health benefit on the host. Perhaps the most commonly used probiotic species belong to the genus *Lactobacillus*. One potential probiotic benefit of probiotic administration is improved resistance to enteric pathogens through competitive exclusion (Nava, G. M., et al., 2005 Anim Health Res Rev 6:105-18). Probiotics are used in the egg and poultry industry to improve performance parameters including mean egg weight, body weight, and feed conversation ratio (Haghighi, H. R. et al., (2005) Clin Diagn Lab Immunol 12:1387-92; Talebi, A., B. et al. 2008, Avian Pathol 37:509-12).

In another aspect of the invention, probiotic organisms were evaluated to explore whether certain species have a novel and beneficial effect on the colonization of *C. jejuni* in chickens. The effect of administration of four probiotic lactobacilli on the colonization of *C. jejuni* in chickens was evaluated (Example 5). The four probiotic lactobacilli examined were *Lactobacillus* strains (*L. acidophilus* NCFM, *Lactobacillus crispatus* JCM 5810, *Lactobacillus gallinarum* ATCC 33199 and *Lactobacillus helveticus* CNRZ32). The strain of *C. jejuni* utilized in these studies was F38011, because it was found to be most sensitive to inhibition by lactobacilli.

In order to determine the effect of administration of probiotic lactobacilli on the chicken immune system, serum antibodies for *C. jejuni* (FIG. 12) were determined at 21 and 28 days post-hatching. Anti-*C. jejuni* antibodies were not detected in birds belonging to groups that were not challenged with *C. jejuni* or in birds not found to be colonized with *C. jejuni*. Antibodies were detected in sera of colonized chickens at 2 weeks post inoculation with *C. jejuni*. Antibody production against *C. jejuni* did not clear the organism from the cecum. The results from Example 5 indicate that it is likely that immune modulation with probiotic *Lactobacillus* strains did not affect the ability of *C. jejuni* to colonize the gastrointestinal tract of chickens.

The ability of probiotic lactobacilli to inhibit the growth of *C. jejuni* in vitro and the effect of the administration of these lactobacilli on *C. jejuni* colonization of chickens were further evaluated. The results unexpectedly showed that birds receiving *L. crispatus* JCM 5810 exhibited a low rate of colonization by *C. jejuni*. Additionally, birds receiving *L. crispatus* had a high rate of recovery of lactobacilli from the cecum of chickens. Strain typing by PCR confirmed that lactobacilli recovered from the cecum of chickens are in fact, *L. crispatus*. Additionally, several isolates from chickens not receiving *L. acidophilus, L. gallinarum*, and *L. helveticus* were also positively identified as *L. crispatus*. *L. crispatus* is commonly isolated from chickens and has been identified as a predominant *Lactobacillus* species in the alimentary tract of chickens (Abbas Hilmi, H. T. et al. (2007), Appl Environ Microbiol 73:7867-73). The fact that *L. crispatus* is able to remain in the alimentary tract of chickens for prolonged periods of time likely enhances the probiotic ability of this species. Moreover, when this fact is considered in view of the data presented that *L. crispatus* exhibited a low rate of colonization by *C. jejuni*, provides evidence that this species might be a good candidate for the development of a recombinant bacterial vaccine.

The four *Lactobacillus* species evaluated are known to have genes encoding S-layer proteins (Avall-Jaaskelainen, S., and A. Palva. (2005), FEMS Microbiol Rev 29:511-29). S-layer protein has been shown to be involved in adherence to host tissues (Doig, P., L. Emody, and T. J. Trust (1992), J Biol Chem 267:43-9) and, in particular, the S-layer of *L. acidophilus* isolated from fowl has been shown to be involved in interaction with avian intestinal epithelial cells (Schneitz, C., L. Nuotio, and K. Lounatma (1993), J Appl Bacteriol 74:290-4). The S-layer protein of *L. crispatus* JCM 5810, the strain evaluated in Example 5, was shown to be responsible for the strain's ability to adhere to collagen containing regions in the chicken colon. The S-layer protein from a different *L. crispatus* strain, ZJ001, was shown to inhibit adhesion of *Salmonella typhimurium* and *E. coli* to HeLa cells. Thus, it is likely that the S-layer protein of *L. crispatus* is important for colonization of the chicken gastrointestinal tract and for inhibition of *C. jejuni* colonization.

Several mechanisms for competitive exclusion have been considered, including the saturation and obstruction of attachment sites for the pathogen by native and probiotic flora, competition for essential nutrients limiting the ability of the pathogen to grow, production of antagonistic molecules including organic acids, hydrogen peroxide and bacteriocins, and modulation of immune responses. Lactobacilli produce a number of anti-microbial products including bacteriocins, organic acids, and hydrogen peroxide (Barefoot, S. F., and C. G. Nettles (1993), J Dairy Sci 76:2366-79), which may inhibit *C. jejuni* and other pathogens in vitro. *Lactobacillus salivarus* NRRL B-30514 has previously been identified as having anti-*C. jejuni* activity (Stern, N. J. et al. (2006), Antimicrob Agents Chemother 50:3111-6). Its bacteriocin, OR-7, has been shown to reduce colonization of *C. jejuni* in chickens when administered in feed. Heat treatment of supernatants and trypsin and proteinase K treatment of supernatants and agar plates did not effect inhibition of *C. jejuni* by the *Lactobacillus* strains evaluated, suggesting inhibition was not due to the production of a bacteriocin. These data strongly suggest that the combination of organic acids and hydrogen peroxide produced by the lactobacilli are responsible for inhibiting *C. jejuni* in vitro.

*Lactobacillus* Bacterial Vaccines and Other Host-Based Vaccines

Another aspect of the invention involves the administration of a *Lactobacillus* strain to chickens that has probiotic as well as vaccine properties. While not wishing to be bound by theory, it is believed that a *Lactobacillus* strain that displays *C. jejuni* epitopes stimulates production of *C. jejuni*-specific IgA antibodies, resulting in a reduction in *C. jejuni* colonization. In Example 5, three species of *Lactobacillus* (i.e., *L. acidophilus, L. crispatus*, and *L. helveticus*) were tested for probiotic properties in order to select one to develop as a vaccine. Some species of *Lactobacillus* synthesize an surface (S)-layer protein (Avall-Jaaskelainen, S., and A. Palva (2005) FEMS Microbiol. Rev. 29:511-529, Boot, H. J. et al. (1996), Microbiology. 142 (Pt 9):2375-2384). These three species were chosen because they normally colonize the ilea of chickens and synthesize a surface (S)-layer protein. Moreover, the S-layer protein, which coats the surface of the bacterium, can tolerate incorporation of foreign epitopes (Ashgar, S. S. et al. (2007), J. Bacteriol. 189:1856-1865). Generally, the S-layer is composed of one to three proteins ranging from 40 to 200 kDa, and comprises 10-15% of the total cellular protein. The S-layer of *L. acidophilus* ATCC 4365 is encoded by two genes slpA and slpB, which are located in opposite orientation from one another and separated by a 3 kb DNA-region. *L. crispatus* JCM 5810 contains two S-layer encoding genes, cbsA and cbsB, but only the cbsA gene is expressed. *L. helveticus* contains one S-layer gene, termed slpA. The genetic techniques for *Lactobacillus* species are advanced (Mota, R. M. et al. (2006), BMC Biotechnol. 6:2), and it is feasible to insert relatively large genetic segments within the S-layer gene, thereby achieving secretion, cell surface attachment, and high-density presentation of foreign epitopes (Avall-Jaaskelainen, S., and A. Palva (2005) FEMS Microbiol. Rev. 29:511-529).

Colonization of the ileum by *Lactobacillus* is desirable, as this section of the digestive tract contains a high number of Peyer's patches that are involved in antigen sampling and antibody production (Vaughn, L. E. et al. (2006), Avian Dis. 50:298-302). A mucosal immune response against *C. jejuni* results in antibodies that bind to the surface of bacterium and prevent or inhibit it from colonizing the digestive tract. To ensure that *C. jejuni* proteins that have the potential to generate neutralizing antibodies are incorporated into the S-layer, the specific *C. jejuni* proteins and the regions within those proteins against which poultry normally generate antibodies are identified.

*C. jejuni* genes could also be combined with various viral hosts or vectors, (e.g. adenovirus, baculovirus, herpes virus, pox virus vectors, etc.). or other bacterial hosts or vectors (e.g. *Escherichia coli*). Such hosts may be attenuated.

Recombinantly Engineered S-Layer Protein

Other embodiments of this invention are directed to engineered recombinant S-layer proteins that have one or more antigenic *C. jejuni* antigenic sequences inserted into the S-layer protein. A particular S-layer protein can be engineered to have, for example, one, two, three, four, five or more antigenic polypeptide sequences inserted into the S-protein. One embodiment has polypeptide sequences from each of the CadF, FlaA, and FlpA proteins inserted into the S-layer protein. The polypeptide may be inserted at a location where the polypeptide is exposed at the surface of a bacterial cell when the surface layer protein is expressed. When expressed at the surface, the heterologous polypeptide can more readily interact with another moiety, for example in a ligand/receptor with another polypeptide (e.g., an antibody). Alternatively, the heterologous peptide may be inserted such that it is not expressed at the surface of the S-protein such as proximal to a cell wall anchor or binding domain.

Two main domains have been identified for the S-layer protein of *Lactobacillus acidophilus* (see Pouwels, P H et al., (1998), Int J Food Microbiol. 41:155-167; Seegers, J F (2002) 20:508-15; U.S. patent application Ser. No. 10/500,307, published as US20050233408, the complete contents of which is herein incorporated by reference). The N-terminal region constitutes about two thirds of the molecule, and it is involved in crystallisation and assembly. This region makes up amino acids 1 to 290 and forms the S-layer above the cell wall. The second main domain consists of amino acids 290 to 412. This portion of the protein is buried in the S-layer and it constitutes the cell wall anchor. The N-terminal region of the *Lactobacillus acidophilus* S-layer protein can subdivided into three portions; residues 1 to about 114, residues from about 115 to about 155 or so, and residues from about 160 to 290. The region comprising amino acid residues from about 115 to about 155 or 160 appears to be loop region that is exposed at the bacterial surface. This region is a preferred site for insertion of heterologous polypeptides, including insertion at a position from 100 to 160, such as from 110 to 150, 110 to 140, preferably from 120 to 140, 120 to 130, or at about position 125. A different amino acid residue numbering scheme will apply to alternative species of *Lactobacillus*.

Antibodies

The present invention also provides antibodies that are specifically immunoreactive with the proteins described herein. Accordingly, the antibodies of the invention will specifically recognize and bind polypeptides that have an amino acid sequence identical, or substantially identical, to the amino acid sequence disclosed herein, or an immunogenic fragment thereof. The antibodies of the invention usually exhibit a specific binding affinity of at least about $10^7$, $10^8$, $10^9$, or $10^{11}$ $M^{-1}$. Antibodies may be polyclonal or monoclonal, and can be made and purified by a variety of means well known to those of skill in the art. See, for example, Coligan, Current Protocols in Immunology, Wiley/Greene, NY (1991); Stites et al. (eds.) BASIC AND Clinical Immunology (7th ed.) Lange Medical Publications, Los Altos, Calif., and references cited therein ("Stites"); Goding, Monoclonal antibodies: Principles and Practice (2d ed.) Academic Press, New York, N.Y. (1986); Kohler and Milstein, 1975, Nature 256: 495-97; and Harlow and Lane. The antibodies of the invention may be of any isotype, for example, IgM, IgD, IgG, IgA, and IgE, with IgG, IgA and IgM most referred. Some monoclonal antibodies of the present invention are humanized, human or chimeric, and may be multifunctional. See, for example, Queen, et al., Proc. Nat'l Acad. Sci. USA 86: 10029 (1989); U.S. Pat. Nos. 5,563,762; 5,693,761; 5,585,089 and 5,530,101. Useful antibodies can also be produced using phage display technology (see, for example, Dower et al., WO 91/17271 and McCafferty et al., WO 92/01047). Single chain antibodies can be produced using methods well known in the art (see, for example, Colcher et al., Ann. NY Acad. Sci. 880: 263-80 (1999); Reiter, Clin. Cancer Res. 2: 245-52 (1996); U.S. Pat. Nos. 4,946,778; 5,260,203; 5,455,030; 5,518,889; and 5,534,621). The antibodies of the invention have a variety of uses, for example for example, isolation or detection of polypeptides, inhibition of activity, etc.

Other Uses of *C. jejuni* Antigens

Those of skill in the art will recognize that the antigens described herein can be used in a variety of other applications, including but not limited to: diagnostics, research reagents (e.g. for investigational purposes), etc. All such uses are intended to be encompassed by the invention.

Various aspects of the invention will now be described with reference to the following experimental section that will be understood to be provided by way of illustration only and not to constitute a limitation on the scope of the invention.

EXAMPLE 1

Identification of *Campylobacter jejuni* Proteins Recognized by Chicken Maternal Antibodies In a previous study, chicks with maternal antibodies generated against the S3B strain of *C. jejuni* provided protection against *Campylobacter* colonization (Sahin et al., 2003. AEM.69:5372). Serum samples, collectively referred to as the Cj S3B-SPF sera, were obtained from the previous study. These sera were determined to contain maternal antibodies that reacted against *C. jejuni* whole cell lysates as judged by ELISA. The antigens recognized by the Cj S313-SPF antibodies were identified by immunoblot analysis, coupled with mass spectrometry, of *C. jejuni* outer membrane protein extracts. This approach led to the identification of *C. jejuni* proteins recognized by the maternal antibodies, including the flagellin proteins and CadF adhesin. In vitro assays revealed that the Cj S3B-SPF sera retarded the motility of the *C. jejuni* S3B homologous strain, but did not retard the motility of a heterologous strain of *C. jejuni* (81-176). Collectively, this Example provides a list of *C. jejuni* proteins against which protective antibodies are generated in hens and passed to chicks.

Materials and Methods

Bacterial Cultures and Chicken Sera.

The *Campylobacter jejuni* S3B strain was isolated from a chicken. The *C. jejuni* 81-176 strain was isolated from an individual with diarrhea containing blood and leukocytes (Korlath, J. A., et al., 1985, J. Infect. Dis. 152:592-596). *C. jejuni* S3B and 81-176 were cultured on Mueller Hinton (MH) agar plates containing 5% citrate buffered bovine blood (MH-blood) under microaerobic conditions (5% $O_2$, 10% $CO_2$, 85% $N_2$) at 37° C. The bacteria were subcultured to a fresh MH-blood plate every 48 h.

The generation of the sera is described in detail elsewhere (Sahin, O. et al., 2003, Appl. Environ. Microbiol. 69:5372-5379). Briefly, specific pathogen-free (SPF) from White Leghorn chickens were obtained from a supplier and hatched in isolation. The chickens were examined for the absence of *C. jejuni* colonization by cloacal swabs, bred at 22 weeks of age, and after an additional 2 weeks were inoculated with the *C. jejuni* S3B strain. Fertilized eggs were collected from the inoculated hens and hatched in isolation. In total, blood was collected from nine SPF White Leghorn chickens at 2 days of age. The serum was harvested from each blood sample and stored at −20° C. 25 to 100 µl of each serum sample were obtained. Throughout this paper those serum samples are referred to as the Cj S3B-SPF sera.

Preparation of *C. jejuni* Outer Membrane Proteins.

Outer membrane proteins (OMPs) were prepared using N-lauroyl-sarcosine as previously described by de Melo and Pechere (de Melo, M. A., and J. C. Pecherè, 1990, Infect. Immun. 58:1749-1756) with slight modifications. Briefly, bacteria were grown overnight in MH broth with shaking at 37° C. under microaerobic conditions. The bacterial cells were harvested and suspended in 10 mM phosphate buffer (pH 7.4) containing 1 mM phenylmethylsulphonyl fluoride (Sigma, St. Louis, Mo.). The bacterial cell suspensions were sonicated five times (30 s each) with a 30 s cooling period on ice between each pulse with a Branson Sonifier Cell Disruptor (model 250; Branson Sonic Power Co., Danbury, Conn.). Cell debris was removed by centrifugation at 6,000×g for 10 min. The crude membranes were obtained by centrifugation at 100,000×g at 4° C. for 2 h. The resulting pellets were suspended in 10 mM Tris (pH 7.5), and the protein concentration of each sample was determined using the bicinchoninic acid (BCA) assay as outlined in the manufacturer's instructions (Pierce, Rockford, Ill.). N-lauroyl-sarcosine (Sigma) was added to the crude extracts at a protein to detergent ratio of 1:4 total (w/w). The samples were incubated at room temperature with gentle rocking for 30 min. The OMPs were obtained by centrifugation at 100,000×g at 15° C. for 2 h. The pellets were washed with 50 mM Tris (pH 7.5), suspended in the same buffer, and stored at −20° C. The protein concentration of the OMP extracts was determined by bicinchoninic acid BCA assay.

Enzyme-linked immunosorbant assays. ELISAs were performed to determine the level of $C. jejuni$-specific IgG antibodies the Cj S3B-SPF sera. Microtiter plates (Corning Incorporated, Corning, N.Y.) were coated with 100 µl of ovalbumin (negative control), $C. jejuni$ S3B whole cell lysates, or 81-176 whole cell lysates diluted to 10 µg/ml in coating buffer (50 mM $Na_2CO_3$, 51 mM $NaHCO_3$, pH 9.6). After incubation at 4° C. for 18 h, the coated plates were incubated with 0.5% (w/v) bovine serum albumin (BSA; Sigma) in phosphate buffer (PBS; 0.14 M NaCl, 5 mM $Na_2HPO_4$ $2H_2O$, 1.5 mM $KH_2PO_{4+}$, 19 mM KCl, pH 7.4) at room temperature for 2 h to reduce the non-specific binding of antibodies. The Cj S3B-SPF serum samples were diluted 1:200 in PBS containing 0.5% BSA. 100 µl of each sample was added to wells in triplicate, and incubated for 2 h at room temperature. The plates were rinsed 3 times with wash buffer [(0.15 M NaCl, 0.1% (v/v) the polysorbate surfactant TWEEN® 20, a polyoxyethylene derivative of sorbitan monolaurate, pH 7.4)] and rabbit anti-chicken IgG conjugated to peroxidase (1:1000; Sigma) diluted in PBS containing 0.5% (w/v) BSA and 0.1% (v/v) TWEEN® 20 was added to the wells. After 1 h of incubation at room temperature, the plates were rinsed 2 times with wash buffer and 2 times with PBS. Tetramethy-benzidine (TMB) substrate (Pierce-Endogen) was added to the wells and the reaction was stopped with 0.18 N $H_2SO_4$ after 10 min of development. Absorbances ($A_{490}$) were determined at 49 nm. The absorbances obtained using the chicken sera incubated with ovalbumin were subtracted from the appropriate serum sample values to remove background signal. Student's t-test was performed on $A_{490}$ values to determine statistical significance between sample groups (P<0.005). Nine sera were collected from chickens not colonized with $C. jejuni$ and used to calculate the negative cutoff using Student's t-distribution. Absorbance values greater than the negative cutoff value were considered positive for $C. jejuni$-specific antibodies (8).

SDS-PAGE and immunoblot analysis. Bacterial OMPs (0.5 µg/µl) were solubilized in single-strength electrophoresis sample buffer and boiled for 5 min. Proteins were separated by SDS-polyacrylamide gel electrophoresis (PAGE) using 12.5% polyacrylamide minigels as previously described by Laemmli (Laemmli, U. K., 1970, Nature. 227:680-685). Separated proteins were either stained with Coomassie brilliant blue R250 (CBB-R250) or transferred to polyvinylidene fluoride (PVDF) membranes. Membranes were blocked in PBS containing 0.05% (v/v) the polysorbate surfactant TWEEN® 20, a polyoxyethylene derivative of sorbitan monolaurate, (PBS-T) with 20% fetal bovine serum and incubated with the Cj S3B-SPF sera (1:200 dilution) overnight at 4° C. Subsequently, blots were washed 3 times with PBS-T. Bound antibodies were detected with rabbit anti-chicken peroxidase-conjugated IgG (1:1000 dilution, Sigma). CadF was detected using a goat anti-CadF specific serum (#461) coupled with a rabbit anti-goat peroxidase-conjugated IgG (1:1000, Sigma). The FlaA and FlaB flagellin proteins were detected using a rabbit anti-$C. jejuni$ flagellin specific serum with goat anti-rabbit peroxidase-conjugated IgG (1:1000, Sigma). The blots were washed 3 times with PBS-T and developed with 4-chloro-1-naphthol peroxidase chromogenic substrate (Thermo Scientific, Rockford, Ill.) as outlined by the manufacturer.

LC/MALDI/TOF-TOF and Data Analysis.

OMP extracts were trichloroacetic acid (TCA) precipitated and washed 3 times with acetone. The dried pellets were resuspended in 25 µl 8 M urea, 100 mM $NH_4HCO_3$, and the pH was adjusted to 7.5-8.0 with $NH_4HCO_3$. Proteins were reduced with DTT at a final concentration of 5 mM at 37° C. for 30 min and then alkylated with iodoactemide at a final concentration of 25 mM at 37° C. for 30 min in the dark. The solution was diluted 4 times with 100 mM $NH_4HCO_3$ and 1 µg trypsin (Sequence grade, Promega, Madison, Wis.) was added for overnight digestion at 37° C. The digest solution was concentrated with speed vacuum to a final volume of 20-30 µl. The LC MALDI plate was prepared. 5 µl digest solution was loaded onto the analytical column by the autosampler and separated at a flow rate of 2 µl/min using the following gradient: 5% B for 0-2 min, 5-20% B for 2-25 min, 20-60% B for 25-50 min, 95% B for 50-60 min, and 0% B for 60-70 min. Mobile phase A was 0.1% trifluoroacetic acid (TFA) in 2% acetonitrile and mobile phase B was 0.1% TFA in 95% acetonitrile. 5 mg/ml MALDI matrix, a-cyano-4-hydroxycinnamic acid (CHCA), was prepared in the solution of 50% acetonitrile, 0.1% TFA, and 5 mM ammonium monophosphate and delivered at a flow rate of 2 µl/min. The LC effluent and matrix solution were mixed via an Upchurch T connector and the mixtures were then spotted on a blank MALDI plate (123×81 mm) every 4 s during the 50 min LC gradient. The MS and MS/MS spectra were acquired with a 4800 MALDI/TOF-TOF mass spectrometer (Applied Biosystems, Foster City, Calif.). 1000 laser shots were used for each reflector MS spectrum and 2500 laser shots were collected for each MS/MS spectrum. The precursor peaks with S/N>40 were selected for MSMS experiment and the 25 strongest precursors were allowed for MSMS per spot with the weakest precursor submitted first. Peaks with S/N>10 were extracted and searched against the $C. jejuni$ 81-176 database (CJJ81176 downloaded from NCBI, 1758 ORFs) using PROTEIN PILOT™ data analysis software (version 2.0.1, revision 67476, Applied Biosystems, Foster City, Calif.). Search parameters were set as follows: enzyme, trypsin; Cys alkylation, iodoacetamide; Special factor, urea denaturation; Species, none; and ID focus, biological modification. The protein confidence threshold cutoff for this report is ProtScore 2.0 (unused) with at least one peptide with 99% confidence. See the supplemental data for the complete ProteinPilot results. Protein subcellular localization was determined by PSORTb (see the website located at www.psort.org/psortb/).

Nano-LC/MS/MS and Data Analysis.

Nano-LC/MS/MS was performed as described previously (Tang, X., et al. 2005, Anal. Chem. 77:311-318), and used to identify the reactive bands as determined by immunoblotting with the Cj S3B-SPF sera. Briefly, bands representing immunoreactive proteins were excised from SDS—12.5% polyacrylamide gels that had been stained with CBB-R250. After band excision, each gel piece was destained with a solution containing 50% methanol and 5% acetic acid. The disulfide bonds within the proteins were dissociated within the gel by performic acid oxidation. The gel was dried, and the proteins were digested with trypsin overnight at 37° C. Nano-LC/MS/MS analysis was done using an electrospray-ion trap (Esquire HCT, Broker Daltonics, Billerica, Mass.) mass spectrometer coupled with a nano-HPLC. The resulting data were used to perform searches against the C. jejuni 81-176 genome database using the program MASCOT licensed in house (Version 2.1.0, MatrixScience Ltd, London). Protein hits with probability-based Mowse scores exceeding their thresholds (p<0.05) were automatically reported. The protein hits were further filtered using more stringent MudPIT scoring and an ions score cutoff of 0.05, which removed all the peptides with expect value (E)>0.05.

Motility Assay.

To evaluate the function attributes of the anti-Campylobacter maternal antibodies, motility assays were performed as described previously with slight modifications (Konkel, M. E. et al., 2004, J. Bacteriol. 186:3296-3303). C. jejuni S3B and 81-176 strains were grown for 24 h on MH-blood plates, harvested by centrifugation at 6,000×g, and suspended to an $OD_{540}$=0.18 in Minimal Essential Medium (MEM; Invitrogen) supplemented with 10% fetal bovine serum (FBS; HyClone Laboratories, Logan, Utah). Bacterial suspensions were then diluted 1:100 in the same media that contained either sera from C. jejuni uninoculated chickens, pooled Cj S3B-SPF sera, or heat-inactivated Cj S3B-SPF pooled sera. Complement was inactivated through heat treatment at 56° C. for 30 min. The bacterial suspensions were mixed, and 10 µl aliquots were spotted onto the surface of semisolid MH medium with 0.4% agar. Motility plates were incubated for 48 h at 37° C. under microaerobic conditions.

Results

Chicks Hatched from Hens Colonized with Campylobacter Possess Anti-C. jejuni Maternal Antibodies.

Nine serum samples (designated 121, 123, 129, 132, 135, 139, 140, 144, and 147) generated in a previous study were obtained and termed the Cj S3B-SPF sera. These sera were collected from 2-day old SPF White Leghorn chicks hatched from hens inoculated with the C. jejuni S3B strain. To determine the level of C. jejuni-specific IgG maternal antibodies in each serum, ELISA were performed with wells coated with whole cell lysates (WCL) prepared from C. jejuni homologous (S3B) and heterologous (81-176) strains (FIG. 1). Non-specific antibody reactivity was determined by calculating the negative cutoff value of antibody reactivity for the sera harvested from nine chickens not colonized with C. jejuni (control sera). The reactivity of the control sera against the WCL of the C. jejuni S3B strain was less than (P<0.005) that obtained for the WCL of the C. jejuni 81-176 strain (FIG. 1, horizontal lines).

Each of the Cj S3B-SPF serum samples contained antibodies that reacted specifically against the WCLs of the C. jejuni S3B and 81-176 strains as judged by ELISA. However, an increase was observed in the reactivity of the Cj S3B-SPF sera against the WCL of the S3B homologous strain (mean $A_{490}$ 0.665) when compared to WCLs from prepared from the 81-176 heterologous strain (mean $A_{490}$ 0.463) (P<0.005). The differences in reactivity with the WCLs suggested that the Cj S3B-SPF sera either contained antibodies that react with antigens unique to the C. jejuni S3B strain or that variations in the amino acid composition of strain specific antigens occur that contribute to the increase in reactivity of the sera against a specific strain. The increase in the reactivity of the Cj S3B-SPF sera against the WCLs from the C. jejuni S3B strain versus the 81-176 strain may partially explain an observed delay in onset of colonization with the C. jejuni S3B challenged chicks and reduced rate of horizontal spread among the flock.

Identification of Outer Membrane Proteins (OMPs).

LC/MALDI/TOF-TOF was performed with the total OMP extracts prepared from the C. jejuni 81-176 strain, for which the genome has been sequenced, to ensure that the composition of the preparations was predominantly outer membrane proteins and not cytoplasmic proteins (FIG. 5). The ProteinPilot™ software was employed as the search engine for protein identification using LC/MALDI/TOF-TOF data. Since the unused ProtScore is a measurement of all the peptide evidence for a protein that is not explained by a higher ranking protein and is a true indicator of protein evidence, we set the unused score at 2.0 as the threshold cutoff for protein identification with at least one peptide with 99% confidence. With these criteria, 60 proteins were identified with 2944 MS/MS spectra searching against the C. jejuni 81-176 database (total 1758 ORFs) (FIG. 5). Of the 60 proteins identified, approximately 32% were localized in the cytoplasm as determined by PSORTb. Additional analysis of the proteins contained within the OMP extracts revealed that 18% were categorized as unknown subcellular location and 50% were identified as extracellular, outer membrane, periplasmic, inner membrane proteins, or designated as unknown subcellular location with a signal peptide.

Reactivity of the Cj S3B-SPF Sera Against the OMPs of Homologous and Heterologous C. jejuni Strains.

To determine the reactivity of the antibodies contained within the Cj S3B-SPF sera, OMP extracts were separated by SDS-PAGE, transferred to PVDF membranes, and immunoblot analysis was performed with the S3B-SPF sera. The Cj S3B-SPF sera produced repeatable banding profiles for the OMP extracts from both the C. jejuni S3B homologous strain and 81-176 heterologous strain as judged by immunoblot analysis (FIG. 2A). The reactive bands in the OMP extracts ranged from 16 to 90 kDa. The representative banding profiles generated against the C. jejuni S3B and 81-176 strains were similar, but some bands were unique to a particular strain.

Inspection of blots revealed that the S3B-SPF sera contained antibodies that reacted against strain-specific proteins and against proteins shared amongst the C. jejuni S3B and 81-176 strains. Proteins with apparent molecular masses of 90, 83, 65, 60, 56, 54, 42, 37, 26, and 20 kDa (bands 1-6, 9, 11, 14, and 16, respectively, see FIG. 2) were cross-reactive with both the C. jejuni S3B homologous and 81-176 heterologous strains. Immunoreactive proteins specific to C. jejuni S3B were observed at approximately 32, 28, 16 kDa (bands 12, 13, and 17, respectively) (FIG. 2). Immunoreactive proteins unique to C. jejuni 81-176 were observed at approximately 50, 45, 40 and 23 kDa (bands 7, 8, 10 and 15, respectively) (FIG. 2). These results indicated that the chicks possessed both maternal antibodies that reacted against the particular C. jejuni strain with which the hens were colonized and maternal antibodies that reacted with proteins shared amongst C. jejuni strains.

Immunoblots were performed to determine if the Cj S3B-SPF sera contained antibodies reactive against CadF protein.

A reactive band (band 11), corresponding to a protein with a $M_r$ of 37 kDa, was observed in the OMP extracts from the C. jejuni S3B and 81-176 strains using each of the nine Cj S3B-SPF sera (FIG. 2). The bands observed at 37 kDa with the Cj S3B-SPF sera had the same relative migration as the CadF protein detected using a goat anti-CadF specific serum (FIG. 2).

Identification of the Bands Recognized by the Cj S3B-SPF Sera.

Nano-LC/MS/MS was used to identify the C. jejuni membrane-associated antigens recognized by the Cj S3B-SPF sera. The OMP extracts from the C. jejuni S3B and 81-176 strains were separated by SDS-PAGE, and either stained with CBB-R250 or transferred to PVDF membrane. The blot was incubated with a representative C. jejuni S3B-specific serum to identify the reactive proteins. Seventeen reactive bands were identified; fourteen of the seventeen bands were subjected to nano-LC/MS/MS.

Bands 1, 2, 4-10, and 12-16 were excised individually from the gel and subjected to tryptic digestion followed by nano-LC/MS/MS. Careful attention was paid to excise those protein bands that were in perfect alignment with the reactive bands in the corresponding immunoblot. The proteins identified are listed in FIG. 4. The predicted "best fit" protein matches were OMPs with significant MASCOT scores and had a molecular weight corresponding to the migration of the protein in a SDS-12.5% polyacrylamide gel. Confidence in protein matches was established using MudPIT scoring and an ion score cutoff of 0.05.

Bands 3 and 11 were identified via immunoblot analysis using protein specific sera, and band 17 was identified based on its apparent molecular mass. The 65 kDa protein (band 3) was identified as flagellin using an anti-C. jejuni flagellin serum and the 37 kDa protein (band 11) was identified as CadF using an anti-C. jejuni CadF serum. It is likely that the 16 kDa immunoreactive band (band 17), which was detected only in the OMP extracts prepared from the C. jejuni S3B strain, is lipooligosaccharide (LOS) (Stern, N. J., and S. Pretanik (2006), J. Food Prot. 69:1034-1039).

The Cj S3B-SPF Bands Unique to C. jejuni 81-176 are Flagellin.

A number of the bands were found to contain peptides that matched the FlaA or FlaB sequence as judged by nano-LC/MS/MS (FIG. 4). This finding raised the possibility that a particular band may have been immunoreactive because of the presence of flagellin protein subunits. To determine whether the reactivity of these bands was due to flagellin subunits or another protein distinct from flagellin, C. jejuni S3B and 81-176 OMP extracts were probed with the anti-C. jejuni flagellin serum. As expected, the 65 kDa protein (bands 3) reacted with the anti-C. jejuni flagellin serum. In addition, proteins of 50 kDa (band 7), 45 kDa (band 8), 40 kDa (band 10) and 23 kDa (band 15) were detected in the OMP extracts from C. jejuni strain 81-176 but not in C. jejuni S3B strain. The immunoreactive bands of 50 kDa, 45 kDa, 40 kDa, and 23 kDa were the only proteins unique to the C. jejuni 81-176 OMP extracts (i.e., not detected in the C. jejuni S3B OMP extracts). The bands of 50 kDa, 45 kDa, 40 kDa, and 23 kDa in the C. jejuni 81-176 OMP extracts were determined to be FlaA or FlaB by nano-LC/MS/MS.

C. jejuni S3B-Specific Antibodies Inhibit the Motility of the Homologous Strain, but not the Heterologous Strain.

Motility assays were performed with the Cj S3B-SPF sera and both the C. jejuni S3B (FIG. 3A) and 81-176 strains (FIG. 3B). In contrast with the C. jejuni 81-176 strain, only the C. jejuni S3B strain showed a reduction in motility when compared with the same strain with control sera harvested from birds not colonized with C. jejuni. This observation was true for both the Cj S3B-SPF heat-inactivated sera, as well as the Cj S3B-SPF untreated sera, demonstrating that the reduction in motility is due to antibodies binding to the bacteria, and not due to the action of complement.

EXAMPLE 2

Examination of Campylobacter jejuni Putative Adhesins and Identification of a New Protein, Designated FLpA, Required for Chicken Colonization Campylobacter jejuni colonization of chickens is presumably dependent upon multiple surface exposed proteins termed adhesins. Putative C. jejuni adhesins include CadF, CapA, JlpA, MOMP, PEB1, Cj1279c, and Cj1349c. The genetic relatedness of 97 C. jejuni isolates recovered from human, poultry, bovine, porcine, ovine, and canine sources was examined by multilocus sequence typing (MLST) and their profile of putative adhesin-encoding genes was determined ed by dot blot hybridization. To assess the individual contribution of each protein in bacteria-host cell adherence, the C. jejuni genes encoding the putative adhesins were disrupted by insertional mutagenesis. The phenotype of each mutant was judged by performing in vitro cell adherence assays with chicken LMH hepatocellular carcinoma epithelial cells and in vivo colonization assays with broiler chicks. MLST analysis indicated that the C. jejuni isolates utilized in this study were genetically diverse. Dot blot hybridization revealed that the C. jejuni genes encoding the putative adhesins, with the exception of capA, were conserved amongst the isolates. The C. jejuni CadF, CapA, Cj1279c, and Cj1349c proteins were found to play a significant role in the bacterium's in vitro adherence to chicken epithelial cells, while CadF, PEB1, and Cj1279c were determined to play a significant role in the bacterium's in vivo colonization of broiler chicks. Collectively, the data indicate that Cj1279c is a novel adhesin. Because Cj1279c harbors fibronectin type III domains, the protein was designated FlpA for Fibronectin-like protein A.

Materials and Methods

Bacterial Strains and Growth Conditions.

Ninety-seven C. jejuni isolates were obtained from human clinical cases, poultry, bovine, porcine (swine), ovine, and canine sources (data not shown). All human isolates were obtained from individuals with clinical signs of campylobacteriosis. C. jejuni F38011 was isolated from an individual with bloody diarrhea. In total, we used 43 human strains (F38011, 81-176, 81116, M129, H1, H2, H4-7, H9-24, H26-32, and H34-43), 41 poultry strains (RM1221, Turkey, S1, S2B, USDA02-833L, A2a, A5a, A18a, D34a, G11a, Iowa 2, Iowa 4-9, Iowa 11-13, Iowa 15, Iowa 21-26, Iowa 33-36, Iowa 39, Iowa 42, Iowa 44, Iowa 77-81, and Iowa 83), five bovine strains (C913, C973, C1086, C1129, and C1144), five porcine strains (93-55, 93-58, 93-338, 93-343, and 92-1578), two ovine strains (ov48 and ov112), and one canine strain (can1979858). C. jejuni isolates were cultured at 37° C. under microaerobic conditions (5% $O_2$, 10% $CO_2$, 85% $N_2$) on Mueller-Hinton agar plates supplemented with 5% citrated bovine blood (MH-blood agar plates). C. jejuni strains were subcultured to a fresh plate every 48 h. The C. jejuni F38011 cadF (kanamycin resistant, $Kan^R$), capA (tetracycline resistant, $Tet^R$), jlpA ($Kan^R$), peb1A ($Kan^R$), Cj1278c ($Tet^R$), Cj1279c ($Kan^R$), and Cj1349c ($Kan^R$) mutants were generated as outlined below. When appropriate, the growth media were supplemented with antibiotics at the following concentrations: Kan, 50 µg/ml (Sigma, St. Louis, Mo.) and Tet, 2.0 µg/ml (Sigma).

Motility Assay.

Motility was determined using MH medium supplemented with 0.4% Select agar (Invitrogen, Carlsbad, Calif.). Briefly, 10 µl of each bacterial suspension in MH broth was added to the surface of the agar and the plates were incubated at 37° C. under microaerobic conditions. Motility was determined by measuring the diameter of the bacterial migration zone after 48 h of incubation.

Multilocus Sequence Typing.

Genomic DNA was isolated from the *C. jejuni* isolates using phenol chloroform extractions. Briefly, bacteria were cultured on MH-blood agar plates and harvested in 5 ml of phosphate-buffered saline (PBS). After incubation for 1 h at 37° C. with 500 µl 10% sodium dodecyl sulfate (SDS) and 5 µl proteinase K (20 mg/ml), three phenol and isoamyl chloroform extractions (24 parts chloroform and 1 part isoamyl alcohol) were performed with the aqueous layer retained each time. An equal volume of cold isopropanol and 250 µl of 2.5 M sodium acetate were added to the aqueous layer, prior to incubation at −20° C. for 5 min. The DNA was pelleted by centrifugation at 11,600×g for 15 min. The pellet was washed with 70% ethanol, spun at 11,600×g for 15 min. resuspended in sterile water, and RNase treated at 37° C. for 1 h. DNA purity, using an $OD_{260}/OD_{280}$ ratio, and concentration was determined.

*C. jejuni* housekeeping genes aspartase A (aspA), glutamine synthetase (glnA), citrate synthase (gltA), serine hydroxymethyl transferase (glyA), phosphoglucomutase (pgm), transketolase (tkt), and the ATP synthase alpha subunit (uncA) were amplified and sequenced, using the primers described elsewhere (26). PCR was performed using approximately 50 ng of genomic DNA and 1 U Taq polymerase (New England Biolabs, Beverly. Mass.) in a 50 µl reaction volume with 50 pmol of each primer, 1×PCR buffer 1×PCR enhancer, 2.5 mM $MgCl_2$, and 250 µM (each) dNTPs. Genes were amplified using the following amplification parameters: 94CC for 30 sec, 53° C. for 30 sec, and 72° C. for 2 min (30 cycles). Amplicons were confirmed by agarose gel electrophoresis and purified. Cycle sequencing reactions were performed on a Tetrad thermocycler (Bio-Rad, Hercules, Calif.), using a terminator cycle sequencing kit and standard protocols. Cycle sequencing extension products were purified DNA sequencing was performed using POP-7 polymer and ABI data collection and sequencing analysis software. Nucleotide sequences were aligned and analyzed Alleles and sequence types were assigned using MLSTparser3 (Miller et al., unpublished); novel alleles and sequence types were submitted to the PubMLST *C. jejuni/C. coli* database see the website located at pubmlst.orgicampylobacter/)

Dot Blot Hybridization.

The *C. jejuni* putative adhesin-encoding genes examined in this study were porA, cadF, capA, jlpA, peb1A, Cj1279c, and Cj1349c. The sequence of each gene from *C. jejuni* NCTC 11168 was obtained from on-line resources (web site located at sanger.ac.uk/Projects/C_jejuni/). Gene-specific probes were generated as outlined below. An internal fragment of each gene was amplified via PCR using the primers listed in Table 2. The amplifications were performed using high fidelity Taq DNA polymerase (Invitrogen) with *C. jejuni* NCTC 11168 chromosomal DNA as the template. Genes were amplified using the following parameters: 94° C. for 2 min (1 cycle); 94° C. for 45 see, 60° C. (−1° C. per cycle) for 30 sec, 70° C. for 1.5 min (10 cycles); 94° C. for 45 see, 50° C. for 30 sec, 70° C. for 1.5 min (25 cycles); 70° C. for 8 min (1 cycle).

The amplified PCR fragments were ligated into the vector pCR2.1 according to the manufacturer's directions and electroporated into *Escherichia coli* InvαF'. The purified plasmids were nick-translated using a Nick Translation Kit according to the manufacturer's directions (Roche Applied Science. Indianapolis, Ind.). One-hundred ng of *C. jejuni* genomic DNA, isolated via phenol chloroform extractions as described above, were vacuum transferred to a genescreen membrane (PerkinElmer, Waltham, Mass.) using a slotblotter. Depurinating solution (0.25 M HCl) was added to each slot for 4 min, followed by denaturating solution (1.5 M NaOH and 0.5 NaCl) for 3 min, neutralizing solution (1.0 M Tris and 1.5 M NaCl, pH 8.0) for 3 min, and 20×SSC (3.0 M NaCl and 0.3 M sodium citrate) for 20 min. DNA was UV cross-linked to the membrane. Each membrane was blocked for 15 min at room temperature with 100 µl denatured salmon sperm DNA in hybridization solution [5 ml formamide, 2 ml 5×P buffer (1.0% BSA, 1.0% polyvinyl-pyrrodilone, 1.0% Ficoll, 0.5% sodium pyrophosphate, 5.0% SDS, and 250 mM Tris pH 7.5), 2 ml 50% dextran sulfate, and 0.58 g NaCl] that had been warmed to 50° C. The radioactively-labeled probe was denatured by heating for 15 min at 95° C., chilled on ice for 15 min, and added to the hybridization solution. The membrane was incubated with the hybridization solution at 35° C. in a hybridization incubator (Robbins Scientific, Hudson, N.H.) overnight. Membranes were washed twice with 2×SSC at 25° C. for 10 min, and twice with a 2×SSC and 1% SDS solution at 35° C. for 20 min. Autoradiography was performed with Kodak BioMax MR film at −80° C. for approximately 2 h.

Generation of *C. jejuni* cadF, jlpA, peb1A, Cj1279c, and Cj1349c Suicide Vectors.

The PCR amplicons used as probes for the dot blot hybridizations were removed from the pCR2.1 multiple-cloning site (MCS) and ligated into pBSK-Kan2. The pBSK-Kan2 vector is identical to pBlueScript (Invitrogen), except that the original kanamycin cassette was replaced with one that functions in both *C. jejuni* and *E. coli* (Labigne-Roussel, A. et al. (1987), *Campylobacter jejuni*. J. Bacteriol. 169:5320-5323). The resulting pBSK-Kan2 vectors (pMEK252-pMEK256) were confirmed by DNA sequencing, and were electroporated into *E. coli* InvαF' electrocompetent cells.

Generation of *C. jejuni* capA and Cj1278c Suicide Vectors.

DNA regions upstream and downstream of the *C. jejuni* capA and Cj1278c genes were amplified by PCR using Taq DNA Polymerase (Invitrogen) and the primers listed in Table 2. *C. jejuni* NCTC 11168 chromosomal DNA was used for the amplification of DNA regions flanking capA, while *C. jejuni* F38011 chromosomal DNA was used for the regions flanking Cj1278c. The reaction conditions were: 94° C. for 2 min (1 cycle); 94° C. for 45 sec, 63° C. (−1° C. per cycle) for 30 sec, 70° C. for 4 min (8 cycles); 94° C. for 45 sec, 50° C. for 30 sec, 70° C. for 4 min (25 cycles); 70° C. for 8 min (1 cycle). The two flanking regions were cloned individually in pCR2.1. Thereafter, one fragment was cloned into the pCR2.1 vector harboring the other fragment, and a tetracycline resistance cassette was inserted between the two flanking regions. The resulting fragment was then moved into the MCS of pBSK-Kan2. The mutation construct was verified by DNA sequencing.

Generation of *C. jejuni* F38011 Mutants.

*C. jejuni* F38011 was gown overnight in MH broth with shaking at 37° C. under microaerobic conditions to a final $OD_{540}$ of 1.0. Two-hundred ml of culture was centrifuged at 6,000×g for 5 min to pellet the cells. The cells were washed once in sterile water and once in 10% glycerol, and resuspended in 350 µl of 10% glycerol. Approximately 2 µg of a CsCl-concentrated suicide vector was mixed with 50 μl of the electrocompetent *C. jejuni* and pulsed at 2.50 kV. The cells were immediately suspended in 200 μl of MH broth and plated on MH-blood agar plates. After overnight incubation at 37° C. in a microaerobic environment, one-half of the growth was streaked onto MH-blood plates containing the appropriate antibiotic (50 μg/ml Kan or 2 μg/ml Tet). After 48 h of incubation, the isolated colonies were screened by PCR using gene-specific primers. Each *C. jejuni* mutant was confirmed using gene-specific primers, and in the case of the *C. jejuni* capA and Cj1278c mutants by sequencing the DNA flanking regions. The motility of each *C. jejuni* mutant was assessed prior to use.

Tissue Culture.

Chicken LMH hepatocellular carcinoma cells (ATCC CRL-2117) were obtained from the American Type Culture Collection (Manassas, Va.). Stock cultures of LMH cells were grown in flasks coated with 0.1% gelatin in Waymouth's MB 752/1 medium supplemented with 10% fetal bovine serum (PBS; HyClone Laboratories, Logan, Utah). Cells were maintained at 37° C. in a humidified, 5% $CO_2$ incubator.

*C. jejuni*-LMH Binding Assay.

LMH cells were seeded to a cell density of $3.0 \times 10^5$ cells/ml and incubated for 24 h at 37° C. in a humidified, 5% $CO_2$ incubator. The cells were rinsed once with Minimal Essential Medium (MEM; Invitrogen) supplemented with 1% FBS and inoculated with approximately $3.0 \times 10^7$ CFU bacteria. Each plate was then subjected to centrifugation at 600×g for 5 min to promote bacteria-host cell contact and incubated at 37° C. for 30 min. To quantitate cell adherence, the *C. jejuni*-inoculated cells were rinsed three times with PBS, and lysed. Ten-fold serial-dilutions of the samples were made and plated on MH-blood agar plates to determine the number of adherent bacteria. The reported values represent the mean counts +/− standard deviation from triplicate wells.

TABLE 2

Genes targeted for mutagenesis

| Locus Tag (Gene Designation)[a] | Gene Product (protein) | # of nucleotides/ residues | Amplified Fragment(s) in nucleotides | Primers |
|---|---|---|---|---|
| Cj1478c (cadF) | CadF | 960/320 | 620 | cadF-F[b] TATTTCTATGGTTTAGCAGGTGGAG (SEQ ID NO: 85) |
| | | | | cadF-R[b] GCTCTACCTTCTTTAGTGTCATTGC (SEQ ID NO: 86) |
| Cj0628/ Cj0629 (capA) | CapA | 3436/1145 | 1321, 1635 | capA-F[b] TGAATCGAAGTGGAAAAATAGAAG (SEQ ID NO: 87) |
| | | | | capA-R[b] CCCATTTTTGTATCTTCATAACCT (SEQ ID NO: 88) |
| | | | | capA-SstI-F[c] ATGAGCTCAAAGTTGTTCCTAAGGGTAAAGC (SEQ ID NO: 89) |
| | | | | capA-SstII-R[c] ATACCGCGGAGTTTTATTCATAAATATTCCCTTTCC (SEQ ID NO: 90) |
| | | | | capA-SstII-F[c] ATACCGCGGGCTCAGTTTAATTATCTTTGGTAATC (SEQ ID NO: 91) |
| | | | | capA-XhoI-R[c] ATACTCGAGCATTTTACAAGCCCTATAAGAAGG (SEQ ID NO: 92) |
| Cj0983 (jlpA) | JlpA | 1119/373 | 868 | JlpA-F[b] TCTCAGGACTCTGGAATAAAGATTG (SEQ ID NO: 93) |
| | | | | jlpA-R[b] GTGTGCTATAGTCACTAACAGGGATG (SEQ ID NO: 94) |

TABLE 2-continued

Genes targeted for mutagenesis

| Locus Tag (Gene Designation)[a] | Gene Product (protein) | # of nucleotides/ residues | Amplified Fragment(s) in nucleotides | Primers |
|---|---|---|---|---|
| Cj0921c (peb1A) | PEB1 | 780/260 | 560 | peb1A-F[b] TCTAGGTGCTTGTGTTGCATTTAG (SEQ ID NO: 95) |
| | | | | peb1A-R[b] TGTCTACAGAAAACGCATCAACTC (SEQ ID NO: 96) |
| Cj1279c | Cj1279c (FlpA) | 1233/411 | 832 | cj1279c-F[b] TCAGAAGATGGCAAGGTTATAGAAG (SEQ ID NO: 97) |
| | | | | Cj1279c-R[b] GTTATTGCTATTGATTCAGCTGGAC (SEQ ID NO: 98) |
| Cj1349c | Cj1349c | 1308/436 | 1115 | Cj1349c-F[b] TATTTTTGATCTTACTCGTGCAATG (SEQ ID NO: 99) |
| | | | | Cj1349c-R[b] TTAAGGTATAATCGACCCAATACGA (SEQ ID NO: 100) |
| Cj1278c | Cj1278c | 1179/393 | 1033, 991 | Cj1278c-BamHI-F[c] ATATAGGATCCGTATCGTTCTAGTGAT GAAAATCC (SEQ ID NO: 101) |
| | | | | Cj1278c-SstII-R[c] ATATACCGCGGTTTTAAAATTTGGCAC TACTGAGC (SEQ ID NO: 102) |
| | | | | Cj1278c-SstII-F[c] ATATACCGCGGGTTTAAAATATAATTT TTCTTGAA AATTAAGC (SEQ ID NO: 103) |
| | | | | Cj1278c-BamHI-R[c] ATATAGGATCCTTTTCAGAAACATCAT TTTTCAAACG (SEQ ID NO: 104) |

[a]The gene number is from the genome sequence from *C. jejuni* NCTC11168.
[b]Indicates the primers used to amplify a DNA fragment for the generation of a suicide vector (gene knockout) and the probe for dot-blot hybridization.
[c]Indicates the primers used to amplify the DNA fragments for construction of the vectors to generate the mutants (i.e., capA and Cj1278c) via a double-crossover event; the two fragments were cloned into pBSK-Kan2, and disrupted by the insertion of a tetracycline resistance cassette.

Chicken Colonization Experiments.

All the experiments and procedures described below were performed in compliance with protocols approved by the Institutional Animal Care and Use Committee (IACUC protocol #3248) at Washington State University. A total of 80 one-week-old chicks were obtained, divided into eight groups, and placed into isolation chambers (Horsfall Bauer isolators) on wire mesh. Water and a commercial chick starter feed were provided ad libitum. Each isolator was equipped with two removable metal trays. Fecal matter was collected and autoclaved before disposal. The chicks were inoculated with *C. jejuni* by oral gavage with 0.5 ml of a bacterial suspension (~$10^7$ bacteria); the *C. jejuni* F38011 strain was cultured in Bolton's broth at 42° C. for 16 h under microaerobic conditions prior to inoculation of the birds. One group of 10 chicks was kept as the uninoculated control group. The remaining groups of chicks were inoculated with the *C. jejuni* F38011:1) wild-type strain; 2) cadF mutant; 3) capA mutant; 4) jlpA mutant; 5) peb1A mutant; 6) Cj1279c mutant; and 7) Cj1349c mutant. After the chicks were inoculated, the remaining bacterial suspensions were serially diluted and plated on Campy-Cefex agar (30) to confirm the CPU of each inoculum.

The chicks were euthanized and necropsied at 7 days post-inoculation (DPI). The cecum was dissected from each chick, weighed, diluted 1:10 (wt/v) in Bolton's broth media, and thoroughly stomached. For enumeration, serial 10-fold dilutions of the cecal contents were made and plated onto Campy-Cefex agar plates. The plates were incubated in a microaerobic environment at 37° C. and the CFUs were counted after 72 h of incubation. PCR was performed with *C. jejuni* cadF and capA specific primers (Table 2) to confirm that the counted colonies were *C. jejuni*.

Results

The *C. jejuni* Strains Used in this Study are Genetically Diverse.

Multilocus sequence typing (MLST) is commonly used for molecular typing of *C. jejuni* isolates (Dingle, K. E. et al.

(2001), 3. Clin. Microbiol. 39:14-23; Levesque, S. et al. (2008), 3. Clin. Microbiol. 46:3404-3411). A total of 97 isolates from humans, poultry, bovine, porcine, ovine, and canine sources were collected and their genetic relatedness was assessed by MLST. The C. jejuni isolates comprised 45 sequence types (data not shown). Eighty-four isolates were assigned to one of 18 clonal complexes (CC). The complexes with the greatest number of isolates were CC 21, CC 48, and CC 45 that were comprised of 19, 10, and 10 isolates, respectively. In total, two human isolates and eleven animal isolates did not belong to a CC in the MLST database. We also compared the allelic profiles, or sequence type (ST) of each isolate. The most common ST was ST-21, represented by isolates H2, H10, H12, Iowa 11, Iowa 13, Iowa 15, Iowa 35, and C1129. The second most common ST was ST-50, represented by isolates H6, H34, H36, H37, H40, S1, and 93-58. Several STs were comprised of three to five isolates, whereas 27 STs were represented by a single isolate. Newly identified STs were generated with four human isolates, F38011, H11, H14, and H30, and one poultry isolate USDA02-833L. In total, 105 alleles were identified amongst the seven loci, and a new pgm allele (pgm431) was reported. Based on the MLST analysis, we concluded that the C. jejuni strains used in this study were genetically diverse.

The Adhesin-Encoding Genes, Except capA, are Conserved Amongst C. jejuni Strains.

The presence of genes encoding putative adhesins in the C. jejuni strains was determined by dot blot hybridization coupled with gene specific probes. The essential features of these genes are listed in Table 3. Six of the seven putative adhesin-encoding genes, i.e., cadF, jlpA, peb1A, porA, Cj1279c, and Cj1349c, were detected in every C. jejuni strain tested (not shown), indicating that these genes are conserved within C. jejuni. One of the seven putative adhesin-encoding genes, capA, was not conserved amongst the strains assayed. C. jejuni capA was absent in 17 of the 43 (40%) human isolates and from 21 of the 54 (39%) animal isolates. The presence or absence of capA often correlated to specific STs. STs 50, 48, and 21, comprising 20 isolates, all possessed capA while STs 464, 459, 61, and 45, comprising 15 isolates, lacked capA.

TABLE 3

C. jejuni genes encoding putative adhesins

| ORF | BLAST | Signal Peptide Cleavage Sites | Genes Within the Putative Operon[a] |
|---|---|---|---|
| porA/Cj1259 | Major outer membrane protein, Campylobacter jejuni | Residues 22-23, SpI cleavage[b] | None Identified |
| cadF/Cj1418c | Structural outer membrane porin OprF, Pseudomonas aeruginos[a] 2e-27 | Residues 26-27, SpI cleavage[b] | Cj1478c, 1477c |
| capA/Cj0628 and Cj0629 | Autotransporter beta-domain, Campylobacter jejuni | None Identified | None Identified |
| jlpA/Cj0983 | Surface-exposed lipoprotein, Campylobacter jejuni | Residues 17-18, SpII cleavage[c] | None Identified |
| peb1A/Cj0921c | Amino acid ABC transporter, amino acid-binding protein, Streptococcus pneumoniae 1e-52 | Residues 26-27, SpI cleavage[b] | Cj0922c 0921c, 0922c, 0919c |
| Cj1279c | Fibronectin Type III domain containing protein lipoprotein, Sulfurimonas denitrificans 1e-57 | Residues 20-21, SpII cleavage[c] | Cj1280c, 1279c, 1278c, 1277c, 1276c, 1275c, 1274c, 1273c, 1272c, 1271c, 1270c, 1269c, 1268c |
| Cj1349c | Fibronectin/fibrinogen-binding protein FBP54, Streptococcus pyogenes 1.7e-05 | None Identified | Cj1350c, 1349c, 1348c, 1347c, 1346c, 1345c, 1344c, 1343c, 1342c |

[a]Genes within the putative operons were determined using NMPDR.
[b]Putative signal peptide cleavage site
[c]Putative lipoprotein signal peptide cleavage site.

CadF, CapA, Cj1279c, and Cj1349c Contribute to C. jejuni Adherence to Chicken LMH Cells.

Figure 6:
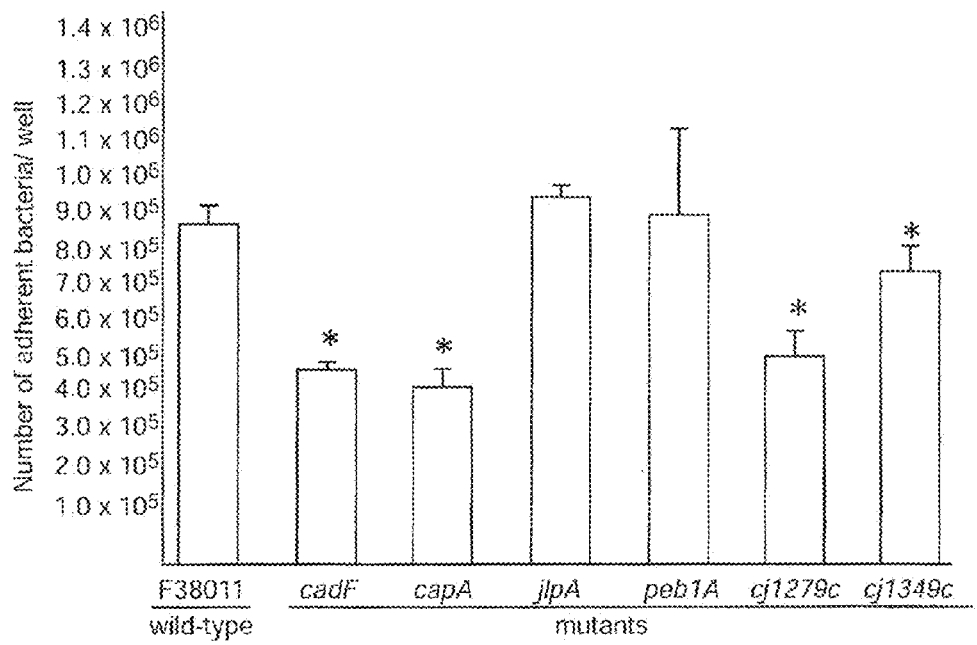
FIG. 6 shows the number of *C. jejuni* bound to chicken LMH hepatocellular carcinoma epithelial cells. Each bar represents the mean±standard deviation of *C. jejuni* bound to the LMH cells per well of a 24-well plate. The asterisk (*) indicates a statistically significant difference (P<0.05) between the *C. jejuni* F38011 wild-type isolate and an isogenic mutant, as determined using Student's t-test.

To determine the role of the putative adhesins in promoting the binding of C. jejuni to cultured chicken epithelial cells, in vitro adherence assays were performed with C. jejuni mutants and chicken LMH hepatocellular carcinoma epithelial cells (FIG. 6). A mutation in the porA gene was not attempted, as a mutation of this gene is hypothesized to be lethal due to its critical structural and pore activity (Amako, K. et al. (1996), Microbiol. Immunol. 40:749-754). All of the C. jejuni mutants (i.e., cadF, capA, jlpA, peb1A, Cj1279c, and Cj1349c) generated were motile (not shown). The LMH cell line was chosen for these experiments because it is the only chicken epithelial cell line readily available to researchers. While LMH cells are derived from the liver, previous C. jejuni adherence studies indicate similar bacterial-host cell adherence efficiency with LMH and human INT 407 epithelial cells (16, 23). Mutations in jlpA and peb1A had little effect on the ability of C. jejuni to bind to the LMH cells. In contrast, a significant reduction (P<0.05) was observed in the binding of the C. jejuni cadF, capA, Cj1279c, and Cj1349c mutants to LMH cells when compared with the C. jejuni wild-type strain. In addition, C. jejuni isolates were genetically matched (H11 and H14; Iowa 80 and Iowa 81) based upon MLST and tested for cell adherence; the H11 and Iowa 81 isolates contained capA and the H14 and Iowa 80 isolates did not. Strains lacking capA showed a significant reduction (P<0.05) in binding to LMH cells relative to strains in possession of the gene (not shown).

CadF, PEB1, and Cj1279c Contribute to *C. jejuni* Colonization of Broiler Chickens.

Figure 7:
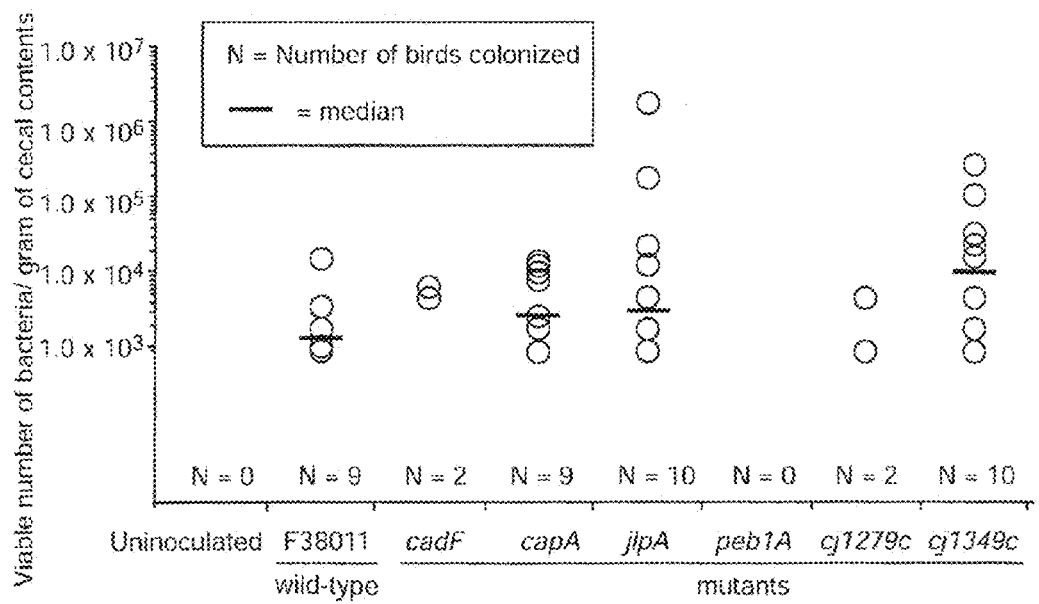
FIG. 7 shows CadF, PEB1, and Cj1279c contribute to *C. jejuni* colonization of broiler chickens. The 'N' indicates the number of chickens in the group of 10 that were colonized with *C. jejuni* (limit of detection $10^3$ CFU/gram cecal contents). The bar indicates the median CFU for each group, which was determined using all birds within the group. The absence of a bar indicates the number of *C. jejuni* was below the limit of detection.

To determine the relative importance of each putative adhesin in chicken colonization, one-week-old chicks were inoculated with the defined *C. jejuni* mutants. Eighty chicks were divided into groups, with each group consisting of ten chicks (FIG. 7). All chicks were euthanized at 7 days post-inoculation and the number of *C. jejuni* per gram of cecal material was determined. *C. jejuni* was not recovered from any of the uninoculated chicks. Mutations in the capA, jlpA, and Cj1349c genes had little effect on the ability of *C. jejuni* to colonize the chicks, as judged by comparison with the wild-type. In contrast, the *C. jejuni* cadF, peb1A, and Cj1279c mutants demonstrated a marked impairment in their ability to colonize chicks, as only two of ten chickens inoculated with the *C. jejuni* cadF and Cj1279c mutants were colonized. None of the ten chicks inoculated with the *C. jejuni* peb1A mutant were colonized.

Cj1279c is Required for Efficient Cell Adherence and Chicken Colonization.

Figure 8:
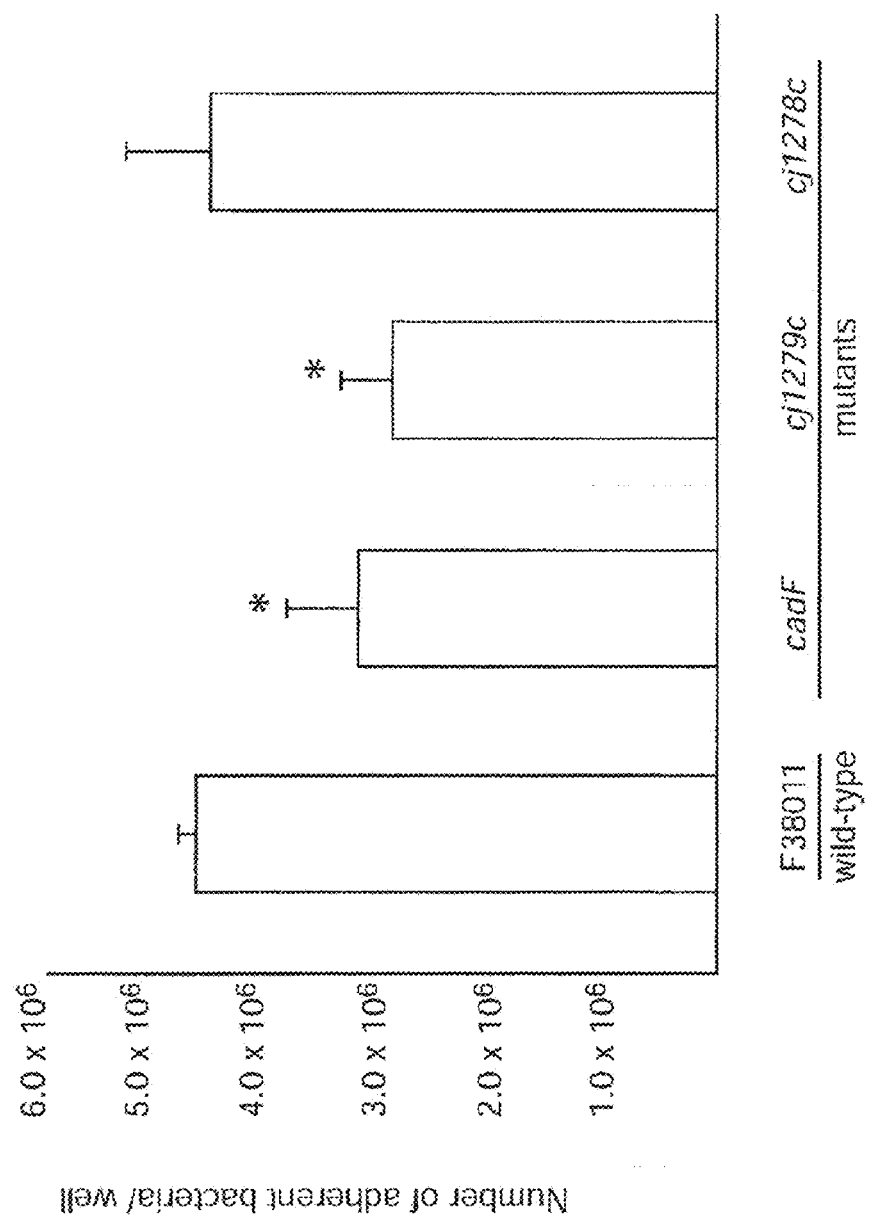
FIG. 8 shows that Cj1279c (flpA) encodes an adhesin. Each bar represents the mean±the standard deviation for the number of *C. jejuni* bound to the LMH cells in each well of a 24-well plate. The asterisk (*) indicates a statistically significance difference (P<0.05) between the *C. jejuni* F38011 wild-type isolate and an isogenic mutant, as determined using Student's t-test.

In silico analysis of Cj1279c revealed that this gene is located within a putative operon consisting of 13 genes (website located at www.microbesonline.org). The Cj1279c gene is situated downstream of Cj1280c that encodes a putative ribosomal pseudouridine synthase and upstream of eleven *C. jejuni* genes involved in various functions including cellular division and metabolism. To alleviate the concern of a polar effect, the Cj1278c gene downstream of Cj1279c was mutated. Adherence assays performed with chicken LMH cells demonstrated that the observed phenotype of the Cj1279c mutant was not due to a polar effect, as a difference in binding was not observed with the Cj1278c mutant relative to the wild-type strain (FIG. 8). Although variations were observed from one experiment to another in the number of *C. jejuni* that bound to the chicken LMH cells (FIGS. 6 and 8), these results appeared to be due to fluctuations in the MOI. Regardless, the *C. jejuni* cadF and Cj1279c mutants consistently showed reductions in cell-binding when compared to the wild-type strain in all experiments performed. Because Cj1279c has not been previously characterized, we propose that it is a novel adhesin. As indicated above, the Cj1279c mutant demonstrates a reduction in both adherence to chicken LMH cells and in the colonization of chickens. Based on these findings and the fact that Cj1279c contains Fn type III domains, the Cj1279c gene is referred to as "flpA" for Fibronectin-like protein A from this point forward.

EXAMPLE 3

*Campylobacter jejuni* FlpA Binds Fibronectin and is Required for Maximal Host Cell Adherence The goal of this study was to characterize the binding properties of FlpA, and to determine if this protein is a member of the Microbial Surface Components Recognizing Adhesive Matrix Molecules (MSCRAMMs) family. Experimental evidence showed that *C. jejuni* FlpA is surface exposed, promotes the bacterium's attachment to host epithelial cells, and has Fn binding activity. Assays were also performed to determine if CadF and FlpA act cooperatively to promote binding of *C. jejuni* to host cells and Fn. The identification of FlpA as a second MSCRAMM in *C. jejuni* highlights the importance of Fn binding in host colonization and disease.

Materials and Methods

Bacterial Strains.

All *Campylobacter jejuni* strains were cultured on Mueller Hinton agar plates supplemented with 5% bovine blood (MH-blood agar) under microaerobic conditions (5% $O_2$, 10% $CO_2$, 85% $N_2$) at 37° C. Strains were passed to fresh plates every 24 to 48 h. The *C. jejuni* F38011 strain was recovered from an individual with campylobacteriosis. The *C. jejuni* F38011 flpA (tetracycline resistant, $Tet^R$) and cadF flpA ($Kan^R$, $Tet^R$) mutants were generated as outlined below. The *C. jejuni* F38011 cadF (kanamycin resistant, $Kan^R$) mutant was generated as outlined elsewhere (5). When appropriate, the growth media were supplemented with chloramphenicol (Chl, 8 µg/ml), kanamycin (Kan, 50 µl/ml), tetracycline (Tet, 2 µg/ml), or cefoperazone (Cef, 30 µg/ml). *Escherichia coli* XL1-Blue MRF' ($Tet^R$, Stratagene, Garden Grove, Calif.), *E. coli* BL21 (Novagen, Madison, Wis.), and *E. coli* LMG194 (streptomycin, $Sm^R$ and $Tet^R$, Invitrogen, Carlsbad, Calif.) were grown aerobically at 37° C. on Luria-Bertani (LB) agar plates or in LB broth. When necessary, growth media were supplemented with ampicillin (Amp, 100 µg/ml), kanamycin (50 µg/ml), tetracycline (12.5 µg/ml), or chloramphenicol (20 µg/ml).

Analysis of the flpA Operon

The *C. jejuni* F38011 wild-type strain was grown to mid-exponential phase in MH broth, and total cellular RNA was extracted Genomic DNA was degraded by treatment with 11 units of RQ1 RNase-free DNase at 37° C. for 30 min. cDNA was synthesized from 500 ng of RNA using random hexamer primers and a reverse-transcriptase (RT) PCR system according to the manufacturer's directions. As a negative control, RT-PCR reactions were performed without RT enzyme. Two separate RNA extractions and cDNA synthesis reactions were performed on different days.

Table 4 lists all primers used in this study. PCR was performed to determine which genes are co-transcribed with flpA using 1 µl of a 1:10 dilution of cDNA as template in a total volume of 25 µl. As a positive control, the reactions were performed using *C. jejuni* F38011 genomic DNA as a template. DNA fragments were amplified using Taq DNA polymerase (Invitrogen, Carlsbad, Calif.) with the following parameters: 94° C. for 4 min, 1 cycle; 94° C. for 45 sec, 60° C. for 30 sec (−1° C. per cycle), and 2 min at 70° C., 10 cycles; 94° C. for 45 sec, 50° C. for 30 sec, and 2 min at 70° C., 25 cycles. PCR products spanning the junctions between genes Cj1280c, flpA, Cj1278c, Cj1277c, Cj1276c, and Cj1275c were amplified using the following primer pairs: MEK2386 and MEK2387, MEK2388 and MEK2389, MEK2412 and MEK2411, MEK2420 and MEK2421, and MEK2422 and MEK2423. The resulting PCR amplicons were analyzed by electrophoresis in a 1% agarose gel.

TABLE 4

| Primer Name | Primers used in this study Sequence 5' > 3' |
|---|---|
| MEK2386 | TAATGCGTTCGCCTTCTAATGC (SEQ ID NO: 105) |
| MEK2387 | AGCTGTGCTCACTTCTATAACC (SEQ ID NO: 106) |
| MEK2388 | TGCCAAAAGATGGTGTAGAAGG (SEQ ID NO: 107) |
| MEK2389 | TAGCCACTTGAGTTAAAGCTGG (SEQ ID NO: 108) |

TABLE 4-continued

Primers used in this study

| Primer Name | Sequence 5' > 3' |
|---|---|
| MEK2412 | ACAAGATGAGAATTTGCTTTTAAAGG (SEQ ID NO: 109) |
| MEK2411 | AAGTTCCTAAAAGCTCTCTAGC (SEQ ID NO: 110) |
| MEK2420 | ATGAGCCAACGGGAAATTTGG (SEQ ID NO: 111) |
| MEK2421 | ACAACAAGCAAATAAACAAAGTAGC (SEQ ID NO: 112) |
| MEK2422 | TTATTTGCTTGTTGTGTGTAAATACG (SEQ ID NO: 113) |
| MEK2423 | ATTCTACCCACTACGGCACC (SEQ ID NO: 114) |
| MEK1672 | ATATAGGATCCAACTTTTTTAGTAGATGAAAATTCAAGG (SEQ ID NO: 115) |
| MEK1671 | ATATACCGCGGCGAAATCTTTTCATCATTCTCTCC (SEQ ID NO: 116) |
| MEK1673 | ATATACCGCGGAGAACCTTCAAGCAAAGTTAAGG (SEQ ID NO: 117) |
| MEK1674 | ATATAGGATCCGTTCTGCTCTATTTTTTTCAAATCC (SEQ ID NO: 118) |
| MEK1681 | ATATACATATGATGATGAAAGATTTCGCTTGAG (SEQ ID NO: 119) |
| MEK1883 | ATATAGGTACCTTTTAAAATTTGGCACTACTGAGC (SEQ ID NO: 120) |
| MEK1687 | ATATAGGATCCCCTTGTGCTCCTGTTGTGC (SEQ ID NO: 121) |
| MEK1688 | ATATACATATGTCCTTTCATTTAAAATGAACCAC (SEQ ID NO: 122) |
| MEK1679 | ATATAGGATCCTGTAAATGAAAGCTTGCCAAAGG (SEQ ID NO: 123) |
| MEK1680 | ATATACTCGAGTTTGCTTGAAGGTTCTGAACG (SEQ ID NO: 124) |
| MEK1765 | ATATACCATGGTGAAAAGATTTCGCTTGAG (SEQ ID NO: 125) |
| MEK1766 | ATATAGGTACCTTACTACTGAGCCGCCTTAAC (SEQ ID NO: 126) |
| MEK1691 | ATATAGGATCCAAGCTTCAAGTAAAGAGCCTGC (SEQ ID NO: 127) |
| MEK1692 | ATATACTCGAGCTGAGCCGCCTTAACTTTGC (SEQ ID NO: 128) |
| MEK2522 | CCCGGATCCCCGGTTTAGCAGGTGGAGGATAT (SEQ ID NO: 129) |
| MEK2523 | CCCGAATTCTTATTTTACTTGTGGAGTTGCACGAGT (SEQ ID NO: 130) |

[a]Restriction endonuclease cleavage sites are underlined.

Generation of the C. jejuni F38011 flpA and cadF flpA Mutant.

A mutation in the flpA gene of C. jejuni F38011 was generated by homologous recombination using a suicide vector harboring a disrupted copy of the flpA gene. The 5' flanking region of the flpA gene was PCR amplified using HiFi Taq (Invitrogen) with the primers MEK1672 and MEK1671 containing BamHI and SstII restriction sites, and ligated into pCR2.1 (Invitrogen). The 3' flanking region of the flpA gene was PCR amplified using primers MEK1673 and MEK1674 containing SstII and BamHI restriction sites, and ligated into pCR2.1. The 3' fragment was restricted with the SstII and BamHI restriction enzymes, gel-purified, and ligated to the 5' fragment in the pCR2.1 vector. The resultant vector was digested with SstII, and the tetO gene conferring Tet resistance was inserted. This vector was then digested with BamHI to liberate the fragment containing the 5' and 3' flpA flanking fragments with the tetO gene, which was subsequently ligated into the suicide vector pBSK (Stratagene, La Jolla, Calif.). The pBSK vector had previously been modified to include an aphA-3 gene cassette encoding Kan resistance. This vector was electroporated into the C. jejuni F38011 wild-type strain and C. jejuni F38011 cadF mutant, and colonies were picked that were Tet resistant. The C. jejuni flpA mutants were confirmed by PCR using flpA gene specific primers.

Complementation of the C. jejuni flpA Mutant.

The flpA ORF with 0 bp of upstream sequence and 15 bp of downstream sequence was PCR amplified from C. jejuni F38011 genomic DNA using HiFi Taq and the primers MEK1681 and MEK1883 harboring the NdeI and KpnI restriction enzymes. The metK promoter sequence was amplified from C. jejuni NCTC11168 using primers MEK1687 and MEK1688 harboring BamHI and NdeI restriction enzymes. The metK promoter-flpA gene product was cloned into the MCS of the pRY111 shuttle vector using BamHI and KpnI sites. The metK promoter flpA in pRY111 was confirmed by DNA sequencing, and the resultant vector was electroporated into E. coli S17-λ-pir for conjugation into the C. jejuni F38011 flpA mutant. The conjugations were performed with overnight cultures of the C. jejuni F38011 flpA mutant grown in MH broth supplemented with Kan and E. coli S17-1 λ-pir harboring the pRY111 metK promoter-flpA construct grown in LB broth supplemented with Chl. The bacteria (the equivalent of 1 $OD_{540}$ units) were pelleted via centrifugation at 6,000×g for 2 min, and the supernatant was discarded. The E. coli S17-1%-pir pellet was resuspended in 500 µl of MH broth and combined with the C. jejuni F38011 flpA mutant pellet. The cells were pelleted again, and the supernatant discarded. The combined pellet was then spotted onto an MH-blood agar plate and incubated at 37° C. in a microaerophilic environment for 14 h. The conjugation spot was then streaked onto MH-blood agar plates supplemented with Chl and Cef, and incubated for 48 h. Isolated transformants were selected and the presence of the recombinant vector in the C. jejuni flpA mutant was confirmed by PCR. The complemented flpA mutant was designated the C. jejuni flpA (flpA+) complemented strain.

Construction of flpA-pET24b, flpA-pBADA, and flpA-pGST Recombinant Vectors.

Recombinant histidine tagged FlpA protein was generated using the pET Expression System from Novagen. A fragment of the flpA gene was PCR amplified using the gene specific primers MEK 1679 and MEK 1680 harboring BamHI and XhoI restriction enzymes, and cloned into the pET24b ($Kan^R$) vector using standard molecular biology techniques. The recombinant plasmid. flpA-pET24b. was introduced into E. coli BL21(DE3). The His-tagged FlpA protein was purified using a metal affinity resin.

To determine if FlpA facilitates the binding of E. coli to epithelial cells, we expressed the flpA gene in E. coli using the pBAD expression vector. The pBAD/Myc-His A vector ($Amp^R$), referred to as the pBADA from this point forward, was obtained from Invitrogen. A fragment of the flpA gene was PCR amplified using the gene specific primers MEK1765 and MEK1766 harboring NcoI and KpnI restriction enzymes and cloned into the pBADA vector using standard molecular biology techniques. The recombinant plasmid, 1279c pBADA, was introduced into E. coli LMG194. Expression of the flpA gene in E. coli LMG194 was induced by the addition of L-arabinose as outlined by the supplier.

The ability of FlpA to bind Fn was determined by ELISA using purified GST-tagged FlpA protein. The flpA gene was PCR amplified using gene specific primers MEK1691 and MEK1692 harboring the BamHI and XhoI restriction enzymes, and ligated into the pGEX-5x-1 vector using standard cloning procedures. The FlpA-GST protein was purified an affinity resin. The cadF gene fragment was cloned into the pGEX-5x-1 vector using primers MEK2522 and MEK2523. The GST-tagged CadF protein was purified.

Generation of FlpA-Specific Serum.

Female New Zealand White rabbits were subcutaneously and intramuscularly injected with 500 μg of purified His-tagged FlpA protein in TiterMax® Gold (CyRx Corporation, Norcross, Ga.). Two booster injections, each containing 50 μg of protein in Freund's incomplete adjuvant (Sigma), were given at 4 and 6 weeks after the primary injection. Blood was collected prior to all immunizations, and 7 days after the second booster injection. The serum was prepared using standard laboratory procedures, and stored at −80° C. FlpA-specific antibody was generated in a New Zealand White rabbit using a protocol approved by the Institutional Animal Care and Use Committee (IACUC protocol #2433) at Washington State University.

Outer Membrane Protein Extracts.

C. jejuni outer membrane proteins (OMPs) were extracted using N-lauroyl-sarcosine as described by de Melo and Pechere (2) with modifications. C. jejuni were grown in MH broth under microaerobic conditions overnight, pelleted by centrifugation, and suspended in 10 mM phosphate buffer (pH 7.4) containing 1 mM phenylmethylsulphonyl fluoride (Sigma, St. Louis, Mo.), 10 μg/ml Deoxyribonuclease 1 (DNase 1, Sigma) and 10 μg/ml Ribonuclease A (RNase, Fermentas, Glen Burnie, Md.). The bacterial cell suspensions were sonicated five times for 30 s each with a 30 s cooling period on ice between each pulse. Cell debris was removed by two successive centrifugations, each at 6,000×g for 10 min. The crude membrane extracts were obtained by centrifugation at 100,000×g at 4° C. for 2 h. The resulting pellets were suspended in 10 mM Tris (pH 7.5), and the protein concentration of each sample was determined using the bicinchoninic acid (BCA) assay as outlined in the manufacturer's instructions (Pierce, Rockford, Ill.). N-lauroyl-sarcosine (Sigma) was added to the crude extracts at a protein to detergent ratio of 1:4 (w/w). The samples were incubated at room temperature with gentle rocking for 30 min, and centrifuged at 100,000×g at 4° C. for 2 h. The pellets were washed with 50 mM Tris (pH 7.5), suspended in the same buffer, and stored at −20° C. The protein concentration of the OMP extracts was determined by BCA assay.

SDS-PAGE and Immunoblot Analysis.

Whole cell lysates (the equivalent of 0.1 $OD_{540}$ units) of the C. jejuni F38011 wild-type strain and mutants were solubilized in single-strength electrophoresis sample buffer and incubated at 95° C. for 5 min. The proteins were separated in SDS-12.5% polyacrylamide gels using the discontinuous system described by Laemmli (7). Following electrophoresis, proteins were stained with Coomassie Brilliant Blue R-250 (CBB R-250, Bio-Rad Laboratories, Hercules, Calif.). For immunoblot analysis, proteins were electrophoretically transferred to a polyvinylidene difluoride (PVDF) membrane. Immunoblots were performed by incubating the membrane overnight at 4° C. with a 1:500 dilution of the α-FlpA serum in phosphate buffered saline [(PBS (20 mM sodium phosphate and 150 mM sodium chloride, pH 7.5) containing 0.01% the polysorbate surfactant TWEEN® 20, a polyoxyethylene derivative of sorbitan monolaurate (v/v)] (PBS-T with 9% non-fat dry milk. After 3 washes with (PBS-T), a HRP-conjugated goat a-rabbit IgG (whole molecule) diluted 1:5000 in (PBS-T) was added as a secondary antibody and incubated at room temperature for 1 h. Following two washes with (PBS-T) and a final wash with PBS, blots were developed using.

Indirect Immunofluorescence Assays.

The C. jejuni F38011 wild-type strain and flpA mutant were harvested from MH-blood agar plates in PBS and 20 μl of the bacterial suspension was air-dried on a glass microscope slide. The air-dried samples were quickly passed over a flame and PBS added onto the surface of the slides. The bacteria were incubated for 45 min at 37° C. in a humidified chamber with either a 1:20 dilution of a rabbit α-C. jejuni whole-cell polyclonal serum (antiserum 1622) (6), rabbit α-FlpA serum, or rabbit pre-bleed serum in PBS containing 0.75% bovine serum albumin (BSA), The slides were washed 3 times with PBS and then incubated for 45 min at 37° C. in a humidified chamber with a 1:1.00 dilution of a Cy2-conjugated AffiniPure goat anti-rabbit IgG (H+L) (Jackson ImmunoResearch, West Grove, Pa.). Following incubation, the samples were rinsed 10 times with PBS, placed on a glass slide with mounting medium containing 4',6-diamidino-2-phenylindole (DAPI, VECTASHIELD®, Vector Laboratories, Inc., Burlingame, Calif.), and visualized using a Nikon Eclipse TE2000 inverted epifluorescence microscope. DAPI, a fluorescent stain that binds to DNA, was used to visualize all bacteria. Images were captured using imaging software and processed using Adobe Photoshop 3.0.4.

Tissue Culture.

INT 407 human intestinal epithelial cells (ATCC CCL6; American Type Culture Collection, Manassas, Va.) were maintained in minimal essential media (MEM, Gibco, Invitrogen, Carlsbad, Calif.) supplemented with 10% fetal bovine serum (FBS; HyClone Laboratories, Logan, Utah) and 5% L-glutamine (1.8 mM). The cells were cultured at 37° C. in a humidified, 5% $CO_2$ incubator and passaged every 48 to 72 h.

Bacteria-Host Cell Adherence Assay.

Each well of a 24-well tissue culture tray was seeded with INT 407 cells (1.5.times.10.sup.5 cells/well) and incubated for 18 h at 37° C. in a humidified, 5% $CO_2$ incubator. The cells were rinsed with the appropriate medium and inoculated with approximately $5 \times 10^7$ CFU of the various C. jejuni strains. Bacteria-host cell contact was promoted by centrifugation at 600×g for 5 min. To determine the viable number of bacteria that adhered to the INT 407 cells, the trays were incubated for 30 min at 37° C. in a humidified, 5% $CO_2$ incubator. Following this incubation period, the epithelial cells were rinsed three times with PBS to remove non-adherent bacteria. The epithelial cells were then lysed. The suspensions were serially diluted and the number of viable, adherent bacteria determined by counting the resultant colonies on MH-blood agar plates. The values reported represent the mean counts +/− standard deviations derived from triplicate wells.

To determine if antibodies against FlpA reduce the binding of C. jejuni to INT 407 cells, different dilutions of the FlpA-specific and pre-bleed sera were added to bacterial suspensions containing approximately $5 \times 10^7$ CFU. The bacterial suspensions were then incubated for 30 minutes at 37° C. under microaerobic conditions (5% $O_2$, 10% $CO_2$, 85% $N_2$). The binding assay was performed as outlined above.

Binding (adherence) assays were also performed with *E. coli* LMG194 harboring flpA-pBADA and *E. coli* LMG194 harboring pBADA without a DNA insert. For these assays, the bacteria were cultured overnight at 37° C. in LB broth supplemented with Amp. The following morning, 5 ml of LB broth containing Amp was inoculated with 250 µl of the overnight culture and incubated with shaking for 90 min at 37° C. Expression of flpA was induced by the addition of L-arabinose; 0.0002% L-arabinose was added to all the cultures for 2 h. The amount of L-arabinose added to the bacterial cultures was determined based on preliminary experiments that examined relative FlpA protein levels versus time and bacterial viability. The adherence assays were performed as described above for the *C. jejuni* strains, with the exception that the INT 407 cells were inoculated with approximately $2 \times 10^7$ CFU of each *E. coli* isolate.

ELISA.

The wells of a 96-well plate were coated overnight at 4° C. with either 1 µg of plasma fibronectin (Fn) (Sigma, St. Louis, Mo.) or BSA-coated wells which served as a negative control. The following day the wells were rinsed with wash buffer [PBS containing 0.005% Tween 20 (v/v)] and blocked with 1% BSA for 1 h at 25° C. and rinsed once with wash buffer. To determine the Fn binding activity of each protein, 2-fold serial dilutions of FlpA-GST and CadF-GST proteins were made in PBS, added to the wells, and incubated for 90 min at 25° C. The CadF-GST protein was used as a positive control for Fn binding affinity. After the wells were washed 3 times with wash buffer, a 1:1000 dilution of rabbit anti-GST antibody (Sigma) in incubation buffer was added to the wells and the plate incubated at 25° C. for 90 min. The wells were then washed 3 times with wash buffer, a 1:5000 dilution of horseradish peroxidase labeled goat anti-GST antibody (Sigma) diluted in PBS was added to the wells and the plate incubated at 25° C. for 90 min. The wells were washed, and bound antibodies were detected by addition of TMB Substrate Solution (Thermo Scientific, Rockford, Ill.). Binding was quantitated by colorimetric detection at 492 nm.

*C. jejuni*-Fn Binding Assay.

The wells of 96-well flat-bottom plates were coated with a 1 mg/ml solution of Fn in 0.05 M Tris Buffered Saline, pH 7.5 (Sigma) overnight at 4° C. For a control, wells were also coated with 1% BSA in PBS. The *C. jejuni* F38011 wild-type, flpA, cadF, and cadF flpA mutants were harvested from overnight plate cultures and resuspended in PBS at an $OD_{540}$ of 0.150 (approximately $10^8$ CFU). Wells were rinsed with PBS, and 100 µl of the bacterial suspensions were added to each well and incubated at 37° C., 5% $CO_2$ for 1 h. The wells were washed three times with PBS and adherent bacteria were removed by the addition of 0.25% trypsin (Gibco, Invitrogen). To enumerate the number of adherent bacteria, serial dilutions of the trypsin suspension were plated on MH-blood agar.

Results

Salient Features of the flpA ORF and the Protein it Encodes

Figure 9:
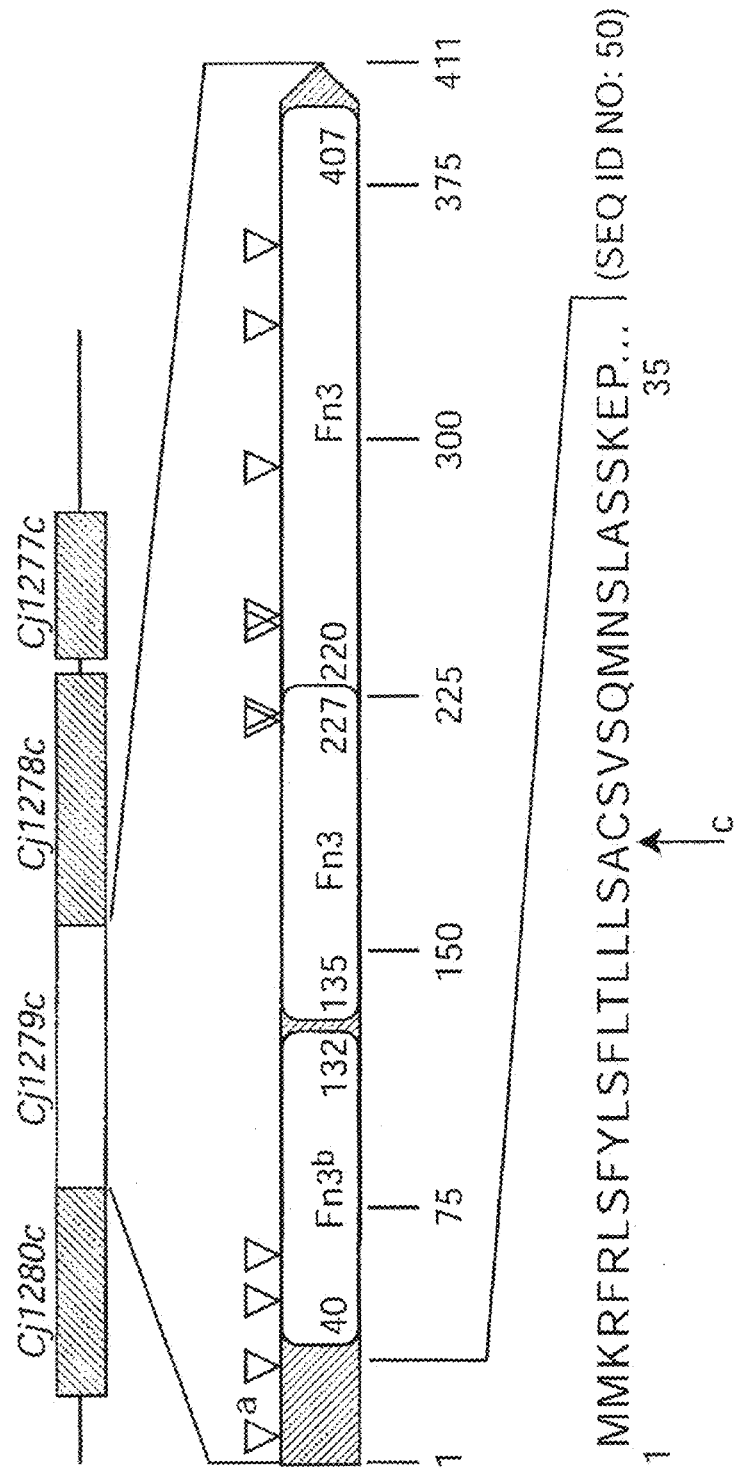
FIG. 9. Salient features of the flpA gene and its deduced amino acid sequence in the *C. jejuni* NCTC 11168 strain. The flpA gene in the *C. jejuni* F38011 strain is the second gene in a polycistronic operon containing a total of 4 genes. The flpA gene in NCTC 11168 is 1236 nucleotides. Examination of the FlpA deduced amino acid sequence revealed few residues differed in the NCTC 11168, RM1221, 81-176, 81116, and F38011 strains (arrowheads), three fibronectin type 3 domains (Fn3, residues 40-132, 135-227, and 220-407), and a prokaryotic membrane lipoprotein lipid attachment site (arrow). "a"=residues that vary in one or more of the four *C. jejuni* sequences strains listed above (SEQ ID NO: 50); "b"=fibronectin, type II domain (SSF49265, residues 40 to 132, 135 to 227, 220 to 407); "c"=prokayotinc membrane lipoprotein attachments site.

Analysis of the flpA gene and predicted operon structure from four *C. jejuni* sequenced strains (i.e., NCTC 11168, RM1221, 81-176, and 811116) revealed conserved features (FIG. 9). The order of the genes flanking flpA in the four *C. jejuni* sequenced strains are identical (i.e., Cj1280c, Cj1279c (flpA), Cj1278c, Cj1277c, and Cj1276c). Apart from in silico analysis of flpA, little is known regarding the operon structure in which this gene resides. To determine number of genes in the operon in which flpA resides, PCR was initially performed using gene specific primers experiments to determine the gene order in the *C. jejuni* F38011 clinical strain. The sizes of the PCR fragments were in agreement with that predicted from NCTC 11168 genome analysis, suggesting that the *C. jejuni* F38011 strain likely has the same gene order (i.e., Cj1280c, Cj1279c (flpA), Cj278c, Cj1277c, and Cj1276c) as the four *C. jejuni* strains indicated above. RT-PCR analysis was then performed with gene specific primers to experimentally determine the number of genes in the flpA operon. In the *C. jejuni* F38011 strain, flpA is the second gene in an operon consisting of Cj1280c, Cj1279c (flpA), Cj1278c, and Cj1277c.

Figure 10:
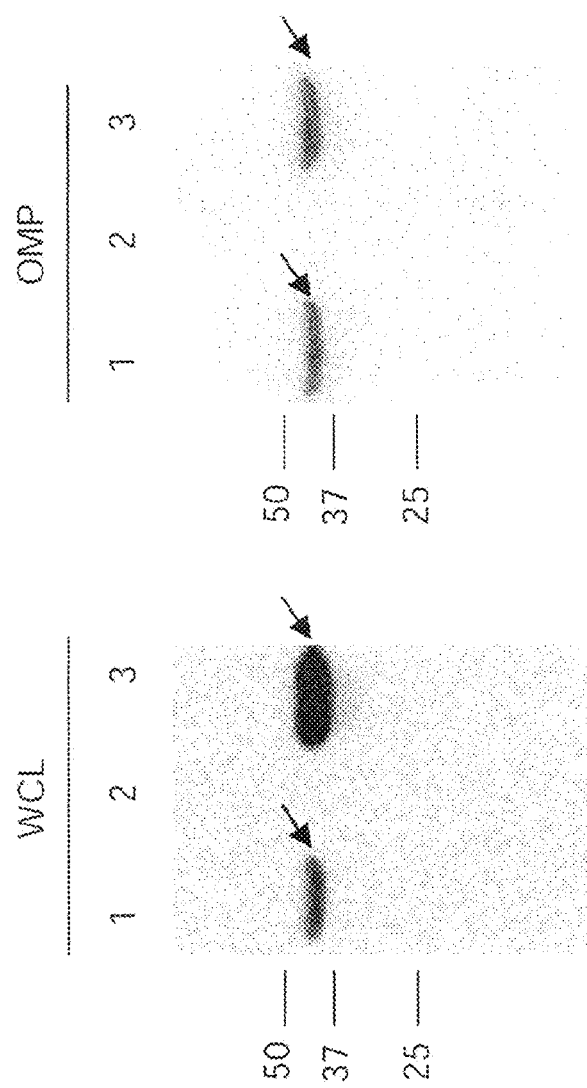
FIGS. 10A and B. Detection of FlpA in *C. jejuni* whole cell lysate (WCL) and outer membrane protein (OMP) extracts prepared from the *C. jejuni* F38011 wild-type strain and flpA isogenic mutant as judged by immunoblot analysis with a FlpA-specific serum. WCL and OMP extracts were resolved by SDS-PAGE (12.5% polyacrylamide) and immunoblot analysis as outlined in "Materials and Methods." The blot on the left side of the panel (A) shows a blot of *C. jejuni* WCLs probed with the FlpA-specific serum and the blot on the right side of the panel (B) shows a blot of *C. jejuni* OMPs probed with the FlpA-specific serum. Lanes: 1, *C. jejuni* F38011 wild-type strain; 2, *C. jejuni* flpA mutant; and 3, *C. jejuni* flpA (flpA$^+$) complemented strain. The position of the FlpA 46 kDa protein is highlighted (arrow). The positions of the molecular mass standards are indicated on the left (in kDa).

The flpA gene in *C. jejuni* NCTC 11168 is 1236 nucleotides. The ORF from *C. jejuni* NCTC 11168 (Cj1279c) begins with two AUG codons in tandem followed by an AAA codon [Lys (K) residue] and is terminated by an UAG termination codon. One discrepancy in the annotation of the flpA ORF from *C. jejuni* NCTC 11168 versus other sequenced strains is that the ORF begins with a single AUG codon followed by an AAA codon in the ORF from *C. jejuni* strains RM1221, 81-176, and 81116. The proposed methionine start codon in all the *C. jejuni* sequenced strains is preceded by a typical Shine-Dalgarno sequence (AGGA). The ORF from *C. jejuni* NCTC 11168 is 411 amino acids and is predicted to synthesize a protein with a calculated mass of 46,124 Da (Table 2). In silico analysis of the FlpA deduced amino acid sequence further revealed that the protein shares greater than 99% identity at the amino acid level among the four *C. jejuni* strains (i.e., NCTC 11168, RM1221, 81-176, and 811116) (Table 2). Other than the one additional methionine at the amino terminus of FlpA from NCTC 11168, only eleven residues differed within the entire deduced amino acid sequence of the four strains. The nucleotide sequence of the flpA gene in the *C. jejuni* F38011 strain is identical to that of the *C. jejuni* NCTC 11168 strain, except for a single silent nucleotide difference at base 882 (i.e., C in strain F38011 versus a T in strain 11168). Examination of the *C. jejuni* NCTC 11168 FlpA predicted amino acid sequence identified an L-S-A-C motif at residues 18-21, which matches the prokaryotic lipoprotein signal consensus [LVI][ASTVI][GAS][C] (FIG. 10). This consensus sequence, found at the C-terminal end of a lipoprotein signal peptide, is referred to as the lipobox. The invariant Cys residue is lipid modified, and presumably inserted into one leaflet of the lipid bilayer. The FlpA deduced amino acid sequence also harbors Fn type III domains.

FlpA is a Membrane-Associated Protein with Surface Exposed Domains

A *C. jejuni* flpA mutant was generated as outlined in 'Materials and Methods,' and demonstrated to have similar growth rates as the *C. jejuni* wild-type strain (not shown). To determine the cellular location of FlpA, whole cell lysates (WCL) and outer membrane protein (OMP) extracts were prepared from a *C. jejuni* wild-type strain, flpA mutant, and flpA (flpA+) complemented strain and analyzed by SDS-PAGE coupled with immunoblot analysis using a FlpA-specific serum. A band with a $M_r$ of 46 kDa was readily observed in WCL extracts of the *C. jejuni* F38011 wild-type and flpA (flpA+) complemented strains but not in the isogenic flpA knockout (FIG. 10). Consistent with the notion that FlpA is a membrane-associated protein, as suggested by its amino-terminal leader, a 46 kDa immunoreactive band was also observed in the OMP extracts of the *C. jejuni* F38011 wild-type strain and the flpA (flpA+) complemented strain.

Figure 11:
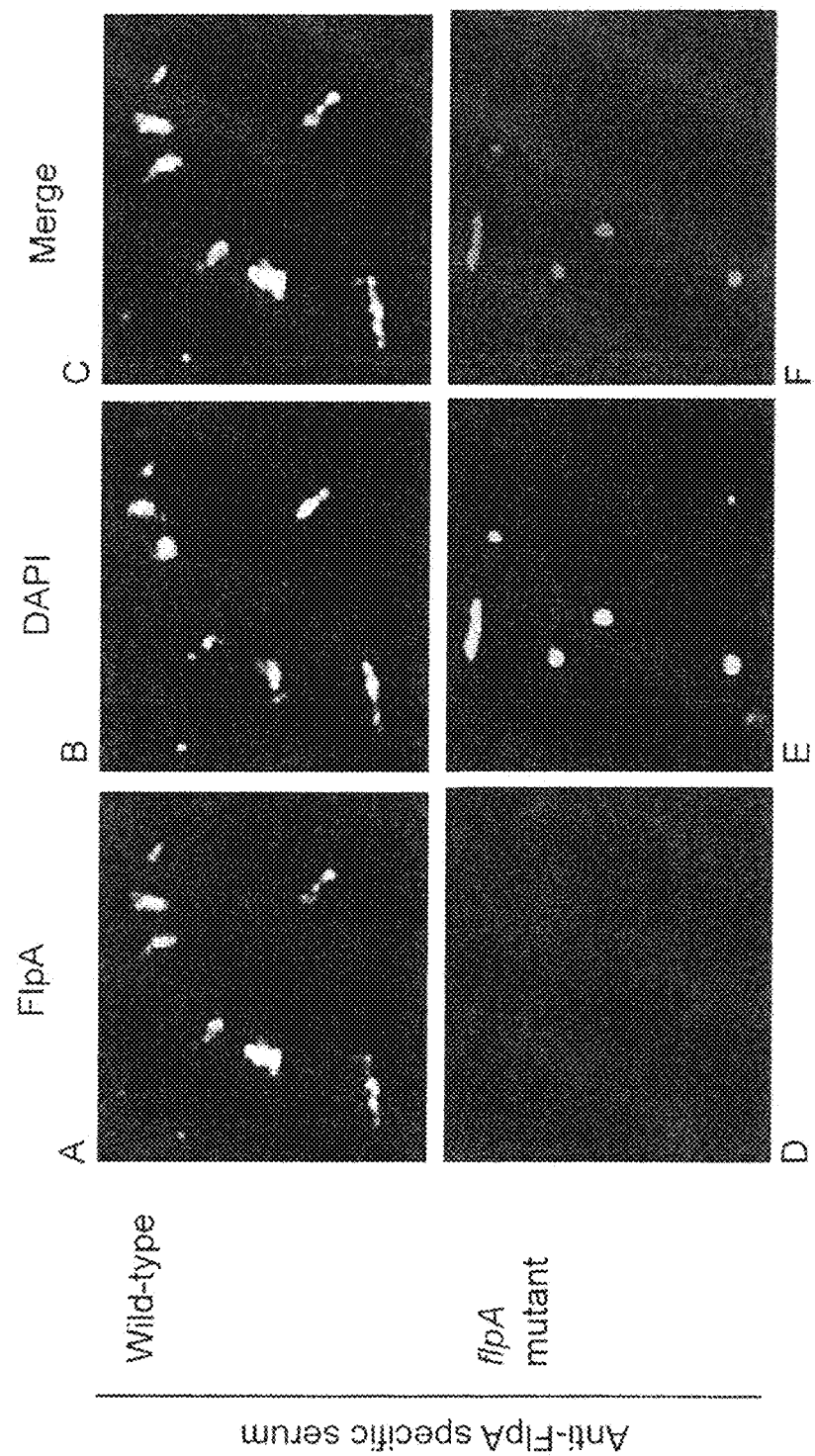
FIG. 11. The FlpA protein contains surface exposed domains. Indirect immunofluorescence microscopy was performed with the *C. jejuni* F38011 wild-type strain (Panels A-C) and flpA isogenic mutant (Panels D-F) as outlined in "Materials and Methods." *C. jejuni* were incubated with the rabbit FlpA-specific serum (Panels A-F) followed by incubation with a Cy2-conjugated goat anti-rabbit secondary antibody. All bacteria were visualized by staining with 4',6-diamidino-2-phenylindole (DAPI). The specimens were visualized using a Nikon Eclipse TE2000 inverted epifluorescence microscope. The *C. jejuni* wild-type strain and flpA mutant incubated with the rabbit α-*C. jejuni* whole-cell serum were readily observed (not shown), whereas only the *C. jejuni* wild-type strain incubated with the rabbit FlpA-specific serum was stained.

To determine if domains of the FlpA protein are surface exposed, *C. jejuni* were incubated with the FlpA-specific serum and indirect immunofluorescence microscopy was performed. All bacteria were incubated with a rabbit α-*C. jejuni* whole-cell serum for a positive control. After the bacteria were incubated with either the rabbit α-*C. jejuni* whole-cell or rabbit FlpA-specific sera, they were incubated with a Cy2-conjugated goat anti-rabbit secondary antibody and examined. The rabbit α-*C. jejuni* whole-cell serum stained both the wild-type and flpA mutant bacteria (not shown). In contrast, the rabbit FlpA-specific serum only stained the wild-type bacteria (FIG. 11). Together, these results indicate that FlpA is a membrane-associated protein with surface exposed domains.

FlpA Promotes the Binding of *C. jejuni* to Human Epithelial Cells

Figure 12:
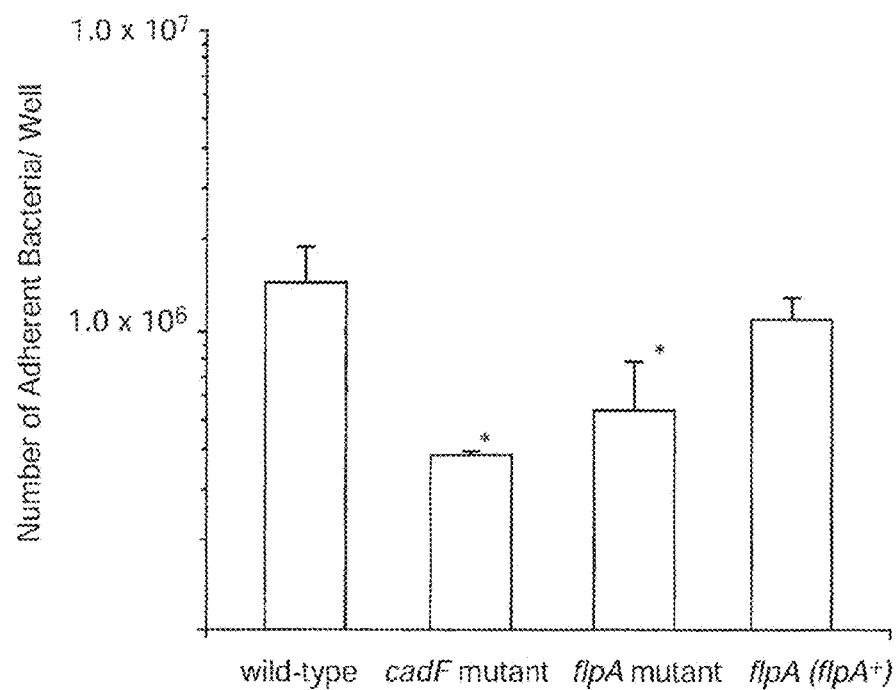
FIG. 12. FlpA promotes the binding of *C. jejuni* to human epithelial cells. In vitro adherence assays were performed with human INT 407 epithelial cells and the *C. jejuni* F38011 wild-type strain, cadF mutant, flpA mutant, and flpA (flpA$^+$) complemented strain as outlined in "Materials and Methods." The *C. jejuni* cadF mutant was included as a negative control, as it is well documented that CadF is an adhesin. Values represent the mean±standard deviation of viable bacteria bound to INT 407 cells per well of a 24-well tissue culture tray. The asterisks (*) indicates that the number of bacteria bound to the INT 407 cells was statistically different (P<0.01) from that of the *C. jejuni* wild-type strain as judged by the Student's t-test.
Figure 13:
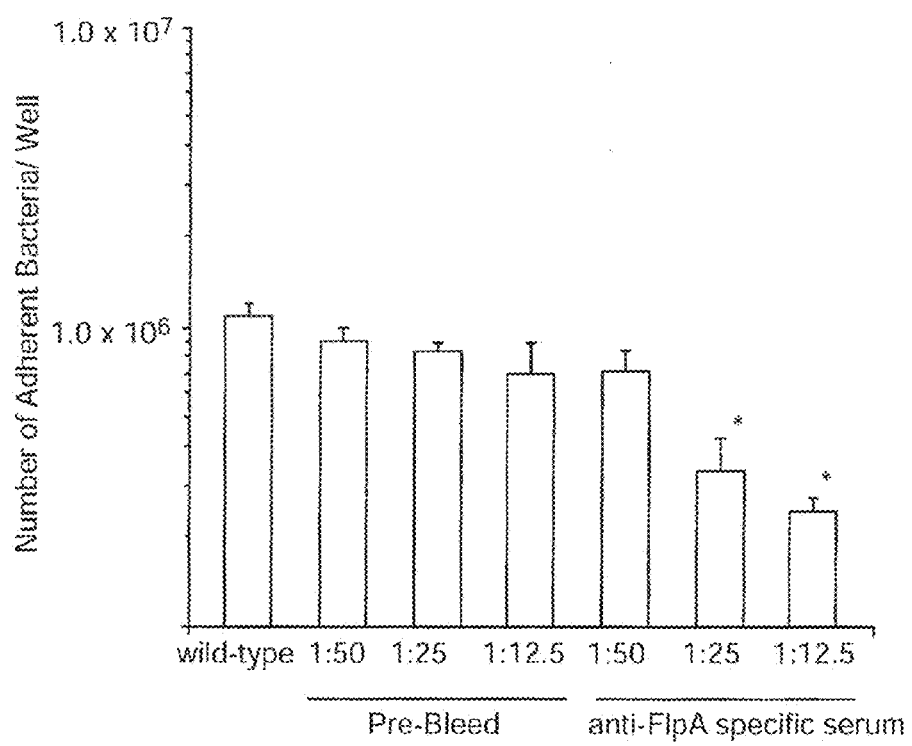
FIG. 13. Inhibition of *C. jejuni* binding to human INT 407 epithelial cells with FlpA-specific serum. The bacteria were incubated with indicated dilutions of the FlpA-specific serum or pre-bleed serum for 30 min prior to inoculation of the INT 407 cells. Adherence assays were performed as outlined in "Materials and Methods." Values represent the mean±standard deviation of viable bacteria bound to INT 407 cells per well of a 24-well tissue culture tray. The asterisks (*) indicates that the number of bacteria bound to the INT 407 cells was statistically different (P<0.01) from that of the *C. jejuni* wild-type strain as judged by the Student's t-test.

Previous work demonstrated that FlpA plays a role in *C. jejuni* colonization of broiler chickens, as only 2 of 10 chickens inoculated with the *C. jejuni* flpA mutant were colonized (3). To build on this initial work, in vitro adherence assays were performed with human INT 407 cells and a *C. jejuni* wild-type strain, cadF mutant, flpA mutant, and flpA (flpA$^+$) complemented strain (FIG. 12). The *C. jejuni* cadF mutant was included in these assays as a negative control (5). At a multiplicity of infection of 30:1, the *C. jejuni* flpA mutant showed a 62% reduction in adherence to INT 407 cells when compared with the *C. jejuni* wild-type strain. In comparison, the *C. jejuni* cadF mutant showed a 72% reduction in adherence to INT 407 cells when compared with the *C. jejuni* wild-type strain. The reduction in the binding of the *C. jejuni* flpA mutant was judged to be specific, as complementation of the mutant in trans with a wild-type copy of the gene driven by the metK promoter restored the organism's binding to the INT 407 cells. To alleviate the concern of a polar effect and to further demonstrate that the phenotype displayed by the *C. jejuni* flpA mutant was due to the presence of the FlpA protein, we tested if the binding of *C. jejuni* to INT 407 cells could be blocked with the FlpA-specific serum (FIG. 13). The FlpA-specific serum reduced the binding of *C. jejuni* to INT 407 cells in a dose-dependent fashion, reaching a maximum value of 77% inhibition at a 1:12.5 dilution of the serum. In contrast, a statistically significant difference was not observed in the binding of *C. jejuni* to INT 407 cells treated with the rabbit pre-bleed serum. Together, these findings demonstrate that FlpA mediates adherence to epithelial cells.

FlpA Promotes the Binding of *E. coli* to Human Epithelial Cells

While a *C. jejuni* flpA mutant exhibited a reduction in binding to INT 407 cells when compared with the wild-type strain, and the FlpA-specific serum blocked adherence, it remained possible that other proteins could act indirectly to potentiate the adhesive property of FlpA. To determine if FlpA is sufficient to promote the binding of bacteria to epithelial cells, adherence assays were performed with *E. coli* expressing flpA. More specifically, we tested the binding properties of an *E. coli* LMG194 strain harboring the pBADA plasmid containing flpA (*E. coli* flpA-pBADA) and the *E. coli* LMG194 strain harboring pBADA without a DNA insert. Prior to these assays, experiments were performed to determine the minimal concentration of L-arabinose and time sufficient to induce flpA expression. A 46 kDa band was readily visible in the whole cell lysates of the *E. coli* flpA-pBADA strain that had been cultured in medium containing 0.0002% of L-arabinose for 2 h as judged by SDS-PAGE (not shown). A statistically significant difference was observed in binding of the *E. coli* flpA-pBADA isolate to INT 407 cells [1.1±0.2]× $10^6$] versus *E. coli* harboring an empty pBADA vector [4.13±1.1]× $10^5$]. This finding further demonstrates that FlpA is an adhesin.

FlpA Binds to Fibronectin

Figure 14:
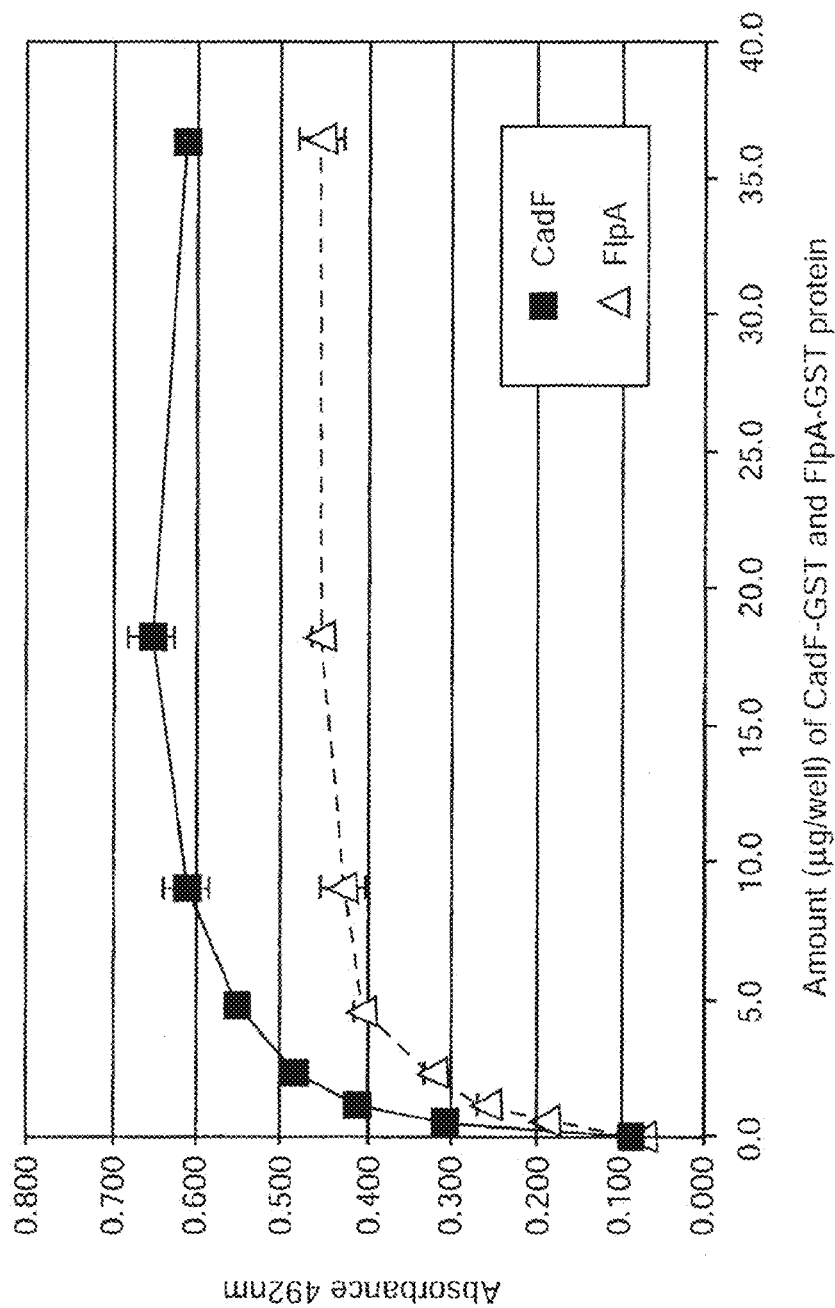
FIG. 14. FlpA binding to fibronectin is saturable. Fibronectin-coated wells were incubated with 2-fold serial dilutions of FlpA-GST and CadF-GST proteins, and bound proteins detected as outlined in "Materials and Methods." The *C. jejuni* CadF protein was included as a positive control. The samples were tested in triplicate, and each data point contains the mean±standard deviation of a representative experiment.

Each Fn monomer has a molecular weight of 250 kDa and contains type I, II, and III repeat units. Sequence analysis of FlpA revealed the presence of at least three domains with similarity to the Fn type III (Fn III) domain (see FIG. 9). The Fn III domain mediates Fn-Fn interactions (9). Based on the presence of the Fn type III domains, ELISAs were performed to determine whether FlpA has Fn binding activity. The *C. jejuni* CadF protein was included in these assays as a positive control because its Fn binding activity is well documented (4, 5). As a negative control, wells were coated with BSA. In addition, we assessed the binding of GST alone. Fn binding activity was evident with both the FlpA-GST and CadF-GST tagged proteins as judged by ELISA (FIG. 14). The specificity of these interactions was demonstrated in that the binding was both dose-dependent and saturable at concentrations between 5 to 10 µg. However, under the conditions used, more CadF bound to Fn than FlpA, suggesting that the two proteins have different affinities for Fn. GST alone did not demonstrate significant Fn binding affinity; background absorbance values of 0.1 were obtained over a range of concentrations (not shown). In addition, all of the GST fusion proteins demonstrated only low-level nonspecific binding to BSA coated wells. The reason for using the GST-recombinant proteins was to alleviate the concern of using different antibodies to detect the bound proteins. The Fn binding activities of FlpA and CadF were also confirmed using FlpA and CadF-specific antibodies (not shown). Based on these results, we concluded that FlpA has Fn binding activity.

Both CadF and FlpA are Required for *C. jejuni* to Bind to Host Cells and Fn

Figure 15A:
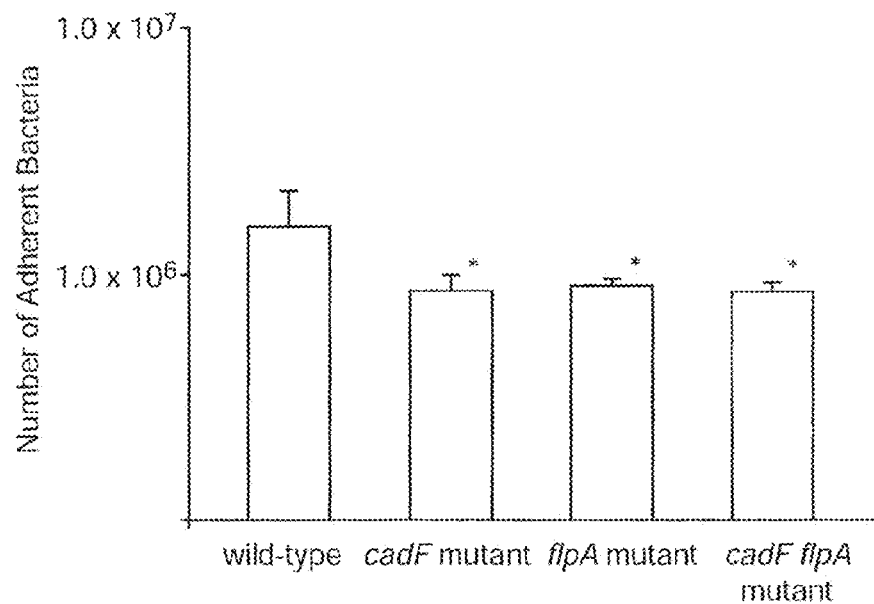
FIGS. 15A and B. CadF and FlpA mediate binding to host cells and Fn. A, In vitro adherence assays were performed with human INT 407 epithelial cells and the *C. jejuni* F38011 wild-type strain, cadF mutant, flpA mutant, and cadF flpA double mutant as outlined in "Materials and Methods." Values represent the mean±standard deviation of viable bacteria bound to INT 407 cells per well of a 24-well tissue culture tray. The asterisks (*) indicates that the number of bacteria bound to the INT 407 cells was statistically different (P<0.01) from that of the *C. jejuni* wild-type strain as judged by the Student's t-test. 13, *C. jejuni*-Fn binding assays were performed with viable bacteria and Fn-coated wells as outlined in "Materials and Methods." The results are presented as the percent bacteria bound relative to the *C. jejuni* F38011 wild-type strain.
Figure 15B:
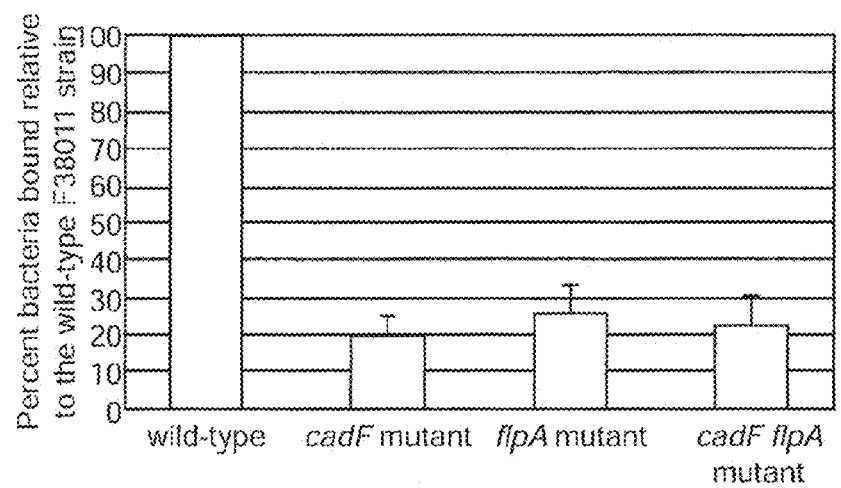

Based on the data shown above, FlpA is a MSCRAMM family member. To determine if FlpA and CadF binding to host cell and Fn is independent of each other, *C. jejuni*-host cell adherence and Fn binding assays were performed with a *C. jejuni* wild-type strain, *C. jejuni* cadF mutant, *C. jejuni* flpA mutant, and *C. jejuni* cadF flpA double mutant (FIG. 15). Each of the *C. jejuni* mutants (i.e., cadF, flpA, and cadF flpA) demonstrated a statistically significant reduction in binding to INT 407 cells and Fn coated wells when compared with the wild-type strain (FIG. 16). In addition, the *C. jejuni* cadF flpA double mutant exhibited a similar reduction in binding to INT 407 cells and Fn coated wells as compared with the individual *C. jejuni* cadF and flpA mutants. Collectively, these data indicate that FlpA and CadF are both needed to facilitate the maximal binding of *C. jejuni* to Fn and host cells.

Discussion

FlpA is a Member of the MSCRAMM Family

Previous work indicates that *C. jejuni* adherence to gastrointestinal cells and extracellular matrix components is crucial for host colonization and subsequent disease. More specifically, a *C. jejuni* cadF mutant shows a significant reduction in adhesion to human INT 407 intestinal cells when compared to a wild-type strain (8). Similar to cadF, disruption of Cj1279c (flpA) results in a *C. jejuni* mutant impaired in its ability to bind to chicken LMH hepatocellular carcinoma epithelial cells and to efficiently colonize broiler chickens when compared with a wild-type strain (3). The product encoded by the Cj1279c gene is termed FlpA for Fibronectin-like protein A, based on the fact that the protein's deduced amino acid sequence harbors Fn type III domains. Here we conclude that FlpA is associated with outer membrane components as judged by SDS-PAGE coupled with immunoblot analysis using FlpA-specific serum and is surface exposed as judged by immunofluorescence microscopy. We also conclude that FlpA acts as an adhesin based on the following experimental findings: 1) The binding of the *C. jejuni* flpA mutant strain to INT 407 epithelial cells was significantly reduced when compared with a wild-type strain; 2) Rabbit polyclonal serum generated against FlpA blocked *C. jejuni* adherence to INT 407 cells in a dose-dependent manner; and 3) The expression of flpA in *E. coli* significantly increased the bacterium's binding to INT 407 cells when compared with *E. coli* containing an empty vector. Finally, we submit that FlpA is a member of the MSCRAMM family because it binds to Fn in a dose-dependent and saturable fashion, as demonstrated by ELISA. Based on the sum of in vitro and in vivo assays, we conclude FlpA is a novel *C. jejuni* adhesin.

FlpA is a Putative Outer Membrane Lipoprotein

While the primary focus of this research was to demonstrate the adhesive properties of FlpA, multiple observations indicate that FlpA is associated with the *C. jejuni* outer membrane. We visualized a 46 kDa band in OMP extracts prepared from *C. jejuni* F38011 using a FlpA-specific serum. In addition, a 46 kDa band was apparent in the OMP extracts prepared from the *C. jejuni* flpA (flpA+) complemented strain. Noteworthy is that the FlpA protein (i.e., CJJ81176_1295) was detected by LC/MALDI/TOF-TOF in *C. jejuni* 81-176 OMP extracts previously (1, 10). We also found that FlpA is exposed on the surface of the bacterium as judged by immunofluorescence microscopy using the FlpA-specific antibodies. Consistent with the notion that the domains of FlpA are surface exposed, the FlpA-specific antibodies used for the immunofluorescence assays reduced the adherence of *C. jejuni* to INT 407 cells in a dose-dependent manner.

Inspection of the amino terminus of FlpA indicated the presence of lipoprotein signal consensus sequence. Although a few experimental methods are available to conclusively demonstrate that a protein is lipid modified, presumptive evidence for the identification of a lipoprotein is evident from inspection of its deduced amino acid sequence. The amino terminal signal sequence of a lipoprotein is characterized by a tripartite structure of positively charged residues at the amino terminus, a hydrophobic core region, and the lipobox with the invariant Cys residue at the carboxy terminus of the signal. The FlpA deduced amino acid sequence contains each of these key features. The presence of the prokaryotic lipoprotein signal consensus sequence strongly suggests that FlpA is a lipoprotein.

Model of CadF and FlpA Binding to Fibronectin

Adherence assays were performed to determine the contribution of FlpA in the binding of *C. jejuni* to human INT 407 epithelial cells. A *C. jejuni* flpA mutant showed a 62% reduction in adherence to INT 407 cells when compared with the *C. jejuni* wild-type strain. In comparison, the *C. jejuni* cadF mutant showed 72% reduction in adherence to INT 407 cells. Given that both proteins demonstrate Fn binding activity, the ability of a *C. jejuni* cadF flpA mutant to exhibit a greater reduction in binding to INT 407 cells than either the *C. jejuni* flpA mutant or *C. jejuni* cadF mutant was tested. It was found that the reduction in binding of the *C. jejuni* cadF flpA double mutant was indistinguishable from a *C. jejuni* cadF or flpA mutants alone. Subsequently, purified FlpA and CadF were tested for competitive binding to Fn-coated wells by ELISA. However, conditions under which the two proteins compete for Fn binding were not identified. Based on these data, it appears likely that CadF binds to one portion of Fn and FlpA binds to another portion, and that both interactions are required for intimate host cell and Fn attachment. Regardless of the specifics of these interactions, it is noteworthy that *C. jejuni* possess at least two Fn binding proteins (i.e., MSCRAMMs).

Summary

In this example, experimental evidence is provided that demonstrates that FlpA promotes the attachment of *C. jejuni* to host epithelial cells and has Fn binding activity. The identification and characterization of FlpA, along with CadF, highlights the potential importance of *C. jejuni* binding to Fn for host colonization and disease.

References for Example 3

1. Cordwell, S. J., A. C. Len, R. G. Touma, N. E. Scott, L. Falconer, D. Jones, A. Connolly, B. Crossett, and S. P. Djordjevic. 2008. Identification of membrane-associated proteins from *Campylobacter jejuni* strains using complementary proteomics technologies. Proteomics. 8:122-139.
2. de Melo, M. A., and J. C. Pechere. 1990. Identification of *Campylobacter jejuni* surface proteins that bind to eucaryotic cells in vitro. Infect. Immun. 58:1749-1756.
3. Flanagan, R. C., J. M. Neal-McKinney, A. S. Dhillon, W. G. Miller, and M. E. Konkel. 2009. Examination of *Campylobacter jejuni* putative adhesins leads to the identification of a new protein, designated FlpA, required for chicken colonization. Infect. Immun. 77:2399-2407.
4. Konkel, M. E., J. E. Christensen, A. M. Keech, M. R. Monteville, J. D. Klena, and S. G. Garvis. 2005. Identification of a fibronectin-binding domain within the *Campylobacter jejuni* CadF protein. Mol. Microbial. 57:1022-1035.
5. Konkel, M. E., S. G. Garvis, S. L. Tipton, D. E. Anderson, Jr., and W. Cieplak, Jr. 1997. Identification and molecular cloning of a gene encoding a fibronectin-binding protein (CadF) from *Campylobacter jejuni*. Mol. Microbiol. 24:953-963.
6. Konkel, M. E., D. J. Mead, and W. Cieplak, Jr. 1993. Kinetic and antigenic characterization of altered protein synthesis by *Campylobacter jejuni* during cultivation with human epithelial cells. J. Infect. Dis. 168:948-954.
7. Laemmli, U. K. 1970. Cleavage of structural proteins during the assembly of the head of bacteriophage T4. Nature. 227:680-685.
8. Monteville, M. R., J. E. Yoon, and M. E. Konkel. 2003. Maximal adherence and invasion of INT 407 cells by *Campylobacter jejuni* requires the CadF outer-membrane protein and microfilament reorganization. Microbiology. 149:153-165.
9. Pankov, R., and K. M. Yamada. 2002. Fibronectin at a glance. J Cell Sci 115:3861-3863.
10. Shoaf-Sweeney, K. D., C. L. Larson, X. Tang, and M. E. Konkel. 2008. Identification of *Campylobacter jejuni* proteins recognized by maternal antibodies of chickens. Appl. Environ. Microbiol. 74:6867-6875.

EXAMPLE 4

Characterization of the FlpA Fibronectin-Binding Domain

In this study, enzyme-linked immunosorbent assays (ELISAs) were used to determine the sites of FlpA and Fn adherence. ELISAs using recombinant proteins encoding each of the three FlpA domains demonstrated FlpA-D2 contained the En-binding domain. Using an array of synthetic peptides spanning the FlpA-D2 amino acid sequence, seven amino acids $^{158}$PHPDFRV$^{164}$ (SEQ ID NO: 51) were identified within FlpA-D2 with maximal Fn-binding activity. Since FN3 repeat are involved in intramolecular interactions with the N-terminus of Fn, the ability of FlpA top bind two thermolytic fragments generated form the N-terminus of Fn the 30 kDa N-terminal domain (NTD) and the gelatin-binding domain (GBD) was determined. FlpA bound the Fn gelatin-binding domain (GBD), but not the NTD. Furthermore, the amounts of FlpA bound to the GBD and full-length Fn were similar, indicating the GBD is the primary site of FlpA adherence to Fn. Collectively, these data demonstrated residues $^{158}$PHPDFRV$^{164}$ within FlpA-D2 mediate adherence to the GBD of Fn.

Materials and Methods.

Bacterial Strains/plasmids. *Escherichia coli* XL-1 Blue (Stratagene, Garden Grove, Calif.) and BL21DE3 (Novagen, Madison, Wis.) were maintained on Luria-Bertani (LB) agar plates or in LB broth aerobically at 37° C. Strains harboring pGEX-5x-1 (GE Healthcare) and pET-24b (Novagen) were grown on media supplemented with 100 µg/ml ampicillin and 50 µg/ml kanamycin, respectively. Construction and expression of the recombinant N-terminal glutathione S-transferase (GST)-tagged and C-terminal 6×-histidine (His)-tagged proteins were performed using standard molecular biology techniques described previously (Konkel et al., 2010). The following primer sets were used to clone the DNA fragment encoding each recombinant peptide for expression: FlpA-His, MEK1679 and MEK1680; FlpA-GST (full-length), MEK1691 and MEK1692; FlpA-D1-GST, MEK1691 and MEK2494; FlpA-D2-GST, MEK2495 and MEK2496; FlpA-D3-GST, MEK2497 and MEK1692 (Table 5).

TABLE 5

Primers used for expression of the recombinant proteins.

| Primer name | Sequence (5' -> 3') |
| --- | --- |
| MEK1679 | ATATAGGATCCTGTAAATGA AAGCTTGCCAAA GG (SEQ ID NO: 131) |
| MEK1680 | ATATACTCGAGTTTGCTTGAAGGTTCTG AAC G (SEQ ID NO: 132) |
| MEK1691 | ATATAGGATCCAA GCTTCA AGTAAA GAG CCTGC (SEQ ID NO: 133) |
| MEK1692 | ATATACTCGAGCTG AGCCGCCTT AACTTTGC (SEQ ID NO: 134) |
| MEK2494 | ATATACTCGAGTGT GCTCACTTCTATAACCTT GC (SEQ ID NO: 135) |
| MEK2495 | ATATAGGATCCAC ACA GCTCCA AGACTTGAA GC (SEQ ID NO: 136) |
| MEK2496 | ATATACTCGAGAGAACTTACAACTTGACTTGA CC (SEQ ID NO: 137) |
| MEK2497 | ATATAGGATCGTCAAGTTGTAAGTTCTACAAGC (SEQ ID NO: 138) |
| MEK2522 | CCCGGATCCCCGGTTTAGCAGGTGGAGGATAT (SEQ ID NO: 139) |
| MEK2523 | CCCGAATTCTTATTTTACTTGTGG AGTTGCACGAGT (SEQ ID NO: 140) |

Protein Purification.

*E. coli* harboring the pGEX-5x-I and pET24b expression vectors were grown aerobically in 1 L of broth cultures supplemented with appropriate antibiotics at 37° C. to an OD$_{540}$=0.6 and induced with 1 mM Isopropyl-.beta.-D-thiogalactoside (IPTG) overnight at 22° C. Cells were harvested in by centrifugation at 6,000×g, 4.degree for 15 min, resuspended in ice-cold 20 mM NaP$_i$, 150 mM NaCl, pH 7.4 buffer (PBS) and lysed by sonication in ice. Lysates were clarified by centrifugation and applied to the appropriate affinity resin for purification. GST fusions were purified on Sepharose 4B GST affinity resin (GE Healthcare/Amersham) according to the manufacturer's instructions. His-tag fusions were purified on a metal affinity resin using a native protein purification protocol. Fractions containing the desired recombinant proteins were pooled, dialyzed in 25 mM Tris pH 7.5 or PBS and concentrated.

Peptide Synthesis.

All FlpA and CadF peptides were synthesized using standard N-9-fluorenyl methoxycarbonyl chemistry on an Applied Biosystems 431A Peptide Synthesizer using instruction supplied by the manufacturer (Applied Biosystems, Foster City, Calif.) by the School of Molecular Biosciences Laboratory for Bioanalysis and Biotechnology at Washington State University (Pullman, Wash.).

ELISA with GST Fusion Proteins.

Human plasma fibronectin (Fn), and the 30-kDa and 40-kDa proteolytic fragments from human Fn were purchased from Sigma (St. Louis, Mo.) 96 well polystyrene plates (Corning, N.Y.) were coated with 40 nM of Fn or Fn fragments (Sigma) in 20 mM NaP$_i$, 150 mM NaCl, pH 7.4 (PBS) overnight at 4° C. Plates were washed once with PBS, 0.01% pH 7.4 (PBST) and then blocked with PBS, 1% BSA (fraction V, Sigma). While the plates incubated with block solution, serial dilutions of the FlpA-GST, FlpA-D1-GST, FlpA-D2-GST, and FlpA-D3-GST were made in PBS to produce concentrations that ranged from 1000 nM to 7.815 nM. After washing the wells with PBST, the GST fusion protein samples were added in triplicate and incubated for 2 h with shaking. Wells were washed three times with PBST and GST antibody (1:1000 in PBS, Sigma) was added for 2 h. Wells were washed and a horseradish peroxidase antibody specific to rabbit IgG (.alpha.-R-HRP, Sigma) was added at a 1:5000 dilution in PBS for 1.5 h. The wells were rinsed and developed using the TMB substrate kit (Thermo Scientific, IL) according to the manufacturer's instructions. Binding was quantitated spectrophotometrically by measuring the absorbance at 450 nm (A450 nm). All samples were assayed in triplicate and the experiments were conducted at room temperature unless otherwise indicated. Each ELISA experiment was performed in triplicate on separate days with fresh reagents to ensure reproducibility. Absorbance measurements recorded from wells coated with Fn but not the GST fusion proteins were subtracted the sample absorbances to control for nonspecific binding by the primary and secondary antibodies. Statistical significance was determined using Student's t-test.

Fn-Binding ELISA.

To investigate the binding of Fn to FlpA, 96 well plates were coated with 250 nM solutions of FlpA-GST, FlpA-D1-GST, FlpA-D2-GST, and FlpA-D3-GST in PBS overnight at 4° C. For coating plates with the FlpA or CadF synthetic peptides a concentration of 2.5 µM was used. Plates were washed with PBST, 0.1% BSA (PBST-BSA) and blocked with PBS 1% BSA for 1 h. Serial dilutions of Fn were made in PBS containing 0.02% BSA such that the concentrations ranged from 20 µg/ml to 9.8 ng/ml. Plates were washed with PBS-BSA and the Fn solutions were added and incubated for 2 h with shaking. Plates were washed extensively and Fn antibody (Sigma) was added at a 1:1000 dilution in PBS 0.02% BSA for 1 h. After another wash step, α-R-HRP was added and the ELISA was developed as previously.

Results:

FlpA Domain 2 Contains the Fn-Binding Domain.

Figure 17A:
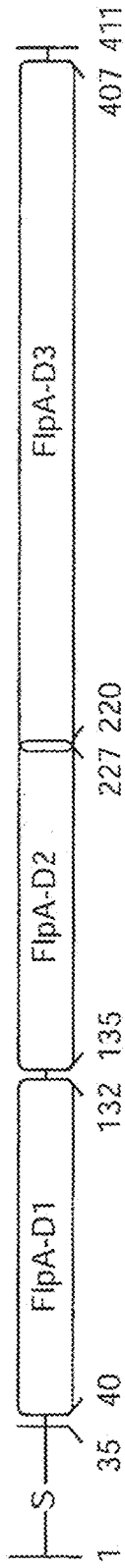
FIG. 17A-C. Primary structure of the FlpA protein, FlpA domains, and synthetic peptides: A, full-length FlpA 'S' marks the signal peptide, B, GST fusion proteins of the three FlpA FN3-like repeats, C, amino acid sequence of the FlpA domain 2 (FlpA-D2) and the seven synthetic peptides P1-P7. Amino acid sequence predicted β-strand secondary structure are indicated with by <-> and gray boxes.
Figure 17B:
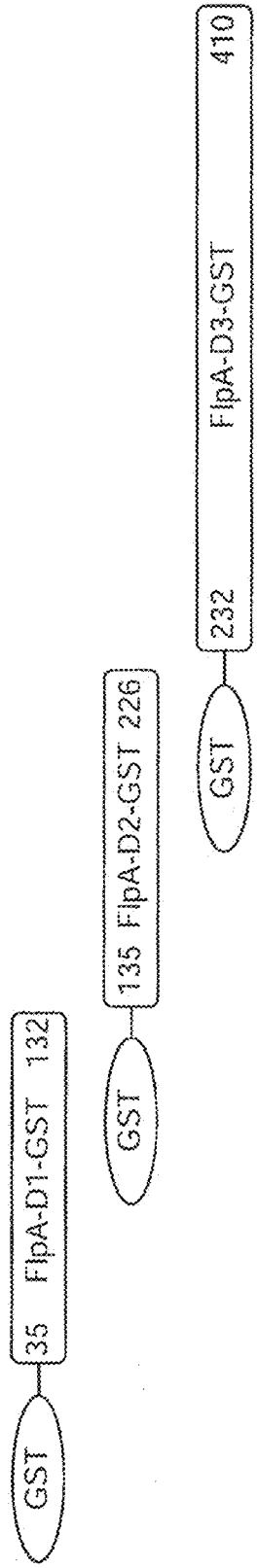
Figure 17C:
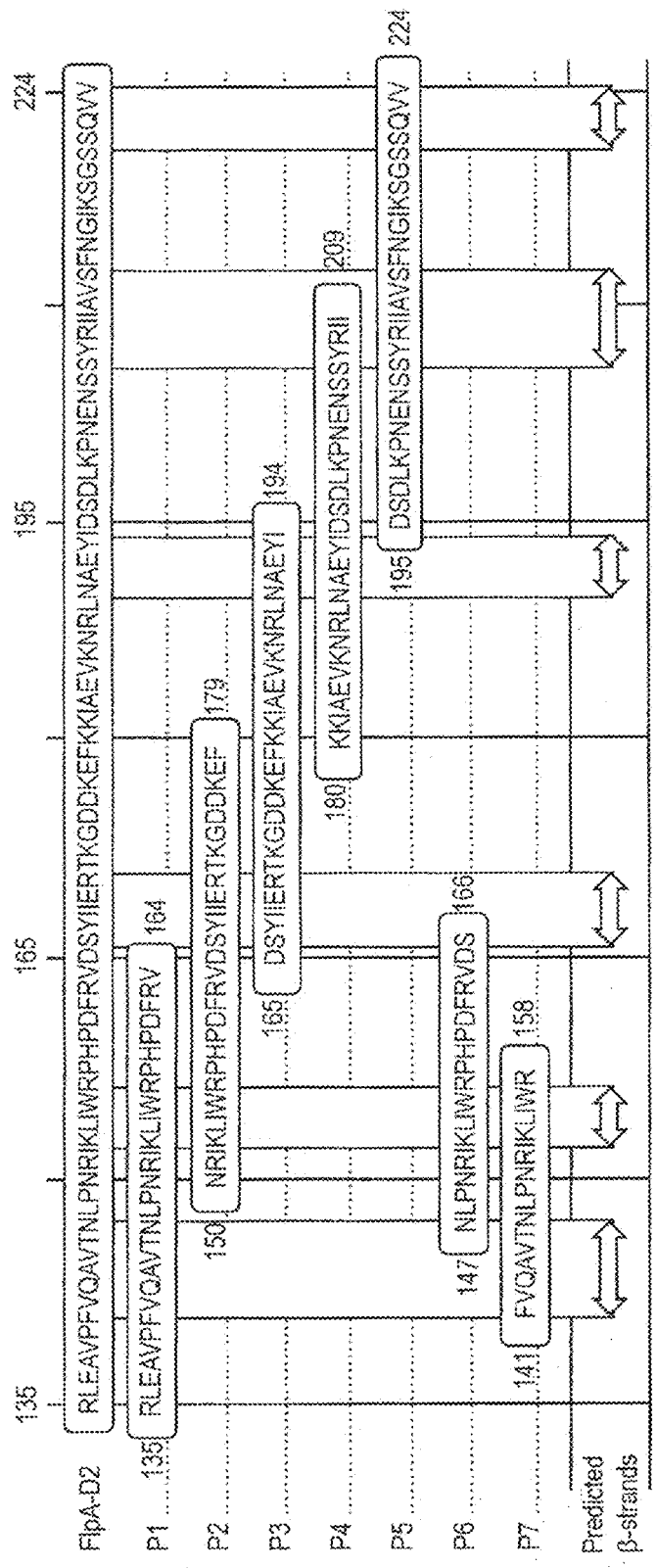
Figure 18A:
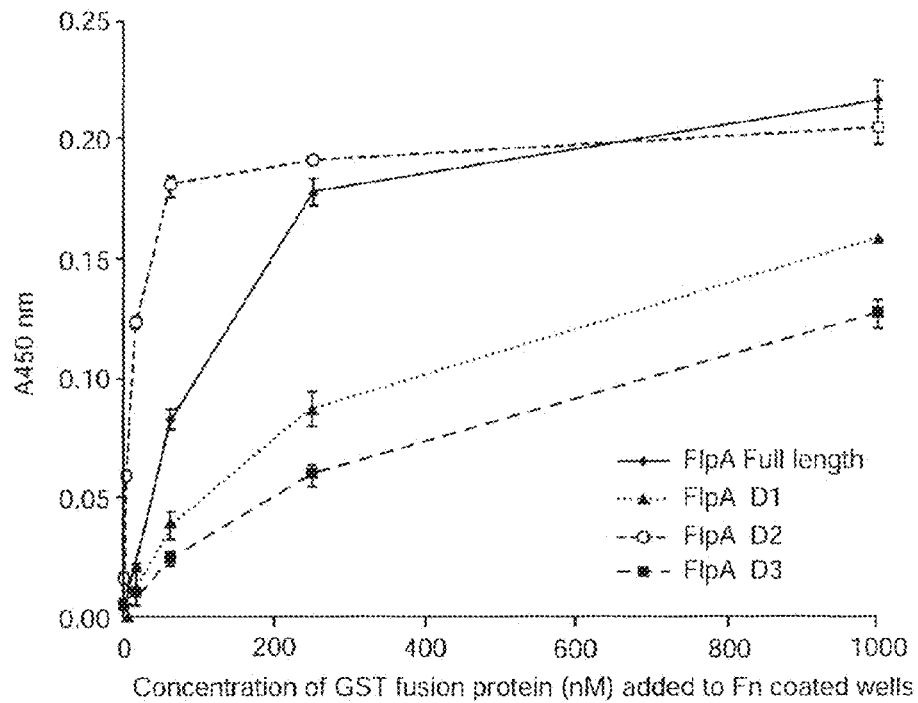
FIGS. 18A and B. A, Adherence of FlpA and the three FlpA FN3-like domains (D1, D2, and D3) to Fn-coated wells. ELISAs were performed with wells coated overnight with 1 ug of Fn. Serial dilutions of the GST fusion proteins (FlpA full-length, FlpA-D1, FLpA-D2, and FlpA-D3) were added to each well. The amount of FlpA protein bound was detected with a primary antibody against GST and a secondary HRP conjugate. All samples were performed in triplicate as described in the Material and Methods. B, Adherence of Fn to wells coated with FlpA and the three FlpA FN3-like domains. For ELISA experiments wells were coated overnight with FlpA full-length, FlpA-D1, FLpA-D2, and FlpA-D3. Serial dilutions of Fn were added to each well. The amount of FlpA protein bound was detected with a primary antibody against Fn and a secondary HRP conjugate.

FlpA binds to human fibronectin (Fn) and mediates adherence of *C. jejuni* to Fn coated surfaces and epithelial cells (Konkel et al. 2010). Bioinformatic analyses of the FlpA amino acid sequences indicates that FlpA contains three domains that resemble Fn type 3 (FN3) repeats: FlpA-D1, FlpA-D2, and FlpA-D3 (Konkel et al. 2010). To determine which of the three FlpA FN3-like domain harbors the Fn-binding domain we cloned each FlpA domain into the pGEX expression vector and produced three GST fusion proteins: FlpA-D1-GST (aa35-132), FlpA-D2-GST (aa135-226), and FlpA-D3-GST (aa232-410) (see FIG. 17). The GST tag served two purposes: 1) purification of the GST fusion proteins, and 2) detection of the four GST fusion proteins with a single antibody. Serial dilutions of FlpA-D1-GST, FlpA-D2-GST, and FlpA-D3-GST fusion proteins were incubated in wells coated with Fn (FIG. 18A). The relative amounts of GST fusion proteins bound were determined by measuring the absorbance of each sample as described in the materials and methods. Full-length FlpA-GST (aa35-410) protein was used as a positive control. Of the three FlpA domain fusion proteins, only FlpA-D2-GST (aa135-226) bound to the Fn-coated wells in similar amounts to the full-length FlpA-GST protein (aa35-410). Binding of the FlpA-D2-GST and FlpA-GST proteins was dose-dependent and saturable. The amount of FlpA-D1-GST and FlpA-D3-GST bound to Fn-coated wells was significantly less than the FlpA-GST and FlpA-D2-GST proteins. These data indicated FlpA-D2 contains the FlpA Fn-binding domain.

Figure 18B:
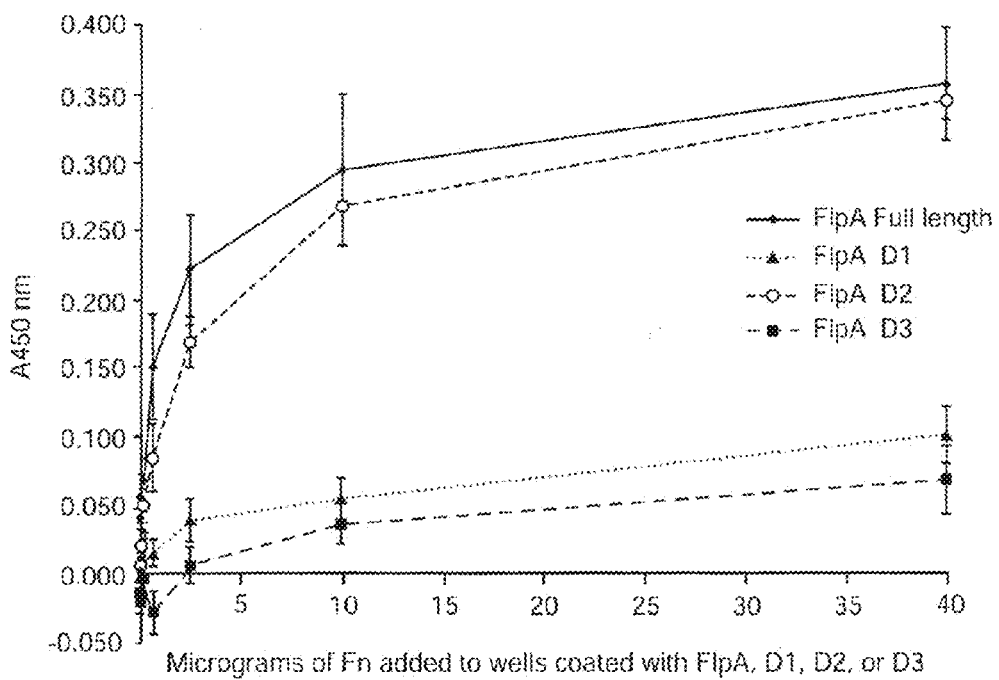

To confirm that FlpA-D2 contained the Fn-binding domain, a second ELISA was performed in which wells were coated with FlpA-GST, FlpA-D1-GST, FlpA-D2-GST, and FlpA-D3-GST. Serial dilutions of Fn were added, and the amount of Fn bound was recorded (FIG. 18B). Fn bound to wells coated with FlpA-GST and FlpA-D2-GST significantly greater than bound to wells coated with FlpA-D1-GST and FlpA-D3-GST. Again, the interaction between Fn and FlpA-D2-GST was dose-dependent and saturable demonstrating specificity. Binding of Fn to wells with FlpA-D1-GST and FlpA-D3-GST was minimal. Collectively, these data demonstrate that the FlpA Fn-binding domain resides within FlpA-D2 (aa135-226).

FlpA Amino Acids N150-F179 have Maximal Fn-Binding Activity.

Figure 19:
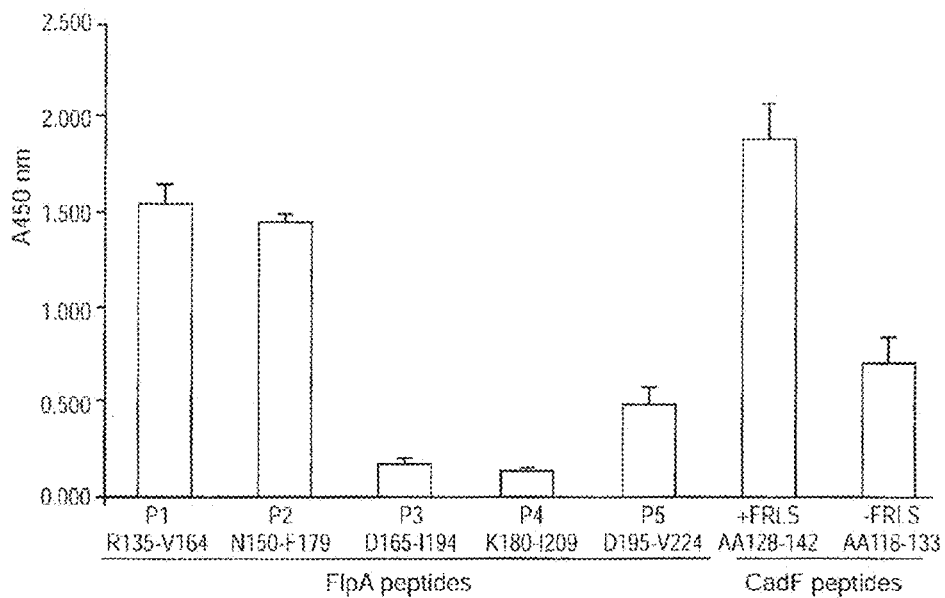
FIG. 19. Adherence of Fn for well coated with FlpA peptides P1-P5. To determine which peptides bound Fn ELISA plates were coated overnight with the five FlpA peptides. Fn was incubated in the wells, and detected as previously.

In addition to FlpA, C. jejuni has another Fn-binding protein termed CadF. In a previous study, the CadF Fn-binding domain was localized to four amino acids FRLS (CadF aa134-137) using a series of synthetic peptides (Konkel et al., 2005). Identification of the amino acids required for FlpA binding to Fn was conducted with a similar approach. Five 30mer peptides, with 15 amino acid overlaps spanning the FlpA-D2 sequence were synthesized: P1 R135-V164, P2 N150-F179, P3 D165-I194, P4 K180-I209, and P5 D195-V224 (FIG. 17). Similar with the previous ELISA, microtiter plates were coated with each of the five FlpA-D2 peptides and serial dilutions of Fn were added to the wells. The amount of Fn bound by each peptide was determined spectrophotometrically (FIG. 19). Two defined CadF peptides, one with the FRLS domain (FRLS$^+$, aa125-140) and one without the FRLS domain (FRLS$^-$, aa118-133), were used as positive and negative controls respectively. Fn bound to the P1 and P2 peptides in significantly greater amounts than the other three FlpA-D2 peptides and the CadF FRLS$^-$ peptide. As with the full-length FlpA and FlpA-D2 proteins, Fn adherence to wells coated with P1 (R135-V164) and P2 (N150-F179) was dose-dependent and saturable. These data revealed that the amino terminus of FlpA-D2 (R135-F179) harbored the FlpA Fn-binding domain.

Replicate ELISA experiments with the FlpA peptides revealed that P1 (R135-V164) and P2 (N150-F179) consistently had comparable affinity for Fn. This observation suggested two possibilities for the spatial distribution of binding site (amino acids) within FlpA-D2 involved in Fn-binding: 1) the FlpA-D2 Fn-binding site is located in the overlapping region of P1 and P2, corresponding to N150-V164, or 2) P1 and P2 each have unique residues responsible for Fn binding, indicating that the amino acid sequence of the Fn-binding domain is extended beyond the overlapping region and possibly non-contiguous. To evaluate the first of these possibilities additional FlpA-D2 peptides were synthesized and ELISAs were performed.

Amino Acids P159-V164 are Required for Maximal Fn-Binding.

Figure 20:
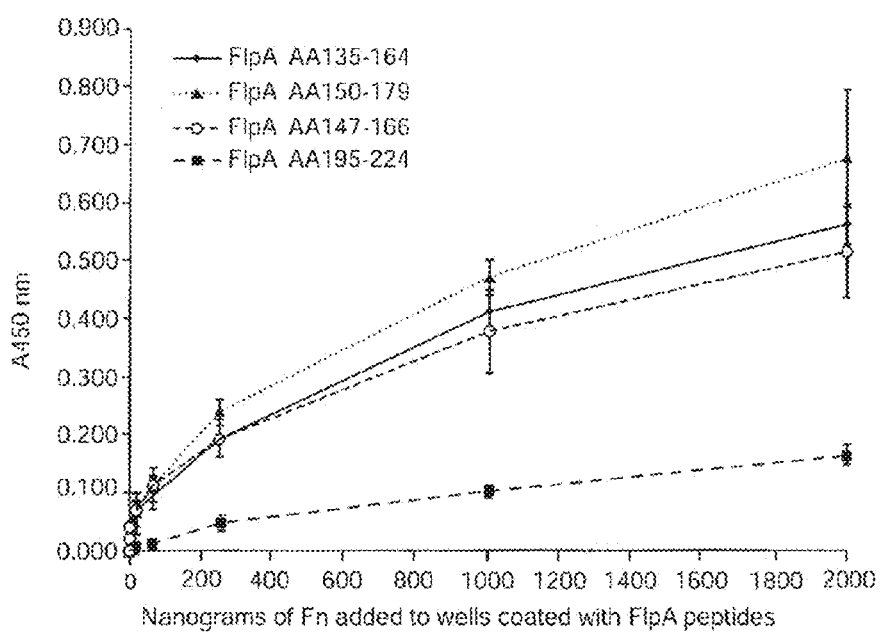
FIG. 20. FlpA P7 (N147-S166) contains the FlpA Fn-binding domain. ELISAs were performed as previously. Microtiter plates were coated with the FlpA peptides and the amount of Fn bound was determined spectrophotometrically.
Figure 22A:
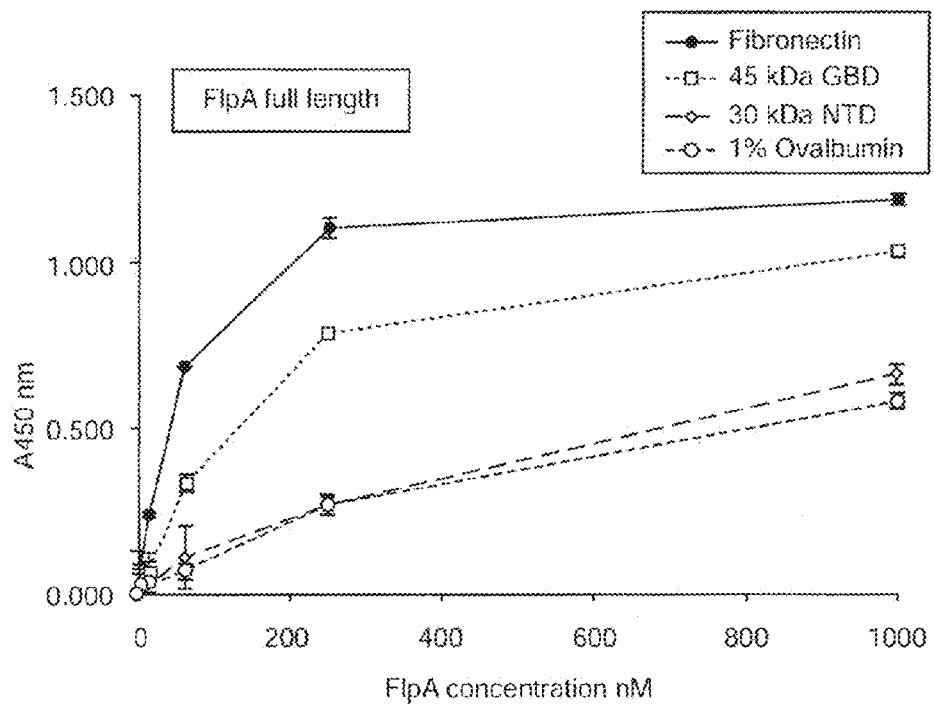
FIG. 22A-D. FlpA binds a site within the gelatin-binding domain (GBD) of Fn. ELISAs were performed to determine if FlpA bound the NTD or GBD of Fn. Microtiter plates were coated with Fn, GBD, NTD, or ovalbumin (negative control) overnight. Serial dilutions of A, FlpA full-length, B, FlpA-D1, C, FLpA-D2, and D, FlpA-D3 were added the wells and the amount of FlpA proteins bound was determined as previously.
Figure 22B:
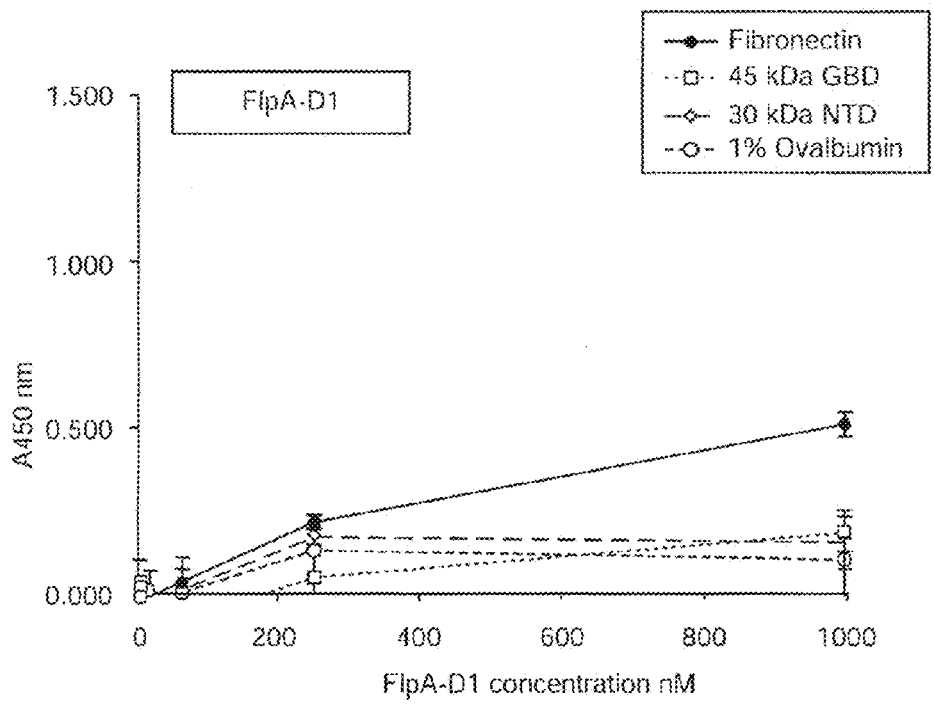
Figure 22C:
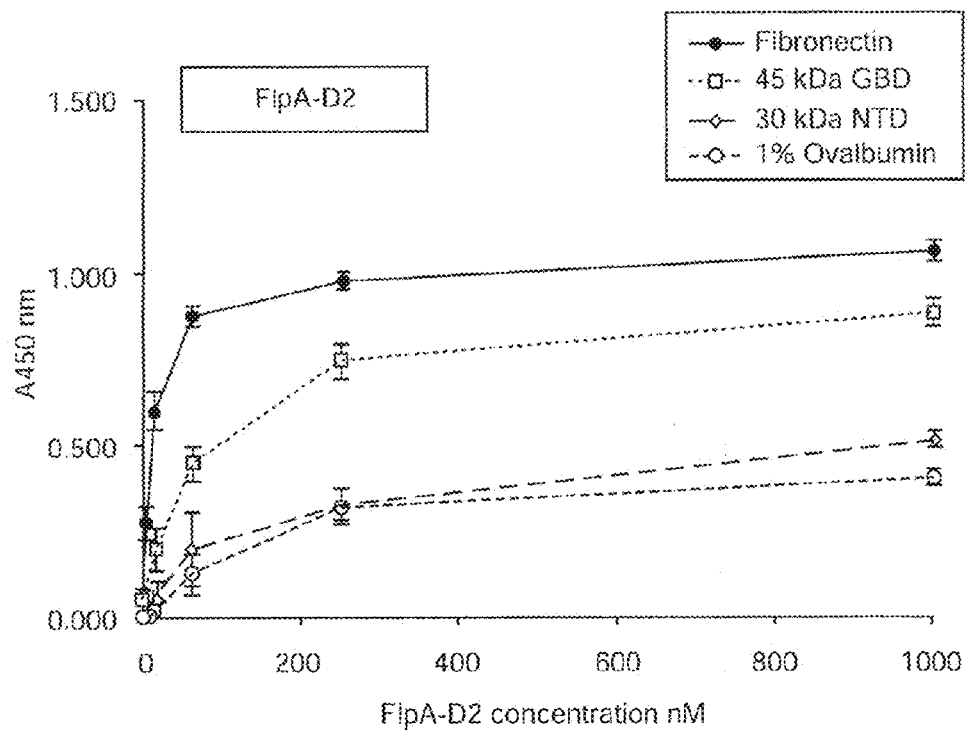
Figure 22D:
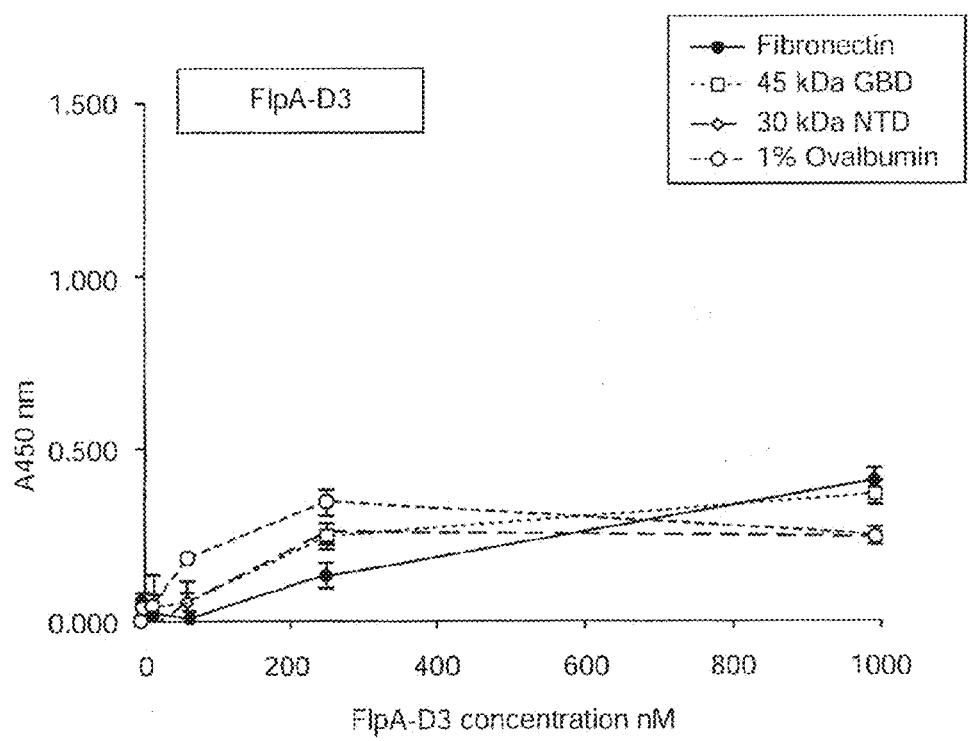

Fn FN3 repeats are composed of seven β-strands arranged in two anti-parallel β-sheets connected by flexible loops (Dickinson et al., 1994). The secondary structure FlpA-D2 is predicted to contain regions of β-strands that alternate with non-β-strand regions (FIG. 17). The over-lapping region of P1 and P2 (N150-V164) corresponds to a portion of FlpA-D2 predicted contain a non-β-strand region at the N-terminus beginning at N147, which is adjacent in the C-terminal direction to a β-strand, and followed by a second non-β-strand region ending at S166 (FIG. 17). Based on the secondary structure prediction, we synthesized a sixth peptide (P6) composed of N147-S166. Fn binding by wells coated with P6 was compared to wells coated with the P1 and P2 peptides, and wells coated with P5 as a negative control (FIG. 20). Fn bound to P6 in comparable amounts as P1 and P2, which demonstrated that P6 (N147-S166) harbored residues critical for maximal Fn-binding.

Data from the initial ELISA using P1 to P5 (FIG. 19) demonstrated that Fn does not bind P3 (D165-I194), which indicates amino acids required for FlpA Fn-binding do not extend much beyond the C-terminus of P6 (V164). To determine the N-terminal boundary of the Fn-binding domain a seventh peptide was synthesized. Again, secondary structure predictions were used to select the sequence of the seventh peptide. Schwarz-Linek et. al. 2003 (Schwarz-Linek et al., 2003) demonstrated that tandem β-strands within SfbI from Streptococcus pyogenes interact with the triple stranded β-sheets of the N-terminal FN1 repeats of Fn using synthetic peptides. Therefore, the seventh peptide, P7 (F141-R157), was designed to span two predicted β-strands and one non-β-strand region (FIG. 17). However, Fn binding to wells coated with P7 minimal, similar to the amount of Fn bound negative control peptides FlpA P5 and CadF FRLS$^-$ (data not shown), and significantly less than Fn binding to P1 and P2. These data indicate the N-terminal boundary of the FlpA Fn-binding domain does not extend significantly beyond P158, and that FlpA amino acids P158-V164 comprise the core of the FlpA Fn-binding domain. High-resolution structural studies are currently underway to further characterize the precise details of the interaction between FlpA and Fn.

FlpA Binds the Gelatin/Collagen Interaction Domain of Fn.

Amino acid sequences alignments of FlpA-D2 with FN3$^{1-15}$ using ClustalW revealed that FlpA-D2 mostly closely aligned with FN3$^1$ (22.9% sequence identity) (FIG. 21). FN3$^1$ binds the to FN1 and FN2 repeats located toward the N-terminus Fn (Mao and Schwarzbauer, 2005). Digestion of Fn with thermolysin produces defined fragments of Fn that retain their physiological activity (FIG. 16) (Pankov and Yamada, 2002). One of the Fn thermolysin fragments produced, termed the N-terminal domain (NTD), is ~30 kDa in size and composed of FN1$^{1-5}$. Another fragment of 40 kDa contains the gelatin/collagen interaction domain (GBD) composed of FN1$^{6-9}$ and FN2$^{1,2}$ (FIG. 16). To determine if FlpA bound the Fn NTD ELISA plates were coated with full-length Fn, the 30 kDa NTD fragment, and the 40 kDa GBD Fn fragment. Interestingly, both full-length FlpA and FlpA-D2 bound the 40 kDa GBD fragment in amounts similar to full-length Fn, whereas binding wells coated with 30 kDa NTD and ovalbumin was minimal (FIG. 22). As with previous assays, the FlpA-D1-GST and the FlpA-D3-GST did not bind Fn or the Fn GBD. These data demonstrate that FlpA-D2 binds a site on Fn within the GBD.

Discussion

Identification of the FlpA Fn-Binding Site.

This study was conducted to further characterize the interaction between FlpA and Fn. FlpA is composed of three domains (D1, D2, and D3) that resemble FN3 repeats from Fn (FIGS. 19 and 20) (Konkel et al., 2010). To determine which domain(s) bound to Fn we expressed each FlpA domain separately as a recombinant protein fused to a GST tag. A series of ELISAs were conducted to determine which of the three FlpA domains bound to Fn. FlpA-D2 was the only FlpA domain to demonstrate significant Fn binding, whereas binding of FlpA-D1 and FlpA-D3 was minimal. Furthermore, the amounts of Fn bound by FlpA-D2 and FlpA full-length were similar—suggesting the major Fn-binding site of resides within FlpA-D2.

Previous studies with CadF employed a panel of synthetic peptides in ELISA experiments to localize the CadF Fn-binding domain to $^{134}$FRLS$^{137}$ (Konkel et al., 2005). We used a similar method to determine the residues within FlpA-D2 bound Fn. Five 30mer peptides, with 15 amino acid overlaps, spanning the FlpA-D2 amino acid sequence were synthesized and assess for Fn binding activity (FIG. 17). FlpA peptides P1 (R135-164) and P2 (N150-F179) bound Fn in amounts comparable to the positive control peptide (CadF FRLS$^+$). The amounts of Fn bound FlpA P1 and P2 were indistinguishable, thus we tested if the Fn-binding domain consisted of amino acids shared between P1 and P2, corresponding to N150-V164. FlpA secondary structure is predicted to contain β-strands that alternate with non-β-strand regions. These characteristics of the FlpA secondary structure are consistent with the structure of the FN3 repeats in Fn, which are comprised of seven β-strands arranged into two anti-parallel β-sheets (Dickinson et al., 1994, Mao and Schwarzbauer, 2005). The sequence shared by P1 and P2 (N150-V164) is predicted to contain a single β-strand region sandwiched between two less ordered (non-β-strand) regions. Previous work with other Fn-binding MSCRAMMs found disordered regions mediate adherence to Fn (Schwarz-Linek et al., 2004). Therefore, P6 was designed to span FlpA N147-S166, which covered the β-strand sandwiched and two less ordered sequences. Fn bound to FlpA P6 in amounts comparable to P1 and P2. In addition, we found that Fn binding was minimal to peptides composed of residues in directions N-terminal to P158 and C-terminal to V 164. This observation indicated that the core of the FlpA Fn-binding domain was composed of $^{158}$PHPDFRV$^{164}$.

FlpA Binds the GBD of Fn.

Fn is a mosaic protein composed of FN1, FN2, and FN3 repeats. The N-terminal region of Fn is composed of FN1 and FN2 repeats, whereas the C-terminus is composed predominantly of FN3 repeats and a few FN1 repeats (FIG. 16) (Pankov and Yamada, 2002). Plasma FN is soluble and maintains a globular structure that is stabilized by interactions between N-terminal FN1 repeats and C-terminal FN3 repeats. For example, FN3$^1$ binds an N-terminal domain of Fn composed of FN1$^{1-6}$. The interactions between FN1 and FN3 repeats are also thought to prevent recognition of epitopes on FN3 domain by cell surface receptors (Mao and Schwarzbauer, 2005, Pankov and Yamada, 2002). For instance, in plasma Fn access to the RGD sequence is limited. This prevents $α_5β_1$-integrin dependent signaling involved in Fn assembly into the ECM and cytoskeletal rearrangements (Mao and Schwarzbauer, 2005, Pierschbacher and Ruoslahti, 1984).

Since FlpA contains putative FN3 domains, we tested to see if FlpA bound the N-terminus of Fn. Digestion of Fn with thermolysin produces well-characterized Fn fragments that maintain their biological activity. Two fragments that comprise the N-terminus of Fn are produced: a ~30 kDa fragment termed the N-terminal domain (NTD) that is composed of FN1$^{1-5}$; and a ~40 kDa fragment termed gelatin-binding domain (GBD) that is composed of FN1$^{6-9}$ and FN2$^{1,2}$ (FIG. 16) (Pankov and Yamada, 2002). In ELISAs FlpA bound to the GBD at levels comparable to full-length Fn, whereas FlpA binding to the NTD was minimal. ITC experiments were conducted to determine the affinity of the FlpA-Fn interaction.

The Impact of FlpA on *C. jejuni* Pathogenesis.

Previous work in our lab established that FlpA is required for *C. jejuni* adherence to host tissues (Flanagan et al., 2009, Konkel et al., 2010). Host cell adherence is a prerequisite for *C. jejuni* invasion, and invasion is associated with the development of acute disease (Babakhani et al., 1993, Konkel et al., 2001). CadF-mediated adherence of *C. jejuni* to Fn in required for maximal invasion efficiency. The reduction in invasiveness by *C. jejuni* cadF mutant is beyond what can be explained by reduced adherence alone (Monteville et al., 2003). This result may be explained by the observation that *C. jejuni* invasion of epithelial cells coincides with the phosphorylation of paxillin and the activation of the Rac1 and Cdc42 (Krause-Gruszczynska et al., 2007, Monteville et al., 2003). Paxillin, Rac1 and Cdc42 are proteins associated with host cell focal complexes (FCs). FCs are composed of integrin receptors, adaptor proteins, and signaling proteins. In response to Fn-integrin engagement, FCs assemble on the cytoplasmic tails of the integrin receptors (Gilcrease, 2007, Small and Kaverina, 2003). Paxillin is one of the first proteins recruited during FC assembly, where it is phosphorylated by FC-associated kinases FAK and Src. FC-mediated signaling can also activate the Rho GTPases, Rac1 and Cdc42, through several downstream effectors. Activated Rac1 and Cdc42 control the formation of actin-based membrane protrusion termed lamellipodia and filopodia, respectively (Broussard et al., 2008, Ridley, 2006, Small and Kaverina, 2003). The transient phosphorylation of paxillin and the activation of the Rac1 and Cdc42 observed during *C. jejuni* infection is dependent CadF adherence to Fn. In addition, *C. jejuni* localized to actin protrusions prior to internalization (Krause-Gruszczynska et al., 2007, Monteville et al., 2003). These observations support a model of *C. jejuni* invasion in which bacterial adherence to Fri stimulates host cell signaling for cytoskeletal rearrangements required for bacterial internalization.

FlpA binding the Fn-GBD has several potential impacts on the FC-dependent model of *C. jejuni* internalization. FlpA adherence to the Fn-GBD may disrupt intramolecular interactions between the N-terminus and the C-terminus of Fn to expose Fn domains involved in Fn fibril assembly, activation of cell surface receptors, or CadF adherence. Assembly of plasma Fn into the ECM has been studied extensively using FN null (−/−) mouse embryonic fibroblasts. Assembly of plasma Fn into the ECM was found to be a cell-dependent process that is initiated at specialized cell-surface sites characterized by active integrin receptors. The display of cell-surface assembly sites is stimulated by cell adherence to C-terminal FN3 repeats (i.e., FN3$^{10}$ RGD). Activated integrin receptors associated with the cell-surface assembly sites recognize and bind the N-terminal FN1 and FN2 repeats of Fn, which results in conformational changes in the structure of plasma Fn and incorporation into the ECM (Mao and Schwarzbauer, 2005, Xu et al., 2009). FCs form at the sites of fibril assembly composed of $\alpha_5\beta_1$-integrin receptor, FAK, vinculin, and paxillin, and attach the newly formed fibrils to the actin cytoskeleton (Mao and Schwarzbauer, 2005). Therefore, if FlpA adherence to Fn promotes Fn fibril assembly, host cell FC components would be brought proximal to sites of *C. jejuni* adherence and participate in bacterial internalization. Alternatively, FlpA may induce conformational changes in Fn to promote CadF adherence to Fn and promote stimulation of FCs-dependent invasion processes. Experiments are currently being conducted to determine if FlpA changes the affinity of CadF for Fn in solution.

FlpA is Unique Among Fn-Binding MSCRAMMs.

The most well-characterized Fn-binding MSCRAMMs belong to a group of proteins produced by *Streptococcus pyogenes* (SfbI), *Staphylococcus aureus* (FnBPA), and *Borrelia Burgdorferi* (BBK32) collectively referred to as FnBPs (for Fn-binding proteins) (Schwarz-Linek et al., 2004). Analyses of the FnBPs have identified conserved Fn-binding domains. FnBPs harbor C-terminal tandem repeats that bind the NTD of Fn by a tandem β-zipper mechanism. In this mechanism structurally disordered Fn-binding repeats of FnBPs form short anti-parallel β-strands, which interact with the triple stranded β-sheets of sequential FN1 modules, resulting in high affinity binding to the NTD of Fn (Schwarz-Linek et al., 2003). Talay et al. (2000) assessed the role of the tandem repeats and a spacer in SfbI (Talay et al., 2000). The C-terminal repeats of Sfb1 were sufficient to confer bacterial adherence, whereas the invasion was dependent on adherence of the spacer domain that bound the GBD of Fn. Interestingly, adherence of the Sfb1 repeats to the Fn NTD was a required for binding of the SfbI spacer domain to Fn (Ozeri et al., 1996, Talay et al., 2000).

FlpA is a putative lipoprotein composed of three FN3-like domains. The primary sites of interaction between FlpA and Fn reside within FlpA-D2 and the GBD of Fn. The $^{158}$PHPDFRV$^{164}$ sequence resides within a region of FlpA-D2 that is predicted to be less ordered and adjacent to β-strands. This putatively disordered structure of the FlpA FN-binding domain is consistent with the disordered structure of the Fn-binding repeats from Sfb1, which may suggest that like Sfb1 the Fn-binding domain of FlpA undergoes a disordered to ordered conversion upon binding to Fn (Schwarz-Linek et al., 2004). However, FlpA-D2 does not appear to harbor the C-terminal repeat domains characteristic of FnBPs. The tandem repeats of FnBPs that bind the Fn NTD, and upstream spacer domains of FnBBPs that bind the Fn GBD, are organized over a span of ~60 amino acids (Schwarz-Linek et al., 2004). The FlpA Fn-binding domain identified in this study consists of a relatively short peptide ($^{158}$PHPDFRV$^{164}$) that does not share sequence identity with any of the FnBP Fn-binding domains. It is difficult to define the exact residues involved in FlpA adherence without detailed structural information, but the results of this study indicate that we have identified critical residues that comprise the core of FlpA Fn-binding site.

In summary, FlpA is a novel MSCRAMM composed of three FN3 repeats that binds a site within the GBD of Fn. Studies are currently underway to: 1) characterize the structure of FlpA, 2) determine the affinities of interactions between FlpA, CadF and Fn, and 3) assess the impact of FlpA-Fn interactions on CadF adherence to Fn.

References for Example 4

Babakhani F K, Bradley G A and Joens L A. Newborn piglet model for campylobacteriosis. Infect Immun. 1993; 61(8): 3466-75. PMCID: PMC281024.

Broussard J A, Webb D J and Kaverina I. Asymmetric focal adhesion disassembly in motile cells. Curr Opin Cell Biol. 2008; 20(1):85-90.

Dickinson C D, Gay D A, Parello J, Ruoslahti E and Ely K R. Crystals of the cell-binding module of fibronectin obtained from a series of recombinant fragments differing in length. J Mol Biol. 1994; 238(1):123-7.

Flanagan R C, Neal-McKinney J M, Dhillon A S, Miller W G and Konkel M E. Examination of *Campylobacter jejuni* putative adhesins leads to the identification of a new protein, designated FlpA, required for chicken colonization. Infect Immun. 2009; 77(6):2399-407.

Gilcrease M Z. Integrin signaling in epithelial cells. Cancer Lett. 2007; 247(1):1-25.

Konkel M E, Larson C L and Flanagan R C. *Campylobacter jejuni* FlpA binds fibronectin and is required for maximal host cell adherence. J Bacteriol. 2010, 192(1):68-76. PMCID: PMC2798237.

Konkel M E, Monteville M R, Rivera-Amill V and Joens L A. The pathogenesis of *Campylobacter jejuni*-mediated enteritis. Curr Issues Intest Microbiol. 2001; 2(2):55-71.

Konkel M E, Christensen J E, Keech A M, Monteville M R, Klena J D and Garvis S G. Identification of a fibronectin-binding domain within the *Campylobacter jejuni* CadF protein. Mol Microbiol. 2005; 57(4):1022-35.

Krause-Gruszczynska M, Rohde M, Hartig R et al. Role of the small Rho GTPases Rac1 and Cdc42 in host cell invasion of *Campylobacter jejuni*. Cell Microbiol. 2007; 9(10): 2431-44.

Mao Y and Schwarzbauer J E. Fibronectin fibrillogenesis, a cell-mediated matrix assembly process. Matrix Biol. 2005; 24(6):389-99.

Monteville M R, Yoon J E and Konkel M E. Maximal adherence and invasion of INT 407 cells by *Campylobacter jejuni* requires the CadF outer-membrane protein and microfilament reorganization. Microbiology. 2003; 149(Pt 1):153-65.

Ozeri V, Tovi A, Burstein I, Natanson-Yaron S, Caparon M G, Yamada K M, Akiyama S K, Vlodaysky I and Hanski E. A two-domain mechanism for group A streptococcal adherence through protein F to the extracellular matrix. EMBO J. 1996; 15(5):989-98. PMCID: PMC449993.

Pankov R and Yamada K M. Fibronectin at a glance. J Cell Sci. 2002; 115(Pt 20):3861-3.

Pierschbacher M D and Ruoslahti E. Variants of the cell recognition site of fibronectin that retain attachment-promoting activity. Proc Natl Acad Sci USA. 1984; 81(19): 5985-8. PMCID: PMC391843.

Ridley A J. Rho GTPases and actin dynamics in membrane protrusions and vesicle trafficking. Trends Cell Biol. 2006; 16(10):522-9.

Schwarz-Linek U, Werner J M, Pickford A R et al. Pathogenic bacteria attach to human fibronectin through a tandem beta-zipper. Nature. 2003; 423(6936):177-81.

Schwarz-Linek U, Hook M and Potts J R. The molecular basis of fibronectin-mediated bacterial adherence to host cells. Mol Microbiol. 2004; 52(3):631-41.

Small J V and Kaverina I. Microtubules meet substrate adhesions to arrange cell polarity. Curr Opin Cell Biol. 2003; 15(1):40-7.

Talay S R, Zock A, Rohde M, Molinari G, Oggioni M, Pozzi G, Guzman C A and Chhatwal G S. Co-operative binding of human fibronectin to Sfb1 protein triggers streptococcal invasion into respiratory epithelial cells. Cell Microbiol. 2000; 2(6):521-35.

Xu J, Bae E, Zhang Q, Annis D S, Erickson H P and Mosher D F. Display of cell surface sites for fibronectin assembly is modulated by cell adherence to (1)F3 and C-terminal modules of fibronectin. PLoS One. 2009; 4(1):e4113. PMCID: PMC2606026.

EXAMPLE 5

Effect of *Lactobacillus* on Colonization of *C. jejuni* in Commercial Broiler Chickens In this Example, the effect of four *Lactobacillus* strains (*L. acidophilus* NCFM, *Lactobacillus crispatus* JCM 5810, *Lactobacillus gallinarum* ATCC 33199 and *Lactobacillus helveticus* CNRZ32) on colonization of *C. jejuni* in commercial broiler chickens was evaluated. Potential mechanisms responsible for competitive exclusion, including production of antagonistic metabolites, modulation of antibody responses and manipulation of the cecal microbiotawere also evaluated.

Materials and Methods

Bacterial strains and growth conditions. The bacterial strains used in this study are listed in Table 6. *C. jejuni* strains were cultured under microaerobic (85% nitrogen, 10% $CO_2$, 5% oxygen) conditions in Mueller-Hinton (MH) (Difco Inc., Detroit, Mich.) broth or on MH agar plates supplemented with 5% citrated bovine blood (MHB agar plates) at 37° C. Cultures were subcultured to a fresh plate every 24 to 48 h. Motility of *C. jejuni* culture was determined prior to inoculation in chickens. *Lactobacillus* strains were propagated statically at 37° C. in deMan, Rogosa and Sharpe (MRS) broth (Difco) or on MRS agar plates under microaerobic conditions.

TABLE 6

Bacterial Strains Used in This Study

| Strain | Relevant Characteristics | Source or Reference |
|---|---|---|
| *C. jejuni* | | |
| F38011 | Human clinical isolate | |
| 81-176 | Human clinical isolate | |
| 81116 | Human clinical isolate | |
| RM1221 | Poultry isolate | |
| S2B | Poultry isolate | |
| Turkey | Poultry isolate | |
| *Caulobacter crescentus* JS4022 | Laboratory strain | |
| *E. coli* TOP10F− | Cloning host | Invitrogen |
| *L. acidophilus* NCFM | Human isolate | |
| *L. crispatus* JCM 5810 | Chicken isolate | JCM[1] |
| *L. gallinarum* ATCC 33199 | Chicken isolate, Neotype Strain | ATCC[2] |
| *L. helveticus* CNRZ32 | Dairy starter strain | CNRZ[3] |
| *L. acidophilus* NCFM-Str | $St^r$ 200 µg/ml | This study |
| *L. crispatus* JCM 5810-Str | $St^r$ 200 µg/ml | This study |
| *L. gallinarum* ATCC 33199-Str | $St^r$ 200 µg/ml | This study |
| *L. helveticus* CNRZ32-Str | $St^r$ 200 µg/ml | This study |

[1]Japan Collection of Microorganisms
[2]American Type Culture Collection
[3]Centre National de Recherche Zootechnique Growth curve analysis. *Lactobacillus* strains were inoculated into from overnight cultures into MRS broth at 1%. Growth was monitored by $O.D._{600}$ using a BioscreenC analyzer (Growth Curves USA, Inc., Piscataway, N.J.). Maximum growth rate ($\mu_m$) was determined by fitting the growth curves to a modified Gompertz model (Zwietering, M. H. et al. (1990) Appl Environ Microbiol 56:1875-1881) using Prism 5.0 (Graphpad Software, Inc., La Jolla, Calif.).

*C. jejuni* Inhibition Assays.

Inhibition of *C. jejuni* cultures by lactobacilli was evaluated using spotted cultures and supernatants. For spotted cultures, overnight cultures of lactobacilli were spotted onto Brain Heart Infusion Agar (Difco) supplemented at 0.1% with TWEEN® 80, (Polysorbate 80, a nonionic surfactant and emulsifier derived from polyethoxylated sorbitan and oleic acid) (Fisher Scientific, Hampton, N.H.) (BHI-T) and incubated overnight under microaerobic conditions. Subsequently, plates were overlaid with molten MH soft agar (0.75% agar) inoculated at 1% with overnight *C. jejuni* cultures standardized to $O.D._{540}$ in MH broth. Plates were incubated for 24 h at 37° C. under microaerobic conditions. Inhibition was evaluated by measuring the zones of inhibition around the *Lactobacillus* cultures and expressed as the ratio of the zone of inhibition to the zone of growth in mm. In order to determine if bacteriocins were contributed to inhibition, plates were treated with proteinase K (20 µg/µl) (Invitrogen, Carlsbad, Calif.) or trypsin (Sigma-Aldrich, St. Louis, Mo.) (10 µg/µl) prior to being overlaid with *C. jejuni*. In order to determine if peroxides contributed to inhibition plates were treated with catalase (10 µg/µl) (Sigma) prior to being overlaid.

Supernatants from *Lactobacillus* cultures were boiled for 6 min, neutralized to pH 7 with 6N NaOH (Fisher), treated with catalase, or left untreated. Supernatants were subsequently filter sterilized (0.22 µM) and spotted onto solidified MH soft agar inoculated at 1% with overnight *C. jejuni* culture and incubated overnight.

Selection of Antibiotic Resistant *Lactobacillus* Strains.

To generate antibiotic-resistant *Lactobacillus* strains for use in further assays, serial transfers of 0.01% were performed in MRS broth containing increasing concentrations of streptomycin (Sigma). Cultures resistant to 200 µg/µl streptomycin were selected for further assays.

Broiler Chickens.

A total of 200 newly hatched chicks were subdivided into ten groups of 20 chicks; the chicks were then placed into isolation chambers (Horsfall-Bauer isolators) on wire mesh. Water and a commercial chick starter feed were provided ad libitum. Fecal matter was collected and autoclaved before disposal. All animal studies were performed using protocols approved by the Institutional Animal Care and Use Committee (IACUC; protocol no. 3248) at Washington State University.

Bacterial Cultures and Chicken Inoculation.

*Lactobacillus* cultures were grown statically in MRS at 37° C. for 18 h. *C. jejuni* F38011 were cultured in MH broth at 37° C. for 18 h prior to inoculation. One group of 20 chickens was kept as the uninoculated control group. The remaining 9 groups of chicks were inoculated as follows: group 2 and 6, *L. acidophilus* NCFM-Str; group 3 and 7, *L. crispatus* JCM5810-Str; group 4 and 8, *L. gallinarum* ATCC 33199-Str; groups 5 & 9, *L. helveticus* CNRZ32-Str; and group 10, *C. crescentus*. Group 10 was administered *C. crescentus*, a non-probiotic bacterium, as a treatment control to demonstrate any observed reduction in *C. jejuni* colonization was due to the probiotic lactobacilli specifically (i.e., positive control for *C. jejuni* colonization, referred to from this point forward as the *C. jejuni* control). Lactobacilli or caulobacter were administered on Days 1 and 4 post-hatching by oral gavage with 0.5 ml bacterial suspension (~$10^8$ CFU). At 14 days post hatching, Groups 5-10 were administered *C. jejuni* F38011 by oral gavage with 0.5 ml bacterial suspension (~$10^8$ CFU). After each inoculation, remaining bacterial suspensions was serially diluted onto appropriate media to confirm the number of CFU in each dose.

Bacterial Enumeration.

Half of the chickens in each group were euthanized and necropsied at day 21 and the remaining chickens on day 28 of the study. A cecum and intestine were dissected from each chicken. The samples were weighed, diluted in an equal volume (w/v) of MH, and thoroughly stomached. Samples were serially diluted in MRS and MH broth for enumeration of *Lactobacillus* and *C. jejuni*, respectively. The MRS dilutions were plated onto Rogosa SL (Difco) agar plates supplemented at 200 µg/ml with streptomycin for enumeration of lactobacilli while MH dilutions were plated on Campy Cefex (Difco) agar plates for enumeration. Plates were incubated microaerobically at 37° C. and CFU counted after 96 h of incubation. To confirm the identity of recovered *Lactobacillus*, PCR was performed on cultures of colonies isolated from plates used for enumeration of lactobacilli using surface layer protein specific primers (Table 7).

Construction of 16S rDNA Clone Libraries.

Total DNA was isolated from cecal contents using a fecal DNA kit. 16S rRNA genes were amplified with PCR Super Mix High Fidelity (Invitrogen) as previously described using three sets of primers: 8F and 1492R (Set A), 8F and 1522R (Set B), and 8F and 926R (Set C) (Table 5) (Lu, J. et al. (2003), Appl Environ Microbiol 69:6816-24). PCR products were pooled and purified using the QiaQuick PCR clean-up kit (Qiagen, Valencia, Calif.). Purified products were ligated to pCR2.1 (Invitrogen) and transformed into chemically competent *Eschcrichia coli* TOP10F'. Clones were screened for a-complementation of β-galactosidase by using X-Gal (5-bromo-4-chloro-3-indolyl-β-D-galactopyranoside) and IPTG (isopropyl-β-D-thiogalactopyranoside) (Ausubel, F. M. et al. (2007), Current Protocols in Molecular Biology. John Wiley and Sons, Inc., New York, N.Y.).

TABLE 7

Primers Used in This Study

| Primer | Sequence (5'-3') | Target |
|---|---|---|
| 8F | AGAGTTTGATCCTGGCTCAG (SEQ ID NO: 141) | 16S rRNA Gene |
| 926R | ACCGCTTGTGCGGGCCC (SEQ ID NO: 142) | 16S rRNA Gene |
| 1492R | TACGGYTACCTTGTTACGACTT (SEQ ID NO: 143) | 16S rRNA Gene |
| 1522R | AAGGAGGTGATCCANCCRCA (SEQ ID NO: 144) | 16S rRNA Gene |
| MEK 1914 | ATACTGCTAACAACACTCCAGC (SEQ ID NO: 145) | *L. acidophilus* slpA |
| MEK 1915 | GCAAAGTATTTTGAATTAATTGCTGC (SEQ ID NO: 146) | *L. acidophilus* slpA |
| MEK 1916 | TGAACACTTCAGCATACGAAGG (SEQ ID NO: 147) | *L. crispatus* cbsA |
| MEK 1917 | CAACATAATTCTTTCTTGCTTCTGC (SEQ ID NO: 148) | *L. crispatus* cbsA |
| MEK 1918 | TTAAATACTGCTGTAGGTAACAGC (SEQ ID NO: 149) | *L. gallinarum* lgsB |
| MEK 1919 | CCGTTACCCTTGTTTTCTAATGG (SEQ ID NO: 150) | *L. gallinarum* lgsB |
| MEK 1920 | GTTATTGGTACTGGTATTACTATCC (SEQ ID NO: 151) | *L. helveticus* slpA |
| MEK 1921 | TGTGCTGCAAAGTACTTAGAGG (SEQ ID NO: 152) | *L. helveticus* slpA |

DNA Sequencing and Sequence Analysis.

Sequencing of constructed libraries was performed at Functional Biosciences, Inc. (Madison, Wis.) using M13F(–20) and M13R(–27) primers. The resulting sequences were processed and aligned using the Ribosomal Database Project (RDP) pipeline tool (website located at rdp.cme.msu.edu) (Cole, J. R. et al. (2009), Nucleic Acids Res 37:D141-5). Aligned sequences were taxonomically classified using the RDP Classifier (Wang, Q. et al., 2007, Appl Environ Microbiol 73:5261-7). Sequences were assigned to operational taxonomic units (OTUs) at 1% sequence dissimilarity using DOTUR (Schloss, P. D., and J. Handelsman, 2005, Appl Environ Microbial 71:1501-6) on the RapidOTU server (website located at genomejouy.inra.fr/rapidotu). DOTUR was also used to generate the Shannon-Weaver (H') and Simpson (D) diversity indices for the eight libraries. Evenness (E) was calculated as described previously (Krebs, C. J. (1989), Ecological Methodology. Harper & Row, Publishers, Inc., New York, N.Y.). Libraries were compared using RDP Library Compare (Cole, J. R. et al., 2009, Nucleic Acids Res 37:D141-5).

Detection of Anti-*C. jejuni* Antibodies in Chick Sera.

ELISA plates were coated plates with 100 µl of 2 µg/ml *C. jejuni* F38011 whole cell lysate diluted in PBS. After incubating plates overnight at 4° C., the wells were washed twice with PBST wash buffer (PBS, 0.05% of the polysorbate surfactant TWEEN® 20, a polyoxyethylene derivative of sorbitan monolaurate) and blocked with 150 µl of PBS, 0.05% TWEEN® 20, and 0.25% gelatin (PBST-G) at 25° C. for 2 h. The plates were washed three times. The chick sera were diluted 1:200 in PBST-G and 100 µl of each serum sample was added in triplicate. After incubation for 2 hours at 25° C., the wells were washed three times and 100 µl of anti-chicken IgG antibody horseradish peroxidase conjugate diluted 1:5000 in PBST-G was added for 2 h at 25° C. Wells were washed three times with PBS and 50 µl of tetramethybenzidine (TMB) substrate (Pierce-Endogen) was added to the wells. The reaction was stopped with 0.18 N $H_2SO_4$ after 10 min of development. Absorbances at 490 nm ($A_{490}$) within wells were determined at 492 nm.

Results

Lactobacilli inhibit *C. jejuni* growth in vitro.

Growth curves were performed in order to characterize the ability of *Lactobacillus acidophilus*, *Lactobacillus crispatus*, *Lactobacillus gallinarum*, and *Lactobacillus helveticus* to grow on MRS (FIG. 22). The $\mu_m$ were determined as follows: *L. acidophilus*, 0.281±0.002 per h; *L. crispatus*, 0.308±0.003 per h; *L. gallinarum*, 0.276±0.002 per h; and *L. helveticus*, 0.265±0.002 per h; and were not dramatically different.

The ability of lactobacilli to inhibit growth of *C. jejuni* in vitro was evaluated. Spotted cultures of all *Lactobacillus* strains tested appeared to inhibit *C. jejuni* F38011 while their ability to inhibit growth of other *C. jejuni* strains was variable. Overnight cultures of *Lactobacillus* were spotted onto BHI-T and allowed to grow O/N at 37° C. Overnight cultures of *C. jejuni* were standardized to $O.D._{540}=1.0$ and inoculated at 1% into 10 ml MH soft agar, overlaid, and incubated 24 h at 37° C. Supernatants from overnight cultures of *Lactobacillus* were left untreated, neutralized with 6.25 N NaOH, or boiled for 6 min. Supernatants from overnight cultures of *Lactobacillus* were left untreated or catalase treated for 1 h. All supernatants were filter sterilized (0.22 µm) and spotted onto 20 ml MH soft agar inoculated at 1% with *C. jejuni*. *Lactobacillus* strains used are indicated as follows: (A) *L. acidophilus*, (B) *L. crispatus*, (C) *L. gallinarum* and (D) *L. helveticus*. Zone of Inhibition (I) and Zone of Growth (G) as used in Table 8 are indicated. *L. acidophilus* and *L. crispatus* were able to effectively inhibit growth of all *C. jejuni* strains tested while *L. gallinarum* and *L. helveticus* were only able to effectively inhibit *C. jejuni* F38011. Additionally, *C. jejuni* F38011 appeared to be the most susceptible strain to inhibition by lactobacilli in vitro.

TABLE 8

Inhibition of *C. jejuni* by lactobacilli*

| LAB Strains | C. jejuni Strains | | | | | |
|---|---|---|---|---|---|---|
| | F38011 | 81-176 | 81116 | RM1221 | S2B | Turkey |
| L. acidophilus | 2.6 ± 0.3$^a$ | 1.6 ± 0.1 | 1.5 ± 0.1 | 1.7 ± 0.1 | 1.5 ± 0.1 | 1.9 ± 0.1 |
| L. crispatus | 4.1 ± 0.8 | 1.8 ± 0.1 | 1.4 ± 0.2 | 1.9 ± 0.2 | 1.4 ± 0.2 | 1.9 ± 0.3 |
| L. gallinarum | 2.4 ± 0.4 | 1.2 ± 0.1 | 1.1 ± 0.1 | 1.2 ± 0.1 | 1.0 ± 0.1 | 1.3 ± 0.2 |
| L. helveticus | 1.5 ± 0.1 | 1.2 ± 0.1 | 1.2 ± 0.1 | 1.2 ± 0.1 | 1.2 ± 0.1 | 1.3 ± 0.1 |

*Expressed as Ratio of Zone of Inhibition (mm)/Zone of Growth (mm)
$^a$Errors represent one standard deviation of triplicate measurements In order to determine whether bacteriocins produced by lactobacilli were involved in inhibition of *C. jejuni*, plates spotted with *Lactobacillus* cultures were treated with trypsin and proteinase K prior to being overlaid with *C. jejuni*. Neither protease treatment reduced inhibition of *C. jejuni* (not shown), suggesting that inhibition was not due to the production of a proteinaceous component and, thus, not due to the production of bacteriocins. Additionally, heat-treatment of supernatants did not effect inhibition, confirming that bacteriocins produced by lactobacilli were not responsible for inhibition of *C. jejuni*. To determine if production of organic acid or hydrogen peroxide contribute to the inhibitory ability of these lactobacilli, supernatants of *Lactobacillus* cultures were neutralized to pH 7 with NaOH or treated with catalase, respectively. Neutralization with NaOH abolished inhibition. Treatment of supernatants with catalase also reduced inhibition of *C. jejuni*, suggesting that peroxides produced by lactobacilli contribute to inhibition. These data suggest the ability of *Lactobacillus* cultures to inhibit growth of *C. jejuni* in vitro is due, at least in part, to the production of organic acids and hydrogen peroxide.

Lactobacilli Reduce *C. jejuni* Colonization of Chickens.

Figure 23A:
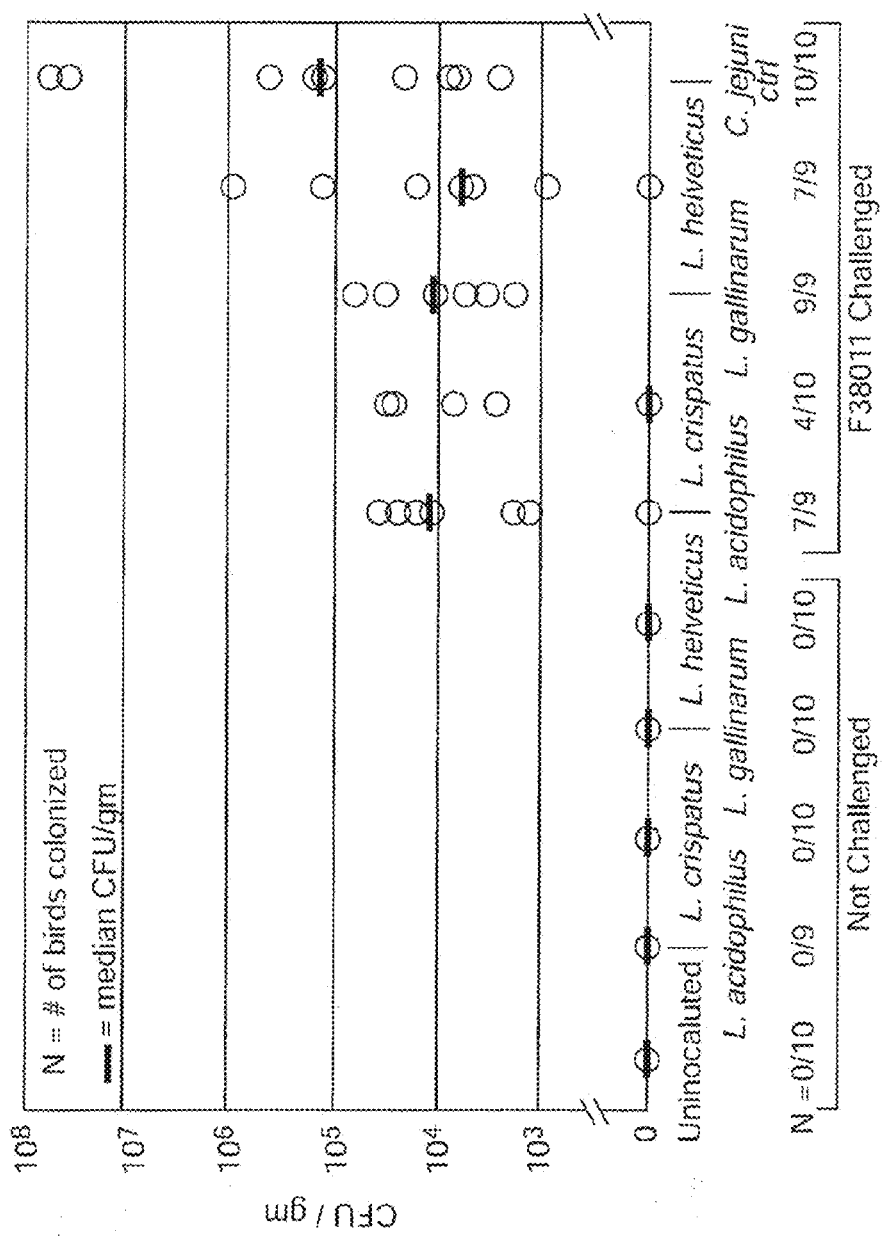
FIG. 23 illustrates the colonization of broiler chickens by *C. jejuni*. Broiler chicks were administered *Lactobacillus* by oral gavage (~$10^8$ CFU) at day one of hatch and 4 days post-hatching. Chicks receiving *C. jejuni* challenge were administered *C. jejuni* F38011 by oral gavage (~$10^8$ CFU) at day 14 post hatching. Half of the chickens were euthanized and necropsied at (A) Day 7 post-challenge and the remaining chickens at (B) Day 14 post-challenge. A cecum was dissected from each chicken, weighed, diluted in an equal volume of MH broth, and thoroughly stomached. Samples were serially diluted and plated onto Campy Cefex agar for enumeration.
Figure 23B:
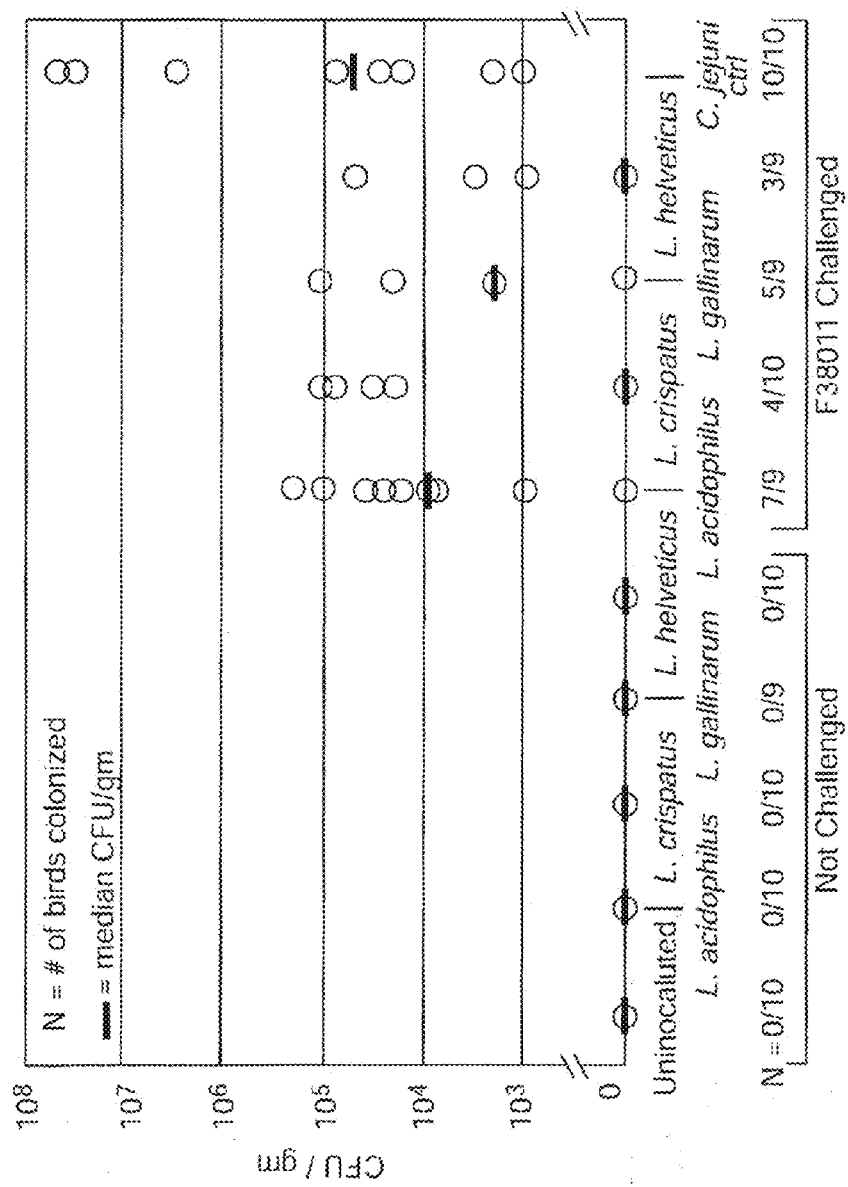

Lactobacilli were administered to commercial broiler chicks as potential competitive exclusion organisms on day-of-hatch and 4 days post-hatching. In order to evaluate the effectiveness of these lactobacilli, the chickens were challenged with *C. jejuni* F38011 14 days post-hatching. Half the chickens were euthanized and necropsied at 7 days post-inoculation with *C. jejuni*. The remaining chickens were euthanized and necropsied at day 14 days post-inoculation. *C. jejuni* present in the cecum of each chicken were enumerated (FIG. 23). The experiment illustrated in FIG. 23 was performed as follows. Broiler chicks were administered *Lactobacillus* by oral gavage (~$10^8$ CFU/ml) at days 1 and 4 post-hatching. Chicks receiving *C. jejuni* challenge were administered *C. jejuni* F38011 by oral gavage (~$10^8$ CFU/ml) at day 14 post hatching. Half of the chickens were euthanized and necropsied at day (A) 21 post-hatching and the remaining chickens at day (B) 28 post-hatching. A cecum was dissected from each chicken, weighed, diluted in an equal volume of MH broth, and thoroughly stomached. Samples were serially diluted and plated onto Campy Cefex agar for enumeration. *C. jejuni* was not detected in the ceca of un-challenged birds indicating containment procedures were effective. In challenged birds receiving *L. acidophilus*, *C. jejuni* was detected in 7 of 9 birds at both 7 and 14 day's post challenge. Colonization of chickens administered *L. gallinarum* and *L. helveticus* by *C. jejuni* appeared to decline from 7 to 14 days post-challenge. Colonization of birds receiving *L. gallinarum* and *L. helveticus* decreased from 9 of 9 to 5 of 9 and 7 of 9 to 3 of 9, respectively. Chickens receiving *L. crispatus* had a low rate of colonization by *C. jejuni* at 4 of 10 birds at both 7 and 14 days post challenge.

Colonization of chickens by administered *Lactobacillus* strains was also determined (Table 7). Chickens receiving *L. helveticus* displayed the highest rate of colonization by lactobacilli (94.4%), followed birds receiving *L. crispatus* (90%), *L. acidophilus* (72.5%), and *L. gallinarum* (51.7%). In chickens that were administered *L. acidophilus*, *L. crispatus* and *L. helveticus*, lactobacilli were recovered in more birds when challenged with *C. jejuni* than when not.

PCR using strain specific primers (Table 5) was used to ascertain whether recovered presumptive lactobacilli were of the same strain administered to the chickens (data not shown). 10 isolates from each group were selected for this analysis. Of all the groups tested, only those groups administered *L. crispatus* JCM5810 were positive for the administered species. Additionally, several presumptive *Lactobacillus* isolates from other groups were also positively identified as *L. crispatus*, as shown in Table 9.

TABLE 9

Cecal Colonization by lactobacili*

| | | C. jejuni Treatment | |
|---|---|---|---|
| LAB Treatment | Total | + | − |
| L. acidophlus | 72.5% | 78.3% | 66.7% |
| L. crispatus | 90.0% | 95.0% | 85.9% |
| L gallinarum | 51.7% | 36.7% | 66.7% |
| L. helveticus | 94.4% | 100.0% | 88.9% |

*Shown as percentage of cecal specimens in which lactobacilli were detected 16S rDNA Microbiome Analysis.

Specimens receiving various treatments were selected for cecal microbiome analysis by 16S rDNA sequencing (Table 10). The 16S rDNA clones were classified using the RDP Classifier. Of the 747 16S rDNA clones, 644 (86%) were classified as Firmicutes, 94 (13%) were classified as Bacteroidetes, 8 (1%) were unclassified, and a single clone was classified as a Proteobacteria. The Firmicutes were the dominant phylum with the Clostridia being the major class across all the specimens accounting for 64% of the total clones in the libraries. While, clones classified as *Lactobacillus* were identified in specimens from groups receiving *L. crispatus*, *L. gallinarum*, and *L. helveticus*, *Lactobacillus* was only appreciably identified from the specimens receiving *L. crispatus*. The single Proteobacteria clone was identified as belonging to the genus *Salmonella* and found in the specimen receiving *L. gallinarum* and *C. jejuni* challenge. No clones were classified as belonging to the genus *Campylobacter*.

Gram-positive flora were dominant across all specimens and regardless of treatment with *Lactobacillus*. While there were some shifts of flora from Bacteroidetes to Firmicutes, the normal flora, aside from the increased number of *Lactobacillus* clones identified, predominate regardless of treatment and the dominant flora was not disrupted by the microbial treatments.

TABLE 10

Features of Specimens Selected for Cecal Microbiome Analysis

| | | Bacterial Counts | | | |
|---|---|---|---|---|---|
| | | Campylobacter | | Lactobacillus | |
| Specimen # | Treatment | Cecum | Illeum | Cecum | Illeum |
| 6 | Uninoculated | ND$^c$ | ND | $4.0 \times 10^4$ | $4.0 \times 10^3$ |
| 21 | L. crispatus | ND | ND | $1.9 \times 10^9$ | $2.3 \times 10^6$ |
| 31 | L. gallinarum | ND | ND | $1.5 \times 10^7$ | ND |
| 41 | L. helveticus | ND | ND | $2.5 \times 10^8$ | $3.0 \times 10^6$ |
| 68 | L. crispatus + C. jejuni | $2.0 \times 10^4$ | ND | $4.8 \times 10^7$ | $5.2 \times 10^7$ |
| 78 | L. helveticus + C. jejuni | $2.0 \times 10^4$ | ND | $2.2 \times 10^6$ | $1.3 \times 10^5$ |
| 89 | L. gallinarum + C. jejuni | ND | ND | $3.5 \times 10^8$ | $9.1 \times 10^6$ |
| C$^a$ | C. jejuni | $2.0 \times 10^6$ | ND | ND | ND |

$^a$Counts shown as CFU/gm of cecal or illeal contents
$^b$Positve control for *C. jejuni* colonization, receiving only *C. jeuni*
$^c$ND—not detected, limit of detection is $1 \times 10^3$ CFU/gm Determination of Serum Antibodies.

Figure 24A:
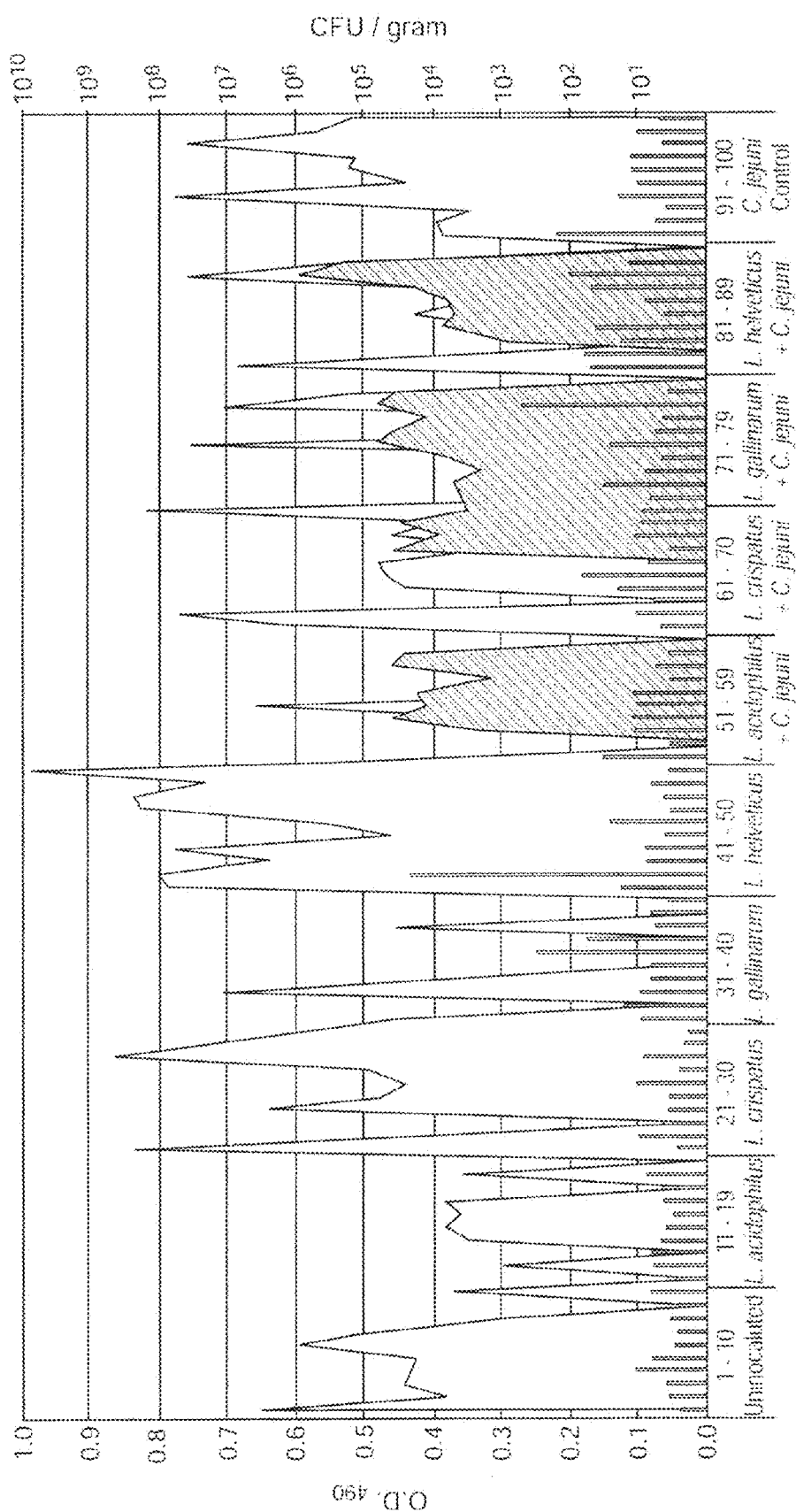
FIGS. 24A and B shows anti-*C. jejuni* serum antibodies. Levels of anti-*C. jejuni* serum antibodies in broiler chickens were determined at (A) Day 7 and (B) Day 14 post-challenge by ELISA as outlined in Materials and Methods. Microtiter plates were coated with *C. jejuni* whole cell lysates, and incubated with sera from the chickens. Chicken sample identification numbers and treatment groups are indicated on the X-axis. Antibody level for each specimen is indicated by white bars. Microbial counts for *C. jejuni* (gray) and *Lactobacillus* (black) are shown as CFU/gram cecal contents.
Figure 24B:
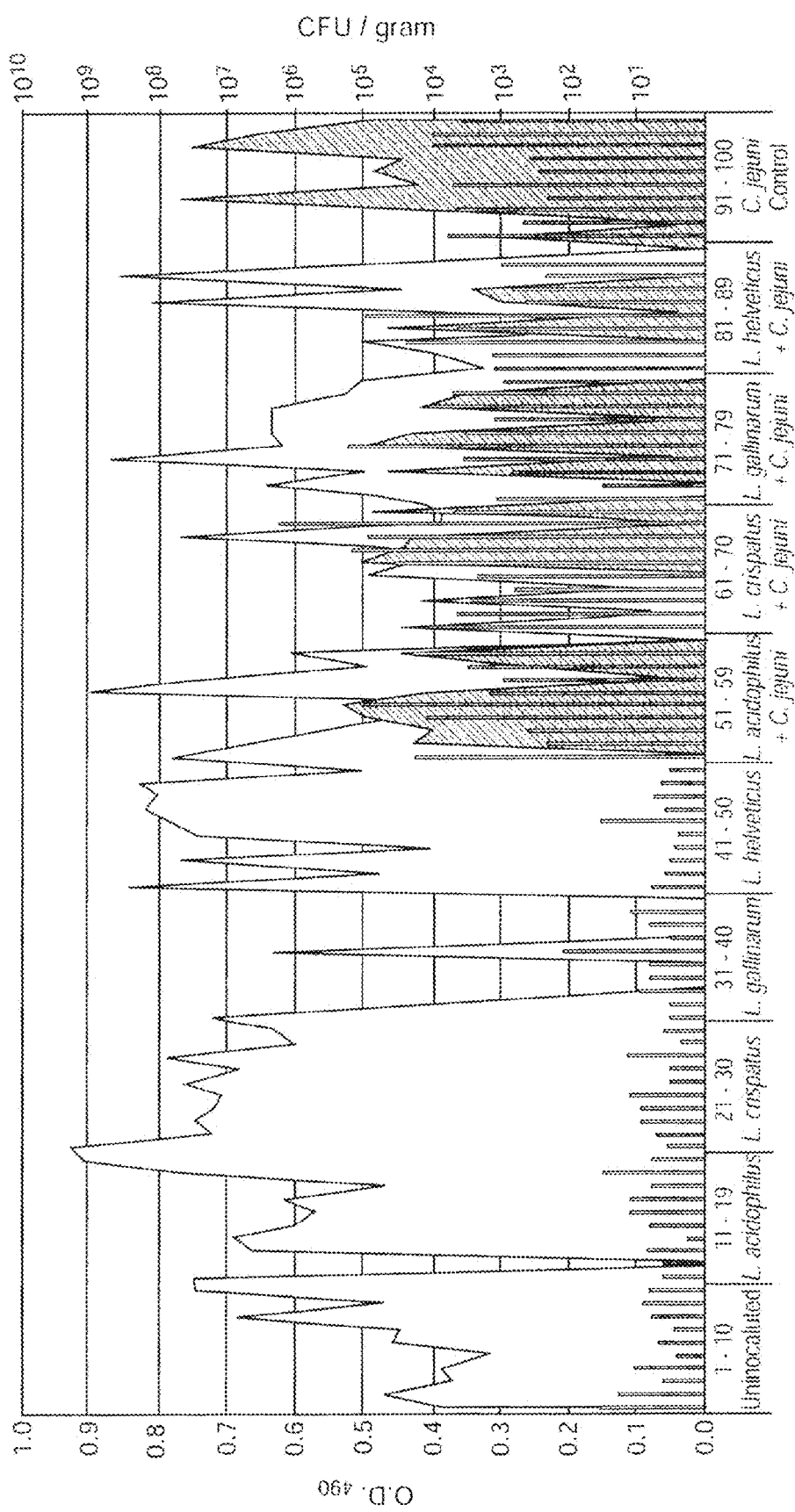
Figure 25A:
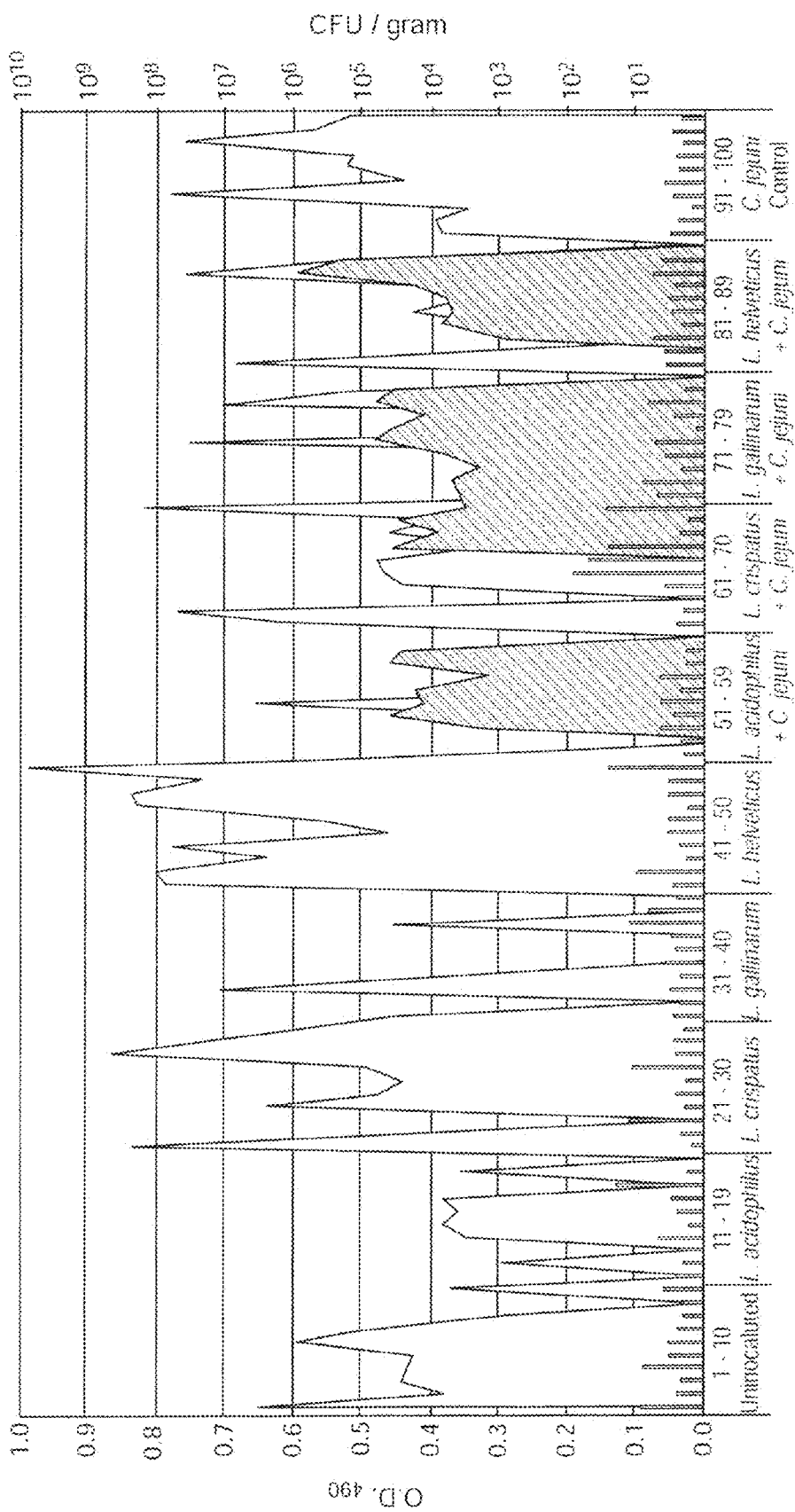
FIGS. 25A and B shows the anti-alpha toxin serum antibodies. Levels of anti-*Clostridium perfringens* alpha-toxin serum antibodies in broiler chickens were determined at (A) Day 7 and (B) Day 14 post-challenge by ELISA as outlined in Materials and Methods. Chicken sample identification numbers and treatment groups are indicated on the X-axis. Antibody level for each specimen is indicated by white bars. Microbial counts for *C. jejuni* (gray) and *Lactobacillus* (black) are shown as CFU/gram cecal contents.
Figure 25B:
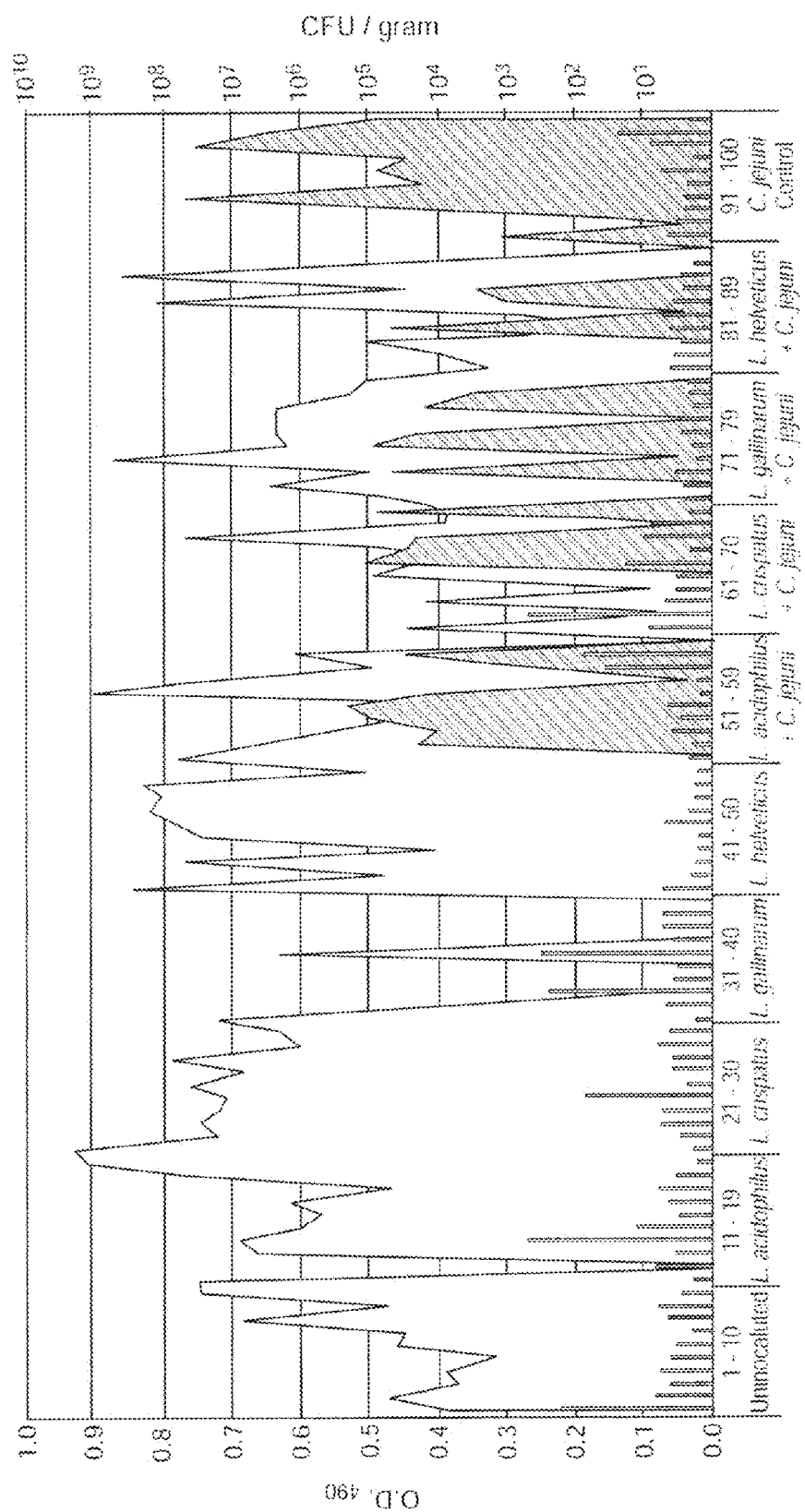

Levels of anti-*C. jejuni* antibodies in sera at 21 and 28 days post-hatch were determined by ELISA (FIG. 24). Anti-*C. jejuni* antibodies were detected in the sera of challenged birds at 14 days post-challenge but not at 7 days post-challenge, while anti-*C. jejuni* antibodies were not detected in the sera of naïve chickens. In challenged birds receiving *L. crispatus*, anti-*C. jejuni* antibodies were detected in fewest birds. This is consistent with their level of colonization. Additionally, the strain of *Lactobacillus* administered did not appear to affect levels of anti-*C. jejuni* antibodies. Natural antibodies to *Clostridium perfringens* present in the chicken sera were also determined (FIG. 25). Antibodies were not detected in significant quantities and did not appear to be affected but the *Lactobacillus* strain administered.

EXAMPLE 6

Use of a Probiotic *Lactobacillus* Strain as an Oral Vaccine to Reduce *Campylobacter jejuni* in Chickens Manipulation of the Gene (slpA) Encoding the S-Layer Protein of *Lactobacillus* Bacterium.

The data below relates to a cloning experiment used to test whether epitopes can be inserted into surface exposed sites of the S-layer protein. The slpA gene from *L. helveticus* CNRZ32 was amplified by PCR using gene specific primers and cloned into the pCR 2.1 vector using the Original TA Cloning Kit (Invitrogen). The promoter and start codon were not included to prevent expression of the slpA gene in *E. coli*, which is toxic (Avall-Jaaskelainen, S. et al. (2002) Appl. Environ. Microbiol. 68:5943-5951). Using inverse PCR, the entire pCR 2.1 vector plasmid containing the slpA gene fragment was amplified using primers whose 5' end each contained one half of the 36 base pair sequence for the Fn-BD from CadF. Blunt-ended ligation of the PCR product resulted in the desired slpA modified construct, with the CadF epitope inserted in-frame. Following sequence-confirmation of the modified slpA construct, it was digested from the pCR 2.1 vector and ligated into the shuttle vector pSA3. This vector has a temperature-sensitive origin of replication, which allows replication in LAB at 37° C. but not 44° C. (Christensen, J. E., and J. L. Steele (2003); J. Bacteriol. 185:3297-3306; Dao, M. L., and J. J. Ferretti (1985); Appl. Environ. Microbiol. 49:115-119). Following electroporation, *L. helveticus* isolates containing the recombinant pSA3 vector were recovered at 37° C. by the pour-plate method using MRS supplemented with 500 ng/ml erythromycin (ERY) and 0.75% agar. The transformants were suspended in MRS broth, plated on MRS+ERY50 plates, and incubated at 44° C. Because pSA3 is unable to replicate at 44° C., the only colonies that were recovered contained the pSA3 plasmid with the modified slpA gene incorporated in the chromosome. To promote excision of the plasmid, the single-crossover isolates were subcultured daily in MRS broth, for 20 days, at 37° C. The broth cultures were then plated on MRS agar plates containing 10 ng/ml ERY. This concentration of antibiotic is inhibitory but not lethal, causing isolates that were cured of pSA3 to appear as pinpoint colonies, whereas the isolates harboring the pSA3 vector were 2-3 cm in diameter. Isolates containing the modified slpA with the CadF Fn-BD were confirmed by PCR amplification and sequencing of the modified slpA gene.

Collection/Generation of Serum Containing *C. jejuni* Protective Antibodies.

The immune response of two groups of birds is analyzed. The first group represents serum samples collected from breeder chickens located at two farms, and the second group represents chickens that have been immunized with *Campylobacter* extracts or whole bacteria. This first experiment has three groups of chickens: 1) non-immunized, non *C. jejuni* challenged; 2) non-immunized, *C. jejuni* challenged; and 3) *C. jejuni* whole cell lysate (wcl) immunized by subcutaneous (SubQ) injection, *C. jejuni* challenged. The wcl was mixed with an adjuvant obtained from a commercial poultry producer (the adjuvant was obtained with the understanding that we would not share the company's name or formulation/composition of the adjuvant with others). The chickens were immunized (primary immunization) at 5 days post-hatch, and again at 12 days post-hatch (boost). At 19 days of age, one half of the chickens (n=10) within group 1, group 2, and group 3 are euthanized and blood collected to assess the antibody responses, whereas the remaining chickens (n=10) in groups 2 and 3 are challenged via oral gavage with $10^6$ cfu of *C. jejuni*. At 26 days of age, the chickens were euthanized and the number of *C. jejuni* per gram of intestinal and cecal contents is determined and compared with chickens that did not receive prior immunization. Immunization of the chickens results in overall reductions in *C. jejuni* colonization of chickens.

A second experiment is performed to compare and contrast two different immunization strategies. Groups 1 and 2 are immunized by SubQ injection with a *C. jejuni* wcl, as above. However, as represented by groups 3 and 4, a total of 40 chickens are immunized by oral administration of formalin-fixed *C. jejuni*. The bacteria are formalin-fixed as outlined by Rice et al. (1997) Vaccine. 15:1922-1932) and Black et al. (1987) Infect. Immun. 55:1116-1120). Groups 5 and 6 serve as non-immunized controls, where only group 6 is being challenged with *C. jejuni*. The load of *C. jejuni* in groups 2 and 4 is less than that of the chickens in group 6 (non-immunized, *C. jejuni* challenged). Serum is obtained that contains antibodies protective against *C. jejuni*.

Determination of C. jejuni Proteins Against which Antibodies are Generated.

Figure 26:
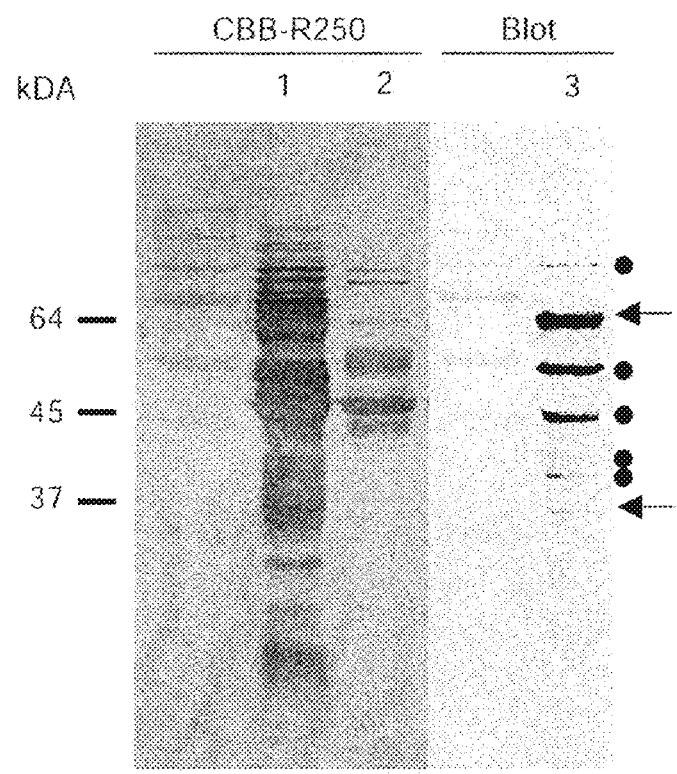
FIG. 26 shows the reactivity of the antibodies in a serum collected from a broiler chicken orally inoculated with *C. jejuni*. The blood was collected from the chicken at 15 days post-inoculation with *C. jejuni* 81116. Lanes: 1, *C. jejuni* 81116 whole cell lysate (wcl); 2, *C. jejuni* 81116 outer membrane protein (omp) preparation; and 3, *C. jejuni* 81116 wcl. The blot shown in the right panel was incubated with a 1:50 dilution of the chicken serum. The arrows highlight the known proteins (62 kDa=FlaA, 37 kDa=CadF), thus far found to react with every sera tested (n=10). The bullets indicate proteins whose identity will be determined by mass spectroscopy.

Sera obtained from chicks immunized with C. jejuni wcl (SubQ) and formalin-fixed C. jejuni (oral administration), as well as non-vaccinated breeder chickens, are analyzed using the following protocol. First, C. jejuni wcl and outer membrane protein (omp) preparations are separated by SDS-PAGE, and proteins transferred to polyvinylidene fluoride membranes. The membranes are rinsed and incubated with chicken sera diluted in PBS (pH 7.4) containing 0.01% Tween 20 and 9% dried milk. Bound immunoglobulins are detected with either α-chicken IgM or α-chicken IgG horseradish peroxidase conjugates. 4-chloro-1-napthol is used as the chromogenic substrate. An example of the expected result is shown in FIG. 26. The identity of the C. jejuni outer membrane proteins against which the chickens generated protective antibodies is identified by coupling SDS-PAGE, immunoblot, and nano-LC/MS/MS/ion trap analysis.

Selection of Epitopes for Incorporation into the Lactobacillus S-Layer Protein.

Two methods are used to select the region of a protein (i.e., residues) that will be incorporated into the S-layer of Lactobacillus. One method relies on determining the specificity/ reactivity of the antibodies generated in the chickens and the second method utilizes a molecular biology approach to determine the conserved regions of a protein. Ideally, the residues incorporated into the S-layer are highly immunogenic and conserved in nature.

Immunoblot and Enzyme-Linked Immunosorbent Assays (ELISAs).

The region within a protein that the antibodies bind is identified via immunoblot analysis of protein fragments. The protein fragments are generated by expression of various gene segments in an expression system (i.e., pET24b, His-tagged) or via enzymatic digestion. The identity of the digested fragment can also be determined using LC/MS/MS/ ion trap analysis. Fine-mapping of a protein's immunoreactive regions is performed by ELISA. As an example, the procedure with the FlaA filament protein is outlined here. FlaA derived synthetic peptides, oligomers (30-mers) are ordered that span the desired region of the protein. Each successive oligomer will overlap the previous oligomer by 10-residues. The oligomers are used to coat the wells of the microtiter plates. As a positive control, wells are coated with the His-tagged recombinant protein. After blocking with PBS/0.5% BSA (wt/vol), chicken sera is added in two-fold serial dilutions (1:50 to 1:6400) and incubated for 90 min at 25° C. The wells are rinsed three times and incubated for 90 min with an .alpha.-chicken IgG/IgM-HRP antibody. The plates are developed using laboratory-established protocols. This method will define the region(s) within a protein to which the antibodies are generated.

Molecular Approach.

Figure 27:
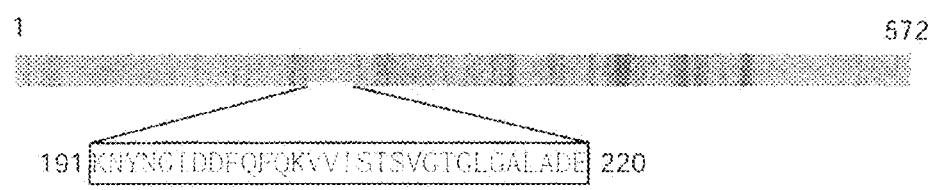
FIG. 27 shows an analysis of the *C. jejuni* FlaA filament protein. The deduced amino acid sequences from 26 FlaA proteins were aligned to determine the conserved regions. Shown with shading are the residues/regions with greater than 90% and 50% amino acid identity, respectively. The black lines indicate regions of increased variability (i.e., non-conservation, insertion, or deletion). The 30-mer indicated below the color graphic (SEQ ID NO: 3) represents a region where 28 of 30 residues are greater than 90% conserved. Relative to the regions downstream of residue 220, the 191-220 region represents a good target for incorporation into a *Lactobacillus* S-layer protein.

Four C. jejuni genomic sequences are currently available. Moreover, the NCBI databases contain numerous entries for any given C. jejuni protein. For the proteins of interest, sequences are aligned to identify regions with greater than 95% identity at the amino acid level. An example of the type of data generated is shown in FIG. 27. In preferred embodiments, epitopes (residues) that are highly immunogenic and conserved in nature are incorporated into the S-layer.

Creation of a Strain of Lactobacillus, that Synthesizes a Recombinant S-Layer Protein Containing Epitopes from C. Jejuni Antigens.

Figure 28:
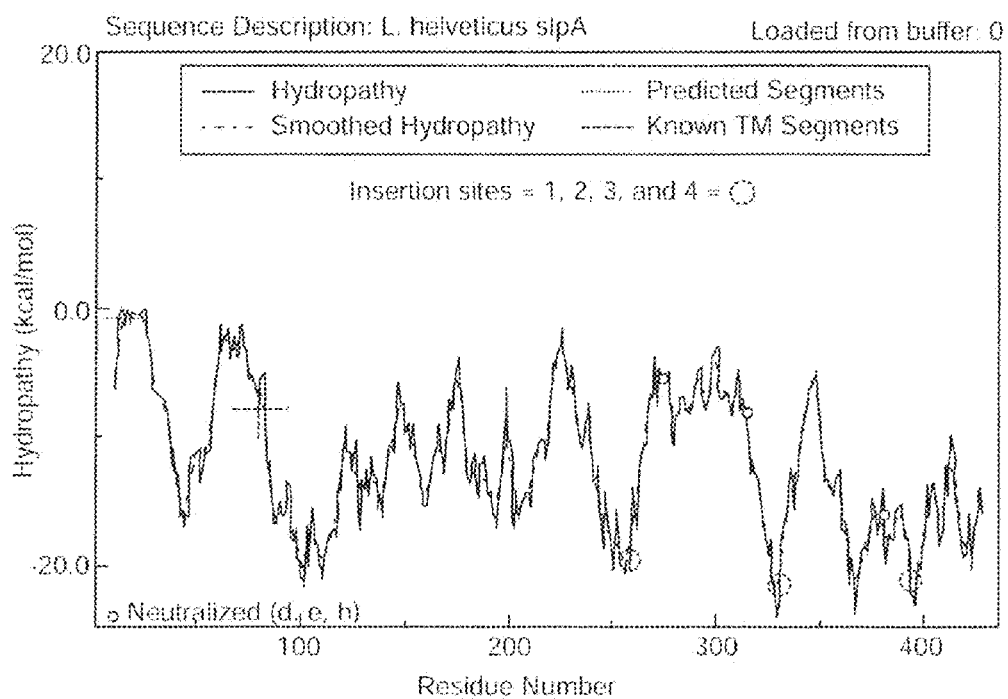
FIG. 28 shows a hydropathy profile of the *L. helveticus* SlpA protein. Shown on the Y-axis is the hydropathy in Kcal/mol, calculated for 19 residue windows centered at the residue numbers listed on the X-axis.

An exemplary cloning strategy using L. helveticus as a model is described below. A difference among the three Lactobacillus species is that the S-layer protein is synthesized by genes unique to the individual species (Avall-Jaaskelainen, S., and A. Palva (2005) FEMS Microbiol. Rev. 29:511-529; Boot, H. J. et al. (1996), Microbiology. 142 (Pt 9):2375-2384). As L. acidophilus has two genes that encode the S-layer, it is necessary to modify both or generate a knockout in one of the two genes. However, the approach is customized depending on the species and strain of Lactobacillus chosen. FIG. 28 shows a hydropathy profile of the L. helveticus SlpA protein. The lower (more negative) hydropathy values correlate to hydrophilic regions of the proteins that are likely to be solvent-exposed, while higher (more positive) hydropathy values indicate more hydrophobic regions that are less likely to be solvent exposed. The four putative solvent-exposed insertion sites are located at residues 104, 259, 333, and 370. Insertion of the CadF 12-mer at site I, residue 104, would increase the hydropathy value, but the value would remain less than −10 Kcal/mol. Thus, based on the results of the membrane protein hydrophobicity prediction tool Membrane Protein Explorer (see the website located at blanco.biomol.u-ci.edu/mpex/) (FIG. 18), we have selected four putative epitope insertion sites in the L. helveticus SlpA S-layer protein.

Figure 29:
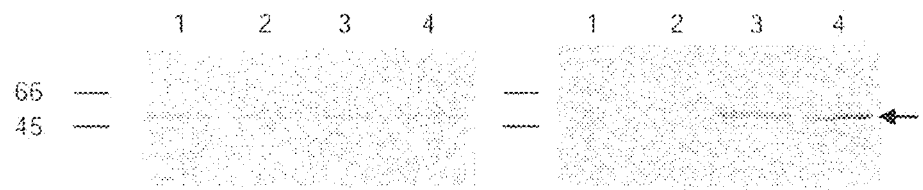
FIG. 29 shows the incorporation of the CadF Fn-BD into the *L. helveticus* S layer protein. Panel A is a CBB-R250 stained gel. Panel B is a blot probed with goat α-CadF serum. Lanes: 1, S-layer protein extracted from a wild-type strain; 2, transformant with a wild-type slpA allele; 3 and 4, independent transformants with the CadF Fn-BD (12mer) in site 1 of the slpA gene. The S-layer with the CadF Fn-BD is indicated (arrow).
Figure 30:
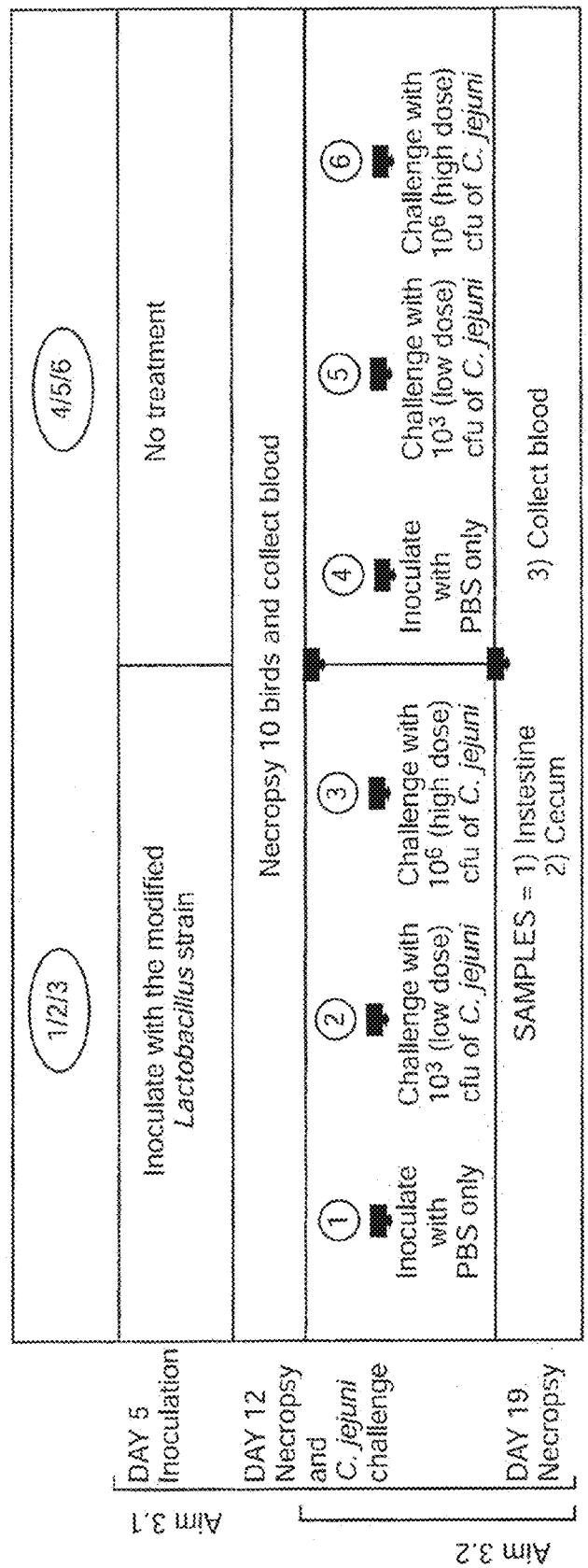
FIG. 30 shows the experimental design to compare the number of *Campylobacter* colonizing chickens inoculated with a *Lactobacillus* vaccine strain versus non-vaccinated chickens. There were 20 birds in each experimental group.

To demonstrate the feasibility of this approach, a 36 base pair DNA fragment encoding the Fn-binding domain (Fn-BD) from residues 130-141 of CadF=AGVKFRLSDSLA (SEQ ID NO: 166), encoded by GCTGGTGT-TAAGTTTCGTTTATCAGATTCACTTGCT, SEQ ID NO: 167) was inserted into target site 1 located in the slpA gene of L. helveticus CNRZ32 (FIG. 28, and FIG. 29). A similar protocol is used to clone other C. jejuni epitopes into the S-layer protein. Where an epitope spans larger regions (i.e., 30 residues, 90 nucleotides), restriction sites are inserted at the desired location in the S-layer gene. The epitopes are PCR amplified with gene specific primers containing restriction sites incorporated into the 5' end, digested with the appropriate enzyme, and then ligated into the S-layer gene. All epitopes inserted into the slpA gene are in-frame with the coding sequence and codon-bias optimized for efficient expression in Lactobacillus.

Analysis of the Surface-Layer in the Modified Lactobacillus Strain.

The CadF epitope is individually inserted into each of the four insertion sites, and the recombinant S-layer is examined for surface display of the epitope and proper conformation. The other C. jejuni epitopes are inserted into the S-layer gene after it is confirmed that an insertion at the four sites will not result in an altered S-layer conformation.

Examination of the S-Layer Protein for C. jejuni Epitope Synthesis.

ELISAs are used to confirm incorporation of a C. jejuni epitope (i.e., the CadF Fn-BD) in the S-layer. Both whole-cell LAB and purified S-layer protein (wild-type and recombinant) are tested. The S-layer protein is extracted from a culture of Lactobacillus bacteria using 6M LiCl as described previously (Johnson-Henry, K. C. et al. (2007) Cell. Microbial. 9:356-367). The ELISA is performed in microtiter wells coated with suspensions of the wild-type and recombinant Lactobacillus bacteria and purified S-layer protein. In the case of the S-layer-CadF Fn-BD, the plates are incubated with α-CadF antibody at 25° C. for 90 min. Bound α-CadF antibody is detected as described previously.

Determining the Level of Recombinant S-Layer Synthesis.

To determine the level of S-layer synthesis in the modified Lactobacillus strain, S-layer extracts from both wild-type and recombinant strains are purified and subjected to SDS-PAGE. Briefly, cultures of the Lactobacillus wild-type and recombinant strains are grown to equivalent densities, and the S-layer extracted (Johnson-Henry, K. C. et al. (2007) Cell. Microbiol. 9:356-367). Equal volumes of the extracted proteins are subjected to protein quantitation assays (i.e., bicinchoninic acid assay) and SDS-PAGE. The protein bands are visualized by staining with Coomassie Brilliant Blue R-250. The amount of S-layer protein in each sample is determined using densitometry scans over a limited range of protein concentration. Both the modified *Lactobacillus* bacteria and purified, recombinant S-layer protein will also be examined by microscopy to determine if introduction of the epitopes has resulted in morphological or conformational changes to the bacteria or protein, respectively. Scanning electron microscopy of purified S-layer extracts are performed as outlined by Johnson-Henry et al. to determine if the S-layer protein will auto-aggregate into characteristic sheets and helices. Transmission electron microscopy analysis of the *Lactobacillus* bacteria is performed as described in Avall-Jaaskelainen et al. ((2002) Appl. Environ. Microbiol. 68:5943-5951). The bacteria are placed on a Formvar coated grid, stained with 1% phosphotungstic acid (PTA, pH 7.0), and examined for morphological irregularities in the S-layer protein.

Assessment of *C. jejuni* Epitope Surface Display.

Surface display of the *C. jejuni* epitopes in the S-layer protein is determined by immuno-flouresence (IF) microscopy. If we do not possess antibodies reactive against a specific *C. jejuni* protein, they are generated by immunization of rabbits with a protein purified from *C. jejuni* or from *E. coli* harboring a recombinant plasmid. IF microscopy is performed with viable bacteria incubated first with a *C. jejuni*-specific antibody and then with α-rabbit IgG conjugated to fluorescein isothiocyanate. The bacteria are visualized using a UV microscope.

Determination of the Efficacy of a *Lactobacillus* Vaccine Strain in Preventing and Reducing *C. jejuni* Colonization and Whether an Immune Response is Generated Against *C. jejuni* Epitopes.

The goal is to bridge the protective response provided from the maternal antibodies with that of the newly produced *C. jejuni* specific-IgA antibodies generated in response to the modified *Lactobacillus* strain. Chickens are inoculated with a strain of *Lactobacillus* that displays three *C. jejuni* epitopes, including portions of the CadF, FlaA, and FlpA proteins. As illustrated in FIG. 30, chickens are inoculated with the modified *Lactobacillus* strain at day 5, which will allow the level of maternal antibodies to begin to decline. Blood is collected, and the sera screened for α-*Campylobacter* IgG and IgM antibodies. IgA antibodies will also be extracted. Briefly, an extraction solution (PBS containing 0.05% Tween 20, 0.1 mg/ml soybean trypsin inhibitor, 0.05 mg/ml EDTA, and 0.35 mg/ml phenylmethylsulfonyl fluoride) is mixed with an intestinal lavage and shaken for 2 hours at 4° C. Following centrifugation (20,000×g) at 4° C. for 30 min, the supernatant is harvested and stored at −20° C. Detection of α-*Campylobacter* antibodies is performed by ELISA and immunoblot analysis.

ELISAs are performed with the *C. jejuni* proteins that contain the antigenic epitopes (purified via a His-tag), as well as a *C. jejuni* wcl. The chicken sera is serially diluted, added to microtiter wells coated with wcl and purified proteins, and incubated at 25° C. for 90 min to allow the antibodies to bind to the *C. jejuni* proteins. After rinsing the wells twice with PBS, α-chicken IgG, IgM, and IgA antibodies conjugated to horseradish peroxidase are added to the wells and incubated at 25° C. for 90 min. Bound antibodies are detected as described previously. Immunoblot analysis is used to confirm the results of the ELISAs. The same wcl used in the ELISA, as well as the purified *C. jejuni* proteins, is probed with chicken sera. The proteins are separated by SDS-12.5% PAGE, and transferred to PVDF membranes. The membranes are washed 3 times in PBS, and incubated with each serum diluted 1:100 in PBS pH 7.4 containing 0.01% Tween 20 with 20% fetal bovine serum. Bound antibodies are detected using α-chicken antibodies (IgG, IgM, and IgA) conjugated to HRP.

Comparison of the Number of *Campylobacter* Colonizing Chickens Inoculated with a *Lactobacillus* Vaccine Strain Versus Non-Vaccinated Chickens.

As part of the experiment outlined in FIG. 30, the number of *Campylobacter* colonizing chickens inoculated with a *Lactobacillus* vaccine strain versus non-vaccinated chickens is compared. One week after inoculation with the modified *Lactobacillus* strain, the chickens are challenged with low ($10^3$ cfu) and high ($10^6$ cfu) doses of *C. jejuni*. One week after the *C. jejuni* challenge, the chickens are euthanized. The *C. jejuni* in the digestive tracts of the birds is enumerated, and compared with one another. The recombinant (modified) strain of *Lactobacillus* colonizes the digestive tract of chickens at densities comparable to that of a *Lactobacillus* wild-type strain. The modified *Lactobacillus* strain is recovered at ~$1\times10^7$ CFU/g in ileal contents and at ~$1\times10^5$ CFU/g in cecal contents (Wise, M. G., and G. R. Siragusa (2007) J. Appl. Microbiol. 102:1138-1149). If the modified *Lactobacillus* strain is unable to persist in the chickens, it will most likely be because antibodies have been generated against the *C. jejuni* epitopes. For this to occur, antibodies reactive against the organism will have been produced, and these are effective in reducing the amount of *Campylobacter* colonizing the cera of chickens. Low and high *C. jejuni* challenge doses are used because the dose that chickens are exposed to in the natural environment is not known; also, many vaccines will fail if the challenge dose is increased beyond the capacity of the immune system to respond effectively. Although not outlined herein, additional experiments are performed to determine if the number of bacteria (inoculum) and day of delivery will affect the efficiency of LAB colonization. Ultimately, the efficacy of the modified *Lactobacillus* strain in reducing the microbial load of *Campylobacter* organisms in chickens is tested with a minimum of ten genetically distinct *C. jejuni* strains. All experiments are performed in a stepwise fashion where each experiment is designed and carried out based on the result of a previous experiment. Should *C. jejuni* neutralizing antibodies not be generated during a one-week time frame (FIG. 30), the experimental design is modified. First, the modified LAB is administered earlier (i.e., day 2, 3, and 4 post-hatch). Although this strategy may result in the clearance of a majority of the modified LAB from the ileum, some bacteria are likely to survive and the number of bacteria in the digestive tract will increase as the level of maternal antibodies decreases. Second, the chickens are challenged with *C. jejuni* at a later date (i.e., day 14, 16, 18, and 21 post-hatch). Either modification will effectively extend the time between when the chickens receive the modified *Lactobacillus* strain and the *C. jejuni* challenge. The goal is to generate an antibody response against *C. jejuni* prior to 3 weeks of age, by which time most chickens become colonized.

EXAMPLE 7

Competitive Exclusion of *Campylobacter jejuni* Colonization of Chickens with Recombinant *Caulobacter crescentus* Expressing *C. jejuni* Antigens The purpose of this experiment was to modify the surface layer of *Caulobacter crescentus* by adding i) a CadF fibronectin binding domain, ii) a PorA conserved epitope, and iii) a conserved flagellin domain. Caulobacter (whole bacterial cells) were administered on day of hatch and 4 days post-hatching by oral gavage with 0.5 ml bacterial suspension (~$10^8$ CFU). At 14 days post hatching, the chicks were administered *C. jejuni* F38011 by oral gavage with 0.5 ml bacterial suspension (~$10^8$ CFU). Half of the chickens in each group were euthanized and necropsied at Day 21 (1 week post-inoculation) and the remaining chickens on Day 28 (2 weeks post-inoculation) of the study.

Materials and Methods
Bacterial Strains, Growth Conditions, Plasmids, and Reagents.

*Escherichia coli* strain DH5 alpha (Invitrogen, Carlsbad, Calif.) was grown at 37° C. in Luria Broth (1% tryptone, 0.5% NaCl, 0.5% yeast extract) The *C. crescentus* strain JS 4022 (Nomellini J. F. et, al. 2007S-layer mediated display of the IgG-binding domain of Streptococcal Protein G on the surface of *Caulobacter crescentus*—Development of an immuno-active reagent. Appl. And Envir. Microb. 73:3245-3253) was propagated in liquid peptone-yeast extract (0.2% peptone, 0.1% yeast extract, 0.01% $CaCl_2$, 0.02% $MgSO_4$), at 30° C. For growth on solid medium, agar was added at 1.3% (wt/vol). Where necessary, media contained chloramphenicol (CM) at 20 g/ml (*E. coli*) or 2 g/ml (*C. crescentus*). Electroporation of *C. crescentus* was performed as previously described (Gilchrist, A., and J. Smit. 1991. Transformation of freshwater and marine caulobacters by electroporation. J. Bacteriol. 173:921-925). Fragments were recovered from agarose gels using a QIAEX II gel extraction kit (QIAGEN). The plasmid DNA was isolated using a QIAprep miniprep plasmid isolation kit (QIAGEN), and DNA segments to construct the 30 peptide epitopes were constructed by GENE-ART AG (Regensburg, Germany)

The epitopes were:

```
                                          (SEQ ID NO: 1)
CadF      (HYGAGVKFRLSDSLALRLETRDQINFNHAN);

(SEQ ID NO: 4)
FlaA2     (INAVKDTTGVEASIDANGQLVLTSADGRGI);
and (SEQ ID NO: 153)
PorA      (YGAAAVGSYDLAGGQFNPQLWLAYW DQVAF).
```

The top strand DNA segments are

CadF:
```
                                          (SEQ ID NO: 154)
5' AGATCTACTAGTCACTACGGCGCCGGCGTCAAGTTCCGCCTGTCGGA

CTCGCTGGCCCTGCGCCTGGAGACCCGCGACCAGATCAACTTCAACCACG

CCAACGCTAGCGCTGCAG 3';
```

FlaA2:
```
                                          (SEQ ID NO: 155)
5' AGATCTACTAGTATCAACGCCGTGAAGGACACCACCGGCGTCGAGGC

GTCGATCGACGCCAACGGCCAGCTGGTCCTGACGTCGGCCGACGGCCGGG

GTATCGCTAGCGCTGCAG 3';
```

PorA:
```
                                          (SEQ ID NO: 156)
5' AGATCTACTAGTTATGGCGCCGCCGCCGTCGGCTCGTATGACCTGGC

CGGCGGCCAGTTCAACCCGCAGCTGTGGCTGGCCTACTGGGACCAGGTCG

CCTTCGCTAGCGCTGCAG 3'.
```

The segments were engineered with BglII and SpeI sites on the 5' end and NheI and PstI sites on the 3' end. The restriction sites arrangement allowed the segments to be directionally cloned into p4ARsaA(723)/GSCC with BglII/PstI as individual epitopes or could be multimerized as desired (Nomellini J. F. et, al. 2007S-layer mediated display of the IgG-binding domain of Streptococcal Protein G on the surface of *Caulobacter crescentus*—Development of an immuno-active reagent. Appl. And Envir. Microb. 73:3245-3253.AEM ref). Multimerization led to the p4ARsaA(723)/CadF/FlaA2/PorA clone.

ELISA

Figure 31:
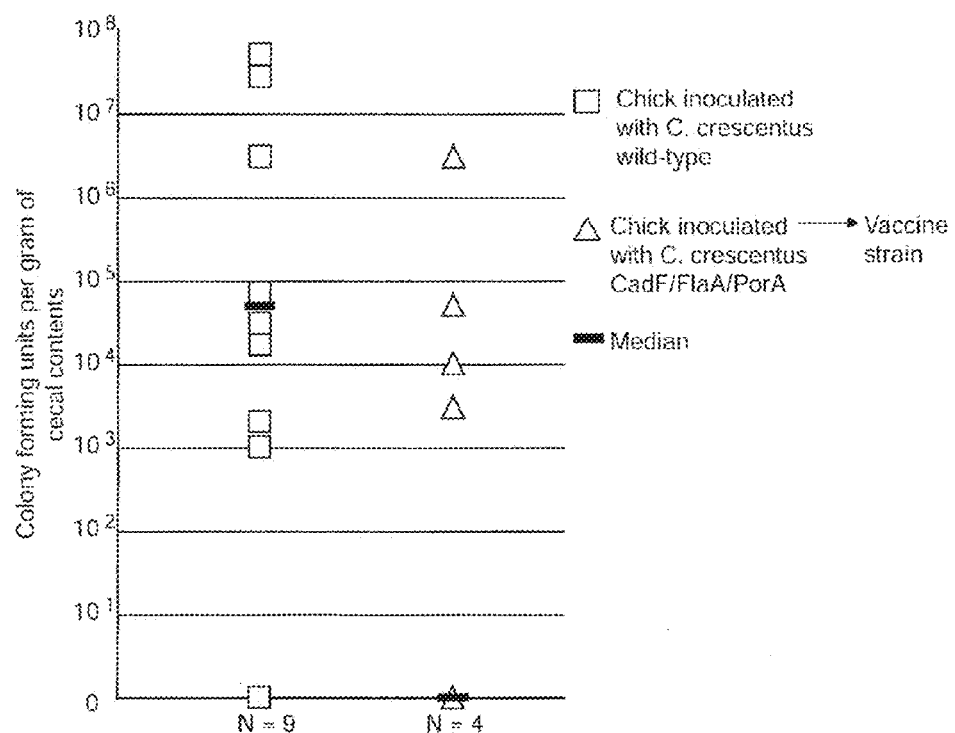
FIG. 31 illustrates the competitive exclusion of *C. jejuni* colonization of chickens with recombinant *Caulobacter crescentus*. N=the number of birds (of 10) that have detectable numbers of *C. jejuni* in their ceca two weeks post-inoculation. *C. crescentur* CadF/FlaA/PorA is the vaccine strain.
Figure 32:
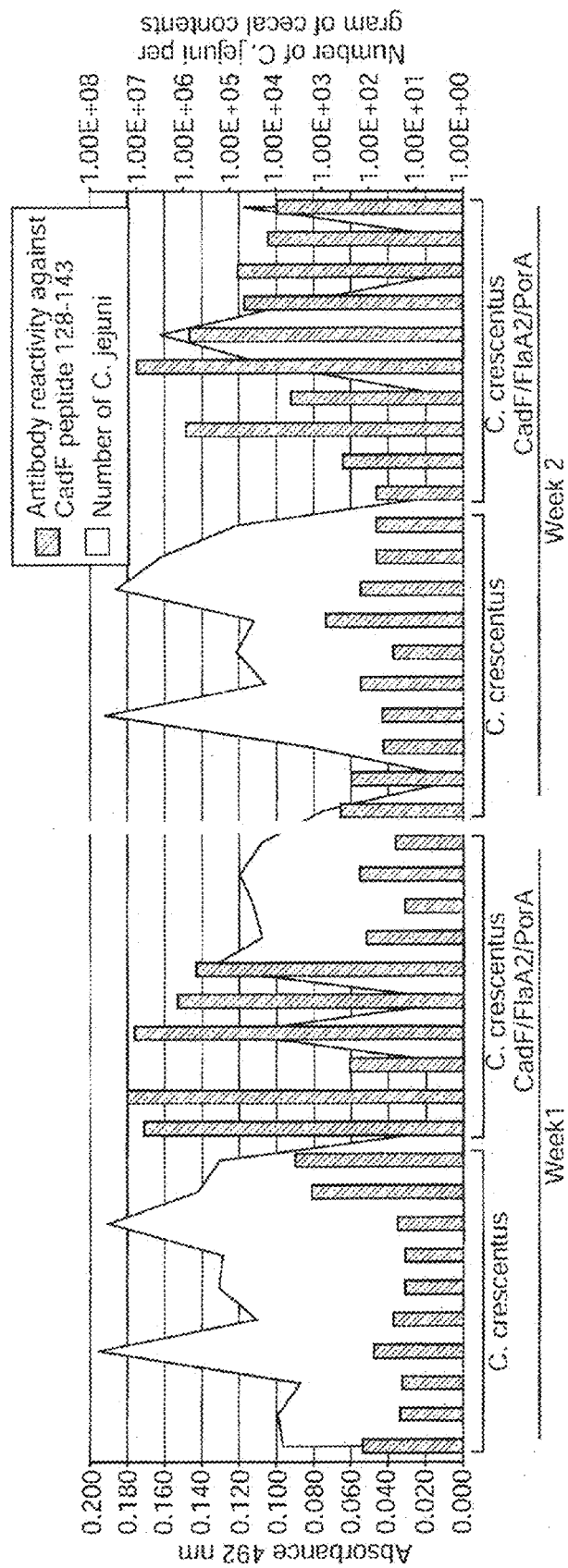
FIG. 32 illustrates a *Caulobacter crescentus* CadF/FlaA2/PorA vaccine strain that inhibits colonization of chickens and stimulates a specific antibody response against a CadF peptide (amino acids 128-143).

ELISA plates were coated plates with 1 µg of the CadF peptide, amino acids 128-142 diluted in PBS (i.e. 100 µl of 10 µg/ml solution). After incubating plates overnight at 4° C., the well were washed twice with PBST wash buffer (PBS, 0.05% of the polysorbate surfactant TWEEN® 20. a polyoxethvylene derivative of sorbitan monolaurate) and blocked with 150 µl of PBS, 0.05% tween20 TWEEN® 20, and 0.25% gelatin (PBST-G) at 25° C. for 2 hours. The plates were washed three times. The chick sera were diluted 1:50 and 1:200 in PBST-G and 100 µl of each serum sample was added in triplicate. After incubation for 2 hours at 25° C., the wells were washed three times and 100 µl of anti-chicken IgG antibody horseradish peroxidase conjugate (Sigma) diluted 1:5000 in PBST-G was added for 2 hours at 25° C. Wells were washed three times with PBS and 50 µl of tetramethybenzidine (TMB) substrate (Pierce-Endogen) was added to the wells. The reaction was stopped with 0.18 $NH_2SO_4$ after 10 min of development. The absorbances ($A_{492}$) within wells were determined at 492 nm. FIGS. 36 and 37 summarize results from this experiment. Only 4 of the 10 birds that received the *C. crescentus* CadF/FlaA/PorA strain were colonized, whereas 9 of the 10 birds that received the *C. crescentus* wild-type strain were colonized. Due to the fact that only 4 of the birds that received the vaccine strain were colonized, the median colony forming units for the *C. crescentus* CadF/FlaA/PorA strain summarized in FIG. 31 is below a detectable level, Elisa assays performed show that the *Caulobacter crescentus* CadF/FlaA2/PorA vaccine strain stimulates a specific antibody response against a CadF peptide (FIG. 32). The data of FIG. 32 is presented in tabular form in Table 11.

TABLE 11

Competitive exclusion of *C. jejuni* colonization of chickens with recombinant *Caulobacter crescentus*

|  |  | CadF | | FlaA2 | | PorA | |
| --- | --- | --- | --- | --- | --- | --- | --- |
|  |  | Ave. Abs. | T-test | Ave. Abs. | T-test | Ave. Abs. | T-test |
| Week 1 | RsaA | 0.047 | 0.013 | 0.035 | 0.163 | 0.022 | 0.857 |
|  | Triflecta | 0.106 |  | 0.042 |  | 0.022 |  |
| Week 2 | RsaA | 0.052 | 0.00002 | 0.052 | 0.2471 | 0.033 | 0.2869 |
|  | Triflecta | 0.111 |  | 0.060 |  | 0.037 |  |

In summary, this experiment shows that the S-layer of *Caulobacter crescentus* can be genetically modified to include multiple *C. jejuni* epitopes. In doing so, a *Caulobacter crecentus* vaccine strain has been generated that reduces the load of *C. jejuni* in the ceca of broilers.

EXAMPLE 8

Comparative Analysis of FlaA Sequences from Several *C. jejuni* Strains

The sequences of the FlaA protein from several *C. jejuni* strains were compared and a consensus sequence was developed (see FIGS. 33A-C). As can be seen, certain domains or regions within the protein are more highly conserved. A highly conserved region was selected sa a vaccine antigen in order to provide protection against the greatest number of *C. jejuni* strains. These residues are predicted to be surface exposed and accessible to protective antibodies. Based on these results, a highly conserved 30 amino acid peptide (residues 278-307 of FlaA: INAVKDTTGVEASIDANGQLVLT-SADGRGI (SEQ ID NO: 4) was identified. This 30 mer represents a candidate antigenic sequence for use in the present invention.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention.

What is claimed is:

1. A *Lactobacillus* host vector genetically engineered to contain nucleic acids which encode and express a protein consisting of the amino acid of SEQ ID NO:3.

2. The *Lactobacillus* host vector of claim 1 wherein said nucleic acids are inserted into an S-layer protein of said *Lactobacillus*.

* * * * *

SEQUENCE LISTING

```
<160> NUMBER OF SEQ ID NOS: 177

<210> SEQ ID NO 1
<211> LENGTH: 30
<212> TYPE: PRT
<213> ORGANISM: Artificial Sequence
<220> FEATURE:
<223> OTHER INFORMATION: Synthetic peptide antigen

<400> SEQUENCE: 1

His Tyr Gly Ala Gly Val Lys Phe Arg Leu Ser Asp Ser Leu Ala Leu
1               5                   10                  15

Arg Leu Glu Thr Arg Asp Gln Ile Asn Phe Asn His Ala Asn
            20                  25                  30

<210> SEQ ID NO 2
<211> LENGTH: 4
<212> TYPE: PRT
<213> ORGANISM: Artificial Sequence
<220> FEATURE:
<223> OTHER INFORMATION: Synthetic antigenic peptide

<400> SEQUENCE: 2

Phe Arg Leu Ser
1

<210> SEQ ID NO 3
<211> LENGTH: 30
<212> TYPE: PRT
<213> ORGANISM: Artificial Sequence
<220> FEATURE:
<223> OTHER INFORMATION: Synthetic antigenic peptide

<400> SEQUENCE: 3

Phe Val Gln Ala Val Thr Asn Leu Pro Asn Arg Ile Lys Leu Ile Trp
1               5                   10                  15

Arg Pro His Pro Asp Phe Arg Val Asp Ser Tyr Ile Ile Glu
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Synthetic antigenic peptide

<400> SEQUENCE: 4

Ile Asn Ala Val Lys Asp Thr Thr Gly Val Glu Ala Ser Ile Asp Ala
1               5                   10                  15

Asn Gly Gln Leu Val Leu Thr Ser Ala Asp Gly Arg Gly Ile
            20                  25                  30
```

<210> SEQ ID NO 5
<211> LENGTH: 960
<212> TYPE: PRT
<213> ORGANISM: Campylobacter jejuni

<400> SEQUENCE: 5

| | | | | | | | | | | | | | | | |
|---|---|---|---|---|---|---|---|---|---|---|---|---|---|---|---|
| Ala | Thr | Gly | Ala | Ala | Ala | Ala | Ala | Thr | Ala | Thr | Thr | Cys | Thr |
| 1 | | | | 5 | | | | | 10 | | | | | 15 |
| Thr | Ala | Thr | Gly | Thr | Thr | Thr | Ala | Gly | Gly | Thr | Thr | Gly | Gly | Cys |
| | | | 20 | | | | | 25 | | | | | 30 |
| Ala | Ala | Gly | Thr | Gly | Thr | Thr | Thr | Ala | Thr | Thr | Thr | Gly | Gly | Thr |
| | | | | 35 | | | | | 40 | | | | | 45 |
| Gly | Cys | Thr | Gly | Ala | Thr | Ala | Ala | Cys | Ala | Ala | Thr | Gly | Thr | Ala | Ala |
| | 50 | | | | | 55 | | | | | 60 | | | | |
| Ala | Ala | Thr | Thr | Thr | Gly | Ala | Ala | Ala | Thr | Cys | Ala | Cys | Thr | Cys | Cys |
| 65 | | | | | 70 | | | | | 75 | | | | | 80 |
| Ala | Ala | Cys | Thr | Thr | Thr | Ala | Ala | Ala | Cys | Thr | Ala | Thr | Ala | Ala | Thr |
| | | | | 85 | | | | | 90 | | | | | 95 |
| Thr | Ala | Cys | Thr | Thr | Thr | Gly | Ala | Ala | Gly | Gly | Thr | Ala | Ala | Thr | Thr |
| | | | | 100 | | | | | 105 | | | | | 110 |
| Thr | Ala | Gly | Ala | Thr | Ala | Thr | Gly | Gly | Ala | Thr | Ala | Ala | Thr | Cys | Gly |
| | | | | 115 | | | | | 120 | | | | | 125 |
| Thr | Thr | Ala | Thr | Gly | Cys | Ala | Cys | Cys | Ala | Gly | Gly | Gly | Ala | Thr | Thr |
| | | | 130 | | | | | 135 | | | | | 140 |
| Ala | Gly | Ala | Cys | Thr | Thr | Gly | Gly | Thr | Thr | Ala | Thr | Cys | Ala | Thr | Thr |
| 145 | | | | | 150 | | | | | 155 | | | | | 160 |
| Thr | Thr | Gly | Ala | Cys | Gly | Ala | Thr | Thr | Thr | Thr | Thr | Gly | Gly | Cys | Thr |
| | | | | 165 | | | | | 170 | | | | | 175 |
| Thr | Gly | Ala | Thr | Cys | Ala | Ala | Thr | Thr | Ala | Gly | Ala | Ala | Thr | Thr | Thr |
| | | | | 180 | | | | | 185 | | | | | 190 |
| Gly | Gly | Gly | Thr | Thr | Ala | Gly | Ala | Gly | Cys | Ala | Thr | Thr | Ala | Thr | Thr |
| | | | 195 | | | | | 200 | | | | | 205 |
| Cys | Thr | Gly | Ala | Thr | Gly | Thr | Thr | Ala | Ala | Thr | Ala | Thr | Ala | Thr | Cys |
| | 210 | | | | | 215 | | | | | 220 | | | | |
| Ala | Ala | Ala | Thr | Ala | Cys | Ala | Ala | Ala | Thr | Ala | Ala | Ala | Ala | Cys | Thr |
| 225 | | | | | 230 | | | | | 235 | | | | | 240 |
| Ala | Cys | Ala | Gly | Ala | Thr | Ala | Thr | Thr | Ala | Cys | Ala | Ala | Gly | Ala | Ala |
| | | | | 245 | | | | | 250 | | | | | 255 |
| Cys | Thr | Thr | Ala | Thr | Thr | Thr | Gly | Ala | Gly | Thr | Gly | Cys | Thr | Ala | Thr |
| | | | | 260 | | | | | 265 | | | | | 270 |
| Thr | Ala | Ala | Ala | Gly | Gly | Thr | Ala | Thr | Thr | Gly | Ala | Thr | Gly | Thr | Ala |
| | | | 275 | | | | | 280 | | | | | 285 |
| Gly | Gly | Thr | Gly | Ala | Gly | Ala | Ala | Ala | Thr | Thr | Thr | Ala | Thr | Thr |
| | | | 290 | | | | | 295 | | | | | 300 |
| Thr | Cys | Thr | Ala | Thr | Gly | Gly | Thr | Thr | Thr | Ala | Gly | Cys | Ala | Gly | Gly |
| 305 | | | | | 310 | | | | | 315 | | | | | 320 |
| Thr | Gly | Gly | Ala | Gly | Gly | Ala | Thr | Ala | Thr | Gly | Ala | Gly | Gly | Ala | Thr |
| | | | | 325 | | | | | 330 | | | | | 335 |
| Thr | Thr | Thr | Thr | Cys | Ala | Ala | Thr | Gly | Cys | Thr | Gly | Cys | Thr | Thr |
| | | | | 340 | | | | | 345 | | | | | 350 |
| Ala | Thr | Gly | Ala | Thr | Ala | Ala | Thr | Ala | Ala | Ala | Gly | Cys | Gly | Gly |
| | | | 355 | | | | | 360 | | | | | 365 |
| Thr | Gly | Gly | Ala | Thr | Thr | Gly | Gly | Ala | Cys | Ala | Thr | Thr | Ala | Thr |
| | | | 370 | | | | | 375 | | | | | 380 |

-continued

```
Gly Gly Cys Gly Cys Gly Gly Thr Gly Thr Ala Ala Ala Ala Thr
385                 390                 395                 400

Thr Cys Cys Gly Thr Cys Thr Thr Ala Gly Thr Gly Ala Thr Thr Cys
            405                 410                 415

Thr Thr Thr Gly Gly Cys Thr Thr Ala Ala Gly Ala Cys Thr Thr
            420                 425                 430

Gly Ala Ala Ala Cys Thr Ala Gly Ala Gly Ala Thr Cys Ala Ala Ala
        435                 440                 445

Thr Thr Ala Ala Thr Thr Thr Cys Ala Ala Thr Cys Ala Thr Gly Cys
    450                 455                 460

Ala Ala Ala Cys Cys Ala Thr Ala Ala Thr Thr Gly Gly Gly Thr Thr
465                 470                 475                 480

Thr Cys Ala Ala Cys Thr Thr Ala Gly Gly Thr Ala Thr Thr Ala
            485                 490                 495

Gly Thr Thr Thr Thr Gly Gly Thr Thr Thr Gly Gly Thr Gly Gly
        500                 505                 510

Cys Ala Ala Ala Ala Gly Gly Ala Ala Ala Ala Gly Cys Thr
    515                 520                 525

Gly Thr Ala Gly Ala Ala Gly Ala Ala Gly Thr Thr Gly Cys Thr Gly
    530                 535                 540

Ala Thr Ala Cys Thr Cys Gly Thr Gly Cys Ala Ala Cys Thr Cys Cys
545                 550                 555                 560

Ala Cys Ala Ala Gly Cys Ala Ala Ala Ala Thr Gly Thr Cys Cys Thr
            565                 570                 575

Gly Thr Thr Gly Ala Ala Cys Cys Ala Ala Gly Ala Gly Ala Ala Gly
            580                 585                 590

Gly Thr Gly Cys Thr Thr Thr Gly Thr Thr Ala Gly Ala Thr Gly Ala
        595                 600                 605

Ala Ala Ala Thr Gly Gly Thr Thr Gly Cys Gly Ala Ala Ala Ala
    610                 615                 620

Ala Cys Thr Ala Thr Thr Thr Cys Thr Thr Gly Gly Ala Ala Gly
625                 630                 635                 640

Gly Thr Cys Ala Thr Thr Thr Gly Gly Thr Thr Thr Thr Gly Ala
        645                 650                 655

Thr Ala Ala Ala Cys Thr Ala Cys Thr Ala Thr Ala Ala Ala Thr
            660                 665                 670

Cys Cys Ala Ala Cys Thr Thr Thr Cys Ala Ala Gly Ala Ala Ala
    675                 680                 685

Ala Ala Ala Thr Cys Ala Ala Ala Gly Ala Ala Thr Thr Gly Cys
    690                 695                 700

Ala Ala Ala Ala Gly Thr Thr Thr Ala Gly Ala Thr Gly Ala Ala
705                 710                 715                 720

Ala Ala Thr Gly Ala Ala Ala Gly Ala Thr Ala Thr Gly Ala Thr Ala
            725                 730                 735

Cys Thr Ala Thr Thr Cys Thr Thr Gly Ala Ala Gly Gly Ala Cys Ala
            740                 745                 750

Thr Ala Cys Ala Gly Ala Thr Ala Ala Thr Ala Thr Cys Gly Gly Thr
        755                 760                 765

Thr Cys Ala Ala Gly Ala Gly Cys Thr Thr Ala Thr Ala Ala Thr Cys
        770                 775                 780

Ala Ala Ala Ala Gly Cys Thr Thr Thr Cys Thr Gly Ala Ala Ala Gly
    785                 790                 795                 800

Ala Cys Gly Thr Gly Cys Thr Ala Ala Ala Ala Gly Thr Gly Thr Thr
```

```
            805                 810                 815
Gly Cys Thr Ala Ala Thr Gly Ala Ala Cys Thr Thr Gly Ala Ala
            820                 825                 830

Ala Ala Thr Ala Thr Gly Gly Thr Gly Thr Ala Gly Ala Ala Ala
            835                 840                 845

Ala Ala Gly Thr Cys Gly Cys Ala Thr Cys Ala Ala Ala Cys Ala
            850                 855                 860

Gly Thr Ala Gly Gly Thr Thr Ala Thr Gly Gly Thr Cys Ala Ala Gly
865                 870                 875                 880

Ala Thr Ala Ala Thr Cys Cys Thr Cys Gly Cys Thr Cys Ala Ala Gly
                885                 890                 895

Cys Ala Ala Thr Gly Ala Cys Ala Cys Thr Ala Ala Ala Gly Ala Ala
                900                 905                 910

Gly Gly Thr Ala Gly Ala Gly Cys Gly Gly Ala Thr Ala Ala Thr Ala
                915                 920                 925

Gly Ala Ala Gly Ala Gly Thr Gly Gly Ala Thr Gly Cys Thr Ala Ala
            930                 935                 940

Ala Thr Thr Thr Ala Thr Thr Thr Thr Ala Gly Ala Thr Ala Ala
945                 950                 955                 960

<210> SEQ ID NO 6
<211> LENGTH: 319
<212> TYPE: PRT
<213> ORGANISM: Campylobacter jejuni

<400> SEQUENCE: 6

Met Lys Lys Ile Phe Leu Cys Leu Gly Leu Ala Ser Val Leu Phe Gly
1               5                   10                  15

Ala Asp Asn Asn Val Lys Phe Glu Ile Thr Pro Thr Leu Asn Tyr Asn
                20                  25                  30

Tyr Phe Glu Gly Asn Leu Asp Met Asp Asn Arg Tyr Ala Pro Gly Ile
            35                  40                  45

Arg Leu Gly Tyr His Phe Asp Asp Phe Trp Leu Asp Gln Leu Glu Phe
        50                  55                  60

Gly Leu Glu His Tyr Ser Asp Val Lys Tyr Thr Asn Thr Asn Lys Thr
65                  70                  75                  80

Thr Asp Ile Thr Arg Thr Tyr Leu Ser Ala Ile Lys Gly Ile Asp Val
                85                  90                  95

Gly Glu Lys Phe Tyr Phe Tyr Gly Leu Ala Gly Gly Tyr Glu Asp
            100                 105                 110

Phe Ser Asn Ala Ala Tyr Asp Asn Lys Ser Gly Gly Phe Gly His Tyr
        115                 120                 125

Gly Ala Gly Val Lys Phe Arg Leu Ser Asp Ser Leu Ala Leu Arg Leu
    130                 135                 140

Glu Thr Arg Asp Gln Ile Asn Phe Asn His Ala Asn His Asn Trp Val
145                 150                 155                 160

Ser Thr Leu Gly Ile Ser Phe Gly Phe Gly Lys Lys Glu Lys Ala
                165                 170                 175

Val Glu Glu Val Ala Asp Thr Arg Ala Thr Pro Gln Ala Lys Cys Pro
            180                 185                 190

Val Glu Pro Arg Glu Gly Ala Leu Leu Asp Glu Asn Gly Cys Glu Lys
        195                 200                 205

Thr Ile Ser Leu Glu Gly His Phe Gly Phe Asp Lys Thr Thr Ile Asn
    210                 215                 220
```

Pro Thr Phe Gln Glu Lys Ile Lys Glu Ile Ala Lys Val Leu Asp Glu
225                 230                 235                 240

Asn Glu Arg Tyr Asp Thr Ile Leu Glu Gly His Thr Asp Asn Ile Gly
            245                 250                 255

Ser Arg Ala Tyr Asn Gln Lys Leu Ser Glu Arg Arg Ala Lys Ser Val
        260                 265                 270

Ala Asn Glu Leu Glu Lys Tyr Gly Val Glu Lys Ser Arg Ile Lys Thr
    275                 280                 285

Val Gly Tyr Gly Gln Asp Asn Pro Arg Ser Ser Asn Asp Thr Lys Glu
290                 295                 300

Gly Arg Ala Asp Asn Arg Arg Val Asp Ala Lys Phe Ile Leu Arg
305                 310                 315

<210> SEQ ID NO 7
<211> LENGTH: 960
<212> TYPE: DNA
<213> ORGANISM: Campylobacter jejuni

<400> SEQUENCE: 7
atgaaaaaaa tattattatg tttaggtttg gcaagtgttt tattcagtgc tgataacaat      60
gtaaaatttg aaatcactcc aactttaaac tataattact tgaaggtaa tttagatatg     120
gataatcgtt atgcaccagg gattagactt ggttatcatt ttgacgattt ttggcttgat    180
caattagaat ttgggttaga gcattattct gatgttaaat atacaaatac aaataaaact    240
acagatatta caagaactta tttgagtgct attaaggta ttgatgtagg tgagaaattt     300
tatttctatg gttagcagg tggaggatat gaggattttt caaatgctgc ttatgataat    360
aaaagcggtg gatttggaca ttatggcgcg ggtgtaaaat tccgccttag tgattctttg    420
gctttaagac ttgaaactag agatcaaatt aattttaatc atgcaaacca taattgggtt   480
tcaactttag gtattagttt tggttttggt ggcaaaaagg aaaaagctgt agaagaagtt    540
gctgatactc gtccagctcc acaagcaaaa tgtcctgtag aaccaagaga aggtgctttg    600
ttagatgaaa atggttgcga aaaaactatt tctttggaag gtcattttgg ttttgataaa    660
actactataa atccaacttt tcaagaaaaa atcaaagaaa ttgcaaaagt tttagatgaa    720
aatgaaagat atgatactat tcttgaagga catacagata tataggttc aagagcttat    780
aatcaaaagc tttcagaaag acgtgctaaa agtgttgcta atgaacttga aaaatatggt    840
gtagaaaaaa gtcgcatcaa aacagtaggt tatggacaag ataatcctcg ctcaagcaat    900
gacactaaag aaggtagagc ggataataga agagtggatg ctaaatttat tttaagataa   960

<210> SEQ ID NO 8
<211> LENGTH: 319
<212> TYPE: PRT
<213> ORGANISM: Campylobacter jejuni

<400> SEQUENCE: 8

Met Lys Lys Ile Leu Leu Cys Leu Gly Leu Ala Ser Val Leu Phe Ser
1               5                   10                  15

Ala Asp Asn Asn Val Lys Phe Glu Ile Thr Pro Thr Leu Asn Tyr Asn
            20                  25                  30

Tyr Phe Glu Gly Asn Leu Asp Met Asp Asn Arg Tyr Ala Pro Gly Ile
        35                  40                  45

Arg Leu Gly Tyr His Phe Asp Asp Phe Trp Leu Asp Gln Leu Glu Phe
    50                  55                  60

Gly Leu Glu His Tyr Ser Asp Val Lys Tyr Thr Asn Thr Asn Lys Thr 65                  70                  75                  80
Thr Asp Ile Thr Arg Thr Tyr Leu Ser Ala Ile Lys Gly Ile Asp Val
                    85                  90                  95
Gly Glu Lys Phe Tyr Phe Tyr Gly Leu Ala Gly Gly Tyr Glu Asp
                100                 105                 110
Phe Ser Asn Ala Ala Tyr Asp Asn Lys Ser Gly Phe Gly His Tyr
            115                 120                 125
Gly Ala Gly Val Lys Phe Arg Leu Ser Asp Ser Leu Ala Leu Arg Leu
130                 135                 140
Glu Thr Arg Asp Gln Ile Asn Phe Asn His Ala Asn His Asn Trp Val
145                 150                 155                 160
Ser Thr Leu Gly Ile Ser Phe Gly Phe Gly Gly Lys Lys Glu Lys Ala
                165                 170                 175
Val Glu Glu Val Ala Asp Thr Arg Pro Ala Pro Gln Ala Lys Cys Pro
                180                 185                 190
Val Glu Pro Arg Glu Gly Ala Leu Leu Asp Glu Asn Gly Cys Glu Lys
            195                 200                 205
Thr Ile Ser Leu Glu Gly His Phe Gly Phe Asp Lys Thr Thr Ile Asn
            210                 215                 220
Pro Thr Phe Gln Glu Lys Ile Lys Glu Ile Ala Lys Val Leu Asp Glu
225                 230                 235                 240
Asn Glu Arg Tyr Asp Thr Ile Leu Glu Gly His Thr Asp Asn Ile Gly
                245                 250                 255
Ser Arg Ala Tyr Asn Gln Lys Leu Ser Glu Arg Arg Ala Lys Ser Val
                260                 265                 270
Ala Asn Glu Leu Glu Lys Tyr Gly Val Glu Lys Ser Arg Ile Lys Thr
            275                 280                 285
Val Gly Tyr Gly Gln Asp Asn Pro Arg Ser Ser Asn Asp Thr Lys Glu
            290                 295                 300
Gly Arg Ala Asp Asn Arg Arg Val Asp Ala Lys Phe Ile Leu Arg
305                 310                 315

<210> SEQ ID NO 9
<211> LENGTH: 1104
<212> TYPE: DNA
<213> ORGANISM: Campylobacter jejuni

<400> SEQUENCE: 9
atgaaattat ttcaaaaaaa tactatttta gctttaggtg ttgtgctttt actcactgct      60
tgcagcaaag aagaagcacc aaaaatacaa atgccgcctc aacctgtaac aaccatgagt     120
gctaaatctg aagatttacc acttagtttt acttaccctg ctaaacttgt cagtgattat     180
gatgtcatta taaagcctca agttagtggc gtaatagaaa ataaactttt aaagctgga      240 gataaagtaa aaaaaggaca aacattattt attatagaac aagacaaatt taaagctagt     300
gttgattcgg cttacggaca agctttgatg gctaaggcaa ctttcgaaaa tgcaagcaag     360
gattttaatc gttctaaagc tcttttttagt aaaagtgcaa tctctcaaaa ggaatacgac     420
tcttctcttg ctacatttaa caattcaaaa gctagtctag caagtgctag agcacagctt     480
gcaaatgcaa gaattgatct agatcatacc gaaataaaag ctcctttga tggtactata     540 ggagatgctt tagttaatat aggagattat gtaagtgctt caacaactga actagttaga     600
gttacaaatt taaatcctat ttcgcagat tcttttattt cagatacaga taaactaaat     660
ttagtccgca atactcaaaa tggaaaatgg gatttagaca gcattcatgc aaatttaaat     720

-continued

```
cttaatggag aaaccgttca aggcaaactt tattttattg attctgttat agatgctaat    780
agtggaacag taaagccaa agctatattt gacaacaaca actcaacact tttaccaggt     840
gcttttgcaa caattacttc agaaggtttt atacaaaaaa atggctttaa agtgcctcaa    900
atagctgtta aacaaaatca aaatgatgtt tatgttcttc ttgttaaaaa tggaaaagta    960
gaaaaatctt ctgtacatat aagctaccaa aacaatgaat atgccattat tgacaaagga   1020
ttacaaaatg gcgataaaat cattttagat aactttaaaa aaattcaagt tggtagcgaa   1080
gttaaagaaa ttggagcaca ataa                                          1104
```

<210> SEQ ID NO 10
<211> LENGTH: 367
<212> TYPE: PRT
<213> ORGANISM: Campylobacter jejuni

<400> SEQUENCE: 10

```
Met Lys Leu Phe Gln Lys Asn Thr Ile Leu Ala Leu Gly Val Val Leu
1               5                   10                  15

Leu Leu Thr Ala Cys Ser Lys Glu Glu Ala Pro Lys Ile Gln Met Pro
            20                  25                  30

Pro Gln Pro Val Thr Thr Met Ser Ala Lys Ser Glu Asp Leu Pro Leu
        35                  40                  45

Ser Phe Thr Tyr Pro Ala Lys Leu Val Ser Asp Tyr Asp Val Ile Ile
    50                  55                  60

Lys Pro Gln Val Ser Gly Val Ile Glu Asn Lys Leu Phe Lys Ala Gly
65                  70                  75                  80

Asp Lys Val Lys Lys Gly Gln Thr Leu Phe Ile Ile Glu Gln Asp Lys
                85                  90                  95

Phe Lys Ala Ser Val Asp Ser Ala Tyr Gly Gln Ala Leu Met Ala Lys
            100                 105                 110

Ala Thr Phe Glu Asn Ala Ser Lys Asp Phe Asn Arg Ser Lys Ala Leu
        115                 120                 125

Phe Ser Lys Ser Ala Ile Ser Gln Lys Glu Tyr Asp Ser Ser Leu Ala
    130                 135                 140

Thr Phe Asn Asn Ser Lys Ala Ser Leu Ala Ser Ala Arg Ala Gln Leu
145                 150                 155                 160

Ala Asn Ala Arg Ile Asp Leu Asp His Thr Glu Ile Lys Ala Pro Phe
                165                 170                 175

Asp Gly Thr Ile Gly Asp Ala Leu Val Asn Ile Gly Asp Tyr Val Ser
            180                 185                 190

Ala Ser Thr Thr Glu Leu Val Arg Val Thr Asn Leu Asn Pro Ile Tyr
        195                 200                 205

Ala Asp Phe Phe Ile Ser Asp Thr Lys Leu Asn Leu Val Arg Asn
    210                 215                 220

Thr Gln Asn Gly Lys Trp Asp Leu Asp Ser Ile His Ala Asn Leu Asn
225                 230                 235                 240

Leu Asn Gly Glu Thr Val Gln Gly Lys Leu Tyr Phe Ile Asp Ser Val
                245                 250                 255

Ile Asp Ala Asn Ser Gly Thr Val Lys Ala Lys Ala Ile Phe Asp Asn
            260                 265                 270

Asn Asn Ser Thr Leu Leu Pro Gly Ala Phe Ala Thr Ile Thr Ser Glu
        275                 280                 285

Gly Phe Ile Gln Lys Asn Gly Phe Lys Val Pro Gln Ile Ala Val Lys
    290                 295                 300
```

Gln Asn Gln Asn Asp Val Tyr Val Leu Leu Val Lys Asn Gly Lys Val
305                 310                 315                 320

Glu Lys Ser Ser Val His Ile Ser Tyr Gln Asn Asn Glu Tyr Ala Ile
            325                 330                 335

Ile Asp Lys Gly Leu Gln Asn Gly Asp Lys Ile Ile Leu Asp Asn Phe
        340                 345                 350

Lys Lys Ile Gln Val Gly Ser Glu Val Lys Glu Ile Gly Ala Gln
        355                 360                 365

<210> SEQ ID NO 11
<211> LENGTH: 1104
<212> TYPE: DNA
<213> ORGANISM: Campylobacter jejuni

<400> SEQUENCE: 11
atgaaattat ttcaaaaaaa tactatttta gctttaggtg ttgtgctttt actcgctgct        60
tgcagcaaag aagaagcacc aaaaatacaa atgccgcctc aacctgtaac aaccatgagt       120
gctaaatctg aagatttacc acttagtttt acttaccctg ctaaacttgt cagtgattat       180
gatgtcatta taaaacctca agttagcggc gtaatagtaa ataaactttt taaagctgga       240
gataaggtaa aaaaggaca acattattt attatagaac aagataaatt taaagctagt        300
gttgattcag cttacggaca agctttaatg gctaaggcaa ctttcgaaaa tgcaagcaag       360
gattttaatc gttctaaagc tcttttttagc aaaagtgcaa tctctcaaaa agaatacgac      420
tcttctcttg ctacatttaa caattcaaaa gctagtctag caagtgctag agcacagctt      480
gcaaatgcaa gaattgatct agatcatacc gagataaaag ctcctttttga tggtactata    540 ggagatgctt tagttaatat aggagattat gtaagtgctt caacaactga actagttaga      600
gttacaaatt taaatcctat ttacgcagat ttcttttattt cagatacaga taaactaaat     660
ttagtccgca atactcaaag tggaaaatgg gatttagaca gcattcatgc aaatttaaat     720
cttaatggag aaaccgttca aggcaaactt tattttattg attcggttat agatgctaat      780
agtggaacag taaaagccaa agccgtattt gataacaata actcaacact tttaccgggt    840
gcttttgcaa caattacttc agaaggtttt atacaaaaaa atggctttaa agtgcctcaa     900
ataggtgtta acaagatca aaatgatgtt tatgttcttc ttgttaaaaa tggaaaagta     960
gaaaaatctt ctgtacatat aagctaccaa acaatgaat acgccattat tgacaaagga     1020
ttgcaaaatg gcgataaaat catttttagat aactttaaaa aaattcaagt tggtagcgaa    1080
gttaaagaaa ttggagcaca ataa                                             1104

<210> SEQ ID NO 12
<211> LENGTH: 367
<212> TYPE: PRT
<213> ORGANISM: Campylobacter jejuni

<400> SEQUENCE: 12

Met Lys Leu Phe Gln Lys Asn Thr Ile Leu Ala Leu Gly Val Val Leu
1               5                   10                  15

Leu Leu Ala Ala Cys Ser Lys Glu Glu Ala Pro Lys Ile Gln Met Pro
            20                  25                  30

Pro Gln Pro Val Thr Thr Met Ser Ala Lys Ser Glu Asp Leu Pro Leu
        35                  40                  45

Ser Phe Thr Tyr Pro Ala Lys Leu Val Ser Asp Tyr Asp Val Ile Ile
    50                  55                  60

Lys Pro Gln Val Ser Gly Val Ile Val Asn Lys Leu Phe Lys Ala Gly

```
                65                  70                  75                  80
Asp Lys Val Lys Lys Gly Gln Thr Leu Phe Ile Ile Glu Gln Asp Lys
                    85                  90                  95

Phe Lys Ala Ser Val Asp Ser Ala Tyr Gly Gln Ala Leu Met Ala Lys
            100                 105                 110

Ala Thr Phe Glu Asn Ala Ser Lys Asp Phe Asn Arg Ser Lys Ala Leu
        115                 120                 125

Phe Ser Lys Ser Ala Ile Ser Gln Lys Glu Tyr Asp Ser Ser Leu Ala
    130                 135                 140

Thr Phe Asn Asn Ser Lys Ala Ser Leu Ala Ser Ala Arg Ala Gln Leu
145                 150                 155                 160

Ala Asn Ala Arg Ile Asp Leu Asp His Thr Glu Ile Lys Ala Pro Phe
                165                 170                 175

Asp Gly Thr Ile Gly Asp Ala Leu Val Asn Ile Gly Asp Tyr Val Ser
            180                 185                 190

Ala Ser Thr Thr Glu Leu Val Arg Val Thr Asn Leu Asn Pro Ile Tyr
        195                 200                 205

Ala Asp Phe Phe Ile Ser Asp Thr Asp Lys Leu Asn Leu Val Arg Asn
    210                 215                 220

Thr Gln Ser Gly Lys Trp Asp Leu Asp Ser Ile His Ala Asn Leu Asn
225                 230                 235                 240

Leu Asn Gly Glu Thr Val Gln Gly Lys Leu Tyr Phe Ile Asp Ser Val
                245                 250                 255

Ile Asp Ala Asn Ser Gly Thr Val Lys Ala Lys Ala Val Phe Asp Asn
            260                 265                 270

Asn Asn Ser Thr Leu Leu Pro Gly Ala Phe Ala Thr Ile Thr Ser Glu
        275                 280                 285

Gly Phe Ile Gln Lys Asn Gly Phe Lys Val Pro Gln Ile Gly Val Lys
    290                 295                 300

Gln Asp Gln Asn Asp Val Tyr Val Leu Leu Val Lys Asn Gly Lys Val
305                 310                 315                 320

Glu Lys Ser Ser Val His Ile Ser Tyr Gln Asn Asn Glu Tyr Ala Ile
                325                 330                 335

Ile Asp Lys Gly Leu Gln Asn Gly Asp Lys Ile Ile Leu Asp Asn Phe
            340                 345                 350

Lys Lys Ile Gln Val Gly Ser Glu Val Lys Glu Ile Gly Ala Gln
        355                 360                 365

<210> SEQ ID NO 13
<211> LENGTH: 1479
<212> TYPE: DNA
<213> ORGANISM: Campylobacter jejuni

<400> SEQUENCE: 13
atgaataaaa taatttcaat tagtgctata gcaagtttta ctcttttgat ttcagcttgc      60
tctttaagtc caaatttaaa tattcccgaa gcaaactata gcattgataa taagcttgga     120
gccttatctt gggaaaaaga aaacaatagc tctatcacaa aaaattggtg aaagactttt     180
gatgatgaaa atttaaataa agtggttgat ttagcactta aaaataataa tgatttaaaa     240
cttgctttca tacacatgga acaagctgct gctcaattag gtatagattt tagcagtttg     300
ttgccaaaat tgatggtag cgcaagcgga agtcgtgcaa aaacagctat aaatgctcca     360
agcaatcgaa ctggggaagt aagttacggt aatgatttta aaatgggact taatttaagc     420
tatgaaatcg atctttgggg aaaatatcgc gatacatatc gcgcctcaaa atcaggcttt     480
```

-continued

```
aaagcaagtg agtatgatta tgaagctgca agactttctg ttatttcaaa tacagttcaa     540
acttatttta atcttgtaaa tgcttatgaa atgaaaatg ctcttaaaga agcctataaa      600
tctgcaaaag aaatttatag gattaatgat gaaaaatttc aagttggtgc tgtaggtgaa     660
tatgaacttg ctcaagcaag agccaactta gaaagtatgg ctttgcaata taatgaagca    720
aagttaaata agaaaatta ccttaaagct ttaaaaattt taacttcaaa tgatttaaat     780
gacatacttt acaaaaatca aagctatcaa gttttttaatc ttaaagaatt tgacattcca    840
actggaattt caagtaccat cttgcttcaa cgtccagata ttggctcttc tttagaaaaa    900
ttaactcagc aaaattatct tgttggagta gctcgcacgg ctttcttacc tagccttttct   960
ttaacaggat tattgggatt tgaaagcggg gatttagata ccttggttaa aggaggttct  1020
aagacttgga atataggtgg aaactttact ctgcctattt tcattggggg tgaaatttac   1080
caaaatgtaa atttagccaa gcttaataaa gatgaagctt ttgtaaatta tcaaaatact   1140
ttgattactg cttttggaga aattcgctat gctttagtag ctagaaaaac tatacgctta  1200
caatacgata atgcacaagc aagcgaacaa tcttacaaaa gaatctatga aattgctaaa   1260
gaacgctatg atataggaga atgtctttg caagattatt tagaggcacg tcaaaattgg    1320
cttaatgctg cggttgcttt taataatatt aaatattctt atgccaattc catagtagat   1380
gtaatcaaag catttggtgg aggatttgag caaagtgaag atacgagtaa aaatataaaa   1440
gaagaatcaa aaaatttaga tatgtctttt agagaatag                          1479
```

<210> SEQ ID NO 14
<211> LENGTH: 492
<212> TYPE: PRT
<213> ORGANISM: Campylobacter jejuni

<400> SEQUENCE: 14

```
Met Asn Lys Ile Ile Ser Ile Ser Ala Ile Ala Ser Phe Thr Leu Leu
1               5                   10                  15

Ile Ser Ala Cys Ser Leu Ser Pro Asn Leu Asn Ile Pro Glu Ala Asn
            20                  25                  30

Tyr Ser Ile Asp Asn Lys Leu Gly Ala Leu Ser Trp Glu Lys Glu Asn
        35                  40                  45

Asn Ser Ser Ile Thr Lys Asn Trp Trp Lys Asp Phe Asp Asp Glu Asn
    50                  55                  60

Leu Asn Lys Val Val Asp Leu Ala Leu Lys Asn Asn Asp Leu Lys
65                  70                  75                  80

Leu Ala Phe Ile His Met Glu Gln Ala Ala Gln Leu Gly Ile Asp
                85                  90                  95

Phe Ser Leu Leu Pro Lys Phe Asp Gly Ser Ala Ser Gly Ser Arg
            100                 105                 110

Ala Lys Thr Ala Ile Asn Ala Pro Ser Asn Arg Thr Gly Glu Val Ser
        115                 120                 125

Tyr Gly Asn Asp Phe Lys Met Gly Leu Asn Leu Ser Tyr Glu Ile Asp
    130                 135                 140

Leu Trp Gly Lys Tyr Arg Asp Thr Tyr Arg Ala Ser Lys Ser Gly Phe
145                 150                 155                 160

Lys Ala Ser Glu Tyr Asp Tyr Glu Ala Ala Arg Leu Ser Val Ile Ser
                165                 170                 175

Asn Thr Val Gln Thr Tyr Phe Asn Leu Val Asn Ala Tyr Glu Asn Glu
            180                 185                 190
```

Asn Ala Leu Lys Glu Ala Tyr Lys Ser Ala Lys Glu Ile Tyr Arg Ile
            195                 200                 205

Asn Asp Glu Lys Phe Gln Val Gly Ala Val Gly Glu Tyr Glu Leu Ala
210                 215                 220

Gln Ala Arg Ala Asn Leu Glu Ser Met Ala Leu Gln Tyr Asn Glu Ala
225                 230                 235                 240

Lys Leu Asn Lys Glu Asn Tyr Leu Lys Ala Leu Lys Ile Leu Thr Ser
            245                 250                 255

Asn Asp Leu Asn Asp Ile Leu Tyr Lys Asn Gln Ser Tyr Gln Val Phe
            260                 265                 270

Asn Leu Lys Glu Phe Asp Ile Pro Thr Gly Ile Ser Ser Thr Ile Leu
            275                 280                 285

Leu Gln Arg Pro Asp Ile Gly Ser Ser Leu Glu Lys Leu Thr Gln Gln
290                 295                 300

Asn Tyr Leu Val Gly Val Ala Arg Thr Ala Phe Leu Pro Ser Leu Ser
305                 310                 315                 320

Leu Thr Gly Leu Leu Gly Phe Glu Ser Gly Asp Leu Asp Thr Leu Val
            325                 330                 335

Lys Gly Gly Ser Lys Thr Trp Asn Ile Gly Asn Phe Thr Leu Pro
            340                 345                 350

Ile Phe His Trp Gly Glu Ile Tyr Gln Asn Val Asn Leu Ala Lys Leu
            355                 360                 365

Asn Lys Asp Glu Ala Phe Val Asn Tyr Gln Asn Thr Leu Ile Thr Ala
            370                 375                 380

Phe Gly Glu Ile Arg Tyr Ala Leu Val Ala Arg Lys Thr Ile Arg Leu
385                 390                 395                 400

Gln Tyr Asp Asn Ala Gln Ala Ser Glu Gln Ser Tyr Lys Arg Ile Tyr
            405                 410                 415

Glu Ile Ala Lys Glu Arg Tyr Asp Ile Gly Glu Met Ser Leu Gln Asp
            420                 425                 430

Tyr Leu Glu Ala Arg Gln Asn Trp Leu Asn Ala Ala Val Ala Phe Asn
            435                 440                 445

Asn Ile Lys Tyr Ser Tyr Ala Asn Ser Ile Val Asp Val Ile Lys Ala
450                 455                 460

Phe Gly Gly Gly Phe Glu Gln Ser Glu Asp Thr Ser Lys Asn Ile Lys
465                 470                 475                 480

Glu Glu Ser Lys Asn Leu Asp Met Ser Phe Arg Glu
            485                 490

<210> SEQ ID NO 15
<211> LENGTH: 1479
<212> TYPE: DNA
<213> ORGANISM: Campylobacter jejuni

<400> SEQUENCE: 15
atgaataaaa taatttcaat tagtgctata gcaagttttta ctcttttgat ttcagcttgc      60
tctttaagtc caaatttaaa tattcccgaa gcaaactata gcattgataa taagcttgga     120
gccttatctt gggaaaaaga aaacaatagc tctatcacaa aaaattggtg gaaagacttt     180
gatgatgaaa atttaaataa agtggttgat ttagcactta aaaataataa tgatttaaaa     240
cttgctttca tacacatgga acaagctgct gctcaattag gtatagattt tagcagtttg     300
ttgccaaaat ttgatggtag cgcaagcgga agtcgtgcaa aaacagctat aaatgctcca     360
agcaatcgaa ctggggaagt aagttacggt aatgatttta aatgggact taatttaagc      420

```
tatgaaatcg atctttgggg aaaatatcgc gatacatatc gcgcctcaaa atcaggcttt    480
aaagcaagtg agtatgatta tgaagctgca agactttctg ttatttcaaa tacagttcaa    540
acttatttta atcttgtaaa tgcttatgaa aatgaaaatg ctcttaaaga agcttatgaa    600
tctgcaaaag aaatttatag gattaatgat gaaaaatttc aagttggcgc tgtaggtgaa    660
tatgaacttg ctcaagcaag agccaactta gaaagtatgg ctttgcaata taatgaagca    720
aagttaaata agaaaatta ccttaaagct taaaaatttt taacttcaaa tgatttaaat    780
gacatacttt acaaaaatca agctatcaa gttttaatc ttaaagaatt tgacattcca    840
actgaatttt caagtaccat cttgcttcaa cgtccagata ttggctcttc tttagaaaaa    900
ttaactcagc aaaattatct tgttggagta gctcgcacgg ctttcttacc tagcctttct    960
ttaacaggat tattgggatt tgaaagcggg gatttagata ccttggttaa aggaggttct   1020
aagacttgga atataggtgg aaactttact ctgcctattt tcattgggg tgaaatttac   1080 caaaatgtaa atttagccaa gcttaataaa gatgaagctt ttgtaaatta tcaaaatact   1140
ttgattactg cttttggaga aattcgctat gctttagtag ctagaaaaac tatacgctta   1200
caatacgata tgcacaagc aagcgaacaa tcttacaaaa gaatctatga aattgctaaa   1260
gaacgctatg atataggaga atgtctttg caagattatt tagaggcacg tcaaaattgg   1320
cttaatgctg cggttgcttt taataatatt aaatattctt atgccaattc catagtagat   1380
gtaatcaaag catttggtgg aggatttgag caaagtgaag atacgagtaa aaatataaaa   1440
gaagaatcaa aaaatttaga tatgtctttt agagaatag                          1479
```

<210> SEQ ID NO 16
<211> LENGTH: 492
<212> TYPE: PRT
<213> ORGANISM: Campylobacter jejuni

<400> SEQUENCE: 16

```
Met Asn Lys Ile Ile Ser Ile Ser Ala Ile Ala Ser Phe Thr Leu Leu
1               5                   10                  15

Ile Ser Ala Cys Ser Leu Ser Pro Asn Leu Asn Ile Pro Glu Ala Asn
            20                  25                  30

Tyr Ser Ile Asp Asn Lys Leu Gly Ala Leu Ser Trp Glu Lys Glu Asn
        35                  40                  45

Asn Ser Ser Ile Thr Lys Asn Trp Trp Lys Asp Phe Asp Asp Glu Asn
    50                  55                  60

Leu Asn Lys Val Val Asp Leu Ala Leu Lys Asn Asn Asn Asp Leu Lys
65                  70                  75                  80

Leu Ala Phe Ile His Met Glu Gln Ala Ala Ala Gln Leu Gly Ile Asp
                85                  90                  95

Phe Ser Ser Leu Leu Pro Lys Phe Asp Gly Ser Ala Ser Gly Ser Arg
            100                 105                 110

Ala Lys Thr Ala Ile Asn Ala Pro Ser Asn Arg Thr Gly Glu Val Ser
        115                 120                 125

Tyr Gly Asn Asp Phe Lys Met Gly Leu Asn Leu Ser Tyr Glu Ile Asp
    130                 135                 140

Leu Trp Gly Lys Tyr Arg Asp Thr Tyr Arg Ala Ser Lys Ser Gly Phe
145                 150                 155                 160

Lys Ala Ser Glu Tyr Asp Tyr Glu Ala Ala Arg Leu Ser Val Ile Ser
                165                 170                 175

Asn Thr Val Gln Thr Tyr Phe Asn Leu Val Asn Ala Tyr Glu Asn Glu
            180                 185                 190
```

```
Asn Ala Leu Lys Glu Ala Tyr Glu Ser Ala Lys Glu Ile Tyr Arg Ile
            195                 200                 205

Asn Asp Glu Lys Phe Gln Val Gly Ala Val Gly Tyr Glu Leu Ala
210                 215                 220

Gln Ala Arg Ala Asn Leu Glu Ser Met Ala Leu Gln Tyr Asn Glu Ala
225                 230                 235                 240

Lys Leu Asn Lys Glu Asn Tyr Leu Lys Ala Leu Lys Ile Leu Thr Ser
            245                 250                 255

Asn Asp Leu Asn Asp Ile Leu Tyr Lys Asn Gln Ser Tyr Gln Val Phe
            260                 265                 270

Asn Leu Lys Glu Phe Asp Ile Pro Thr Gly Ile Ser Ser Thr Ile Leu
            275                 280                 285

Leu Gln Arg Pro Asp Ile Gly Ser Ser Leu Gly Lys Leu Thr Gln Gln
            290                 295                 300

Asn Tyr Leu Val Gly Val Ala Arg Thr Ala Phe Leu Pro Ser Leu Ser
305                 310                 315                 320

Leu Thr Gly Leu Leu Gly Phe Glu Ser Gly Asp Leu Asp Thr Leu Val
            325                 330                 335

Lys Gly Gly Ser Lys Thr Trp Asn Ile Gly Gly Asn Phe Thr Leu Pro
            340                 345                 350

Ile Phe His Trp Gly Glu Ile Tyr Gln Asn Val Asn Leu Ala Lys Leu
            355                 360                 365

Asn Lys Asp Glu Ala Phe Val Asn Tyr Gln Asn Thr Leu Ile Thr Ala
            370                 375                 380

Phe Gly Glu Ile Arg Tyr Ala Leu Val Ala Arg Lys Thr Ile Arg Leu
385                 390                 395                 400

Gln Tyr Asp Asn Ala Gln Ala Ser Glu Gln Ser Tyr Lys Arg Ile Tyr
            405                 410                 415

Glu Ile Ala Lys Glu Arg Tyr Asp Ile Gly Glu Met Ser Leu Gln Asp
            420                 425                 430

Tyr Leu Glu Ala Arg Gln Asn Trp Leu Asn Ala Ala Val Ala Phe Asn
            435                 440                 445

Asn Ile Lys Tyr Ser Tyr Ala Asn Ser Ile Val Asp Val Ile Lys Ala
            450                 455                 460

Phe Gly Gly Phe Glu Gln Ser Glu Asp Thr Ser Lys Asn Ile Lys
465                 470                 475                 480

Glu Glu Ser Lys Asn Leu Asp Met Ser Phe Arg Glu
            485                 490

<210> SEQ ID NO 17
<211> LENGTH: 840
<212> TYPE: DNA
<213> ORGANISM: Campylobacter jejuni

<400> SEQUENCE: 17
atgaaaaaaa tacttctaag tgttttaacg gcctttgttg cagtagtatt ggctgcttgt      60
ggaggaaatt ctgactctaa aactttaaat tctcttgata agatcaagca aaatggagtt     120
gttaggattg gggtatttgg cgataaacca ccttttggtt atgtggatga aaaggaaac     180 aatcaaggct atgatatagc tttagctaaa cgcatagcaa agaacttttt tggcgatgaa     240
aataaggtgc aatttgttct tgttgaagct gcaaataggg ttgagttttt aaaatcaaat     300
aaagtagata ttatttttgg ctaattttact caaactccgc aaagggcaga gcaggttgat     360
ttttgctcgc cttatatgaa ggtagcttta ggcgtagctg taccaaagga tagtaatata     420
```

```
actagcgtag aagatttaaa agataaaacc ttgcttttaa acaaaggcac aacagcagat    480
gcttatttta cgcaaaatta tcctaatatt aaaactttaa aatatgatca aaataccgaa    540
acctttgccg ctttgatgga taaagaggc gatgctttaa gtcatgataa taccttactt    600
tttgcttggg tgaaagatca tcctgatttt aaaatgggta ttaaagagtt aggtaacaaa    660
gatgttatcg caccagcggt taaaaaaggc gataaagaac ttaaagaatt tatcgataat    720
ttgatcatca aactaggcca agagcagttt tttcacaagg cttatgatga aactttaaaa    780
gctcattttg gagatgatgt taaggccgat gatgtagtga ttgaaggtgg aaaaatttaa    840
```

<210> SEQ ID NO 18
<211> LENGTH: 279
<212> TYPE: PRT
<213> ORGANISM: Campylobacter jejuni

<400> SEQUENCE: 18

```
Met Lys Lys Ile Leu Leu Ser Val Leu Thr Ala Phe Val Ala Val Val
1               5                   10                  15

Leu Ala Ala Cys Gly Gly Asn Ser Asp Ser Lys Thr Leu Asn Ser Leu
            20                  25                  30

Asp Lys Ile Lys Gln Asn Gly Val Val Arg Ile Gly Val Phe Gly Asp
        35                  40                  45

Lys Pro Pro Phe Gly Tyr Val Asp Glu Lys Gly Asn Asn Gln Gly Tyr
    50                  55                  60

Asp Ile Ala Leu Ala Lys Arg Ile Ala Lys Glu Leu Phe Gly Asp Glu
65                  70                  75                  80

Asn Lys Val Gln Phe Val Leu Val Glu Ala Ala Asn Arg Val Glu Phe
                85                  90                  95

Leu Lys Ser Asn Lys Val Asp Ile Ile Leu Ala Asn Phe Thr Gln Thr
            100                 105                 110

Pro Gln Arg Ala Glu Gln Val Asp Phe Cys Ser Pro Tyr Met Lys Val
        115                 120                 125

Ala Leu Gly Val Ala Val Pro Lys Asp Ser Asn Ile Thr Ser Val Glu
    130                 135                 140

Asp Leu Lys Asp Lys Thr Leu Leu Leu Asn Lys Gly Thr Thr Ala Asp
145                 150                 155                 160

Ala Tyr Phe Thr Gln Asn Tyr Pro Asn Ile Lys Thr Leu Lys Tyr Asp
                165                 170                 175

Gln Asn Thr Glu Thr Phe Ala Ala Leu Met Asp Lys Arg Gly Asp Ala
            180                 185                 190

Leu Ser His Asp Asn Thr Leu Leu Phe Ala Trp Val Lys Asp His Pro
        195                 200                 205

Asp Phe Lys Met Gly Ile Lys Glu Leu Gly Asn Lys Asp Val Ile Ala
    210                 215                 220

Pro Ala Val Lys Lys Gly Asp Lys Glu Leu Lys Glu Phe Ile Asp Asn
225                 230                 235                 240

Leu Ile Ile Lys Leu Gly Gln Glu Gln Phe Phe His Lys Ala Tyr Asp
                245                 250                 255

Glu Thr Leu Lys Ala His Phe Gly Asp Asp Val Lys Ala Asp Asp Val
            260                 265                 270

Val Ile Glu Gly Gly Lys Ile
        275
```

<210> SEQ ID NO 19

<211> LENGTH: 840
<212> TYPE: DNA
<213> ORGANISM: Campylobacter jejuni

<400> SEQUENCE: 19

```
atgaaaaaaa tacttctaag tgttttaacg acctttgttg cagtagtatt ggctgcttgt      60
ggaggaaatt ctgactctaa aactttaaat tctcttgata agatcaagca aaatggagtt     120
gttaggattg gggtatttgg cgataaacca ccttttggtt atgtggatga aaaaggaaac     180
aatcaaggct atgatatagc tttagctaaa cgcatagcaa agaacttttt ggcgatgaa      240
aataaggtgc aatttgttct tgttgaagct gcaaataggg ttgagttttt aaaatcaaat     300
aaagtagata ttattttggc taattttact caaactccag aaagagccga gcaggttgat     360
ttttgcttgc cttatatgaa ggtagcttta ggcgtagctg taccaaagga tagtaatata     420
actagcgtag aagatttaaa agataaaacc ttgcttttaa acaaaggcac aacagcagat     480
gcttatttta cgcaagatta tcctaatatt aaaactttaa aatatgatca aaataccgaa     540
acctttgccg ctttgatgga taaaagaggc gatgctttaa gtcatgataa taccttactt     600
tttgcttggg tgaaagatca tcctgatttt aaaatgggta tcaaagagtt aggtaacaaa     660
gatgttatcg caccagcggt taaaaaaggc gataaagaac ttaaagaatt tatcgataat     720
ttgatcatca aactaggcca agagcagttt tttcacaagg cttatgatga aactttaaaa     780
gctcattttg gagatgatgt taaggctgat gatgtagtga ttgaaggtgg aaaaatttaa     840
```

<210> SEQ ID NO 20
<211> LENGTH: 279
<212> TYPE: PRT
<213> ORGANISM: Campylobacter jejuni

<400> SEQUENCE: 20

Met Lys Lys Ile Leu Leu Ser Val Leu Thr Thr Phe Val Ala Val Val
1               5                   10                  15

Leu Ala Ala Cys Gly Gly Asn Ser Asp Ser Lys Thr Leu Asn Ser Leu
            20                  25                  30

Asp Lys Ile Lys Gln Asn Gly Val Val Arg Ile Gly Val Phe Gly Asp
        35                  40                  45

Lys Pro Pro Phe Gly Tyr Val Asp Glu Lys Gly Asn Asn Gln Gly Tyr
    50                  55                  60

Asp Ile Ala Leu Ala Lys Arg Ile Ala Lys Glu Leu Phe Gly Asp Glu
65                  70                  75                  80

Asn Lys Val Gln Phe Val Leu Val Glu Ala Ala Asn Arg Val Glu Phe
                85                  90                  95

Leu Lys Ser Asn Lys Val Asp Ile Ile Leu Ala Asn Phe Thr Gln Thr
            100                 105                 110

Pro Glu Arg Ala Glu Gln Val Asp Phe Cys Leu Pro Tyr Met Lys Val
        115                 120                 125

Ala Leu Gly Val Ala Val Pro Lys Asp Ser Asn Ile Thr Ser Val Glu
    130                 135                 140

Asp Leu Lys Asp Lys Thr Leu Leu Leu Asn Lys Gly Thr Thr Ala Asp
145                 150                 155                 160

Ala Tyr Phe Thr Gln Asp Tyr Pro Asn Ile Lys Thr Leu Lys Tyr Asp
                165                 170                 175

Gln Asn Thr Glu Thr Phe Ala Ala Leu Met Asp Lys Arg Gly Asp Ala
            180                 185                 190

Leu Ser His Asp Asn Thr Leu Leu Phe Ala Trp Val Lys Asp His Pro

```
            195                 200                 205
Asp Phe Lys Met Gly Ile Lys Glu Leu Gly Asn Lys Asp Val Ile Ala
    210                 215                 220

Pro Ala Val Lys Lys Gly Asp Lys Glu Leu Lys Glu Phe Ile Asp Asn
225                 230                 235                 240

Leu Ile Ile Lys Leu Gly Gln Glu Gln Phe Phe His Lys Ala Tyr Asp
                245                 250                 255

Glu Thr Leu Lys Ala His Phe Gly Asp Asp Val Lys Ala Asp Asp Val
            260                 265                 270

Val Ile Glu Gly Gly Lys Ile
        275
```

<210> SEQ ID NO 21
<211> LENGTH: 756
<212> TYPE: DNA
<213> ORGANISM: Campylobacter jejuni

<400> SEQUENCE: 21

```
atgaaaaaaa tattaagcat tgctctagtt gctttagttg gtttatttt  aggtgcttgt     60
agtgattcta aaataaaga  atcaaatgca agtgtagaat  taaaggttgg aactgctcca   120
aattataaac cttttaatta  taaagaaaac tcaaaactta caggttttga tactgatttg   180
gttgaagaga ttgccaaaaa  aaatggtatt aaaattgttt gggttgaaac caatttcgat   240
ggattgattc ctgctttaaa  agctggcaaa atcgatatga ttgcctcagc tatgagcgca   300
actgacgaaa gaagacaaag  tgttgatttt accaaacctt actatatgag  taaaaatctt   360
tatcttaagc taaaaaacaa  cgactctctt caaacgaaaa atgatttaga aggtaaaaaa   420
ataggagttc aactaggaac  tttacaagaa aatactgcaa aagctatcaa aaatgcacaa   480
gtacaaagca ataaagattt  aaacatagct gttttagcac taaaaaacaa caaaatcgat   540
gctattgtag ctgatcaaga  tactgctaaa ggttttttag ctgaaaatcc agaattggta   600
agcttctacc aagaaacaga  tggagggaaa ggctttagtt ttgcttttga taaaaataaa   660
caaaaaaata ttattgaaat  atttaacaaa ggcatagatg aagcaaaaac tgatggattt   720
tatgatactt taattaaaaa  atatgaatta gaataa                              756
```

<210> SEQ ID NO 22
<211> LENGTH: 251
<212> TYPE: PRT
<213> ORGANISM: Campylobacter jejuni

<400> SEQUENCE: 22

```
Met Lys Lys Ile Leu Ser Ile Ala Leu Val Ala Leu Val Gly Leu Phe
1               5                   10                  15

Leu Gly Ala Cys Ser Asp Ser Lys Asn Lys Glu Ser Asn Ala Ser Val
            20                  25                  30

Glu Leu Lys Val Gly Thr Ala Pro Asn Tyr Lys Pro Phe Asn Tyr Lys
        35                  40                  45

Glu Asn Ser Lys Leu Thr Gly Phe Asp Thr Asp Leu Val Glu Glu Ile
    50                  55                  60

Ala Lys Lys Asn Gly Ile Lys Ile Val Trp Val Glu Thr Asn Phe Asp
65                  70                  75                  80

Gly Leu Ile Pro Ala Leu Lys Ala Gly Lys Ile Asp Met Ile Ala Ser
                85                  90                  95

Ala Met Ser Ala Thr Asp Glu Arg Arg Gln Ser Val Asp Phe Thr Lys
            100                 105                 110
```

Pro Tyr Tyr Met Ser Lys Asn Leu Tyr Leu Lys Leu Lys Asn Asn Asp
            115                 120                 125

Ser Leu Gln Thr Lys Asn Asp Leu Glu Gly Lys Lys Ile Gly Val Gln
    130                 135                 140

Leu Gly Thr Leu Gln Glu Asn Thr Ala Lys Ala Ile Lys Asn Ala Gln
145                 150                 155                 160

Val Gln Ser Asn Lys Asp Leu Asn Ile Ala Val Leu Ala Leu Lys Asn
                165                 170                 175

Asn Lys Ile Asp Ala Ile Val Ala Asp Gln Asp Thr Ala Lys Gly Phe
            180                 185                 190

Leu Ala Glu Asn Pro Glu Leu Val Ser Phe Tyr Gln Glu Thr Asp Gly
            195                 200                 205

Gly Glu Gly Phe Ser Phe Ala Phe Asp Lys Asn Lys Gln Lys Asn Ile
        210                 215                 220

Ile Glu Ile Phe Asn Lys Gly Ile Asp Glu Ala Lys Thr Asp Gly Phe
225                 230                 235                 240

Tyr Asp Thr Leu Ile Lys Lys Tyr Glu Leu Glu
            245                 250

<210> SEQ ID NO 23
<211> LENGTH: 756
<212> TYPE: DNA
<213> ORGANISM: Campylobacter jejuni

<400> SEQUENCE: 23
atgaaaaaaa tattaagcat tgccctagtt gctttagttg gtttattttt aggtgcttgt        60
agtgattcta aaaataaaga atcaaatgca agtgtagaat taaaggttgg aactgctcca       120
aattataaac ttttaattaa taagaaaaac tcaaaactta caggttttga tactgatttg       180
gttgaagaga tcgccaaaaa aaatggtatt aaaattgttt gggttgaaac caatttcgat       240
ggattgattc ctgctttaaa agctggcaaa tcgatatga ttgcctcagc tatgagcgca        300
actgacgaaa aagacaaag tgttgatttt accaaacctt actatatgag taaaaatctt        360
tatcttaagc taaaaacaa cgactctctt caaacgaaaa atgatttaga aggtaaaaaa        420
ataggagttc aactaggaac tttacaagaa atactgcaa aagctatcaa aaatgcacaa        480
gtacaaagca ataagatttt aaacatagct gttttagcac taaaaacaa caaaatcgat        540 gctattgtag ctgatcaaga tactgctaaa ggttttttag ctgaaaatcc agaattggta       600
agtttctacc aagaaacaga tggaggagaa ggctttagtt ttgcttttga taaaaataaa       660 caaaagata ttattgaaat atttaacaaa ggcatagatg aagcaaaaac tgatggattt        720
tataatactt taattaaaaa atatgaatta gaataa                                  756

<210> SEQ ID NO 24
<211> LENGTH: 251
<212> TYPE: PRT
<213> ORGANISM: Campylobacter jejuni

<400> SEQUENCE: 24

Met Lys Lys Ile Leu Ser Ile Ala Leu Val Ala Leu Val Gly Leu Phe
1               5                   10                  15

Leu Gly Ala Cys Ser Asp Ser Lys Asn Lys Glu Ser Asn Ala Ser Val
            20                  25                  30

Glu Leu Lys Val Gly Thr Ala Pro Asn Tyr Lys Pro Phe Asn Tyr Lys
        35                  40                  45

| | | | | | | | | | | | | | | |
|---|---|---|---|---|---|---|---|---|---|---|---|---|---|---|
Glu | Asn | Ser | Lys | Leu | Thr | Gly | Phe | Asp | Thr | Asp | Leu | Val | Glu | Ile
 | 50 | | | | 55 | | | | 60 | | | | |

Ala Lys Lys Asn Gly Ile Lys Ile Val Trp Val Glu Thr Asn Phe Asp
65              70              75              80

Gly Leu Ile Pro Ala Leu Lys Ala Gly Lys Ile Asp Met Ile Ala Ser
                85              90              95

Ala Met Ser Ala Thr Asp Glu Arg Arg Gln Ser Val Asp Phe Thr Lys
            100             105             110

Pro Tyr Tyr Met Ser Lys Asn Leu Tyr Leu Lys Leu Asn Asn Asp
        115             120             125

Ser Leu Gln Thr Lys Asn Asp Leu Glu Gly Lys Lys Ile Gly Val Gln
    130             135             140

Leu Gly Thr Leu Gln Glu Asn Thr Ala Lys Ala Ile Lys Asn Ala Gln
145             150             155             160

Val Gln Ser Asn Lys Asp Leu Asn Ile Ala Val Leu Ala Leu Lys Asn
                165             170             175

Asn Lys Ile Asp Ala Ile Val Ala Asp Gln Asp Thr Ala Lys Gly Phe
            180             185             190

Leu Ala Glu Asn Pro Glu Leu Val Ser Phe Tyr Gln Glu Thr Asp Gly
        195             200             205

Gly Glu Gly Phe Ser Phe Ala Phe Asp Lys Asn Lys Gln Lys Asp Ile
    210             215             220

Ile Glu Ile Phe Asn Lys Gly Ile Asp Glu Ala Lys Thr Asp Gly Phe
225             230             235             240

Tyr Asn Thr Leu Ile Lys Lys Tyr Glu Leu Glu
                245             250

<210> SEQ ID NO 25
<211> LENGTH: 624
<212> TYPE: DNA
<213> ORGANISM: Campylobacter jejuni

<400> SEQUENCE: 25
atgaaaaaaa caaaaatttt aggaacagct cttattggag ctttgctttt tagtggttgt      60
gcgcaaacag cttatacaga tggaaaggca agtcaggtaa aaaaaggcga tgctttaacc     120
ttgggtcttg atagacaaga ttttgaaagt gcagctgaaa ctatgataaa tagtatgtta     180
agcgatcctg cttttgcaaa tattaaacca ggtacaagaa aggttattgc tattggtagg     240
gttgtgaatg ataccccgca agaatcgat actgaaaaac tcaccgcaaa aatcacttct      300
gcattaagaa aatcaggtaa atttgttcta acttcagcag ttgctgcagg cggagcactt     360
gatagcatga gtgaagatgt aagagaatta agagataatg atgagtttaa tcaaaaaacc     420
atagcaaaaa aagggacatt ggtatcgcct gattttctc ttgcgggtaa aattagacaa      480
gataatgtaa aacttagcaa tggtaaaact caagtagaat acttttctctt actaagactt    540 actgatttaa catcaggttt agtttattgg gaagatgaac aaactattga taaaaccggt     600
tctagtaaat cagttacttg gtaa                                            624

<210> SEQ ID NO 26
<211> LENGTH: 207
<212> TYPE: PRT
<213> ORGANISM: Campylobacter jejuni

<400> SEQUENCE: 26

Met Lys Lys Thr Lys Ile Leu Gly Thr Ala Leu Ile Gly Ala Leu Leu
1               5                   10                  15

```
Phe Ser Gly Cys Ala Gln Thr Ala Tyr Thr Asp Gly Lys Ala Ser Gln
            20                  25                  30

Val Lys Lys Gly Asp Ala Leu Thr Leu Gly Leu Asp Arg Gln Asp Phe
        35                  40                  45

Glu Ser Ala Ala Glu Thr Met Ile Asn Ser Met Leu Ser Asp Pro Ala
    50                  55                  60

Phe Ala Asn Ile Lys Pro Gly Thr Arg Lys Val Ile Ala Ile Gly Arg
65                  70                  75                  80

Val Val Asn Asp Thr Pro Gln Arg Ile Asp Thr Glu Lys Leu Thr Ala
                85                  90                  95

Lys Ile Thr Ser Ala Leu Arg Lys Ser Gly Lys Phe Val Leu Thr Ser
            100                 105                 110

Ala Val Ala Ala Gly Gly Ala Leu Asp Ser Met Ser Glu Asp Val Arg
        115                 120                 125

Glu Leu Arg Asp Asn Asp Glu Phe Asn Gln Lys Thr Ile Ala Lys Lys
    130                 135                 140

Gly Thr Leu Val Ser Pro Asp Phe Ser Leu Ala Gly Lys Ile Arg Gln
145                 150                 155                 160

Asp Asn Val Lys Leu Ser Asn Gly Lys Thr Gln Val Glu Tyr Phe Phe
                165                 170                 175

Leu Leu Arg Leu Thr Asp Leu Thr Ser Gly Leu Val Tyr Trp Glu Asp
            180                 185                 190

Glu Gln Thr Ile Asp Lys Thr Gly Ser Ser Lys Ser Val Thr Trp
    195                 200                 205

<210> SEQ ID NO 27
<211> LENGTH: 624
<212> TYPE: DNA
<213> ORGANISM: Campylobacter jejuni

<400> SEQUENCE: 27
atgaaaaaaa caaaaatttt aggaacagct cttattggag ctttgctttt tagtggttgt    60
gcgcaaacag cttatacaga tggaaaggca agtcaggtga aaaaagggga tgctttaacc   120
ttgggtcttg atagacaaga ttttgaaagt gcagctgaaa ctatgataaa tagtatgtta   180
agcgatcctg cttttgcaaa tattaaacca ggtacaagaa aggttattgc tattggtagg   240
gttgtgaatg atacccccgca agaatcgat actgaaaaac tcaccgcaaa atcacttct    300 gcattaagaa aatcaggtaa atttgttcta acttcagcag ttgctgcagg cggagcactt   360
gatagcatga gtgaagatgt aagagaatta agagataatg atgagtttaa tcaaaaaacc   420
atagcaaaaa aagggacatt ggtatcgcct gattttctc ttgcgggtaa aattagacaa    480
gataatgtaa aacttagcaa tggtaaaact caagtagaat acttttttctt actaagactt   540 actgatttaa catcaggttt agtttattgg gaagatgaac aaactatcga taaaaccggt   600
tctagtaaaa cagttacttg gtaa                                          624

<210> SEQ ID NO 28
<211> LENGTH: 207
<212> TYPE: PRT
<213> ORGANISM: Campylobacter jejuni

<400> SEQUENCE: 28

Met Lys Lys Thr Lys Ile Leu Gly Thr Ala Leu Ile Gly Ala Leu Leu
1               5                   10                  15

Phe Ser Gly Cys Ala Gln Thr Ala Tyr Thr Asp Gly Lys Ala Ser Gln
```

```
                  20                  25                  30
Val Lys Lys Gly Asp Ala Leu Thr Leu Gly Leu Asp Arg Gln Asp Phe
             35                  40                  45

Glu Ser Ala Ala Glu Thr Met Ile Asn Ser Met Leu Ser Asp Pro Ala
 50                  55                  60

Phe Ala Asn Ile Lys Pro Gly Thr Arg Lys Val Ile Ala Ile Gly Arg
 65                  70                  75                  80

Val Val Asn Asp Thr Pro Gln Arg Ile Asp Thr Glu Lys Leu Thr Ala
                 85                  90                  95

Lys Ile Thr Ser Ala Leu Arg Lys Ser Gly Lys Phe Val Leu Thr Ser
            100                 105                 110

Ala Val Ala Ala Gly Gly Ala Leu Asp Ser Met Ser Glu Asp Val Arg
            115                 120                 125

Glu Leu Arg Asp Asn Asp Glu Phe Asn Gln Lys Thr Ile Ala Lys Lys
            130                 135                 140

Gly Thr Leu Val Ser Pro Asp Phe Ser Leu Ala Gly Lys Ile Arg Gln
145                 150                 155                 160

Asp Asn Val Lys Leu Ser Asn Gly Lys Thr Gln Val Glu Tyr Phe Phe
                165                 170                 175

Leu Leu Arg Leu Thr Asp Leu Thr Ser Gly Leu Val Tyr Trp Glu Asp
            180                 185                 190

Glu Gln Thr Ile Asp Lys Thr Gly Ser Ser Lys Thr Val Thr Trp
            195                 200                 205

<210> SEQ ID NO 29
<211> LENGTH: 1203
<212> TYPE: DNA
<213> ORGANISM: Campylobacter jejuni

<400> SEQUENCE: 29
atgaaaataa ttaaaattct ttttttaggc ttattttaa gcctaagtct taatgctaaa      60
gttataacca caacttcaac aaaatcaagc acaggtgaag gcacaggctt gactagggaa    120
gatgcgataa acaatgccat tatagaagct ataggaaaaa tgagtggagt aagcatcaat    180
tctcttaaga atctaacac tagcgtttca actgataatt caggttcaaa tatacaagat    240
aattacagcg agcaaatttc aaaagccacc aaaggtagag ctgatactta tgaaatcaat    300
agtgttgaac aagatgcaaa tggtaaatat acagccaatg taacgatttt taaaaccaca    360
acaacaaaaa agtatcaagc tccaggttta agtgcagata atagaagaag tattactgtt    420
tttgattcta ctccagatgc tgcaaaaaga ggtataggct cagctttgca acaaaaaatc    480
atttctgatt tattgcaaag tcgtaaattt aatgtttag accgtgattc tagtggctat    540
tatgaaatgg aaaagctttt aatcaaaagt ggcgacgcag ctagcgatga agtttataaa    600
cttaaaaata tgttagcaac agattatatt ttattgtttt ctatttcagg acttgaaggt    660
aaacaaaaaa caagcaattt aacaggaaaa agcaaaactg aaattgaagt tatcgtagat    720
tatcgtgtgc ttttatttgc tacaagacaa attaaatttt ctaatacttt aagcatgaaa    780
gtcaatctta aagacaatag tcttagtgcc aatgaaaccg cactcaaaca aattgcaaat    840
cgtatagcag agatatttt aaacgcaatt tatcctttga agttgcaag tgttgaaaac    900 aatgaagtaa tattttctca aagcttaaat caaggtgatg tttatgaatg ttttgctctt    960
gggaaggtta taaagatac ttatacaaaa gaaaatacag gaagagtaga aagcaaaaca   1020
ggaagtattg aaatcactcg cacaagccct aaattttctt atgcaaaaat cacagaaggt   1080
```

```
agtgtaaaag tgggcgatat ttgcagacct ttaagtaata ctggtagtgg aaatggctac    1140
actataggtc gtgatgcaaa ttatcaaacc caagaaggcg gcggagtaaa tctaggcttt    1200
taa                                                                  1203
```

<210> SEQ ID NO 30
<211> LENGTH: 400
<212> TYPE: PRT
<213> ORGANISM: Campylobacter jejuni

<400> SEQUENCE: 30

```
Met Lys Ile Ile Lys Ile Leu Phe Leu Gly Leu Phe Leu Ser Leu Ser
1               5                   10                  15

Leu Asn Ala Lys Val Ile Thr Thr Thr Ser Thr Lys Ser Ser Thr Gly
            20                  25                  30

Glu Gly Thr Gly Leu Thr Arg Glu Asp Ala Ile Asn Asn Ala Ile Ile
        35                  40                  45

Glu Ala Ile Gly Lys Met Ser Gly Val Ser Ile Asn Ser Leu Lys Lys
    50                  55                  60

Ser Asn Thr Ser Val Ser Thr Asp Asn Ser Gly Ser Asn Ile Gln Asp
65                  70                  75                  80

Asn Tyr Ser Glu Gln Ile Ser Lys Ala Thr Lys Gly Arg Ala Asp Thr
                85                  90                  95

Tyr Glu Ile Asn Ser Val Glu Gln Asp Ala Asn Gly Lys Tyr Thr Ala
            100                 105                 110

Asn Val Thr Ile Phe Lys Thr Thr Thr Lys Lys Tyr Gln Ala Pro
        115                 120                 125

Gly Leu Ser Ala Asp Asn Arg Arg Ser Ile Thr Val Phe Asp Ser Thr
    130                 135                 140

Pro Asp Ala Ala Lys Arg Gly Ile Gly Ser Ala Leu Gln Gln Lys Ile
145                 150                 155                 160

Ile Ser Asp Leu Leu Gln Ser Arg Lys Phe Asn Val Leu Asp Arg Asp
                165                 170                 175

Ser Ser Gly Tyr Tyr Glu Met Glu Lys Ala Leu Ile Lys Ser Gly Asp
            180                 185                 190

Ala Ala Ser Asp Glu Val Tyr Lys Leu Lys Asn Met Leu Ala Thr Asp
        195                 200                 205

Tyr Ile Leu Leu Phe Ser Ile Ser Gly Leu Glu Gly Lys Gln Lys Thr
    210                 215                 220

Ser Asn Leu Thr Gly Lys Ser Lys Thr Glu Ile Glu Val Ile Val Asp
225                 230                 235                 240

Tyr Arg Val Leu Leu Phe Ala Thr Arg Gln Ile Lys Phe Ser Asn Thr
                245                 250                 255

Leu Ser Met Lys Val Asn Leu Lys Asp Asn Ser Leu Ser Ala Asn Glu
            260                 265                 270

Thr Ala Leu Lys Gln Ile Ala Asn Arg Ile Ala Gly Asp Ile Leu Asn
        275                 280                 285

Ala Ile Tyr Pro Leu Lys Val Ala Ser Val Glu Asn Asn Glu Val Ile
    290                 295                 300

Phe Ser Gln Ser Leu Asn Gln Gly Asp Val Tyr Glu Cys Phe Ala Leu
305                 310                 315                 320

Gly Lys Val Ile Lys Asp Thr Tyr Thr Lys Glu Asn Thr Gly Arg Val
                325                 330                 335

Glu Ser Lys Thr Gly Ser Ile Glu Ile Thr Arg Thr Ser Pro Lys Phe
            340                 345                 350
```

```
Ser Tyr Ala Lys Ile Thr Glu Gly Ser Val Lys Val Gly Asp Ile Cys
        355                 360                 365

Arg Pro Leu Ser Asn Thr Gly Ser Gly Asn Gly Tyr Thr Ile Gly Arg
    370                 375                 380

Asp Ala Asn Tyr Gln Thr Gln Glu Gly Gly Val Asn Leu Gly Phe
385                 390                 395                 400

<210> SEQ ID NO 31
<211> LENGTH: 1203
<212> TYPE: DNA
<213> ORGANISM: Campylobacter jejuni

<400> SEQUENCE: 31
atgaaaataa ttaaaattct ttttttagga ttattttaa gcctaagtct taatgctaaa     60
gttgtgacta caacttcaac aaaatcaagc acaggcgaag cacaggctt gactagggaa    120 gatgcgataa acaatgccat tatagaagct ataggaaaaa tgagtggagt aagcatcaat    180
tctcttaaga aatctaacac tagcgtttca actgataatt caggttcaaa atacaagat    240 aattacagcg agcaaatttc aaaagccacc aaaggtagag ctgatactta tgaaatcaat    300
agtgttgaac aagatgcaaa tggtaaatat acagccaatg taacgatttt taaaaccaca    360
acaacaaaaa agtatcaagt tccaggttta agcgcagata atagaagaag tattactgtt    420
tttgattcta ctctagatgc tgcaaaaaga ggtataggct cagcttttgca acaaaaaatc    480 atttctgatt tattgcaaag tcgtaaattt aatgttttag accgtgattc tagtggctat    540
tatgaaatgg aaaaagcttt aatcaaaagt ggcgacgcag ctagcgatga agtttataaa    600
cttaaaaata tgttagcaac agattatatt ttattgtttt ctatttcagg acttgaaggt    660
aaacaaaaaa caagcaattt aacaggaaaa agcaaaactg aaattgaagt tatcgtagat    720
tatcgtgtgc ttttatttgc tacaagacaa attaaatttt ctaatacttt aagcatgaaa    780
gtcaatctta aagacaatag tcttagtgcc aatgaaaccg cactcaaaca aattgcaaat    840
cgtatagcag gagatatttt aaacgcaatt tatcctttga agttgcaag tgttgaaaac    900 aatgaagtaa tattttctca agcttaaat caaggtgatg tttatgaatg ttttgctctt    960
gggaaggtta taaagatac ttatacaaaa gaaaatacag gaagagtaga aagcaaaaca   1020
ggaagtattg aaatcactcg cacaagccct aaattttctt atgcaaaaat cacagaaggt   1080
agtgtaaaag tgggcgatat ttgcagacct ttaagtaata ctggtagtgg aaatggctac   1140
actataggtc gtgatgcaaa ttatcaaacc caagaaggcg gcggagtaaa tctaggcttt   1200
taa                                                                1203

<210> SEQ ID NO 32
<211> LENGTH: 400
<212> TYPE: PRT
<213> ORGANISM: Campylobacter jejuni

<400> SEQUENCE: 32

Met Lys Ile Ile Lys Ile Leu Phe Leu Gly Leu Phe Leu Ser Leu Ser
1               5                   10                  15

Leu Asn Ala Lys Val Val Thr Thr Thr Ser Thr Lys Ser Ser Thr Gly
            20                  25                  30

Glu Gly Thr Gly Leu Thr Arg Glu Asp Ala Ile Asn Asn Ala Ile Ile
        35                  40                  45

Glu Ala Ile Gly Lys Met Ser Gly Val Ser Ile Asn Ser Leu Lys Lys
    50                  55                  60
```

| | | | | | | | | | | | | | | |
|---|---|---|---|---|---|---|---|---|---|---|---|---|---|---|
|Ser|Asn|Thr|Ser|Val|Ser|Thr|Asp|Asn|Ser|Gly|Ser|Asn|Ile|Gln|Asp|
|65| | | |70| | | |75| | | |80| | | |

Asn Tyr Ser Glu Gln Ile Ser Lys Ala Thr Lys Gly Arg Ala Asp Thr
                85                  90                  95

Tyr Glu Ile Asn Ser Val Glu Gln Asp Ala Asn Gly Lys Tyr Thr Ala
            100                 105                 110

Asn Val Thr Ile Phe Lys Thr Thr Thr Lys Lys Tyr Gln Val Pro
        115                 120                 125

Gly Leu Ser Ala Asp Asn Arg Arg Ser Ile Thr Val Phe Asp Ser Thr
        130                 135                 140

Leu Asp Ala Ala Lys Arg Gly Ile Gly Ser Ala Leu Gln Gln Lys Ile
145                 150                 155                 160

Ile Ser Asp Leu Leu Gln Ser Arg Lys Phe Asn Val Leu Asp Arg Asp
                165                 170                 175

Ser Ser Gly Tyr Tyr Glu Met Glu Lys Ala Leu Ile Lys Ser Gly Asp
            180                 185                 190

Ala Ala Ser Asp Glu Val Tyr Lys Leu Lys Asn Met Leu Ala Thr Asp
        195                 200                 205

Tyr Ile Leu Leu Phe Ser Ile Ser Gly Leu Glu Gly Lys Gln Lys Thr
210                 215                 220

Ser Asn Leu Thr Gly Lys Ser Lys Thr Glu Ile Glu Val Ile Asp
225                 230                 235                 240

Tyr Arg Val Leu Leu Phe Ala Thr Arg Gln Ile Lys Phe Ser Asn Thr
                245                 250                 255

Leu Ser Met Lys Val Asn Leu Lys Asp Asn Ser Leu Ser Ala Asn Glu
            260                 265                 270

Thr Ala Leu Lys Gln Ile Ala Asn Arg Ile Ala Gly Asp Ile Leu Asn
        275                 280                 285

Ala Ile Tyr Pro Leu Lys Val Ala Ser Val Glu Asn Asn Glu Val Ile
290                 295                 300

Phe Ser Gln Ser Leu Asn Gln Gly Asp Val Tyr Glu Cys Phe Ala Leu
305                 310                 315                 320

Gly Lys Val Ile Lys Asp Thr Tyr Thr Lys Glu Asn Thr Gly Arg Val
                325                 330                 335

Glu Ser Lys Thr Gly Ser Ile Glu Ile Thr Arg Thr Ser Pro Lys Phe
            340                 345                 350

Ser Tyr Ala Lys Ile Thr Glu Gly Ser Val Lys Val Gly Asp Ile Cys
        355                 360                 365

Arg Pro Leu Ser Asn Thr Gly Ser Gly Asn Gly Tyr Thr Ile Gly Arg
370                 375                 380

Asp Ala Asn Tyr Gln Thr Gln Glu Gly Gly Val Asn Leu Gly Phe
385                 390                 395                 400

<210> SEQ ID NO 33
<211> LENGTH: 2220
<212> TYPE: DNA
<213> ORGANISM: Campylobacter jejuni

<400> SEQUENCE: 33
atgaaaaaac atcttattag tatttgtgct ttagttgcta tggccaatgc agcaaccatt    60
aaagatatta aatttatcgg attaaatcat ttatcgaaca caagcgctat aaatatcgcg   120
gggcttaaaa taggcgagga aataaatcct gcaaaaatca acactgctat tcttaatctt   180
tataaacaaa attatttcga aaatattgca gtagaaaaca acaatggaat tttggaaatt   240

```
atagttactg aaaaaccaac tatagcaaag gttactatca caggtatagc ttcaaatgat    300
agaaaacaag ttgaaagtat tttagggatt aaaagaggta cactacttga tgaaggaaat    360
ataaaagaag ctattgaacg cattaaagct tattatgaag caaaaagtta ttttgatact    420
attgtagaat acaaaaaaaa gactttagaa aatactgatg gactagagct tgaatttata    480
gtaaatcgtg gtgaaaatat cattattgat aatgttcatt taagtggagc aaagaaattt    540
tcatattctg atatagaacc tgctgttgtt aacaaagaaa aagaatttat gggatggatg    600
tggggacgca atgatggaaa attaaaagtt tttgaactta gtaacgatag ttcaagaatt    660
gctgatgaat atatgaaaaa aggatattta gatgttcaag tatcctcccc ttatcttaaa    720
acctacacag atacttatca agcaaatttg acttatttta tcaaagaagg aaagccttat    780
aaaattaaaa gtataagcat agaaaatcct ttatttgatg ataagcaaaa tgcacaaacc    840
gtaaaagatt taagatcaag cgctggcaaa actatcaata tcgaagacat tagaaaagat    900
gttaaaacca tagaaacaca aagtgctgat tgggttatg cgtttgtaga agtctatcct    960
gatattcaaa aaatgatca aactcaagaa gccaccgttg tatttaaagt aatccctcac   1020
gataaagttt atataagaaa tgttattatt tcaggaaatt cacgcaccgt agatcgcgtc   1080
atacgccgag aattatatat aacagaaggt aatttataca atagaacaga cttaagcgag   1140
tcaaaaaatg ctttaaaaag aacttcttat tttgacgatg taaatatcaa agaagaaaaa   1200
gttgatgata cacatattga tttgattgtt gatgttaaag aagcttctac aggagctatt   1260
tctggaggca ttggctatgg atcaagcgat ggtattttgc ttaacgcttc tttatcggat   1320
acaaatatct ttggttcagg aataaaaagc tctgtaagcg tagataaaag cgatgatact   1380
ttatcgggaa ggattagtct cgtaaatcca cgcgttcttg atagtcaata tagtctgggt   1440
ggaacacttt attcaaatga ctatgaatgg gataattatt cagaaaaaaa ttacggcttt   1500
gatataacaa ttggacgcca atttgcaaga tactataatg taagcttaac ttataatctt   1560
gaacaaagcg atatatatca cttaagtcca actcttttaa gaacaggata tgaacttggc   1620
aaaagtatta aaagctctat aactccagca atcaccttta acgatacaga tgattattat   1680
ctgccacgat caggtattat tgcttcaact agtttagaat acgctggact tggcggagat   1740
caagaattta tttcatcaag ctctaaattt aacttttatc aaggtttgca agactatata   1800
ggatatgatc ttatttatcg ctataaagcg agttttttata agtatgggat gaaggttat   1860
ttaccaatta accaaagaat ttatttaggt ggtattagat cgatacgcgg ttttgaaagc   1920
agaacagtaa gtcctaaaaa tcaatgggga gatgaaatag gcggaaccat agcttttgcc   1980
aattccgtag aacttagttt tcctttgatt gatagaatca aacttcgtgg tagcgtgttt   2040
tttgattatg gtatgatagg gcgtaaaaat ttagatgaaa taaaaagaat gagtacaggt   2100
ataggcattg aatggattac acctattgga cctttacaac ttgtatttgc caaacctctt   2160
aatgataaaa aaggtgatga tactaatagt tttgaattta atcttggaac acgctttttaa  2220
```

<210> SEQ ID NO 34
<211> LENGTH: 739
<212> TYPE: PRT
<213> ORGANISM: Campylobacter jejuni

<400> SEQUENCE: 34

Met Lys Lys His Leu Ile Ser Ile Cys Ala Leu Val Ala Met Ala Asn
1               5                   10                  15

Ala Ala Thr Ile Lys Asp Ile Lys Phe Ile Gly Leu Asn His Leu Ser

```
            20                  25                  30
Asn Thr Ser Ala Ile Asn Ile Ala Gly Leu Lys Ile Gly Glu Glu Ile
            35                  40                  45

Asn Pro Ala Lys Ile Asn Thr Ala Ile Leu Asn Leu Tyr Lys Gln Asn
        50                  55                  60

Tyr Phe Glu Asn Ile Ala Val Glu Asn Asn Gly Ile Leu Glu Ile
 65                  70                  75                  80

Ile Val Thr Glu Lys Pro Thr Ile Ala Lys Val Thr Ile Thr Gly Ile
                85                  90                  95

Ala Ser Asn Asp Arg Lys Gln Val Glu Ser Ile Leu Gly Ile Lys Arg
            100                 105                 110

Gly Thr Leu Leu Asp Glu Gly Asn Ile Lys Glu Ala Ile Glu Arg Ile
        115                 120                 125

Lys Ala Tyr Tyr Glu Ala Lys Ser Tyr Phe Asp Thr Ile Val Glu Tyr
    130                 135                 140

Lys Lys Lys Thr Leu Glu Asn Thr Asp Gly Leu Glu Leu Glu Phe Ile
145                 150                 155                 160

Val Asn Arg Gly Glu Asn Ile Ile Ile Asp Asn Val His Leu Ser Gly
                165                 170                 175

Ala Lys Lys Phe Ser Tyr Ser Asp Ile Glu Pro Ala Val Val Asn Lys
            180                 185                 190

Glu Lys Glu Phe Met Gly Trp Met Trp Gly Arg Asn Asp Gly Lys Leu
        195                 200                 205

Lys Val Phe Glu Leu Ser Asn Asp Ser Ser Arg Ile Ala Asp Glu Tyr
    210                 215                 220

Met Lys Lys Gly Tyr Leu Asp Val Gln Val Ser Ser Pro Tyr Leu Lys
225                 230                 235                 240

Thr Tyr Thr Asp Thr Tyr Gln Ala Asn Leu Thr Tyr Phe Ile Lys Glu
                245                 250                 255

Gly Lys Pro Tyr Lys Ile Lys Ser Ile Ser Ile Glu Asn Pro Leu Phe
            260                 265                 270

Asp Asp Lys Gln Asn Ala Gln Thr Val Lys Asp Leu Arg Ser Ser Ala
        275                 280                 285

Gly Lys Thr Ile Asn Ile Glu Asp Ile Arg Lys Asp Val Lys Thr Ile
    290                 295                 300

Glu Thr Gln Ser Ala Asp Leu Gly Tyr Ala Phe Val Glu Val Tyr Pro
305                 310                 315                 320

Asp Ile Gln Lys Asn Asp Gln Thr Gln Glu Ala Thr Val Val Phe Lys
                325                 330                 335

Val Ile Pro His Asp Lys Val Tyr Ile Arg Asn Val Ile Ser Gly
            340                 345                 350

Asn Ser Arg Thr Val Asp Arg Val Ile Arg Arg Glu Leu Tyr Ile Thr
        355                 360                 365

Glu Gly Asn Leu Tyr Asn Arg Thr Asp Leu Ser Glu Ser Lys Asn Ala
    370                 375                 380

Leu Lys Arg Thr Ser Tyr Phe Asp Asp Val Asn Ile Lys Glu Glu Lys
385                 390                 395                 400

Val Asp Asp Thr His Ile Asp Leu Ile Val Asp Val Lys Glu Ala Ser
                405                 410                 415

Thr Gly Ala Ile Ser Gly Gly Ile Gly Tyr Gly Ser Ser Asp Gly Ile
            420                 425                 430

Leu Leu Asn Ala Ser Leu Ser Asp Thr Asn Ile Phe Gly Ser Gly Ile
        435                 440                 445
```

```
Lys Ser Ser Val Ser Val Asp Lys Ser Asp Asp Thr Leu Ser Gly Arg
    450                 455                 460

Ile Ser Leu Val Asn Pro Arg Val Leu Asp Ser Gln Tyr Ser Leu Gly
465                 470                 475                 480

Gly Thr Leu Tyr Ser Asn Asp Tyr Glu Trp Asp Asn Tyr Ser Glu Lys
            485                 490                 495

Asn Tyr Gly Phe Asp Ile Thr Ile Gly Arg Gln Phe Ala Arg Tyr Tyr
            500                 505                 510

Asn Val Ser Leu Thr Tyr Asn Leu Glu Gln Ser Asp Ile Tyr His Leu
        515                 520                 525

Ser Pro Thr Leu Leu Arg Thr Gly Tyr Glu Leu Gly Lys Ser Ile Lys
    530                 535                 540

Ser Ser Ile Thr Pro Ala Ile Thr Phe Asn Asp Thr Asp Asp Tyr Tyr
545                 550                 555                 560

Leu Pro Arg Ser Gly Ile Ile Ala Ser Thr Ser Leu Glu Tyr Ala Gly
            565                 570                 575

Leu Gly Gly Asp Gln Glu Phe Ile Ser Ser Ser Lys Phe Asn Phe
            580                 585                 590

Tyr Gln Gly Leu Gln Asp Tyr Ile Gly Tyr Asp Leu Ile Tyr Arg Tyr
        595                 600                 605

Lys Ala Ser Phe Tyr Lys Val Trp Asp Glu Gly Tyr Leu Pro Ile Asn
    610                 615                 620

Gln Arg Ile Tyr Leu Gly Gly Ile Arg Ser Ile Arg Gly Phe Glu Ser
625                 630                 635                 640

Arg Thr Val Ser Pro Lys Asn Gln Trp Gly Asp Glu Ile Gly Gly Thr
            645                 650                 655

Ile Ala Phe Ala Asn Ser Val Glu Leu Ser Phe Pro Leu Ile Asp Arg
            660                 665                 670

Ile Lys Leu Arg Gly Ser Val Phe Phe Asp Tyr Gly Met Ile Gly Arg
        675                 680                 685

Lys Asn Leu Asp Glu Ile Lys Arg Met Ser Thr Gly Ile Gly Ile Glu
    690                 695                 700

Trp Ile Thr Pro Ile Gly Pro Leu Gln Leu Val Phe Ala Lys Pro Leu
705                 710                 715                 720

Asn Asp Lys Lys Gly Asp Asp Thr Asn Ser Phe Glu Phe Asn Leu Gly
            725                 730                 735

Thr Arg Phe

<210> SEQ ID NO 35
<211> LENGTH: 2220
<212> TYPE: DNA
<213> ORGANISM: Campylobacter jejuni

<400> SEQUENCE: 35
atgaaaaaac atcttattag tatttgtgct ttagttgcta tagccaatgc agcaaccatt      60
aaagatatta aatttatcgg attaaatcat ttatcgaaca caagcgctat aaatatcacg     120
gggcttaaaa taggcgagga aataaatcct gcaaaaatca acactgctat tcttaatctt     180
tataaacaaa attatttcga aaatattgca gtagaaaaca caatggaat ttggaaatt      240 atagttaccg aaaaaccaac tatagcaaag gttactatca caggtatagc ttcaaatgat     300
agaaaacaag ttgaaagtat tttagggatt aaagaggca cactacttga tgaaggaagt     360 ataaagaag ctattgaacg cattaaagct tattatgaag caaaaagtta ttttgatact     420
```

```
attgtagaat acaaaaaaaa gactttagaa ataccgatg gactagagct tgaatttata     480
gtaaatcgtg gcgaaaatat cattattgat aatgttcatt taagtggagc caagaaattt    540
tcatattctg atatagaacc tgctgttgtt aacaaagaaa aagaattat gggatggatg     600
tggggacgca atgatggaaa attaaaagtt tttgaactta gtaacgatag ttcaagaatt    660
gctgatgaat atatgaaaaa aggatattta gatgttcaag tatcctcgcc ttatcttaaa    720
acctacacag atacttatca agcaaatttg acttatttta tcaaagaagg aaagccttat    780
aaaattaaaa gtataagcat agaaaatcct ttatttgatg ataaacaaaa tgcacaaacc    840
gtaaaagatt taagatcaag tgctggcaaa actatcaata ttgaagacat tagaaaagat    900
gttaaaacca tagaaacaca aagtgctgat ttgggttatg cgtttgtaga agtctatcct   960
gatattcaaa aaaatgatca aactcaagaa gccaccgttg tatttaaagt aatccctcac   1020
gataaagttt atataagaaa tgttattatt tcaggaaatt cacgtactgt agatcgcgtc   1080
atacgccgag aattatatat aacagaaggt aatttataca atagaacaga cttaagcgag   1140
tcaaaaaatg ctttaaaaag aacttcttat tttgacgatg taaatatcaa agaagaaaaa   1200
gttgatgata cacatattga tttgattgtt gatgttaaag aagcttctac aggagctatt   1260
tctggaggca ttggctatgg atcaagcgat ggtattttgc ttaacgcttc tttatcagat   1320
acaaatatct ttggttcagg aataaaaagc tctgtaagcg tagataaaag cgatgatacc   1380
ttatcaggaa ggattagtct cataaatcca cgcgttcttg atagtcaata tagtctgggt   1440
ggaacacttt attcaaatga ctatgaatgg gataattatt cagaaaaaaa ttacggcttt   1500
gatataacag ttggacgcca atttgcaaga tactataatg taagcttaac ttataatctt   1560
gaacaaagcg atatatacca cttaagtcca actcttttaa gaacaggata tgaacttggc   1620
aaaagtatta aaagctctat aactccagca atcacctttta acaatacaga tgattattat   1680
ctgccacgat caggtatcat tgcttcaact agtttagaat acgctggact tggcggagat   1740
caagaattta tttcatcaag ctctaaattt aactttttatc aaggtttaca agactatata   1800
ggatatgatc ttatttatcg ctataaagcg agttttttata aagtatggga tgaaggctat   1860
ttaccgatta atcaaagaat ttatttaggt ggtattagat cgatacgcgg ttttgaaagc   1920
agaacagtaa gtcctaaaaa ccaatgggga gatgaagtag gtggaaccat agcttttgcc   1980
aattctgtag aacttagttt tcctttgatt gatagaatca aacttcgtgg tagcgtgttt   2040
tttgattatg gtatgatagg acgtaaaaat ttagatgaaa taaaaagaat gagtacaggt   2100
ataggcattg aatggattac accaattggg cctttacagc ttgtatttgc caaacctctt   2160
aatgataaaa aaggtgatga tactaatagt tttgaattta atcttggaac acgcttttaa   2220
```

<210> SEQ ID NO 36
<211> LENGTH: 739
<212> TYPE: PRT
<213> ORGANISM: Campylobacter jejuni

<400> SEQUENCE: 36

```
Met Lys Lys His Leu Ile Ser Ile Cys Ala Leu Val Ala Ile Ala Asn
1               5                   10                  15

Ala Ala Thr Ile Lys Asp Ile Lys Phe Ile Gly Leu Asn His Leu Ser
            20                  25                  30

Asn Thr Ser Ala Ile Asn Ile Thr Gly Leu Lys Ile Gly Glu Glu Ile
        35                  40                  45

Asn Pro Ala Lys Ile Asn Thr Ala Ile Leu Asn Leu Tyr Lys Gln Asn
    50                  55                  60
```

```
Tyr Phe Glu Asn Ile Ala Val Glu Asn Asn Gly Ile Leu Glu Ile
 65                  70                  75                  80

Ile Val Thr Glu Lys Pro Thr Ile Ala Lys Val Thr Ile Thr Gly Ile
                 85                  90                  95

Ala Ser Asn Asp Arg Lys Gln Val Glu Ser Ile Leu Gly Ile Lys Arg
                100                 105                 110

Gly Thr Leu Leu Asp Glu Gly Ser Ile Lys Glu Ala Ile Glu Arg Ile
            115                 120                 125

Lys Ala Tyr Tyr Glu Ala Lys Ser Tyr Phe Asp Thr Ile Val Glu Tyr
130                 135                 140

Lys Lys Lys Thr Leu Glu Asn Thr Asp Gly Leu Glu Leu Glu Phe Ile
145                 150                 155                 160

Val Asn Arg Gly Glu Asn Ile Ile Ile Asp Asn Val His Leu Ser Gly
                165                 170                 175

Ala Lys Lys Phe Ser Tyr Ser Asp Ile Glu Pro Ala Val Val Asn Lys
            180                 185                 190

Glu Lys Glu Phe Met Gly Trp Met Trp Gly Arg Asn Asp Gly Lys Leu
        195                 200                 205

Lys Val Phe Glu Leu Ser Asn Asp Ser Ser Arg Ile Ala Asp Glu Tyr
210                 215                 220

Met Lys Lys Gly Tyr Leu Asp Val Gln Val Ser Ser Pro Tyr Leu Lys
225                 230                 235                 240

Thr Tyr Thr Asp Thr Tyr Gln Ala Asn Leu Thr Tyr Phe Ile Lys Glu
                245                 250                 255

Gly Lys Pro Tyr Lys Ile Lys Ser Ser Ile Glu Asn Pro Leu Phe
            260                 265                 270

Asp Asp Lys Gln Asn Ala Gln Thr Val Lys Asp Leu Arg Ser Ser Ala
        275                 280                 285

Gly Lys Thr Ile Asn Ile Glu Asp Ile Arg Lys Asp Val Lys Thr Ile
    290                 295                 300

Glu Thr Gln Ser Ala Asp Leu Gly Tyr Ala Phe Val Glu Val Tyr Pro
305                 310                 315                 320

Asp Ile Gln Lys Asn Asp Gln Thr Gln Glu Ala Thr Val Phe Lys
                325                 330                 335

Val Ile Pro His Asp Lys Val Tyr Ile Arg Asn Val Ile Ile Ser Gly
            340                 345                 350

Asn Ser Arg Thr Val Asp Arg Val Arg Arg Glu Leu Tyr Ile Thr
        355                 360                 365

Glu Gly Asn Leu Tyr Asn Arg Thr Asp Leu Ser Glu Ser Lys Asn Ala
    370                 375                 380

Leu Lys Arg Thr Ser Tyr Phe Asp Asp Val Asn Ile Lys Glu Glu Lys
385                 390                 395                 400

Val Asp Asp Thr His Ile Asp Leu Ile Val Asp Val Lys Glu Ala Ser
                405                 410                 415

Thr Gly Ala Ile Ser Gly Gly Ile Gly Tyr Gly Ser Ser Asp Gly Ile
            420                 425                 430

Leu Leu Asn Ala Ser Leu Ser Asp Thr Asn Ile Phe Gly Ser Gly Ile
        435                 440                 445

Lys Ser Ser Val Ser Val Asp Lys Ser Asp Asp Thr Leu Ser Gly Arg
    450                 455                 460

Ile Ser Leu Ile Asn Pro Arg Val Leu Asp Ser Gln Tyr Ser Leu Gly
465                 470                 475                 480
```

Gly Thr Leu Tyr Ser Asn Asp Tyr Glu Trp Asp Asn Tyr Ser Glu Lys
            485                 490                 495

Asn Tyr Gly Phe Asp Ile Thr Val Gly Arg Gln Phe Ala Arg Tyr Tyr
        500                 505                 510

Asn Val Ser Leu Thr Tyr Asn Leu Glu Gln Ser Asp Ile Tyr His Leu
        515                 520                 525

Ser Pro Thr Leu Leu Arg Thr Gly Tyr Glu Leu Gly Lys Ser Ile Lys
        530                 535                 540

Ser Ser Ile Thr Pro Ala Ile Thr Phe Asn Asn Thr Asp Tyr Tyr
545                 550                 555                 560

Leu Pro Arg Ser Gly Ile Ile Ala Ser Thr Ser Leu Glu Tyr Ala Gly
            565                 570                 575

Leu Gly Gly Asp Gln Glu Phe Ile Ser Ser Ser Lys Phe Asn Phe
            580                 585                 590

Tyr Gln Gly Leu Gln Asp Tyr Ile Gly Tyr Asp Leu Ile Tyr Arg Tyr
            595                 600                 605

Lys Ala Ser Phe Tyr Lys Val Trp Asp Glu Gly Tyr Leu Pro Ile Asn
        610                 615                 620

Gln Arg Ile Tyr Leu Gly Gly Ile Arg Ser Ile Arg Gly Phe Glu Ser
625                 630                 635                 640

Arg Thr Val Ser Pro Lys Asn Gln Trp Gly Asp Glu Val Gly Gly Thr
            645                 650                 655

Ile Ala Phe Ala Asn Ser Val Glu Leu Ser Phe Pro Leu Ile Asp Arg
            660                 665                 670

Ile Lys Leu Arg Gly Ser Val Phe Phe Asp Tyr Gly Met Ile Gly Arg
            675                 680                 685

Lys Asn Leu Asp Glu Ile Lys Arg Met Ser Thr Gly Ile Gly Ile Glu
        690                 695                 700

Trp Ile Thr Pro Ile Gly Pro Leu Gln Leu Val Phe Ala Lys Pro Leu
705                 710                 715                 720

Asn Asp Lys Lys Gly Asp Asp Thr Asn Ser Phe Glu Phe Asn Leu Gly
            725                 730                 735

Thr Arg Phe

<210> SEQ ID NO 37
<211> LENGTH: 930
<212> TYPE: DNA
<213> ORGANISM: Campylobacter jejuni

<400> SEQUENCE: 37
ttgaaaaaat atttattttc ctgtgtttta gcctccattt taacccaatc agctacggct      60
gtagaatttc aagaaggttt tagtggaaat ttaagcatag gtgtgggtgc aagggatatt     120
aaaagtaata tttcaacctt ggcaaacagt gattatctaa gcagtcacaa tgctgataat     180
tcagactcct ctttcattcc ttttatcggt gcagaacttt actatggtaa tcttatagat     240
aatgatagaa ttttattaa aaactacaat ggaagagata tcagcggtat agctttaggc     300
tacgaaagag cttatttaga gcgttttagc acttcttttt ctgtaatttc ctctttaaga     360
gaaaaagctt atgcaaatcc ttatgcaata ggaaatagag aagaaactga tgttgataga     420
tatggtttta aaatctctca actttatgaa agtgattttg ggaaatttac cacttcatat     480
ttatttagca aaaacaaata tgataaagac actatcgcac aaagctcttt aaaaagggag     540
ggatattatc acgaaattga attaaactat aattatagct tattaaacct agggttaaat     600
tatgattaca atgatgcaga cggaaaagct caaagctatt caagatatgg ttttagtata     660

```
ggaacaaatt tggcttttgc taatgattac atcttcactc caaatttaaa tcttagcaaa      720
tatgaagcag taggaactga tcctatcttc cacaaaaaac aagatggtaa tatagttaag      780
cttaatttaa aagttgttaa aaatcaattt ttgggttata acggacttta tggttttgca      840
aattatggca tagaaaaaag aaatagcgat ataggatttt atgatgaaac ctatcaaatt      900
gtcctaactg gtataggata taaattctaa                                        930
```

```
<210> SEQ ID NO 38
<211> LENGTH: 309
<212> TYPE: PRT
<213> ORGANISM: Campylobacter jejuni

<400> SEQUENCE: 38
```

Met Lys Lys Tyr Leu Phe Ser Cys Val Leu Ala Ser Ile Leu Thr Gln
1               5                   10                  15

Ser Ala Thr Ala Val Glu Phe Gln Glu Gly Phe Ser Gly Asn Leu Ser
            20                  25                  30

Ile Gly Val Gly Ala Arg Asp Ile Lys Ser Asn Ile Ser Thr Leu Ala
        35                  40                  45

Asn Ser Asp Tyr Leu Ser Ser His Asn Ala Asp Asn Ser Asp Ser Ser
    50                  55                  60

Phe Ile Pro Phe Ile Gly Ala Glu Leu Tyr Tyr Gly Asn Leu Ile Asp
65                  70                  75                  80

Asn Asp Arg Ile Phe Ile Lys Asn Tyr Asn Gly Arg Asp Ile Ser Gly
                85                  90                  95

Ile Ala Leu Gly Tyr Glu Arg Ala Tyr Leu Glu Arg Phe Ser Thr Ser
            100                 105                 110

Phe Ser Val Ile Ser Ser Leu Arg Glu Lys Ala Tyr Ala Asn Pro Tyr
        115                 120                 125

Ala Ile Gly Asn Arg Glu Glu Thr Asp Val Asp Arg Tyr Gly Phe Lys
    130                 135                 140

Ile Ser Gln Leu Tyr Glu Ser Asp Phe Gly Lys Phe Thr Thr Ser Tyr
145                 150                 155                 160

Leu Phe Ser Lys Asn Lys Tyr Asp Lys Asp Thr Ile Ala Gln Ser Ser
                165                 170                 175

Leu Lys Arg Glu Gly Tyr Tyr His Glu Ile Glu Leu Asn Tyr Asn Tyr
            180                 185                 190

Ser Leu Leu Asn Leu Gly Leu Asn Tyr Asp Tyr Asn Asp Ala Asp Gly
        195                 200                 205

Lys Ala Gln Ser Tyr Ser Arg Tyr Gly Phe Ser Ile Gly Thr Asn Leu
    210                 215                 220

Ala Phe Ala Asn Asp Tyr Ile Phe Thr Pro Asn Leu Asn Leu Ser Lys
225                 230                 235                 240

Tyr Glu Ala Val Gly Thr Asp Pro Ile Phe His Lys Lys Gln Asp Gly
                245                 250                 255

Asn Ile Val Lys Leu Asn Leu Lys Val Val Lys Asn Gln Phe Leu Gly
            260                 265                 270

Tyr Asn Gly Leu Tyr Gly Phe Ala Asn Tyr Gly Ile Glu Lys Arg Asn
        275                 280                 285

Ser Asp Ile Gly Phe Tyr Asp Glu Thr Tyr Gln Ile Val Leu Thr Gly
    290                 295                 300

Ile Gly Tyr Lys Phe
305

<210> SEQ ID NO 39
<211> LENGTH: 930
<212> TYPE: DNA
<213> ORGANISM: Campylobacter jejuni

<400> SEQUENCE: 39

```
ttgaaaaaat atttattttc ctgtgtttta gcctccattt taacccaatc agctacggct      60
gtagaatttc aagaaggttt tagtggaaat ttaagcatag gtgtgggtgc aagggatatt     120
aaaagtaata tttcaacctt ggcaaacagt gattatctaa gcagttacaa tgctgataat     180
tcagactcct ctttcattcc ttttatcggt gcagaacttt actatggtaa tcttatagat     240
aatgatagaa tttttattaa aaactacaat ggaagagata tcagcggtat agctttaggc     300
tacgaaagag cttatttaga gcgttttagc acttctttt ctgtaatttc ctctttaaga      360
gaaaaagctt atgcaaatcc ttatgcaata ggaaatagag aagaaactga tgttgataga     420
tatggtttta aaatctctca actttatgaa agtgattttg ggaaatttac cacttcatat     480
ttatttagca aaaacaaata tgataaagac actatcgcac aaagctcttt aaaaagggag     540
ggatattatc acgaaattga attaaactat aattatagct tattaaacct agggttaaat     600
tatgattaca atgatgcaga cggaaaagct caaagctatt caagatatgg ttttagcata     660
ggaacaaatt tggcttttgc taatgattac atcttcactc caaatttaaa tcttagcaaa     720
tatgaagcag taggaactga tcctatcttc cacaaaaaac aagatggtaa tatagttaag     780
cttaatttaa aagttgttaa aaatcaattt ttgggttata acggacttta tggttttgca     840
aattatggca tagaaaaaag aaatagcgat ataggatttt atgatgaaac ctatcaaatt     900
atcctaactg gtataggata taaattctaa                                       930
```

<210> SEQ ID NO 40
<211> LENGTH: 309
<212> TYPE: PRT
<213> ORGANISM: Campylobacter jejuni

<400> SEQUENCE: 40

Met Lys Lys Tyr Leu Phe Ser Cys Val Leu Ala Ser Ile Leu Thr Gln
1               5                   10                  15

Ser Ala Thr Ala Val Glu Phe Gln Glu Gly Phe Ser Gly Asn Leu Ser
            20                  25                  30

Ile Gly Val Gly Ala Arg Asp Ile Lys Ser Asn Ile Ser Thr Leu Ala
        35                  40                  45

Asn Ser Asp Tyr Leu Ser Ser Tyr Asn Ala Asp Asn Ser Asp Ser Ser
    50                  55                  60

Phe Ile Pro Phe Ile Gly Ala Glu Leu Tyr Tyr Gly Asn Leu Ile Asp
65                  70                  75                  80

Asn Asp Arg Ile Phe Ile Lys Asn Tyr Asn Gly Arg Asp Ile Ser Gly
                85                  90                  95

Ile Ala Leu Gly Tyr Glu Arg Ala Tyr Leu Glu Arg Phe Ser Thr Ser
            100                 105                 110

Phe Ser Val Ile Ser Ser Leu Arg Glu Lys Ala Tyr Ala Asn Pro Tyr
        115                 120                 125

Ala Ile Gly Asn Arg Glu Glu Thr Asp Val Asp Arg Tyr Gly Phe Lys
    130                 135                 140

Ile Ser Gln Leu Tyr Glu Ser Asp Phe Gly Lys Phe Thr Thr Ser Tyr
145                 150                 155                 160

Leu Phe Ser Lys Asn Lys Tyr Asp Lys Asp Thr Ile Ala Gln Ser Ser

|  | 165 | | | 170 | | | | 175 | | | |
|---|---|---|---|---|---|---|---|---|---|---|---|

Leu Lys Arg Glu Gly Tyr Tyr His Glu Ile Glu Leu Asn Tyr Asn Tyr
           180                      185                190

Ser Leu Leu Asn Leu Gly Leu Asn Tyr Asp Tyr Asn Asp Ala Asp Gly
    195                   200                205

Lys Ala Gln Ser Tyr Ser Arg Tyr Gly Phe Ser Ile Gly Thr Asn Leu
    210                   215                220

Ala Phe Ala Asn Asp Tyr Ile Phe Thr Pro Asn Leu Asn Leu Ser Lys
225               230                 235              240

Tyr Glu Ala Val Gly Thr Asp Pro Ile Phe His Lys Lys Gln Asp Gly
            245                 250              255

Asn Ile Val Lys Leu Asn Leu Lys Val Val Lys Asn Gln Phe Leu Gly
        260                 265                270

Tyr Asn Gly Leu Tyr Gly Phe Ala Asn Tyr Gly Ile Glu Lys Arg Asn
    275                 280                 285

Ser Asp Ile Gly Phe Tyr Asp Glu Thr Tyr Gln Ile Ile Leu Thr Gly
    290                 295               300

Ile Gly Tyr Lys Phe
305

<210> SEQ ID NO 41
<211> LENGTH: 1422
<212> TYPE: DNA
<213> ORGANISM: Campylobacter jejuni

<400> SEQUENCE: 41

```
atgaaaacta ggttttcact tattttaagt gcttgtcttc tttcatcttc acttttgct     60 aaaaatacag atgatgagat aactaagctt caaaaacagc ttgcacaaat tcaagctgaa    120
cttgcacaaa tcagaaaaga agagaagct caagttaaac aaaatgaagc tgtaaaagct    180
gaacttgccg atcttaatga tagagccgat gaaacagaat ttcaagctgc tttgagcaag    240
gttaaatttg acttgagtt ttcaacagcg gtttcaaata caaactataa agttagcgga    300
caagattata gtgctaataa caaatggatg aatgagcttc atttaaatat gaatgctgat    360
attaatgata aaaccaaatt ctatggtcgt ttatctatgg ctaaaaattg gtctcaaatg    420
ggttggagtg gtactcctta tgacttagat gcaggaagaa acacaagatc aagtgggcct    480
gtactttatg tagatagagc ttatcttgac tactatatca cacctgagtg gattgcaacc    540
gtaggaagac agccaggaac cgatggtccg ggaagtaatc ttagaaacaa tgctttaaga    600
caatcaactt atccagcctt agcgattaat gctctaggtg atgcagcagt gatcacttat    660
aagcctgaaa gtttgcaaga tcataaggta gctatccgtg cagcttatgg taaaacctat    720
caatgggatg aagaaagtgg taagtaaga gactggatga gtgatcaaaa agatgctgat    780
gcaaatcttt actatgctgc agtagaagga gagcttccta gaaaggtat gggagataat    840 cttattatct tcaatgtggc tcatatgact gattttgcat tgcctattcc aggatctatg    900
ttattgggtg atgatgatga agttgttaat ttaggtaatc ttactttagc taatattcat    960
tttgaaaatt acaaagcttt tggaacaaat tttaattggt tcgcatcttt gggatattct   1020
aatggaagca ataatgagat aaatccatta ttaagcacag ctcttcaaag taaaggttat   1080
ggcaatggta agttcaatga aaaagacggc tatgctgtgc atgtaggcgg acgctatgat   1140
tttactaagg cttaaaaagt agggtatgag ttcttctggg gaagtagata ctggtatact   1200
atgagccgtc caagtatcaa tgatccgctt aatataagaa tgacaagagg aacggcacat   1260
```

-continued

```
gatttttatg tgatttatca acttgataga tatcaattct tacgcttaag ctacaccaat    1320
atccaaaaca tttggggtaa tcgtggctta ccatttggtg gagcgaaaaa agataaagca    1380
agagctgata atatcatgtt aatgtataat gtaaaattct aa                      1422
```

<210> SEQ ID NO 42
<211> LENGTH: 473
<212> TYPE: PRT
<213> ORGANISM: Campylobacter jejuni

<400> SEQUENCE: 42

| Met | Lys | Thr | Arg | Phe | Ser | Leu | Ile | Leu | Ser | Ala | Cys | Leu | Leu | Ser | Ser |
|---|---|---|---|---|---|---|---|---|---|---|---|---|---|---|---|
| 1 | | | | 5 | | | | | 10 | | | | | 15 | |

| Ser | Leu | Phe | Ala | Lys | Asn | Thr | Asp | Asp | Glu | Ile | Thr | Lys | Leu | Gln | Lys |
|---|---|---|---|---|---|---|---|---|---|---|---|---|---|---|---|
| | | | 20 | | | | | 25 | | | | | 30 | | |

| Gln | Leu | Ala | Gln | Ile | Gln | Ala | Glu | Leu | Ala | Gln | Ile | Arg | Lys | Glu | Arg |
|---|---|---|---|---|---|---|---|---|---|---|---|---|---|---|---|
| | | 35 | | | | | 40 | | | | | 45 | | | |

| Glu | Ala | Gln | Val | Lys | Gln | Asn | Glu | Ala | Val | Lys | Ala | Glu | Leu | Ala | Asp |
|---|---|---|---|---|---|---|---|---|---|---|---|---|---|---|---|
| | 50 | | | | | 55 | | | | | 60 | | | | |

| Leu | Asn | Asp | Arg | Ala | Asp | Glu | Thr | Glu | Phe | Gln | Ala | Ala | Leu | Ser | Lys |
|---|---|---|---|---|---|---|---|---|---|---|---|---|---|---|---|
| 65 | | | | | 70 | | | | | 75 | | | | | 80 |

| Val | Lys | Phe | Gly | Leu | Glu | Phe | Ser | Thr | Ala | Val | Ser | Asn | Thr | Asn | Tyr |
|---|---|---|---|---|---|---|---|---|---|---|---|---|---|---|---|
| | | | | 85 | | | | | 90 | | | | | 95 | |

| Lys | Val | Ser | Gly | Gln | Asp | Tyr | Ser | Ala | Asn | Asn | Lys | Trp | Met | Asn | Glu |
|---|---|---|---|---|---|---|---|---|---|---|---|---|---|---|---|
| | | | 100 | | | | | 105 | | | | | 110 | | |

| Leu | His | Leu | Asn | Met | Asn | Ala | Asp | Ile | Asn | Asp | Lys | Thr | Lys | Phe | Tyr |
|---|---|---|---|---|---|---|---|---|---|---|---|---|---|---|---|
| | | 115 | | | | | 120 | | | | | 125 | | | |

| Gly | Arg | Leu | Ser | Met | Ala | Lys | Asn | Trp | Ser | Gln | Met | Gly | Trp | Ser | Gly |
|---|---|---|---|---|---|---|---|---|---|---|---|---|---|---|---|
| | 130 | | | | | 135 | | | | | 140 | | | | |

| Thr | Pro | Tyr | Asp | Leu | Asp | Ala | Gly | Arg | Asn | Thr | Arg | Ser | Ser | Gly | Pro |
|---|---|---|---|---|---|---|---|---|---|---|---|---|---|---|---|
| 145 | | | | | 150 | | | | | 155 | | | | | 160 |

| Val | Leu | Tyr | Val | Asp | Arg | Ala | Tyr | Leu | Asp | Tyr | Tyr | Ile | Thr | Pro | Glu |
|---|---|---|---|---|---|---|---|---|---|---|---|---|---|---|---|
| | | | | 165 | | | | | 170 | | | | | 175 | |

| Trp | Ile | Ala | Thr | Val | Gly | Arg | Gln | Pro | Gly | Thr | Asp | Gly | Pro | Gly | Ser |
|---|---|---|---|---|---|---|---|---|---|---|---|---|---|---|---|
| | | | 180 | | | | | 185 | | | | | 190 | | |

| Asn | Leu | Arg | Asn | Asn | Ala | Leu | Arg | Gln | Ser | Thr | Tyr | Pro | Ala | Leu | Ala |
|---|---|---|---|---|---|---|---|---|---|---|---|---|---|---|---|
| | | 195 | | | | | 200 | | | | | 205 | | | |

| Ile | Asn | Ala | Leu | Gly | Asp | Ala | Val | Ile | Thr | Tyr | Lys | Pro | Glu | Ser |
|---|---|---|---|---|---|---|---|---|---|---|---|---|---|---|
| | 210 | | | | | 215 | | | | | 220 | | | |

| Leu | Gln | Asp | His | Lys | Val | Ala | Ile | Arg | Ala | Ala | Tyr | Gly | Lys | Thr | Tyr |
|---|---|---|---|---|---|---|---|---|---|---|---|---|---|---|---|
| 225 | | | | | 230 | | | | | 235 | | | | | 240 |

| Gln | Trp | Asp | Glu | Glu | Ser | Gly | Lys | Val | Arg | Asp | Trp | Met | Ser | Asp | Gln |
|---|---|---|---|---|---|---|---|---|---|---|---|---|---|---|---|
| | | | | 245 | | | | | 250 | | | | | 255 | |

| Lys | Asp | Ala | Asp | Ala | Asn | Leu | Tyr | Tyr | Ala | Ala | Val | Glu | Gly | Glu | Leu |
|---|---|---|---|---|---|---|---|---|---|---|---|---|---|---|---|
| | | | 260 | | | | | 265 | | | | | 270 | | |

| Pro | Ile | Glu | Gly | Met | Gly | Asp | Asn | Leu | Ile | Ile | Phe | Asn | Val | Ala | His |
|---|---|---|---|---|---|---|---|---|---|---|---|---|---|---|---|
| | | 275 | | | | | 280 | | | | | 285 | | | |

| Met | Thr | Asp | Phe | Ala | Leu | Pro | Ile | Pro | Gly | Ser | Met | Leu | Leu | Gly | Asp |
|---|---|---|---|---|---|---|---|---|---|---|---|---|---|---|---|
| | 290 | | | | | 295 | | | | | 300 | | | | |

| Asp | Asp | Glu | Val | Val | Asn | Leu | Gly | Asn | Leu | Thr | Leu | Ala | Asn | Ile | His |
|---|---|---|---|---|---|---|---|---|---|---|---|---|---|---|---|
| 305 | | | | | 310 | | | | | 315 | | | | | 320 |

| Phe | Glu | Asn | Tyr | Lys | Ala | Phe | Gly | Thr | Asn | Phe | Asn | Trp | Phe | Ala | Ser |
|---|---|---|---|---|---|---|---|---|---|---|---|---|---|---|---|
| | | | | 325 | | | | | 330 | | | | | 335 | |

| Leu | Gly | Tyr | Ser | Asn | Gly | Ser | Asn | Asn | Glu | Ile | Asn | Pro | Leu | Leu | Ser |
|---|---|---|---|---|---|---|---|---|---|---|---|---|---|---|---|
| | | | 340 | | | | | 345 | | | | | 350 | | |

```
Thr Ala Leu Gln Ser Lys Gly Tyr Gly Asn Gly Lys Phe Asn Glu Lys
        355                 360                 365

Asp Gly Tyr Ala Val His Val Gly Gly Arg Tyr Asp Phe Thr Lys Ala
    370                 375                 380

Leu Lys Val Gly Tyr Glu Phe Phe Trp Gly Ser Arg Tyr Trp Tyr Thr
385                 390                 395                 400

Met Ser Arg Pro Ser Ile Asn Asp Pro Leu Asn Ile Arg Met Thr Arg
                405                 410                 415

Gly Thr Ala His Asp Phe Tyr Val Ile Tyr Gln Leu Asp Arg Tyr Gln
            420                 425                 430

Phe Leu Arg Leu Ser Tyr Thr Asn Ile Gln Asn Ile Trp Gly Asn Arg
        435                 440                 445

Gly Leu Pro Phe Gly Gly Ala Lys Lys Asp Lys Ala Arg Ala Asp Asn
    450                 455                 460

Ile Met Leu Met Tyr Asn Val Lys Phe
465                 470

<210> SEQ ID NO 43
<211> LENGTH: 1401
<212> TYPE: DNA
<213> ORGANISM: Campylobacter jejuni

<400> SEQUENCE: 43
atgaaaacta gttttcact tattttaagt gcttgtcttc tttcatcttc acttttgct      60 aaaaatgcag atgatgagat aaccaagctt caaaaacagc ttgcacaaat tcaagctgaa    120
cttgcacaaa tcagaaaaga agagaagct caagctaagc aaaatgaagc tgtaaaagct    180
gaacttgctg atcttaatga tagagccgat gaaacagaat tcaagctgc tttaagcaag    240 gttaaatttg acttgagtt tcaacagcg gtttcaaata caaactataa agttagcgga    300
caagattata gtgctaataa caaatggatg aatgagcttc atttaaatat gaatgctgat    360
attaatgata aaaccaaatt ctatggtcgt ttatctatgg ctaaaaactg gtctcaaatg    420
gattggagtg gaagcccta tgacctagat gcaggaagaa cacaagatc aagcgggcct    480 gtgctttatg tagatagagc ttatcttgac tactatatca cacctgagtg gattgcaacc    540
ataggaagac agccaggaac cgatggccca ggaagtaatc ttagaaacaa tgctttaaga    600
caatcaactt atccagcctt agcaatcaat gctctaggtg atgcagcagt gatcacttat    660
aaacctgaaa gtttgcaaga tcataaggtg gctatccgtg cagcttatgg taaaacttat    720
caatgggatg aagaaggcaa ggtaagagac tggatgagcg atcaaaaaga tgctgatgca    780
aatctttact atgctgcagt agaaggagag cttcctatag aaggtatggg agataatctt    840
attatcttca atgtggctca tatgactgat tttgcattac cattgcctag tattccttct    900
attctaaatc aaggtgttta taatcttgga gattaactt tagcaaatat tcattttgaa    960
aactataatg cttttggtac aaattttaat tattttgtat ctttagggta ttctaacgga   1020
gcaaatgcgc atactctaag tgcaaatcct gttgcgcaat ctcaattgga atttaatgaa   1080
aaagatggtt atgctgtgca tgtaggtgga cgttatgatt ttactaaggc tttaaaagtg   1140
gggtatgagt tcttctgggg aagtagatac tggtatacta tgagccgtcc aagtattaat   1200
gatccactta atataagaat gacaagagga acagcacatg atttttatgt gatttatcaa   1260
ctcgatagat atcaattctt acgcttaagc tatactaata tccaaaatat ttggggtaat   1320
cgtggtatac catttggtgg agcgaaaaaa gataaagcaa gagctgataa tatcatgtta   1380
```
atgtataatg taaaattcta a                                              1401

<210> SEQ ID NO 44
<211> LENGTH: 466
<212> TYPE: PRT
<213> ORGANISM: Campylobacter jejuni

<400> SEQUENCE: 44

Met Lys Thr Lys Phe Ser Leu Ile Leu Ser Ala Cys Leu Leu Ser Ser
1               5                   10                  15

Ser Leu Phe Ala Lys Asn Ala Asp Asp Glu Ile Thr Lys Leu Gln Lys
            20                  25                  30

Gln Leu Ala Gln Ile Gln Ala Glu Leu Ala Gln Ile Arg Lys Glu Arg
        35                  40                  45

Glu Ala Gln Ala Lys Gln Asn Glu Ala Val Lys Ala Glu Leu Ala Asp
    50                  55                  60

Leu Asn Asp Arg Ala Asp Glu Thr Glu Phe Gln Ala Ala Leu Ser Lys
65                  70                  75                  80

Val Lys Phe Gly Leu Glu Phe Ser Thr Ala Val Ser Asn Thr Asn Tyr
                85                  90                  95

Lys Val Ser Gly Gln Asp Tyr Ser Ala Asn Lys Trp Met Asn Glu
            100                 105                 110

Leu His Leu Asn Met Asn Ala Asp Ile Asn Asp Lys Thr Lys Phe Tyr
        115                 120                 125

Gly Arg Leu Ser Met Ala Lys Asn Trp Ser Gln Met Asp Trp Ser Gly
    130                 135                 140

Ser Pro Tyr Asp Leu Asp Ala Gly Arg Asn Thr Arg Ser Ser Gly Pro
145                 150                 155                 160

Val Leu Tyr Val Asp Arg Ala Tyr Leu Asp Tyr Tyr Ile Thr Pro Glu
                165                 170                 175

Trp Ile Ala Thr Ile Gly Arg Gln Pro Gly Thr Asp Gly Pro Gly Ser
            180                 185                 190

Asn Leu Arg Asn Asn Ala Leu Arg Gln Ser Thr Tyr Pro Ala Leu Ala
        195                 200                 205

Ile Asn Ala Leu Gly Asp Ala Ala Val Ile Thr Tyr Lys Pro Glu Ser
    210                 215                 220

Leu Gln Asp His Lys Val Ala Ile Arg Ala Ala Tyr Gly Lys Thr Tyr
225                 230                 235                 240

Gln Trp Asp Glu Glu Gly Lys Val Arg Asp Trp Met Ser Asp Gln Lys
                245                 250                 255

Asp Ala Asp Ala Asn Leu Tyr Tyr Ala Ala Val Glu Gly Glu Leu Pro
            260                 265                 270

Ile Glu Gly Met Gly Asp Asn Leu Ile Ile Phe Asn Val Ala His Met
        275                 280                 285

Thr Asp Phe Ala Leu Pro Leu Pro Ser Ile Pro Ser Ile Leu Asn Gln
    290                 295                 300

Gly Val Tyr Asn Leu Gly Asp Leu Thr Leu Ala Asn Ile His Phe Glu
305                 310                 315                 320

Asn Tyr Asn Ala Phe Gly Thr Asn Phe Asn Tyr Phe Val Ser Leu Gly
                325                 330                 335

Tyr Ser Asn Gly Ala Asn Ala His Thr Leu Ser Ala Asn Pro Val Ala
            340                 345                 350

Gln Ser Gln Leu Glu Phe Asn Glu Lys Asp Gly Tyr Ala Val His Val
        355                 360                 365

```
Gly Gly Arg Tyr Asp Phe Thr Lys Ala Leu Lys Val Gly Tyr Glu Phe
    370                 375                 380

Phe Trp Gly Ser Arg Tyr Trp Tyr Thr Met Ser Arg Pro Ser Ile Asn
385                 390                 395                 400

Asp Pro Leu Asn Ile Arg Met Thr Arg Gly Thr Ala His Asp Phe Tyr
                405                 410                 415

Val Ile Tyr Gln Leu Asp Arg Tyr Gln Phe Leu Arg Leu Ser Tyr Thr
            420                 425                 430

Asn Ile Gln Asn Ile Trp Gly Asn Arg Gly Ile Pro Phe Gly Gly Ala
        435                 440                 445

Lys Lys Asp Lys Ala Arg Ala Asp Asn Ile Met Leu Met Tyr Asn Val
    450                 455                 460

Lys Phe
465

<210> SEQ ID NO 45
<211> LENGTH: 1236
<212> TYPE: DNA
<213> ORGANISM: Campylobacter jejuni

<400> SEQUENCE: 45
```

| | | | | | |
|---|---|---|---|---|---|
| atgatgaaaa | gatttcgctt | gagttttac | ttgagtttt | taactctttt | gcttagcgct | 60 |
| tgtagtgttt | cgcaaatgaa | ttcgctagct | tcaagtaaag | agcctgctgt | aaatgaaagc | 120 |
| ttgccaaagg | ttgaaagttt | aaaaagtctt | agtgatatga | gtaatattgc | ttttgaatgg | 180 |
| gagcctttat | ataatgaaaa | tattaaagga | ttttatttgt | atcgttctag | tgatgaaaat | 240 |
| cctgatttta | aacttgtagg | cactattaaa | gataagtttc | aaactcatta | tgtagatact | 300 |
| aaattagagc | ctggtactaa | gtatcgttat | atgatgaaaa | gctttaatga | gcaaggacaa | 360 |
| atttcagaag | atggcaaggt | tatagaagtg | agcacagctc | caagacttga | agctgttcct | 420 |
| tttgttcaag | ctgtgactaa | tttgcctaat | cgtattaaac | ttatttggcg | tccgcatcct | 480 |
| gattttaggg | ttgattctta | tattattgaa | agaaccaaag | gtgatgataa | agaatttaaa | 540 |
| aaaattgcag | aagtaaaaaa | tcgtttaaac | gctgaataca | tcgatagtga | tttaaagcct | 600 |
| aatgaaaatt | caagttatag | aattattgct | gtgagttta | atgggataaa | gagtgggtca | 660 |
| agtcaagttg | taagttctac | aagcaaggct | ttacctcctc | aagttgagca | tttaagtgct | 720 |
| agcacagatg | gttctagtaa | aatcatttta | acttgggatg | ctcctacgta | tgaagatttt | 780 |
| tcttattata | agtttattc | tacgagctca | agcttccttc | cttttagtgt | tttggcaaag | 840 |
| actgataaaa | attcttatga | ggatatagta | gaaggagcag | gtaaaagcaa | gtattataaa | 900 |
| gtaacaatgg | tggataaaga | tggtcttgaa | agtcctatgc | caaagatgg | tgtagaaggt | 960 |
| aaaactttag | gcaacccttt | ggctcctagt | attattttgg | ctcaaagtac | aagcgaaggg | 1020 |
| ataaatttag | aatggagtga | taatgatact | agagctgttg | agtatgaagt | aagacgctat | 1080 |
| ggcggggagc | aaaatgcagt | ttttaaaggc | attaaagaaa | agcgattaaa | agatgtaaaa | 1140 |
| gctttgccag | gggtggaata | tagttatgaa | gttattgcta | ttgattcagc | cgggcttcgt | 1200 |
| tcagaaccctt | caagcaaagt | taaggcggct | cagtag | | | 1236 |

```
<210> SEQ ID NO 46
<211> LENGTH: 411
<212> TYPE: PRT
<213> ORGANISM: Campylobacter jejuni

<400> SEQUENCE: 46
```

```
Met Met Lys Arg Phe Arg Leu Ser Phe Tyr Leu Ser Phe Leu Thr Leu
1               5                   10                  15

Leu Leu Ser Ala Cys Ser Val Ser Gln Met Asn Ser Leu Ala Ser Ser
            20                  25                  30

Lys Glu Pro Ala Val Asn Glu Ser Leu Pro Lys Val Glu Ser Leu Lys
            35                  40                  45

Ser Leu Ser Asp Met Ser Asn Ile Ala Phe Glu Trp Glu Pro Leu Tyr
50                  55                  60

Asn Glu Asn Ile Lys Gly Phe Tyr Leu Tyr Arg Ser Ser Asp Glu Asn
65                  70                  75                  80

Pro Asp Phe Lys Leu Val Gly Thr Ile Lys Asp Lys Phe Gln Thr His
                85                  90                  95

Tyr Val Asp Thr Lys Leu Glu Pro Gly Thr Lys Tyr Arg Tyr Met Met
            100                 105                 110

Lys Ser Phe Asn Glu Gln Gly Gln Ile Ser Glu Asp Gly Lys Val Ile
            115                 120                 125

Glu Val Ser Thr Ala Pro Arg Leu Glu Ala Val Pro Phe Val Gln Ala
        130                 135                 140

Val Thr Asn Leu Pro Asn Arg Ile Lys Leu Ile Trp Arg Pro His Pro
145                 150                 155                 160

Asp Phe Arg Val Asp Ser Tyr Ile Ile Glu Arg Thr Lys Gly Asp Asp
                165                 170                 175

Lys Glu Phe Lys Lys Ile Ala Glu Val Lys Asn Arg Leu Asn Ala Glu
            180                 185                 190

Tyr Ile Asp Ser Asp Leu Lys Pro Asn Glu Asn Ser Ser Tyr Arg Ile
            195                 200                 205

Ile Ala Val Ser Phe Asn Gly Ile Lys Ser Gly Ser Ser Gln Val Val
        210                 215                 220

Ser Ser Thr Ser Lys Ala Leu Pro Pro Gln Val Glu His Leu Ser Ala
225                 230                 235                 240

Ser Thr Asp Gly Ser Ser Lys Ile Ile Leu Thr Trp Asp Ala Pro Thr
                245                 250                 255

Tyr Glu Asp Phe Ser Tyr Tyr Lys Val Tyr Ser Thr Ser Ser Ser Phe
            260                 265                 270

Leu Pro Phe Ser Val Leu Ala Lys Thr Asp Lys Asn Ser Tyr Glu Asp
            275                 280                 285

Ile Val Glu Gly Ala Gly Lys Ser Lys Tyr Tyr Lys Val Thr Met Val
        290                 295                 300

Asp Lys Asp Gly Leu Glu Ser Pro Met Pro Lys Asp Gly Val Glu Gly
305                 310                 315                 320

Lys Thr Leu Gly Asn Pro Leu Ala Pro Ser Ile Ile Leu Ala Gln Ser
                325                 330                 335

Thr Ser Glu Gly Ile Asn Leu Glu Trp Ser Asp Asn Asp Thr Arg Ala
            340                 345                 350

Val Glu Tyr Glu Val Arg Arg Tyr Gly Gly Gln Asn Ala Val Phe
            355                 360                 365

Lys Gly Ile Lys Glu Lys Arg Leu Lys Asp Val Lys Ala Leu Pro Gly
        370                 375                 380

Val Glu Tyr Ser Tyr Glu Val Ile Ala Ile Asp Ser Ala Gly Leu Arg
385                 390                 395                 400

Ser Glu Pro Ser Ser Lys Val Lys Ala Ala Gln
                405                 410
```

<210> SEQ ID NO 47
<211> LENGTH: 1233
<212> TYPE: DNA
<213> ORGANISM: Campylobacter jejuni

<400> SEQUENCE: 47

```
atgaaaagat tcgcttggg tttttacttg agtttttaa ctcttttgct tagcgcttgt      60
agtgtttcgc aaatgaattc gctagcttca gtaaagagc ctgctgtaaa tgaaagcttg    120
ccaaaggttg aaagtttaaa aagtcttagc gatatgagta atattgcttt tgaatgggag   180
tctttatata atgaaaatat taaaggattt tatttatatc gttctagtga tgaaaatcct   240
gatttaaac ttgtaggcac tattaaagat aagtttcaaa ctcattatgt agatactaaa   300
ttagagcctg gtactaagta tcgttatatg atgaaaagct taatgagca aggacaaatt    360
tcagaagatg gcaaggttat agaagtgagc acagctccaa gacttgaagc tgttcctttt    420
gttcaagctg tgactaattt gcctaatcgt attaaactta tttggcgtcc gcatcctgat   480
tttagagttg attcttatat tattgaaaga actaaaggtg atgataaaga atttaaaaaa   540
attgcagaag taaaaatcg tttaaacgct gaatacatcg atagtgattt aaaacctaat   600
gaaaattcaa gctatagaat cattgctgtg agttttaatg ggataaagag tgaaccaagt   660
caagttgtaa gttctacaag caaggctttg cctcctcaag ttgagcattt aagtgctagc   720
acagatggtt ctaataaaat catgttaact tgggatgctc ctacatatga agatttttct   780
tattataaag tttattctac aagctcaagc ttccttcctt ttagtgtttt ggcaaagact   840
gataaaaatt cttatgagga tatagtagaa ggagtaggta aaagcaagta ttataaagta   900
acaatggtgg ataaagatgg tcttgaaagt cctatgccaa agatggtgt agaaggtaaa   960
actttaggta acccttttggc tcctagtatt attttggctc aaagcacaag cgaaggata  1020
aatttagaat ggagcgataa tgatactaga gctgttgagt atgaagtaag acgctatggc  1080
ggggagcaaa atgctgtttt taaaggcatt aagaaaagc gattaaaaga tgtaaaagct  1140
ttaccagggg tggaatatag ttatgaagtt attgctattg attcggctgg gcttcgttca  1200
gaaccttcaa gcaaagttaa ggcagctcag tag                                1233
```

<210> SEQ ID NO 48
<211> LENGTH: 410
<212> TYPE: PRT
<213> ORGANISM: Campylobacter jejuni

<400> SEQUENCE: 48

```
Met Lys Arg Phe Arg Leu Gly Phe Tyr Leu Ser Phe Leu Thr Leu Leu
1               5                   10                  15

Leu Ser Ala Cys Ser Val Ser Gln Met Asn Ser Leu Ala Ser Ser Lys
            20                  25                  30

Glu Pro Ala Val Asn Glu Ser Leu Pro Lys Val Glu Ser Leu Lys Ser
        35                  40                  45

Leu Ser Asp Met Ser Asn Ile Ala Phe Glu Trp Glu Ser Leu Tyr Asn
    50                  55                  60

Glu Asn Ile Lys Gly Phe Tyr Leu Tyr Arg Ser Ser Asp Glu Asn Pro
65                  70                  75                  80

Asp Phe Lys Leu Val Gly Thr Ile Lys Asp Lys Phe Gln Thr His Tyr
                85                  90                  95

Val Asp Thr Lys Leu Glu Pro Gly Thr Lys Tyr Arg Tyr Met Met Lys
            100                 105                 110

Ser Phe Asn Glu Gln Gly Gln Ile Ser Glu Asp Gly Lys Val Ile Glu
```

|  |  |  | 115 |  |  |  | 120 |  |  |  | 125 |  |  |
|---|---|---|---|---|---|---|---|---|---|---|---|---|---|

Val Ser Thr Ala Pro Arg Leu Glu Ala Val Pro Phe Val Gln Ala Val
    130                       135                   140

Thr Asn Leu Pro Asn Arg Ile Lys Leu Ile Trp Arg Pro His Pro Asp
145                   150                   155                 160

Phe Arg Val Asp Ser Tyr Ile Ile Glu Arg Thr Lys Gly Asp Asp Lys
                165                   170                 175

Glu Phe Lys Lys Ile Ala Glu Val Lys Asn Arg Leu Asn Ala Glu Tyr
         180                   185               190

Ile Asp Ser Asp Leu Lys Pro Asn Glu Asn Ser Ser Tyr Arg Ile Ile
              195                 200            205

Ala Val Ser Phe Asn Gly Ile Lys Ser Glu Pro Ser Gln Val Val Ser
    210                     215                   220

Ser Thr Ser Lys Ala Leu Pro Pro Gln Val His Leu Ser Ala Ser
225                   230                   235                 240

Thr Asp Gly Ser Asn Lys Ile Met Leu Thr Trp Asp Ala Pro Thr Tyr
                245                   250                 255

Glu Asp Phe Ser Tyr Tyr Lys Val Tyr Ser Thr Ser Ser Ser Phe Leu
         260                   265               270

Pro Phe Ser Val Leu Ala Lys Thr Asp Lys Asn Ser Tyr Glu Asp Ile
              275                 280            285

Val Glu Gly Val Gly Lys Ser Lys Tyr Tyr Lys Val Thr Met Val Asp
    290                     295                   300

Lys Asp Gly Leu Glu Ser Pro Met Pro Lys Asp Gly Val Glu Gly Lys
305                   310                   315                 320

Thr Leu Gly Asn Pro Leu Ala Pro Ser Ile Ile Leu Ala Gln Ser Thr
                325                   330               335

Ser Glu Gly Ile Asn Leu Glu Trp Ser Asp Asn Asp Thr Arg Ala Val
         340                   345               350

Glu Tyr Glu Val Arg Arg Tyr Gly Gly Glu Gln Asn Ala Val Phe Lys
    355                     360                   365

Gly Ile Lys Glu Lys Arg Leu Lys Asp Val Lys Ala Leu Pro Gly Val
370                   375                   380

Glu Tyr Ser Tyr Glu Val Ile Ala Ile Asp Ser Ala Gly Leu Arg Ser
385                   390                   395                 400

Glu Pro Ser Ser Lys Val Lys Ala Ala Gln
         405                   410

<210> SEQ ID NO 49
<211> LENGTH: 810
<212> TYPE: DNA
<213> ORGANISM: Campylobacter jejuni

<400> SEQUENCE: 49

| atgaaaaaaa | tcatttcttt | agcccttgct | ttagctttaa | gtgcaagtgc | agcagaactt | 60 |
|---|---|---|---|---|---|---|
| aaaatggcaa | ctacaacaag | cactgacaat | acaggacttt | tagatgctct | aaaacctctt | 120 |
| tatgaaaaag | aaagtggcaa | taccttaaaa | tgggttgccg | taggaacagg | tgcggcttta | 180 |
| aaaatgggtg | aagattgcaa | tgctgatgtg | cttttgtgc | attctccaaa | ggctgaaaaa | 240 |
| gaatttatga | aaaaaggctt | tggtgtagat | agaactcctg | tgatgtataa | tgattttatc | 300 |
| atcatcgcag | ataaatcttt | agcttctaaa | tttaaggta | aaatttaaa | agaaagctta | 360 |
| gaacttatca | aaatgaaaaa | gcttactttc | atctcaagag | gcgataaatc | aggcactgac | 420 |
| aataaagaaa | aaagcctttg | gaaaaatctt | ggcggtgttc | ctgaaaagca | agctggtat | 480 |

-continued

```
caacaaagcg gacaaggtat gttagcaagc attaaaatcg ctgaagaaaa aaaaggtgtg      540
attttaaccg atcgtggtac ttatatcaaa tatgaagcca atgaaaaagg caaaccaaac      600
ttagtcattg taaatgaagg cgatgatagt cttaaaaatt tttattctgt tatagcgaca      660
aatcctaagc attgtaaaaa tgtaaattat acagaagcta gtaaatttat caatgggta       720 acaagtgata agactttaaa tttcattgct gattttaaac ttcttaataa acctttattt      780
gtaattgatg caaaaacaag aaaagactaa                                       810
```

<210> SEQ ID NO 50
<211> LENGTH: 269
<212> TYPE: PRT
<213> ORGANISM: Campylobacter jejuni

<400> SEQUENCE: 50

```
Met Lys Lys Ile Ile Ser Leu Ala Leu Ala Leu Ser Ala Ser
 1               5                   10                  15
Ala Ala Glu Leu Lys Met Ala Thr Thr Thr Ser Thr Asp Asn Thr Gly
             20                  25                  30
Leu Leu Asp Ala Leu Lys Pro Leu Tyr Glu Lys Glu Ser Gly Asn Thr
         35                  40                  45
Leu Lys Trp Val Ala Val Gly Thr Gly Ala Ala Leu Lys Met Gly Glu
     50                  55                  60
Asp Cys Asn Ala Asp Val Leu Phe Val His Ser Pro Lys Ala Glu Lys
 65                  70                  75                  80
Glu Phe Met Lys Lys Gly Phe Gly Val Asp Arg Thr Pro Val Met Tyr
                 85                  90                  95
Asn Asp Phe Ile Ile Ile Ala Asp Lys Ser Leu Ala Ser Lys Phe Lys
            100                 105                 110
Gly Lys Asn Leu Lys Glu Ser Leu Glu Leu Ile Lys Asn Glu Lys Leu
        115                 120                 125
Thr Phe Ile Ser Arg Gly Asp Lys Ser Gly Thr Asp Asn Lys Glu Lys
    130                 135                 140
Ser Leu Trp Lys Asn Leu Gly Gly Val Pro Glu Lys Gln Ser Trp Tyr
145                 150                 155                 160
Gln Gln Ser Gly Gln Gly Met Leu Ala Ser Ile Lys Ile Ala Glu Glu
                165                 170                 175
Lys Lys Gly Val Ile Leu Thr Asp Arg Gly Thr Tyr Ile Lys Tyr Glu
            180                 185                 190
Ala Asn Glu Lys Gly Lys Pro Asn Leu Val Ile Asn Glu Gly Asp
        195                 200                 205
Asp Ser Leu Lys Asn Phe Tyr Ser Val Ile Ala Thr Asn Pro Lys His
    210                 215                 220
Cys Lys Asn Val Asn Tyr Thr Glu Ala Ser Lys Phe Ile Lys Trp Val
225                 230                 235                 240
Thr Ser Asp Lys Thr Leu Asn Phe Ile Ala Asp Phe Lys Leu Leu Asn
                245                 250                 255
Lys Pro Leu Phe Val Ile Asp Ala Lys Thr Arg Lys Asp
            260                 265
```

<210> SEQ ID NO 51
<211> LENGTH: 810
<212> TYPE: DNA
<213> ORGANISM: Campylobacter jejuni

<400> SEQUENCE: 51

```
atgaaaaaaa tcatttcttt agcccttgct ttagctttaa gtgcaagtgc agcagaactt      60
aaaatggcaa ctacaacaag cactgacaat acaggacttt agatgctct aaaacctctt     120 tatgaaaaag aaagtggcaa taccttaaaa tggggttgccg taggaacagg tgcggcttta    180
aaaatgggtg aagattgcaa tgctgatgtg cttttttgtgc attctccaaa ggctgaaaaa   240
gaatttatga aaaaggcttt tggtgtagat agaactcctg tgatgtataa tgattttatc    300
atcatcgcag ataaatcttt agcttctaaa tttaaaggta aaaatttaaa agaaagctta    360
gaacttatca aaatgaaaa gcttactttc atctcaagag gcgataaatc aggcactgac     420
aataaagaaa aagcctttg gaaaatcttt ggcggtgttc ctgaaaagca aagctggtat     480
caacaaagcg gacaaggtat gttagcaagc attaaaatcg ctgaagaaaa aaaggtgtg    540 atttaaccg atcgtggtac ttatatcaaa tatgaagcca atgaaaaagg caaaccaaac    600
ttagtcattg taaatgaagg cgatgatagt cttaaaaatt tttattctgt tatagcgaca    660
aatcctaagc attgtaaaaa tgtaaattat acagaagcta gtaaatttat caaatgggta    720
acaagtgata agactttaaa tttcattgct gattttaaac ttcttaataa accttatt     780 gtaattgatg caaaaacaag aaaagactaa                                     810
```

<210> SEQ ID NO 52
<211> LENGTH: 269
<212> TYPE: PRT
<213> ORGANISM: Campylobacter jejuni

<400> SEQUENCE: 52

```
Met Lys Lys Ile Ile Ser Leu Ala Leu Ala Leu Ser Ala Ser
 1               5                  10                  15

Ala Ala Glu Leu Lys Met Ala Thr Thr Thr Ser Thr Asp Asn Thr Gly
            20                  25                  30

Leu Leu Asp Ala Leu Lys Pro Leu Tyr Glu Lys Glu Ser Gly Asn Thr
        35                  40                  45

Leu Lys Trp Val Ala Val Gly Thr Gly Ala Ala Leu Lys Met Gly Glu
    50                  55                  60

Asp Cys Asn Ala Asp Val Leu Phe Val His Ser Pro Lys Ala Glu Lys
65                  70                  75                  80

Glu Phe Met Lys Lys Gly Phe Gly Val Asp Arg Thr Pro Val Met Tyr
                85                  90                  95

Asn Asp Phe Ile Ile Ile Ala Asp Lys Ser Leu Ala Ser Lys Phe Lys
            100                 105                 110

Gly Lys Asn Leu Lys Glu Ser Leu Glu Leu Ile Lys Asn Glu Lys Leu
        115                 120                 125

Thr Phe Ile Ser Arg Gly Asp Lys Ser Gly Thr Asp Asn Lys Glu Lys
    130                 135                 140

Ser Leu Trp Lys Asn Leu Gly Gly Val Pro Glu Lys Gln Ser Trp Tyr
145                 150                 155                 160

Gln Gln Ser Gly Gln Gly Met Leu Ala Ser Ile Lys Ile Ala Glu Glu
                165                 170                 175

Lys Lys Gly Val Ile Leu Thr Asp Arg Gly Thr Tyr Ile Lys Tyr Glu
            180                 185                 190

Ala Asn Glu Lys Gly Lys Pro Asn Leu Val Ile Val Asn Glu Gly Asp
        195                 200                 205

Asp Ser Leu Lys Asn Phe Tyr Ser Val Ile Ala Thr Asn Pro Lys His
    210                 215                 220
```

Cys Lys Asn Val Asn Tyr Thr Glu Ala Ser Lys Phe Ile Lys Trp Val
225                 230                 235                 240

Thr Ser Asp Lys Thr Leu Asn Phe Ile Ala Asp Phe Lys Leu Leu Asn
            245                 250                 255

Lys Pro Leu Phe Val Ile Asp Ala Lys Thr Arg Lys Asp
            260                 265

<210> SEQ ID NO 53
<211> LENGTH: 1719
<212> TYPE: DNA
<213> ORGANISM: Campylobacter jejuni

<400> SEQUENCE: 53

| | | | | | |
|---|---|---|---|---|---|
| atgggatttc | gtattaacac | caatgttgca | gctttaaatg | caaaagcaaa | cgctgattta | 60 |
| aatagtaaaa | gtttagatgc | ttctttaagc | agacttagtt | caggtcttag | aatcaactcc | 120 |
| gcagcagatg | atgcttcagg | gatggcgata | gcagatagtt | aagatctca | agctaatact | 180 |
| ttaggtcaag | ctatatctaa | tggtaatgat | gctttaggta | tcttacaaac | tgctgataag | 240 |
| gctatggatg | agcaacttaa | aatcttagat | acaatcaaaa | ctaaggcaac | tcaagcggct | 300 |
| caagatggac | aaagtttaaa | aacaagaacc | atgcttcaag | cagatatcaa | ccgtttaatg | 360 |
| gaagaacttg | acaatattgc | aaatactact | tcatttaacg | gtaaacaact | tttaagtggg | 420 |
| aattttatca | atcaagaatt | tcaaatcggt | gcaagttcaa | atcaaactgt | aaaagctact | 480 |
| ataggagcaa | ctcaatcttc | taagataggt | ttaacacgct | ttgaaacagg | aggaagaatt | 540 |
| tcaactagtg | gcgaagtaca | atttactctt | aaaaattaca | atggtataga | tgattttcag | 600 |
| tttcaaaaag | ttgtgatttc | aacttcagtt | ggaacaggac | ttggagcttt | agcagatgag | 660 |
| atcaataaaa | atgctgataa | acaggtgtt | agagctactt | ttacagtaga | aactagaggt | 720 |
| atagctgcag | ttagagcagg | agctacttca | gatactttg | ctatcaatgg | ggtaaaaatc | 780 |
| ggtaaagtag | attacaaaga | tggtgatgct | aatggagcct | tagttgctgc | aatcaattcg | 840 |
| gttaaagata | ccactggagt | tgaagcttcg | atcgatgcta | atggacaact | tttacttact | 900 |
| tcaagagaag | gtagagggat | taaaatcgat | ggtaatatag | gtggaggtgc | ctttatcaat | 960 |
| gctgatatga | agaaaaacta | tggccgcttg | tctttagtta | aaaatgatgg | taagatatt | 1020 |
| ttaatcagcg | gtagcaatct | ttcttctgca | ggttttggtg | caactcaatt | tatctctcaa | 1080 |
| gcttctgttt | ctttaagaga | gtcaaaagga | caaattgatg | ctaatatcgc | tgatgctatg | 1140 |
| ggatttggtt | ctgcaaacaa | aggagttgtg | ttaggtggtt | attcttctgt | tagtgcctat | 1200 |
| atgagtagcg | caggaagtgg | atttctttca | ggttcaggtt | attctgtagg | tagcggtaaa | 1260 |
| aattattcca | caggttttgc | aaacgctata | gctatttcag | ctgcttcgca | actttctacg | 1320 |
| gtatataatg | tttctgcagg | ctcaggtttt | tcaagtggtt | caacactttc | tcagtttgca | 1380 |
| actatgaaaa | caactgcttt | tggagtaaaa | gatgaaacag | caggtgttac | cacacttaaa | 1440 |
| ggcgctatgg | ctgtgatgga | tatagctgaa | acagctataa | caaatcttga | tcaaatcaga | 1500 |
| gccgacattg | gttcggtaca | aaatcaagtt | acatcaacta | taacaacat | caccgtaact | 1560 |
| caagtaaacg | ttaaagcagc | agaatcgcaa | atccgtgatg | tagactttgc | agccgagagt | 1620 |
| gcaaactact | ctaaagcaaa | tatcttagct | caaagcggct | cttatgccat | ggcacaggct | 1680 |
| aattctgttc | aacaaaatgt | tttaagatta | ctacagtag | | | 1719 |

<210> SEQ ID NO 54
<211> LENGTH: 572
<212> TYPE: PRT

<213> ORGANISM: Campylobacter jejuni

<400> SEQUENCE: 54

Met Gly Phe Arg Ile Asn Thr Asn Val Ala Ala Leu Asn Ala Lys Ala
1               5                   10                  15

Asn Ala Asp Leu Asn Ser Lys Ser Leu Asp Ala Ser Leu Ser Arg Leu
            20                  25                  30

Ser Ser Gly Leu Arg Ile Asn Ser Ala Ala Asp Asp Ala Ser Gly Met
        35                  40                  45

Ala Ile Ala Asp Ser Leu Arg Ser Gln Ala Asn Thr Leu Gly Gln Ala
    50                  55                  60

Ile Ser Asn Gly Asn Asp Ala Leu Gly Ile Leu Gln Thr Ala Asp Lys
65                  70                  75                  80

Ala Met Asp Glu Gln Leu Lys Ile Leu Asp Thr Ile Lys Thr Lys Ala
                85                  90                  95

Thr Gln Ala Ala Gln Asp Gly Gln Ser Leu Lys Thr Arg Thr Met Leu
            100                 105                 110

Gln Ala Asp Ile Asn Arg Leu Met Glu Glu Leu Asp Asn Ile Ala Asn
        115                 120                 125

Thr Thr Ser Phe Asn Gly Lys Gln Leu Leu Ser Gly Asn Phe Ile Asn
    130                 135                 140

Gln Glu Phe Gln Ile Gly Ala Ser Ser Asn Gln Thr Val Lys Ala Thr
145                 150                 155                 160

Ile Gly Ala Thr Gln Ser Ser Lys Ile Gly Leu Thr Arg Phe Glu Thr
                165                 170                 175

Gly Gly Arg Ile Ser Thr Ser Gly Glu Val Gln Phe Thr Leu Lys Asn
            180                 185                 190

Tyr Asn Gly Ile Asp Asp Phe Gln Phe Gln Lys Val Val Ile Ser Thr
        195                 200                 205

Ser Val Gly Thr Gly Leu Gly Ala Leu Ala Asp Glu Ile Asn Lys Asn
    210                 215                 220

Ala Asp Lys Thr Gly Val Arg Ala Thr Phe Thr Val Glu Thr Arg Gly
225                 230                 235                 240

Ile Ala Ala Val Arg Ala Gly Ala Thr Ser Asp Thr Phe Ala Ile Asn
                245                 250                 255

Gly Val Lys Ile Gly Lys Val Asp Tyr Lys Asp Gly Asp Ala Asn Gly
            260                 265                 270

Ala Leu Val Ala Ala Ile Asn Ser Val Lys Asp Thr Thr Gly Val Glu
        275                 280                 285

Ala Ser Ile Asp Ala Asn Gly Gln Leu Leu Leu Thr Ser Arg Glu Gly
    290                 295                 300

Arg Gly Ile Lys Ile Asp Gly Asn Ile Gly Gly Ala Phe Ile Asn
305                 310                 315                 320

Ala Asp Met Lys Glu Asn Tyr Gly Arg Leu Ser Leu Val Lys Asn Asp
                325                 330                 335

Gly Lys Asp Ile Leu Ile Ser Gly Ser Asn Leu Ser Ser Ala Gly Phe
            340                 345                 350

Gly Ala Thr Gln Phe Ile Ser Gln Ala Ser Val Ser Leu Arg Glu Ser
        355                 360                 365

Lys Gly Gln Ile Asp Ala Asn Ile Ala Asp Ala Met Gly Phe Gly Ser
    370                 375                 380

Ala Asn Lys Gly Val Val Leu Gly Gly Tyr Ser Ser Val Ser Ala Tyr
385                 390                 395                 400

Met Ser Ser Ala Gly Ser Gly Phe Ser Gly Ser Gly Tyr Ser Val
            405                 410                 415

Gly Ser Gly Lys Asn Tyr Ser Thr Gly Phe Ala Asn Ala Ile Ala Ile
        420                 425                 430

Ser Ala Ala Ser Gln Leu Ser Thr Val Tyr Asn Val Ser Ala Gly Ser
        435                 440                 445

Gly Phe Ser Ser Gly Ser Thr Leu Ser Gln Phe Ala Thr Met Lys Thr
    450                 455                 460

Thr Ala Phe Gly Val Lys Asp Glu Thr Ala Gly Val Thr Thr Leu Lys
465                 470                 475                 480

Gly Ala Met Ala Val Met Asp Ile Ala Glu Thr Ala Ile Thr Asn Leu
                485                 490                 495

Asp Gln Ile Arg Ala Asp Ile Gly Ser Val Gln Asn Gln Val Thr Ser
            500                 505                 510

Thr Ile Asn Asn Ile Thr Val Thr Gln Val Asn Val Lys Ala Ala Glu
        515                 520                 525

Ser Gln Ile Arg Asp Val Asp Phe Ala Ala Glu Ser Ala Asn Tyr Ser
    530                 535                 540

Lys Ala Asn Ile Leu Ala Gln Ser Gly Ser Tyr Ala Met Ala Gln Ala
545                 550                 555                 560

Asn Ser Val Gln Gln Asn Val Leu Arg Leu Leu Gln
                565                 570

<210> SEQ ID NO 55
<211> LENGTH: 1731
<212> TYPE: DNA
<213> ORGANISM: Campylobacter jejuni

<400> SEQUENCE: 55
atgggatttc gtattaacac aaatgttgca gcattgaatg caaaagcaaa ctctgatctt      60
aatgctaaaa gtttagatgc ttctttaagc agacttagtt caggtcttag aattaactca     120
gcagcagatg atgcttcagg gatggcgata gcagatagct taagatctca agcaaatact     180
ttaggtcaag ctatatcaaa tggtaatgat gctttaggta tcttacaaac cgcagataaa     240
gctatggatg agcaattaaa aattcttgat actatcaaga ctaaagctac tcaagcagct     300
caagatggac aaagtttaaa acaagaact atgcttcaag cagatattaa taaattaatg     360
gaagagcttg ataatatcgc aaatactact tcatttaatg gtaagcaact tttaagtgga     420
aattttacca atcaagaatt ccaaatcggc gcaagttcaa accaaactgt gaaagcaact     480
atcggtgcta ctcaatcttc taaaatcggt gttacaagat ttgaaaccgg tgctcaaagt     540
tttacttcag gtgtggttgg tcttactatt aaaaactaca atggtataga agattttaaa     600
tttgataatg ttgtgatttc aacttcagtt ggaacaggac ttggagcttt ggctgaagag     660
atcaataaaa gcgctgataa acaggagtt cgcgcaactt acgatgtaaa aacaactggc     720
gtttatgcta taaagaagg aactacttct caagaatttg ccattaatgg agtaactata     780
ggaaaaattg aatacaaaga cggagatggt aacggctctt tgatttcagc tatcaatgcg     840
gttaaagata ccacaggagt tcaagcttct aaagatgaaa acggcaagct tgttcttaca     900
tcggctgatg cagggtat taaaattact ggagatatag tgttggttc tggtatttg      960 gcaaatcaaa aagaaaacta tgggcgatta tctttagtta aaaatgatgg tagagatatc     1020
aatataagtg gaaccaatct tagtgctata ggtatgggta acacagatat gatttctcaa     1080
tcttcagtgt ctttaagaga atcaaaaggt caaatttcag caaccaatgc cgatgctatg     1140

```
ggatttaatt cttataaagg tggtggaaaa tttgttttta ctcaaaatgt aagttcaatt    1200
tctgcattta tgagtgcaca aggttcagga ttttctagag gttcaggatt ttctgtgggt    1260
agtggtaaaa atttatctgt tggattgagt caaggaatac aaattatttc aagtgcggct    1320
tcaatgagca atacttatgt tgtttcagca ggttcaggat tttcttctgg ctcaggaaat    1380
tctcaatttg cagcccttaa aactactgct gctaatacaa ctgatgagac tgcaggtgta    1440
accactctta aaggtgcaat ggcggttatg gatatagcag aaactgctat aacaaatcta    1500
gatcaaatca gagcagatat tggttctata caaaatcaag ttacatcaac tataaataac    1560
attactgtaa ctcaagttaa tgttaaagca gcagaatcgc aaatcagaga tgtagacttt    1620
gcaagtgaga gtgcaaacta ctctaaagct aacatcttag cccaaagtgg ttcttatgca    1680
atggctcaag caaattctag tcagcaaaat gttttaagat tattacaata g             1731
```

<210> SEQ ID NO 56
<211> LENGTH: 576
<212> TYPE: PRT
<213> ORGANISM: Campylobacter jejuni

<400> SEQUENCE: 56

```
Met Gly Phe Arg Ile Asn Thr Asn Val Ala Ala Leu Asn Ala Lys Ala
1               5                   10                  15

Asn Ser Asp Leu Asn Ala Lys Ser Leu Asp Ala Ser Leu Ser Arg Leu
            20                  25                  30

Ser Ser Gly Leu Arg Ile Asn Ser Ala Ala Asp Asp Ala Ser Gly Met
        35                  40                  45

Ala Ile Ala Asp Ser Leu Arg Ser Gln Ala Asn Thr Leu Gly Gln Ala
    50                  55                  60

Ile Ser Asn Gly Asn Asp Ala Leu Gly Ile Leu Gln Thr Ala Asp Lys
65                  70                  75                  80

Ala Met Asp Glu Gln Leu Lys Ile Leu Asp Thr Ile Lys Thr Lys Ala
                85                  90                  95

Thr Gln Ala Ala Gln Asp Gly Gln Ser Leu Lys Thr Arg Thr Met Leu
            100                 105                 110

Gln Ala Asp Ile Asn Lys Leu Met Glu Glu Leu Asp Asn Ile Ala Asn
        115                 120                 125

Thr Thr Ser Phe Asn Gly Lys Gln Leu Leu Ser Gly Asn Phe Thr Asn
    130                 135                 140

Gln Glu Phe Gln Ile Gly Ala Ser Ser Asn Gln Thr Val Lys Ala Thr
145                 150                 155                 160

Ile Gly Ala Thr Gln Ser Ser Lys Ile Gly Val Thr Arg Phe Glu Thr
                165                 170                 175

Gly Ala Gln Ser Phe Thr Ser Gly Val Val Gly Leu Thr Ile Lys Asn
            180                 185                 190

Tyr Asn Gly Ile Glu Asp Phe Lys Phe Asp Asn Val Val Ile Ser Thr
        195                 200                 205

Ser Val Gly Thr Gly Leu Gly Ala Leu Ala Glu Glu Ile Asn Lys Ser
    210                 215                 220

Ala Asp Lys Thr Gly Val Arg Ala Thr Tyr Asp Val Lys Thr Thr Gly
225                 230                 235                 240

Val Tyr Ala Ile Lys Glu Gly Thr Thr Ser Gln Glu Phe Ala Ile Asn
                245                 250                 255

Gly Val Thr Ile Gly Lys Ile Glu Tyr Lys Asp Gly Asp Gly Asn Gly
            260                 265                 270
```

```
Ser Leu Ile Ser Ala Ile Asn Ala Val Lys Asp Thr Thr Gly Val Gln
            275                 280                 285
Ala Ser Lys Asp Glu Asn Gly Lys Leu Val Leu Thr Ser Ala Asp Gly
        290                 295                 300
Arg Gly Ile Lys Ile Thr Gly Asp Ile Val Gly Ser Gly Ile Leu
305                 310                 315                 320
Ala Asn Gln Lys Glu Asn Tyr Gly Arg Leu Ser Leu Val Lys Asn Asp
                325                 330                 335
Gly Arg Asp Ile Asn Ile Ser Gly Thr Asn Leu Ser Ala Ile Gly Met
            340                 345                 350
Gly Thr Thr Asp Met Ile Ser Gln Ser Ser Val Ser Leu Arg Glu Ser
        355                 360                 365
Lys Gly Gln Ile Ser Ala Thr Asn Ala Asp Ala Met Gly Phe Asn Ser
    370                 375                 380
Tyr Lys Gly Gly Gly Lys Phe Val Phe Thr Gln Asn Val Ser Ser Ile
385                 390                 395                 400
Ser Ala Phe Met Ser Ala Gln Gly Ser Gly Phe Ser Arg Gly Ser Gly
                405                 410                 415
Phe Ser Val Gly Ser Gly Lys Asn Leu Ser Val Gly Leu Ser Gln Gly
            420                 425                 430
Ile Gln Ile Ile Ser Ser Ala Ala Ser Met Ser Asn Thr Tyr Val Val
        435                 440                 445
Ser Ala Gly Ser Gly Phe Ser Ser Gly Ser Gly Asn Ser Gln Phe Ala
    450                 455                 460
Ala Leu Lys Thr Thr Ala Ala Asn Thr Thr Asp Glu Thr Ala Gly Val
465                 470                 475                 480
Thr Thr Leu Lys Gly Ala Met Ala Val Met Asp Ile Ala Glu Thr Ala
                485                 490                 495
Ile Thr Asn Leu Asp Gln Ile Arg Ala Asp Ile Gly Ser Ile Gln Asn
            500                 505                 510
Gln Val Thr Ser Thr Ile Asn Asn Ile Thr Val Thr Gln Val Asn Val
        515                 520                 525
Lys Ala Ala Glu Ser Gln Ile Arg Asp Val Asp Phe Ala Ser Glu Ser
    530                 535                 540
Ala Asn Tyr Ser Lys Ala Asn Ile Leu Ala Gln Ser Gly Ser Tyr Ala
545                 550                 555                 560
Met Ala Gln Ala Asn Ser Ser Gln Gln Asn Val Leu Arg Leu Leu Gln
                565                 570                 575

<210> SEQ ID NO 57
<211> LENGTH: 1719
<212> TYPE: DNA
<213> ORGANISM: Campylobacter jejuni

<400> SEQUENCE: 57
atgggtttta ggataaacac caacatcggt gcattaaatg cacatgcaaa ttcagttgtt      60
aatgctagag aactggataa gtctttaagc agacttagtt caggtcttag aatcaactcc     120
gcagcagatg atgcttcagg gatggcgata gcagattctt tgcgttcaca agcagccact     180
ttaggtcaag ctatcaacaa tggtaatgat gctataggta tcttacaaac tgctgataag     240
gctatggatg agcaacttaa aatcttagat acaatcaaaa ctaaggcaac tcaagcggct     300
caagatggac aaagtttaaa acaagaacc atgcttcaag cagatatcaa ccgtttaatg     360
gaagaacttg acaatatcgc aaatactact tcatttaacg gtaaacaact tttaagtggg     420
```

```
aattttatca atcaagaatt tcaaatcggt gcaagttcaa atcaaactat aaaagctact    480
ataggagcaa ctcaatcttc taagataggt ttaacacgct ttgaaacagg aggaagaatt    540
tcatctagtg gtgaagtaca atttactctt aaaaattaca atggtataga tgattttcag    600
tttcaaaaag ttgtgatttc aacttcagtt ggaacaggac ttggagcttt agcagaagag    660
atcaataaaa gtgctgataa acaggtgtt agagctactt ttacagtaga aactagaggt     720
atagctgcag ttagagcagg aactacttca gatactttg ctatcaatgg agtaactata     780
ggtcaagtag cctatgaaga tggtgatgga acggtgctt tagttgctgc aatcaattcg     840
gttaaagata ccactggagt tgaagcttcg atcgatgcta atggacaact tttacttact    900
tcaagagaag gtagagggat taaaatcgat ggtaatatag gtggaggtgc ctttatcaat    960
gctgatatga aagaaaacta tggccgcttg tctttagtta aaaatgatgg taaagatatt   1020
ttaatcagcg gtagcaatct ttcttctgca ggttttggtg caactcaatt tatctctcaa   1080
gcttctgttt cttttaagaga gtcaaaagga gatttgatg ctaatatcgc tgatgctatg    1140
ggatttggtt ctgcaaacaa aggagttgtg ttaggtggtt attcttctgt tagtgcctat   1200
atgagtagcg caggaagtgg attttcttca ggttcaggtt attctgtagg tagcggtaaa   1260
aattattcca caggttttgc aaacgctata gctatttcag ctgcttcgca actttctacg   1320
gtatataatg tttctgcagg ctcaggtttt tcaagtggtt caacactttc tcagtttgca   1380
actatgaaaa caactgcttt tggagtaaaa gatgaaacag caggtgttac cacacttaaa   1440
ggcgctatgg ctgtgatgga tatagctgaa acagccacaa caaatcttga tcaaatcaga   1500
gcagacattg gttcggtgca aaatcaactt caagttacta taaacaacat tactgttact   1560
caagtcaatg ttaaagcagc tgaatcaacc ataagagatg tagactttgc agctgagagt   1620
gcaaattttt ctaaatataa catccttgcg caatcaggtt cttatgctat gagtcaggct   1680
aatgcagtgc agcaaaatgt tttaaaactt cttcaataa                          1719
```

<210> SEQ ID NO 58
<211> LENGTH: 572
<212> TYPE: PRT
<213> ORGANISM: Campylobacter jejuni

<400> SEQUENCE: 58

```
Met Gly Phe Arg Ile Asn Thr Asn Ile Gly Ala Leu Asn Ala His Ala
1               5                   10                  15

Asn Ser Val Val Asn Ala Arg Glu Leu Asp Lys Ser Leu Ser Arg Leu
            20                  25                  30

Ser Ser Gly Leu Arg Ile Asn Ser Ala Ala Asp Asp Ala Ser Gly Met
        35                  40                  45

Ala Ile Ala Asp Ser Leu Arg Ser Gln Ala Ala Thr Leu Gly Gln Ala
    50                  55                  60

Ile Asn Asn Gly Asn Asp Ala Ile Gly Ile Leu Gln Thr Ala Asp Lys
65                  70                  75                  80

Ala Met Asp Glu Gln Leu Lys Ile Leu Asp Thr Ile Lys Thr Lys Ala
                85                  90                  95

Thr Gln Ala Ala Gln Asp Gly Gln Ser Leu Lys Thr Arg Thr Met Leu
            100                 105                 110

Gln Ala Asp Ile Asn Arg Leu Met Glu Glu Leu Asp Asn Ile Ala Asn
        115                 120                 125

Thr Thr Ser Phe Asn Gly Lys Gln Leu Leu Ser Gly Asn Phe Ile Asn
    130                 135                 140
```

-continued

```
Gln Glu Phe Gln Ile Gly Ala Ser Ser Asn Gln Thr Ile Lys Ala Thr
145                 150                 155                 160

Ile Gly Ala Thr Gln Ser Ser Lys Ile Gly Leu Thr Arg Phe Glu Thr
                165                 170                 175

Gly Gly Arg Ile Ser Ser Ser Gly Glu Val Gln Phe Thr Leu Lys Asn
            180                 185                 190

Tyr Asn Gly Ile Asp Asp Phe Gln Phe Gln Lys Val Val Ile Ser Thr
        195                 200                 205

Ser Val Gly Thr Gly Leu Gly Ala Leu Ala Glu Glu Ile Asn Lys Ser
    210                 215                 220

Ala Asp Lys Thr Gly Val Arg Ala Thr Phe Thr Val Glu Thr Arg Gly
225                 230                 235                 240

Ile Ala Ala Val Arg Ala Gly Thr Thr Ser Asp Thr Phe Ala Ile Asn
                245                 250                 255

Gly Val Thr Ile Gly Gln Val Ala Tyr Glu Asp Gly Asp Gly Asn Gly
            260                 265                 270

Ala Leu Val Ala Ala Ile Asn Ser Val Lys Asp Thr Thr Gly Val Glu
        275                 280                 285

Ala Ser Ile Asp Ala Asn Gly Gln Leu Leu Leu Thr Ser Arg Glu Gly
    290                 295                 300

Arg Gly Ile Lys Ile Asp Gly Asn Ile Gly Gly Ala Phe Ile Asn
305                 310                 315                 320

Ala Asp Met Lys Glu Asn Tyr Gly Arg Leu Ser Leu Val Lys Asn Asp
                325                 330                 335

Gly Lys Asp Ile Leu Ile Ser Gly Ser Asn Leu Ser Ser Ala Gly Phe
            340                 345                 350

Gly Ala Thr Gln Phe Ile Ser Gln Ala Ser Val Ser Leu Arg Glu Ser
        355                 360                 365

Lys Gly Arg Phe Asp Ala Asn Ile Ala Asp Ala Met Gly Phe Gly Ser
    370                 375                 380

Ala Asn Lys Gly Val Val Leu Gly Gly Tyr Ser Ser Val Ser Ala Tyr
385                 390                 395                 400

Met Ser Ser Ala Gly Ser Gly Phe Ser Ser Gly Ser Gly Tyr Ser Val
                405                 410                 415

Gly Ser Gly Lys Asn Tyr Ser Thr Gly Phe Ala Asn Ala Ile Ala Ile
            420                 425                 430

Ser Ala Ala Ser Gln Leu Ser Thr Val Tyr Asn Val Ser Ala Gly Ser
        435                 440                 445

Gly Phe Ser Ser Gly Ser Thr Leu Ser Gln Phe Ala Thr Met Lys Thr
    450                 455                 460

Thr Ala Phe Gly Val Lys Asp Glu Thr Ala Gly Val Thr Thr Leu Lys
465                 470                 475                 480

Gly Ala Met Ala Val Met Asp Ile Ala Glu Thr Ala Thr Asn Leu
                485                 490                 495

Asp Gln Ile Arg Ala Asp Ile Gly Ser Val Gln Asn Gln Leu Gln Val
            500                 505                 510

Thr Ile Asn Asn Ile Thr Val Thr Gln Val Asn Val Lys Ala Ala Glu
        515                 520                 525

Ser Thr Ile Arg Asp Val Asp Phe Ala Ala Glu Ser Ala Asn Phe Ser
    530                 535                 540

Lys Tyr Asn Ile Leu Ala Gln Ser Gly Ser Tyr Ala Met Ser Gln Ala
545                 550                 555                 560

Asn Ala Val Gln Gln Asn Val Leu Lys Leu Leu Gln
```

<210> SEQ ID NO 59
<211> LENGTH: 1731
<212> TYPE: DNA
<213> ORGANISM: Campylobacter jejuni

<400> SEQUENCE: 59

```
atgggtttta ggataaacac caacatcggt gcattaaatg cacatgcaaa ttcagttgtt      60
aactctaatg aacttgacaa gtctttaagt agactaagtt caggtcttag aattaactca     120
gcagcagatg atgcttcagg gatggcagata gcagattctt tgcgttcaca agcagcaact    180
ttaggtcaag ctataaacaa tggtaatgat gccataggta ttttgcaaac tgcagataaa     240
gctatggatg agcaattaaa aattcttgat actatcaaga ctaaagctac tcaagcagct     300
caagatggac aaagtttaaa aacaagaact atgcttcaag cagatattaa taaattaatg    360
gaagagcttg ataatatcgc aaatactact tcatttaatg gtaagcaact tttaagtgga     420
aattttacca atcaagaatt ccaaatcggc gcaagttcaa accaaactgt gaaagcaact     480
atcggtgcta ctcaatcttc taaaatcggt gttacaagat tgaaaccgg tgctcaaagt     540
tttacttcag gtgtggttgg tcttactatt aaaaactaca atggtataga agattttaaa     600
tttgataatg ttgtgatttc aacttcagtt ggaacaggac ttggagcttt ggctgaagag     660
atcaataaaa gcgctgataa acaggagtt cgcgcaactt acgatgtaaa acaactggc      720
gtttatgcta taaagaagg aactacttct caagactttg ccattaatgg agttgtaatt     780
ggtcagatta ttataaaga tggtgataat aacggccaat tggtttcagc tatcaatgcg     840
gttaaagata ccacaggagt tcaagcttct aaagatgaaa acggcaagct tgttcttaca     900
tcggctgatg cagggtgtat taaaattact ggagatatag tgttggttc tggtattttg      960
gcaaatcaaa agaaaacta tgggcgatta tctttagtta aaaatgatgg tagagatatc    1020
aatataagtg gaaccaatct tagtgctata ggtatgggta caacagatat gatttctcaa    1080
tcttcagtgt ctttaagaga atcaaaaggt caaatttcag caaccaatgc cgatgctatg    1140
ggatttaatt cttataaagg tggtggaaaa tttgttttta ctcaaaatgt aagttcaatt    1200
tctgcattta tgagtgcaca aggttcagga ttttctagag gttcaggatt ttctgtgggt    1260
agtggtaaaa atttatctgt tggattgagt caaggaatac aaattattc aagtgcggct    1320
tcaatgagca atacttatgt tgtttcagca ggttcaggat tttcttctgg ctcaggaaat    1380
tctcaatttg cagcccttaa aactactgct gctaatacaa ctgatgagac tgcaggtgta    1440
accactctta aggtgcaat ggcggttatg gatatagcag aaactgctat aacaaatcta    1500
gatcaaatca gagcagatat tggttctgta caaaatcaac ttcaagttac tataaacaat    1560
attactgtaa ctcaagttaa tgttaaagca gccgaatcaa ccataagaga tgtagacttt    1620
gcaagtgaga gtgcgaattt ttctaaatat aacattcttg cacaatcagg ctcatatgct    1680
atgagtcaag ctaacgctgt acagcaaaat gttttaaaac tattacaata a            1731
```

<210> SEQ ID NO 60
<211> LENGTH: 576
<212> TYPE: PRT
<213> ORGANISM: Campylobacter jejuni

<400> SEQUENCE: 60

```
Met Gly Phe Arg Ile Asn Thr Asn Ile Gly Ala Leu Asn Ala His Ala
1               5                   10                  15
```

-continued

Asn Ser Val Val Asn Ser Asn Glu Leu Asp Lys Ser Leu Ser Arg Leu
            20                  25                  30

Ser Ser Gly Leu Arg Ile Asn Ser Ala Ala Asp Asp Ala Ser Gly Met
        35                  40                  45

Ala Ile Ala Asp Ser Leu Arg Ser Gln Ala Ala Thr Leu Gly Gln Ala
50                  55                  60

Ile Asn Asn Gly Asn Asp Ala Ile Gly Ile Leu Gln Thr Ala Asp Lys
65                  70                  75                  80

Ala Met Asp Glu Gln Leu Lys Ile Leu Asp Thr Ile Lys Thr Lys Ala
                85                  90                  95

Thr Gln Ala Ala Gln Asp Gly Gln Ser Leu Lys Thr Arg Thr Met Leu
            100                 105                 110

Gln Ala Asp Ile Asn Lys Leu Met Glu Glu Leu Asp Asn Ile Ala Asn
        115                 120                 125

Thr Thr Ser Phe Asn Gly Lys Gln Leu Leu Ser Gly Asn Phe Thr Asn
130                 135                 140

Gln Glu Phe Gln Ile Gly Ala Ser Ser Asn Gln Thr Val Lys Ala Thr
145                 150                 155                 160

Ile Gly Ala Thr Gln Ser Ser Lys Ile Gly Val Thr Arg Phe Glu Thr
                165                 170                 175

Gly Ala Gln Ser Phe Thr Ser Gly Val Val Gly Leu Thr Ile Lys Asn
            180                 185                 190

Tyr Asn Gly Ile Glu Asp Phe Lys Phe Asp Asn Val Val Ile Ser Thr
        195                 200                 205

Ser Val Gly Thr Gly Leu Gly Ala Leu Ala Glu Glu Ile Asn Lys Ser
210                 215                 220

Ala Asp Lys Thr Gly Val Arg Ala Thr Tyr Asp Val Lys Thr Thr Gly
225                 230                 235                 240

Val Tyr Ala Ile Lys Glu Gly Thr Thr Ser Gln Asp Phe Ala Ile Asn
                245                 250                 255

Gly Val Val Ile Gly Gln Ile Asn Tyr Lys Asp Gly Asp Asn Asn Gly
            260                 265                 270

Gln Leu Val Ser Ala Ile Asn Ala Val Lys Asp Thr Thr Gly Val Gln
        275                 280                 285

Ala Ser Lys Asp Glu Asn Gly Lys Leu Val Leu Thr Ser Ala Asp Gly
290                 295                 300

Arg Gly Ile Lys Ile Thr Gly Asp Ile Gly Val Gly Ser Gly Ile Leu
305                 310                 315                 320

Ala Asn Gln Lys Glu Asn Tyr Gly Arg Leu Ser Leu Val Lys Asn Asp
                325                 330                 335

Gly Arg Asp Ile Asn Ile Ser Gly Thr Asn Leu Ser Ala Ile Gly Met
            340                 345                 350

Gly Thr Thr Asp Met Ile Ser Gln Ser Ser Val Ser Leu Arg Glu Ser
        355                 360                 365

Lys Gly Gln Ile Ser Ala Thr Asn Ala Asp Ala Met Gly Phe Asn Ser
370                 375                 380

Tyr Lys Gly Gly Gly Lys Phe Val Phe Thr Gln Asn Val Ser Ser Ile
385                 390                 395                 400

Ser Ala Phe Met Ser Ala Gln Gly Ser Gly Phe Ser Arg Gly Ser Gly
                405                 410                 415

Phe Ser Val Gly Ser Gly Lys Asn Leu Ser Val Gly Leu Ser Gln Gly
            420                 425                 430

Ile Gln Ile Ile Ser Ser Ala Ala Ser Met Ser Asn Thr Tyr Val Val

```
                    435                 440                 445
Ser Ala Gly Ser Gly Phe Ser Ser Gly Ser Gly Asn Ser Gln Phe Ala
    450                 455                 460

Ala Leu Lys Thr Thr Ala Ala Asn Thr Thr Asp Glu Thr Ala Gly Val
465                 470                 475                 480

Thr Thr Leu Lys Gly Ala Met Ala Val Met Asp Ile Ala Glu Thr Ala
                485                 490                 495

Ile Thr Asn Leu Asp Gln Ile Arg Ala Asp Ile Gly Ser Val Gln Asn
            500                 505                 510

Gln Leu Gln Val Thr Ile Asn Asn Ile Thr Val Thr Gln Val Asn Val
        515                 520                 525

Lys Ala Ala Glu Ser Thr Ile Arg Asp Val Asp Phe Ala Ser Glu Ser
    530                 535                 540

Ala Asn Phe Ser Lys Tyr Asn Ile Leu Ala Gln Ser Gly Ser Tyr Ala
545                 550                 555                 560

Met Ser Gln Ala Asn Ala Val Gln Gln Asn Val Leu Lys Leu Leu Gln
                565                 570                 575

<210> SEQ ID NO 61
<211> LENGTH: 2598
<212> TYPE: DNA
<213> ORGANISM: Campylobacter jejuni

<400> SEQUENCE: 61
atgatgagat cactttggtc tggcgtaagc ggactacaag cacatcaagt tgcgatggat      60
gttgaaggta ataacatttc aaatgttaat accactggtt ttaaatattc tcgtgcagat     120
tttgggacta tgtttagcca aactgtgaaa atcgctacag ctccaactga tggaagaggc     180
ggatctaatc cacttcaaat cggtcttggc gtttcagtaa gttctacaac tagaattcat     240
tctcaaggtt cagttcaaac cacagataaa acactgacg ttgctataaa tggcgatggt     300 tttttatgg taagcgatga tggtggtctt acaaactatc ttacaaggag cggggatttt     360
aaactagatg cttatggaaa ttttgttaat aatgcaggtt tgttgtcca agggtggaat      420 atcaactggg atgatcaaac tatagatagt tcaagaactc acaaaatat ttttatcgat     480 ccaggtatgc atatccctgc agcaaaatct actgaagttg ctatcaaagc gaatttaaat     540
agtggtttaa ataggaac ttcaagtaga atctttatg cacttgattc tgttcatgga      600
tggaatacta aacccaaag agcagaagat gaaaatgata caggaactac tcagttttat     660
acgacttcta agaattctgt agaagtgaca gaaaagggtg tggatgcggg atcacttttt     720
aacgcgaaag gacaaggact taatcttaga gatggacaag gaatttgggt atcttatgca     780
gatgcaacat attctaccaa taaagtagga gtaaatgctt ttgatccaaa tttacagcaa     840
aatcaaactg ctgctttttg gggaacagct aatcaaaaag tgaatttaga tataacttta     900
aatggggtta gaattcaaaa tgctgatatt caaagtattg atgatgctat tgcttatatc     960
aataccttta ctgcaccaac ggatacaagg gatggaacag tgtaaaaagc ggttaaaaat    1020
aaggatggta gtggaattga ttttgtcaat gataatgccg atggtactac agataatatg    1080
aaaaatatca atcttgtggt tgccaatacc aatacagcag gtgagctttg gaatgctgta    1140
tggaataaca acaatcaaac atttacattt aataataatg gtaatggaca ggctggaaca    1200
ccgactatta taaaaaatgg ttcttctttg tggacagcta caaatattac atttacacca    1260
caacctcctc aagcagctac gaatgttcag cttactggtg gactaaatgc acaaataata    1320
acagcacata atatattta gttcaaac cctgtggata taggtcctat gtataatcct    1380
```

-continued

```
gacggtggac cagcattcca gcctggtgct aatgcaacta caagaccaac tgaaccaggt    1440
tcagcagctt attgggatgc tgttaatggt ggacttttaa atactaatgt aagaactttt    1500
agaaccacag aagatttaag agaacttta caaagggatg ctagatatgg ggttgattat     1560 gatgaagtg gaacttttgc tgcagctgat attaatcaaa atataaaagt agtagtaacg     1620
gcagatggac attttgctat ttccaatgct aatgaacaat caactgttcc accaaatgct    1680
attaatggtg taggaaatgc cactacaaca gatccaaaaa atatgagttt taatataaca    1740
gcttatagta acaaacaagg aactgtaagt actaatgatg ctttcactgc tattttaaa    1800 gctttcgatg gtcctttggt tataggaaat cagatcaaag aaagcgaaca acttaagctt    1860 tctgctttt cggcggggct tgaaatttat gattctttag gttcaaaaca cactttagaa    1920
gtgcagtttg ttaagcaaag taccactcaa gatgggggta atgaatggca aatgatcatc    1980
cgtgtacctg aacctgcaga gattaacact acaggcgaag gaccaaacaa tatcatcgta    2040
ggaacagcta gatttaacaa tgacggctct ttagctagtt atacaccaag aacgataaat    2100
ttctcaccaa acaatggtgc cgcaccaaat caacaaatca aactttcctt tggaacaagt    2160
ggaagcaatg acggccttgt aagctcaaat tctgcttcaa ctctaacagg acaggcaact    2220
gatggttata cttcaggtaa cttaaaacct gatgctatcc gtgtggatga taaaggtaat    2280
atcttaggtg aatttactaa tggcaaaacc tttgctgtag caaaaatcgc aatggcttca    2340
gtggcaaata actcaggtct tgaggaaatt ggtggaaatc tttttaaagt tactgcaaat    2400
agtggtaata tcgtggtagg tgaagcagga acaggaggtc gtggtgagat gaaaaccctca    2460 gctcttgaaa tgtcaaatgt ggatttaagt cgttctttaa cagagcttat tatcattcaa    2520
agaggttatc aagcaaactc aaaaaccatt tcaacgagtg atcaaatgct ccaaactcta    2580
atccagctta aacaataa                                                   2598
```

<210> SEQ ID NO 62
<211> LENGTH: 865
<212> TYPE: PRT
<213> ORGANISM: Campylobacter jejuni

<400> SEQUENCE: 62

```
Met Met Arg Ser Leu Trp Ser Gly Val Ser Gly Leu Gln Ala His Gln
1               5                   10                  15

Val Ala Met Asp Val Glu Gly Asn Asn Ile Ser Asn Val Asn Thr Thr
            20                  25                  30

Gly Phe Lys Tyr Ser Arg Ala Asp Phe Gly Thr Met Phe Ser Gln Thr
        35                  40                  45

Val Lys Ile Ala Thr Ala Pro Thr Asp Gly Arg Gly Gly Ser Asn Pro
    50                  55                  60

Leu Gln Ile Gly Leu Gly Val Ser Val Ser Ser Thr Thr Arg Ile His
65                  70                  75                  80

Ser Gln Gly Ser Val Gln Thr Thr Asp Lys Asn Thr Asp Val Ala Ile
                85                  90                  95

Asn Gly Asp Gly Phe Phe Met Val Ser Asp Asp Gly Gly Leu Thr Asn
            100                 105                 110

Tyr Leu Thr Arg Ser Gly Asp Phe Lys Leu Asp Ala Tyr Gly Asn Phe
        115                 120                 125

Val Asn Asn Ala Gly Phe Val Val Gln Gly Trp Asn Ile Asn Trp Asp
    130                 135                 140

Asp Gln Thr Ile Asp Ser Ser Arg Thr Pro Gln Asn Ile Phe Ile Asp
```

-continued

```
145                 150                 155                 160
Pro Gly Met His Ile Pro Ala Ala Lys Ser Thr Glu Val Ala Ile Lys
                165                 170                 175

Ala Asn Leu Asn Ser Gly Leu Asn Ile Gly Thr Ser Ser Arg Asn Leu
                180                 185                 190

Tyr Ala Leu Asp Ser Val His Gly Trp Asn Thr Lys Thr Gln Arg Ala
                195                 200                 205

Glu Asp Glu Asn Asp Thr Gly Thr Thr Gln Phe Tyr Thr Thr Ser Lys
210                 215                 220

Asn Ser Val Glu Val Thr Glu Lys Gly Val Asp Ala Gly Ser Leu Phe
225                 230                 235                 240

Asn Ala Lys Gly Gln Gly Leu Asn Leu Arg Asp Gly Gln Gly Ile Trp
                245                 250                 255

Val Ser Tyr Ala Asp Ala Thr Tyr Ser Thr Asn Lys Val Gly Val Asn
                260                 265                 270

Ala Phe Asp Pro Asn Leu Gln Gln Asn Gln Thr Ala Ala Phe Trp Gly
                275                 280                 285

Thr Ala Asn Gln Lys Val Asn Leu Asp Ile Thr Leu Asn Gly Val Arg
                290                 295                 300

Ile Gln Asn Ala Asp Ile Gln Ser Ile Asp Asp Ala Ile Ala Tyr Ile
305                 310                 315                 320

Asn Thr Phe Thr Ala Pro Thr Asp Thr Arg Asp Gly Thr Gly Val Lys
                325                 330                 335

Ala Val Lys Asn Lys Asp Gly Ser Gly Ile Asp Phe Val Asn Asp Asn
                340                 345                 350

Ala Asp Gly Thr Thr Asp Asn Met Lys Asn Ile Asn Leu Val Val Ala
                355                 360                 365

Asn Thr Asn Thr Ala Gly Glu Leu Trp Asn Ala Val Trp Asn Asn Asn
                370                 375                 380

Asn Gln Thr Phe Thr Phe Asn Asn Gly Asn Gly Gln Ala Gly Thr
385                 390                 395                 400

Pro Thr Ile Asn Lys Asn Gly Ser Ser Leu Trp Thr Ala Thr Asn Ile
                405                 410                 415

Thr Phe Thr Pro Gln Pro Pro Gln Ala Ala Thr Asn Val Gln Leu Thr
                420                 425                 430

Gly Gly Leu Asn Ala Gln Ile Ile Thr Ala His Lys Tyr Ile Tyr Ser
                435                 440                 445

Ser Asn Pro Val Asp Ile Gly Pro Met Tyr Asn Pro Asp Gly Gly Pro
                450                 455                 460

Ala Phe Gln Pro Gly Ala Asn Ala Thr Thr Arg Pro Thr Glu Pro Gly
465                 470                 475                 480

Ser Ala Ala Tyr Trp Asp Ala Val Asn Gly Leu Leu Asn Thr Asn
                485                 490                 495

Val Arg Thr Phe Arg Thr Thr Glu Asp Leu Arg Glu Leu Leu Gln Arg
                500                 505                 510

Asp Ala Arg Tyr Gly Val Asp Tyr Asp Gly Ser Gly Thr Phe Ala Ala
                515                 520                 525

Ala Asp Ile Asn Gln Asn Ile Lys Val Val Thr Ala Asp Gly His
                530                 535                 540

Phe Ala Ile Ser Asn Ala Asn Glu Gln Ser Thr Val Pro Pro Asn Ala
545                 550                 555                 560

Ile Asn Gly Val Gly Asn Ala Thr Thr Thr Asp Pro Lys Asn Met Ser
                565                 570                 575
```

```
Phe Asn Ile Thr Ala Tyr Ser Asn Lys Gln Gly Val Ser Thr Asn
            580                 585                 590
Asp Ala Phe Thr Ala Ile Phe Lys Ala Phe Asp Gly Pro Leu Val Ile
    595                 600                 605
Gly Asn Gln Ile Lys Glu Ser Glu Gln Leu Lys Leu Ser Ala Phe Ser
    610                 615                 620
Ala Gly Leu Glu Ile Tyr Asp Ser Leu Gly Ser Lys His Thr Leu Glu
625                 630                 635                 640
Val Gln Phe Val Lys Gln Ser Thr Thr Gln Asp Gly Gly Asn Glu Trp
                645                 650                 655
Gln Met Ile Ile Arg Val Pro Glu Pro Ala Glu Ile Asn Thr Thr Gly
            660                 665                 670
Glu Gly Pro Asn Asn Ile Ile Val Gly Thr Ala Arg Phe Asn Asn Asp
        675                 680                 685
Gly Ser Leu Ala Ser Tyr Thr Pro Arg Thr Ile Asn Phe Ser Pro Asn
    690                 695                 700
Asn Gly Ala Ala Pro Asn Gln Gln Ile Lys Leu Ser Phe Gly Thr Ser
705                 710                 715                 720
Gly Ser Asn Asp Gly Leu Val Ser Ser Asn Ser Ala Ser Thr Leu Thr
                725                 730                 735
Gly Gln Ala Thr Asp Gly Tyr Thr Ser Gly Asn Leu Lys Pro Asp Ala
            740                 745                 750
Ile Arg Val Asp Asp Lys Gly Asn Ile Leu Gly Glu Phe Thr Asn Gly
        755                 760                 765
Lys Thr Phe Ala Val Ala Lys Ile Ala Met Ala Ser Val Ala Asn Asn
    770                 775                 780
Ser Gly Leu Glu Glu Ile Gly Gly Asn Leu Phe Lys Val Thr Ala Asn
785                 790                 795                 800
Ser Gly Asn Ile Val Val Gly Glu Ala Gly Thr Gly Arg Gly Glu
                805                 810                 815
Met Lys Thr Ser Ala Leu Glu Met Ser Asn Val Asp Leu Ser Arg Ser
            820                 825                 830
Leu Thr Glu Leu Ile Ile Gln Arg Gly Tyr Gln Ala Asn Ser Lys
        835                 840                 845
Thr Ile Ser Thr Ser Asp Gln Met Leu Gln Thr Leu Ile Gln Leu Lys
    850                 855                 860
Gln
865

<210> SEQ ID NO 63
<211> LENGTH: 2517
<212> TYPE: DNA
<213> ORGANISM: Campylobacter jejuni

<400> SEQUENCE: 63
atgatgagat cactttggtc tggcgtaagc ggactacaag cacatcaagt tgcgatggat     60
gttgaaggta ataacatttc aaatgttaat accactggtt ttaaatactc ccgtgcagat    120
tttgggacta tgtttagcca aactgtgaaa atcgctacag ctccaactga tggaagaggt    180
ggatctaatc cacttcaaat cggtcttggc gtttcagtaa gttctacaac tagaattcat    240
tctcaaggtt cagttcaaac cacagataaa acactgatg tggctataaa tggtgatggt    300 tttttatgg tgagtgatga tgggggggctt actcgctatc ttacaaggag cggggatttt    360
aaactagatg cttatggaaa ttttgttaat aatgcaggtt tgttgtccaa agggtggaat    420
```

```
atcaactggg atactcaaag tatagatagc tcaagaactc cgcaaaatat ttttatcgat      480
cccggtatgc atatccctgc agcaaaatca accgaagtag ccatcaaagc gaatttaaat      540
agtggtttaa gcgtaggaac agcaaaaact cctatatatg gacttgattc tgttcatggt      600
tttaacaaaa aagatggaac tgcaaaaaat gaaaatgata caggtataac tcaattttac      660
acaacttcaa aaaattcagt agaagttaca gaaaaggggt tgactgtgc tgctttattt      720 aatggtaaag gcgatggttt aaatttaaga gatggacaag gtatatgggt aagctatgca      780
gattctaaat ttagcacaga tgttccaaat ggtgtaaatg tatttaatcc aaatactcaa      840
gctactcaaa atggtgttat attttgggga gatgaaaaca atgctgtaaa tcttgatata      900
acattaaatg gagttagaat acaaaataat tctataaaaa gtttagatca agctatagaa      960
tacataaata cttttacagc tcctacagat acaagagaag gaacgggagt aaaagcagta     1020
agaaaagccg atggtagcgg tatagaattt ataaatacta atgctgatgg cactacagat     1080
aatatgaaaa atatagactt ggttgtaaat caagcaaata cagccggaga aagacacaat     1140
cttacatggc aagcaaataa taatagtttt caagctacat ctagaaaaca aggtgcaaac     1200
tcagtatgga tacctggaaa taatcctgta aatggaactg aaagaataca aatagtaaca     1260
gcgcataaat atgtatacag ttcaactcca gttcaactag atcctatgta taatccagat     1320
ggtggtcctg cttttaatca agccaatata aacacacctg gaacagctga aaataactat     1380
cgtaatgccg ttaatggttc tttattaaat acaacagtaa gaacttttag aactactgaa     1440
gatttaagag aacttttaca aagagatgct agatatggtg ttgattatga tggaagtggt     1500
ggatttgaag ctgatggtag tgatgttaat gaaggtgtaa aagtaacagt tggtgcaaca     1560
ggtgaattta taatatcaaa tccaaatgtt caatcaactc ctccaaatgg tatagttcaa     1620
aataatagaa gacctcatga tataagttttt aatgttacag cttatacaga tgcaaaaggc     1680
aaagtaagca caaatatggc atttacaaat atatttaaag gttttgatgg agttttaaca     1740 gtaggaaaatt caaatcgcca aagcgaacaa cttttcttaa gtgcatttttc tgctggactt     1800 gaaatttatg attctttagg ttcaaaacat actttagaag tgcagtttgt taagcaaagc     1860
acaactcaag atggtggtaa tgaatggcag atgatcatcc gtgtgccaga acctgctgag     1920
attaacacta caggcgaagg accaaataat atcatcgtag gaacggcaag atttaacaat     1980
gatggctctt tggcaaatta tagtccaaaa actataaatt tctcaccaaa caatggtgcc     2040
gcaccaaatc aacaaataaa acttagcttt ggaacaagtg gaagcaatga cggccttgta     2100
agctcaaatt ctgcttcaac tctaacagga caagcaactg atggttatac ttcaggtaac     2160
ttaaagcctg atgctatccg tgtggatgat aaaggaaata tcttaggtga atttacaaat     2220
ggtaaaacct tcgctgtggc aaaaatggcg atggcttcag tagcaaataa ctcaggcctt     2280
gaagaaatcg gcggaaatct ttttaaagtc actgcaaata gtggggctat agtagtaggt     2340
gaagcaggaa caggaggtcg tggtgagatg aaaacctcag ctcttgaaat gtcaaatgtg     2400
gatttaagtc gttctttaac agagcttatc atcattcaaa gaggttatca agcaaactca     2460
aaaaccattt caacgagtga tcaaatgctt caaactctaa tccagcttaa acaataa         2517
```

<210> SEQ ID NO 64
<211> LENGTH: 838
<212> TYPE: PRT
<213> ORGANISM: Campylobacter jejuni

<400> SEQUENCE: 64

-continued

```
Met Met Arg Ser Leu Trp Ser Gly Val Ser Gly Leu Gln Ala His Gln
1               5                   10                  15

Val Ala Met Asp Val Glu Gly Asn Asn Ile Ser Asn Val Asn Thr Thr
            20                  25                  30

Gly Phe Lys Tyr Ser Arg Ala Asp Phe Gly Thr Met Phe Ser Gln Thr
            35                  40                  45

Val Lys Ile Ala Thr Ala Pro Thr Asp Gly Arg Gly Gly Ser Asn Pro
50                      55                  60

Leu Gln Ile Gly Leu Gly Val Ser Val Ser Ser Thr Thr Arg Ile His
65                  70                  75                  80

Ser Gln Gly Ser Val Gln Thr Thr Asp Lys Asn Thr Asp Val Ala Ile
                85                  90                  95

Asn Gly Asp Gly Phe Phe Met Val Ser Asp Asp Gly Gly Leu Thr Arg
            100                 105                 110

Tyr Leu Thr Arg Ser Gly Asp Phe Lys Leu Asp Ala Tyr Gly Asn Phe
        115                 120                 125

Val Asn Asn Ala Gly Phe Val Val Gln Gly Trp Asn Ile Asn Trp Asp
    130                 135                 140

Thr Gln Ser Ile Asp Ser Ser Arg Thr Pro Gln Asn Ile Phe Ile Asp
145                 150                 155                 160

Pro Gly Met His Ile Pro Ala Ala Lys Ser Thr Glu Val Ala Ile Lys
                165                 170                 175

Ala Asn Leu Asn Ser Gly Leu Ser Val Gly Thr Ala Lys Thr Pro Ile
                180                 185                 190

Tyr Gly Leu Asp Ser Val His Gly Phe Asn Lys Asp Gly Thr Ala
        195                 200                 205

Lys Asn Glu Asn Asp Thr Gly Ile Thr Gln Phe Tyr Thr Thr Ser Lys
    210                 215                 220

Asn Ser Val Glu Val Thr Glu Lys Gly Val Asp Cys Ala Ala Leu Phe
225                 230                 235                 240

Asn Gly Lys Gly Asp Gly Leu Asn Leu Arg Asp Gly Gln Gly Ile Trp
                245                 250                 255

Val Ser Tyr Ala Asp Ser Lys Phe Ser Thr Asp Val Pro Asn Gly Val
            260                 265                 270

Asn Val Phe Asn Pro Asn Thr Gln Ala Thr Gln Asn Gly Val Ile Phe
    275                 280                 285

Trp Gly Asp Glu Asn Asn Ala Val Asn Leu Asp Ile Thr Leu Asn Gly
        290                 295                 300

Val Arg Ile Gln Asn Asn Ser Ile Lys Ser Leu Asp Gln Ala Ile Glu
305                 310                 315                 320

Tyr Ile Asn Thr Phe Thr Ala Pro Thr Asp Thr Arg Glu Gly Thr Gly
            325                 330                 335

Val Lys Ala Val Arg Lys Ala Asp Gly Ser Gly Ile Glu Phe Ile Asn
                340                 345                 350

Thr Asn Ala Asp Gly Thr Thr Asp Asn Met Lys Asn Ile Asp Leu Val
            355                 360                 365

Val Asn Gln Ala Asn Thr Ala Gly Glu Arg His Asn Leu Thr Trp Gln
    370                 375                 380

Ala Asn Asn Asn Ser Phe Gln Ala Thr Ser Arg Lys Gln Gly Ala Asn
385                 390                 395                 400

Ser Val Trp Ile Pro Gly Asn Asn Pro Val Asn Gly Thr Glu Arg Ile
            405                 410                 415

Gln Ile Val Thr Ala His Lys Tyr Val Tyr Ser Ser Thr Pro Val Gln
```

```
                420            425            430
Leu Asp Pro Met Tyr Asn Pro Asp Gly Gly Pro Ala Phe Asn Gln Ala
            435                440                445
Asn Ile Asn Thr Pro Gly Thr Ala Glu Asn Asn Tyr Arg Asn Ala Val
        450                455                460
Asn Gly Ser Leu Leu Asn Thr Thr Val Arg Thr Phe Arg Thr Thr Glu
465                470                475                480
Asp Leu Arg Glu Leu Leu Gln Arg Asp Ala Arg Tyr Gly Val Asp Tyr
                485                490                495
Asp Gly Ser Gly Gly Phe Glu Ala Asp Gly Ser Asp Val Asn Glu Gly
            500                505                510
Val Lys Val Thr Val Gly Ala Thr Gly Glu Phe Ile Ile Ser Asn Pro
        515                520                525
Asn Val Gln Ser Thr Pro Pro Asn Gly Ile Val Gln Asn Asn Arg Arg
        530                535                540
Pro His Asp Ile Ser Phe Asn Val Thr Ala Tyr Thr Asp Ala Lys Gly
545                550                555                560
Lys Val Ser Thr Asn Met Ala Phe Thr Asn Ile Phe Lys Gly Phe Asp
                565                570                575
Gly Val Leu Thr Val Gly Asn Ser Asn Arg Gln Ser Glu Gln Leu Phe
            580                585                590
Leu Ser Ala Phe Ser Ala Gly Leu Glu Ile Tyr Asp Ser Leu Gly Ser
        595                600                605
Lys His Thr Leu Glu Val Gln Phe Val Lys Gln Ser Thr Thr Gln Asp
        610                615                620
Gly Gly Asn Glu Trp Gln Met Ile Ile Arg Val Pro Glu Pro Ala Glu
625                630                635                640
Ile Asn Thr Thr Gly Glu Gly Pro Asn Asn Ile Ile Val Gly Thr Ala
                645                650                655
Arg Phe Asn Asn Asp Gly Ser Leu Ala Asn Tyr Ser Pro Lys Thr Ile
            660                665                670
Asn Phe Ser Pro Asn Asn Gly Ala Ala Pro Asn Gln Gln Ile Lys Leu
        675                680                685
Ser Phe Gly Thr Ser Gly Ser Asn Asp Gly Leu Val Ser Ser Asn Ser
        690                695                700
Ala Ser Thr Leu Thr Gly Gln Ala Thr Asp Gly Tyr Thr Ser Gly Asn
705                710                715                720
Leu Lys Pro Asp Ala Ile Arg Val Asp Lys Gly Asn Ile Leu Gly
                725                730                735
Glu Phe Thr Asn Gly Lys Thr Phe Ala Val Ala Lys Met Ala Met Ala
            740                745                750
Ser Val Ala Asn Asn Ser Gly Leu Glu Glu Ile Gly Gly Asn Leu Phe
        755                760                765
Lys Val Thr Ala Asn Ser Gly Ala Ile Val Val Gly Glu Ala Gly Thr
        770                775                780
Gly Gly Arg Gly Glu Met Lys Thr Ser Ala Leu Glu Met Ser Asn Val
785                790                795                800
Asp Leu Ser Arg Ser Leu Thr Glu Leu Ile Ile Gln Arg Gly Tyr
                805                810                815
Gln Ala Asn Ser Lys Thr Ile Ser Thr Ser Asp Gln Met Leu Gln Thr
            820                825                830
Leu Ile Gln Leu Lys Gln
            835
```

<210> SEQ ID NO 65
<211> LENGTH: 738
<212> TYPE: DNA
<213> ORGANISM: Campylobacter jejuni

<400> SEQUENCE: 65

```
atgaaaaaaa tattaatttt aagtttagca gcaagttttt taaatgctga aattttagtt      60
tatggtccag gtggtcctgc tcctgtgcta aaagagcttg ctttaaaatt tgaagaaaaa     120
acaaaagaaa aggtgattgt aaccgcaggt ccaactccag cttgggtaga caaagcaaaa     180
gaaaatgcag atttgatttt ttcaggcaat acttcaatga tggatgattt tgctaaaaaa     240
attccaagtt taagtttgga aaatttaagc gttttaaatg tgcgtccatc aggtattatc     300
gtgcgtccaa ataatccaaa aaatattaaa aattttgaag acattttaaa agatggcata     360
aatgttatgg tggttgatgg tgcaggacaa gttggacttt atgaagatat ggctttaaaa     420
agtgcaaaaa gagaaaattt ggtaaaatta cgtaaaaata taaaaattta tgctaaaaat     480
tccaaagctg ctgtagatga gtggaataac aatccaaata ttgatgcttt aatcatttgg     540
tctcattggg caaaggcttt aggcgatgat aaagctttat ttatcaaaga taaaaatgca     600
gtgatttatc gtgcagctga aatagctcct acaaaaaaag gtttagaaaa taaaaaagct     660
ttagaatttg tagattttat taagagtcag gaagctcaaa aagtgtggaa aaaatatact     720
tggaaagaag taaaataa                                                   738
```

<210> SEQ ID NO 66
<211> LENGTH: 245
<212> TYPE: PRT
<213> ORGANISM: Campylobacter jejuni

<400> SEQUENCE: 66

```
Met Lys Lys Ile Leu Ile Leu Ser Leu Ala Ala Ser Phe Leu Asn Ala
1               5                   10                  15

Glu Ile Leu Val Tyr Gly Pro Gly Gly Pro Ala Pro Val Leu Lys Glu
            20                  25                  30

Leu Ala Leu Lys Phe Glu Glu Lys Thr Lys Lys Val Ile Val Thr
        35                  40                  45

Ala Gly Pro Thr Pro Ala Trp Val Asp Lys Ala Lys Glu Asn Ala Asp
    50                  55                  60

Leu Ile Phe Ser Gly Asn Thr Ser Met Met Asp Asp Phe Ala Lys Lys
65                  70                  75                  80

Ile Pro Ser Leu Ser Leu Glu Asn Leu Ser Val Leu Asn Val Arg Pro
                85                  90                  95

Ser Gly Ile Ile Val Arg Pro Asn Asn Pro Lys Asn Ile Lys Asn Phe
            100                 105                 110

Glu Asp Ile Leu Lys Asp Gly Ile Asn Val Met Val Val Asp Gly Ala
        115                 120                 125

Gly Gln Val Gly Leu Tyr Glu Asp Met Ala Leu Lys Ser Ala Lys Arg
    130                 135                 140

Glu Asn Leu Val Lys Leu Arg Lys Asn Ile Lys Ile Tyr Ala Lys Asn
145                 150                 155                 160

Ser Lys Ala Ala Val Asp Glu Trp Asn Asn Asn Pro Asn Ile Asp Ala
                165                 170                 175

Leu Ile Ile Trp Ser His Trp Ala Lys Ala Leu Gly Asp Asp Lys Ala
            180                 185                 190
```

```
Leu Phe Ile Lys Asp Lys Asn Ala Val Ile Tyr Arg Ala Glu Ile
            195                 200                 205

Ala Pro Thr Lys Lys Gly Leu Glu Asn Lys Lys Ala Leu Glu Phe Val
        210                 215                 220

Asp Phe Ile Lys Ser Gln Glu Ala Gln Lys Val Trp Lys Lys Tyr Thr
225                 230                 235                 240

Trp Lys Glu Val Lys
                245

<210> SEQ ID NO 67
<211> LENGTH: 741
<212> TYPE: DNA
<213> ORGANISM: Campylobacter jejuni

<400> SEQUENCE: 67
atgaaaaaaa tattaatttt aagtttagca gcagcaagtt tttttaaatgc tgaaatttta      60 gtttatggtc caggtggtcc cgctcctgtg ctaaaagagc ttgctttaaa atttgaagaa     120
aaaacaaaag aaaaggtgat tgtaaccgca ggtccaactc cagcttggat agataaagca     180
aaagaaaatg cagatttgat tttttcaggc aatacttcaa tgatggatga ttttgctaaa     240
aaaattccaa gtttaagttt ggaaaattta agcgttttaa atgtgcgtcc atcaggtatt     300
atcgtgcgtc caaataatcc aaaaaatatt aaaaattttg aagacatttt aaaagatggc     360
ataaatgtta tggtggttga tggtgcagga caagttggac tttatgaaga tatggcttta     420
aaaagtgcaa aagagaaaa tttggtaaaa ttacgtaaaa atataaaaat ttatgctaaa     480
aattccaaag ctgctgtaga tgagtggaat aacaatccaa atattgatgc tttaatcatt     540
tggtctcatt gggcaaaggc tttaggcgat gataaagctt tatttatcaa agataaaaat     600
gcagtgattt atcgtgcagc tgaaattgct cctacaaaaa aaggtttaga aaataaaaaa     660
gctttagaat ttgtagattt tattaagagt aaggaagctc aaaaagtgtg gaaaaaatat     720
acttggaaag aagtaaaata a                                                741

<210> SEQ ID NO 68
<211> LENGTH: 246
<212> TYPE: PRT
<213> ORGANISM: Campylobacter jejuni

<400> SEQUENCE: 68

Met Lys Lys Ile Leu Ile Leu Ser Leu Ala Ala Ala Ser Phe Leu Asn
1               5                   10                  15

Ala Glu Ile Leu Val Tyr Gly Pro Gly Gly Pro Ala Pro Val Leu Lys
            20                  25                  30

Glu Leu Ala Leu Lys Phe Glu Glu Lys Thr Lys Glu Lys Val Ile Val
        35                  40                  45

Thr Ala Gly Pro Thr Pro Ala Trp Ile Asp Lys Ala Lys Glu Asn Ala
    50                  55                  60

Asp Leu Ile Phe Ser Gly Asn Thr Ser Met Met Asp Asp Phe Ala Lys
65                  70                  75                  80

Lys Ile Pro Ser Leu Ser Leu Glu Asn Leu Ser Val Leu Asn Val Arg
                85                  90                  95

Pro Ser Gly Ile Ile Val Arg Pro Asn Asn Pro Lys Asn Ile Lys Asn
            100                 105                 110

Phe Glu Asp Ile Leu Lys Asp Gly Ile Asn Val Met Val Val Asp Gly
        115                 120                 125

Ala Gly Gln Val Gly Leu Tyr Glu Asp Met Ala Leu Lys Ser Ala Lys
```

```
                130                 135                 140
Arg Glu Asn Leu Val Lys Leu Arg Lys Asn Ile Lys Ile Tyr Ala Lys
145                 150                 155                 160

Asn Ser Lys Ala Ala Val Asp Glu Trp Asn Asn Pro Asn Ile Asp
                165                 170                 175

Ala Leu Ile Ile Trp Ser His Trp Ala Lys Ala Leu Gly Asp Asp Lys
                180                 185                 190

Ala Leu Phe Ile Lys Asp Lys Asn Ala Val Ile Tyr Arg Ala Ala Glu
                195                 200                 205

Ile Ala Pro Thr Lys Lys Gly Leu Glu Asn Lys Lys Ala Leu Glu Phe
                210                 215                 220

Val Asp Phe Ile Lys Ser Lys Glu Ala Gln Lys Val Trp Lys Lys Tyr
225                 230                 235                 240

Thr Trp Lys Glu Val Lys
                245
```

<210> SEQ ID NO 69
<211> LENGTH: 753
<212> TYPE: DNA
<213> ORGANISM: Campylobacter jejuni

<400> SEQUENCE: 69

```
atgaaaaaaa ttattacttt atttggtgca tgtgccttag cttttagtat ggcaaatgca    60
gatgtaaacc tttacggacc aggtggccca cacacggcct aaaagatat agcaaacaaa   120
tatagcgaaa aaacaggcgt taaagtaaat gtaaattttg gccctcaagc gacttggttt   180
gaaaaggcta aaaagatgc agatatttta tttggcgctt cagatcaatc ggctttagct   240
atagcgagtg attttggaaa agattttaat gtgagtaaaa tcaagccttt atattttaga   300
gaagccatca tacttactca aaaggcaat cctttaaaaa tcaaggtttt aaaagatttg   360
gctaataaaa aagtaagaat cgttgtgcct gaaggtgctg aaagagcaa tacttctgga   420
actggagttt gggaagatat gataggtaga actcaagata taaaaaccat acaaaatttt   480
agaaacaata tcgtggcctt tgttccaaat agtggaagtg caagaaagct tttcgcacaa   540
gatcaagccg atgcttggat cacttggatt gactggtcaa aaagcaatcc tgacatagga   600
actgccgtag ctatagaaaa agatttggtt gtttatagaa cttttaatgt gatagctaaa   660
gaaggtgcga gcaaagaaac acaagatttt attgcttatt taagttctaa ggaagctaaa   720
gaaattttta aaaatacgg ctggagagaa taa                                 753
```

<210> SEQ ID NO 70
<211> LENGTH: 250
<212> TYPE: PRT
<213> ORGANISM: Campylobacter jejuni

<400> SEQUENCE: 70

```
Met Lys Lys Ile Ile Thr Leu Phe Gly Ala Cys Ala Leu Ala Phe Ser
1               5                   10                  15

Met Ala Asn Ala Asp Val Asn Leu Tyr Gly Pro Gly Gly Pro His Thr
                20                  25                  30

Ala Leu Lys Asp Ile Ala Asn Lys Tyr Ser Glu Lys Thr Gly Val Lys
            35                  40                  45

Val Asn Val Asn Phe Gly Pro Gln Ala Thr Trp Phe Glu Lys Ala Lys
        50                  55                  60

Lys Asp Ala Asp Ile Leu Phe Gly Ala Ser Asp Gln Ser Ala Leu Ala
65                  70                  75                  80
```

Ile Ala Ser Asp Phe Gly Lys Asp Phe Asn Val Ser Lys Ile Lys Pro
            85                  90                  95

Leu Tyr Phe Arg Glu Ala Ile Ile Leu Thr Gln Lys Gly Asn Pro Leu
            100                 105                 110

Lys Ile Lys Gly Leu Lys Asp Leu Ala Asn Lys Lys Val Arg Ile Val
        115                 120                 125

Val Pro Glu Gly Ala Gly Lys Ser Asn Thr Ser Gly Thr Gly Val Trp
    130                 135                 140

Glu Asp Met Ile Gly Arg Thr Gln Asp Ile Lys Thr Ile Gln Asn Phe
145                 150                 155                 160

Arg Asn Asn Ile Val Ala Phe Val Pro Asn Ser Gly Ser Ala Arg Lys
                165                 170                 175

Leu Phe Ala Gln Asp Gln Ala Asp Ala Trp Ile Thr Trp Ile Asp Trp
            180                 185                 190

Ser Lys Ser Asn Pro Asp Ile Gly Thr Ala Val Ala Ile Glu Lys Asp
        195                 200                 205

Leu Val Val Tyr Arg Thr Phe Asn Val Ile Ala Lys Glu Gly Ala Ser
    210                 215                 220

Lys Glu Thr Gln Asp Phe Ile Ala Tyr Leu Ser Ser Lys Glu Ala Lys
225                 230                 235                 240

Glu Ile Phe Lys Lys Tyr Gly Trp Arg Glu
                245                 250

<210> SEQ ID NO 71
<211> LENGTH: 753
<212> TYPE: DNA
<213> ORGANISM: Campylobacter jejuni

<400> SEQUENCE: 71
atgaaaaaaa ttattacttt atttggcgca tgtgccttag cttttagtat ggcaaatgca     60
gatgtaaatc tttacggacc aggtggccca cacacggcct aaaagatat agcaagtaaa    120 tatagcgaaa aaacaggcgt taaagtaaat gtaaattttg cccctcaagc gacttggttt    180
gaaaaggcta aaaagatgc agatatttta tttggcgctt cagatcaatc ggctttagct    240
atagcaagtg attttggaaa agattttaat gtgagtaaaa tcaagccttt gtattttaga    300
gaagccatca tacttactca aaaaggcaat ccttttaaaaa tcaaggtttt aaagatttg    360 gctaataaaa aagtaagaat cgttgtacct gaaggtgctg gaaagagcaa tacttctgga    420
acgggagttt gggaagatat gataggtaga actcaagata taaaaaccat acaaaatttt    480
agaaacaata tcgtagcttt tgttccaaat agtggaagtg caagaaagct tttcgcacaa    540
gatcaagccg atgcttggat cacttggatt gactggtcaa aaagcaatcc tgacatagga    600
actgccgtag ctatagaaaa agatttggtt gtttatagaa cttttaatgt ggtagctaaa    660
gaaggtgcga gcaaagaaac acaagatttt attgcttatt taagttctaa ggaagctaaa    720
gaaattttta aaaatacgg ctggagagaa taa                                  753

<210> SEQ ID NO 72
<211> LENGTH: 250
<212> TYPE: PRT
<213> ORGANISM: Campylobacter jejuni

<400> SEQUENCE: 72

Met Lys Lys Ile Ile Thr Leu Phe Gly Ala Cys Ala Leu Ala Phe Ser
1               5                   10                  15

```
Met Ala Asn Ala Asp Val Asn Leu Tyr Gly Pro Gly Gly Pro His Thr
             20                  25                  30
Ala Leu Lys Asp Ile Ala Ser Lys Tyr Ser Glu Lys Thr Gly Val Lys
         35                  40                  45
Val Asn Val Asn Phe Gly Pro Gln Ala Thr Trp Phe Glu Lys Ala Lys
 50                  55                  60
Lys Asp Ala Asp Ile Leu Phe Gly Ala Ser Asp Gln Ser Ala Leu Ala
 65                  70                  75                  80
Ile Ala Ser Asp Phe Gly Lys Asp Phe Asn Val Ser Lys Ile Lys Pro
                 85                  90                  95
Leu Tyr Phe Arg Glu Ala Ile Ile Leu Thr Gln Lys Gly Asn Pro Leu
             100                 105                 110
Lys Ile Lys Gly Leu Lys Asp Leu Ala Asn Lys Lys Val Arg Ile Val
         115                 120                 125
Val Pro Glu Gly Ala Gly Lys Ser Asn Thr Ser Gly Thr Gly Val Trp
130                 135                 140
Glu Asp Met Ile Gly Arg Thr Gln Asp Ile Lys Thr Ile Gln Asn Phe
145                 150                 155                 160
Arg Asn Asn Ile Val Ala Phe Val Pro Asn Ser Gly Ser Ala Arg Lys
                165                 170                 175
Leu Phe Ala Gln Asp Gln Ala Asp Ala Trp Ile Thr Trp Ile Asp Trp
            180                 185                 190
Ser Lys Ser Asn Pro Asp Ile Gly Thr Ala Val Ala Ile Glu Lys Asp
        195                 200                 205
Leu Val Val Tyr Arg Thr Phe Asn Val Val Ala Lys Glu Gly Ala Ser
210                 215                 220
Lys Glu Thr Gln Asp Phe Ile Ala Tyr Leu Ser Ser Lys Glu Ala Lys
225                 230                 235                 240
Glu Ile Phe Lys Lys Tyr Gly Trp Arg Glu
                245                 250

<210> SEQ ID NO 73
<211> LENGTH: 1275
<212> TYPE: DNA
<213> ORGANISM: Campylobacter jejuni

<400> SEQUENCE: 73
atgaaactag ttaaacttag tttagttgca gctcttgctg caggtgcttt ttcagcagct      60
aacgctactc cacttgaaga agcgatcaaa gatgttgatg tatcaggtgt attaagatac    120
agatacgata caggtaattt tgataaaaat ttcgttaaca actcaaattt aaacaacagc    180
aaacaagatc acaaatatag agcacaagtt aacttcagtg ctgctatagc tgataacttc    240
aaagcttttg ttcaatttga ctataatgct gctgatggtg ttatggtgc taatggaata    300 aaaaatgatc aaaaaggact ttttgttcgt caattatact taacttatac aaatgaagat    360
gttgctacaa gtaatcgc tggtaaacaa caattaaacc ttatctggac ggataacgct    420
attgatggtt tagttggcac aggtgttaaa gtagtaaata acagcatcga tggtttaact    480
ctagctgctt tgctgtagac tagcttcatg gctgcagagc aaggtgcaga tttattagaa    540
catagtaata tttcaacaac atcaaatcaa gctccttta aagtagattc agtaggaaat    600
ctttacggtg ctgctgctgt aggttcttat gatcttgctg gtggacaatt caacccacaa    660
ttatggttag cttattggga tcaagtagca ttcttctatg ctgtagatgc agcttatagt    720
acaactatct tgatggaat caactggaca cttgaaggtg cttacttagg aaatagcctt    780
```

```
gatagcgaac ttgatgataa acacacgct aatggcaatt tatttgcttt aaaaggtagc    840
attgaagtaa atggttggga tgctagcctt ggtggtttat actacggtga taaagaaaaa    900
gcttctacag ttgtaatcga agatcaaggt aatcttggtt ctttacttgc aggtgaggaa    960
attttctata ctactggttc aagactaaat ggtgatactg gtagaaatat cttcggttat   1020
gtaactggtg gatatacttt caacgaaaca gttcgcgttg gtgctgactt cgtatatggt   1080
ggaacaaaaa cagaagctgc taatcattta ggtggtggta aaaaacttga agctgttgca   1140
agagtagatt acaaatactc tccaaaactt aacttctcag cattctattc ttatgtgaac   1200
ctagatcaag gtgtaaacac taatgaaagt gctgatcata gcactgtaag acttcaagct   1260
ctttacaaat tctaa                                                    1275
```

<210> SEQ ID NO 74
<211> LENGTH: 424
<212> TYPE: PRT
<213> ORGANISM: Campylobacter jejuni

<400> SEQUENCE: 74

```
Met Lys Leu Val Lys Leu Ser Leu Val Ala Ala Leu Ala Ala Gly Ala
1               5                   10                  15

Phe Ser Ala Ala Asn Ala Thr Pro Leu Glu Glu Ala Ile Lys Asp Val
                20                  25                  30

Asp Val Ser Gly Val Leu Arg Tyr Arg Tyr Asp Thr Gly Asn Phe Asp
            35                  40                  45

Lys Asn Phe Val Asn Asn Ser Asn Leu Asn Asn Ser Lys Gln Asp His
        50                  55                  60

Lys Tyr Arg Ala Gln Val Asn Phe Ser Ala Ala Ile Ala Asp Asn Phe
65                  70                  75                  80

Lys Ala Phe Val Gln Phe Asp Tyr Asn Ala Ala Asp Gly Gly Tyr Gly
                85                  90                  95

Ala Asn Gly Ile Lys Asn Asp Gln Lys Gly Leu Phe Val Arg Gln Leu
            100                 105                 110

Tyr Leu Thr Tyr Thr Asn Glu Asp Val Ala Thr Ser Val Ile Ala Gly
        115                 120                 125

Lys Gln Gln Leu Asn Leu Ile Trp Thr Asp Asn Ala Ile Asp Gly Leu
    130                 135                 140

Val Gly Thr Gly Val Lys Val Val Asn Asn Ser Ile Asp Gly Leu Thr
145                 150                 155                 160

Leu Ala Ala Phe Ala Val Asp Ser Phe Met Ala Ala Glu Gln Gly Ala
                165                 170                 175

Asp Leu Leu Glu His Ser Asn Ile Ser Thr Thr Ser Asn Gln Ala Pro
            180                 185                 190

Phe Lys Val Asp Ser Val Gly Asn Leu Tyr Gly Ala Ala Ala Val Gly
        195                 200                 205

Ser Tyr Asp Leu Ala Gly Gly Gln Phe Asn Pro Gln Leu Trp Leu Ala
    210                 215                 220

Tyr Trp Asp Gln Val Ala Phe Phe Tyr Ala Val Asp Ala Ala Tyr Ser
225                 230                 235                 240

Thr Thr Ile Phe Asp Gly Ile Asn Trp Thr Leu Glu Gly Ala Tyr Leu
                245                 250                 255

Gly Asn Ser Leu Asp Ser Glu Leu Asp Asp Lys Thr His Ala Asn Gly
            260                 265                 270

Asn Leu Phe Ala Leu Lys Gly Ser Ile Glu Val Asn Gly Trp Asp Ala
        275                 280                 285
```

```
Ser Leu Gly Gly Leu Tyr Tyr Gly Asp Lys Glu Lys Ala Ser Thr Val
        290                 295                 300

Val Ile Glu Asp Gln Gly Asn Leu Gly Ser Leu Leu Ala Gly Glu Glu
305                 310                 315                 320

Ile Phe Tyr Thr Thr Gly Ser Arg Leu Asn Gly Asp Thr Gly Arg Asn
                325                 330                 335

Ile Phe Gly Tyr Val Thr Gly Gly Tyr Thr Phe Asn Glu Thr Val Arg
                340                 345                 350

Val Gly Ala Asp Phe Val Tyr Gly Gly Thr Lys Thr Glu Ala Ala Asn
                355                 360                 365

His Leu Gly Gly Gly Lys Lys Leu Glu Ala Val Ala Arg Val Asp Tyr
        370                 375                 380

Lys Tyr Ser Pro Lys Leu Asn Phe Ser Ala Phe Tyr Ser Tyr Val Asn
385                 390                 395                 400

Leu Asp Gln Gly Val Asn Thr Asn Glu Ser Ala Asp His Ser Thr Val
                405                 410                 415

Arg Leu Gln Ala Leu Tyr Lys Phe
            420

<210> SEQ ID NO 75
<211> LENGTH: 1275
<212> TYPE: DNA
<213> ORGANISM: Campylobacter jejuni

<400> SEQUENCE: 75
atgaaactag ttaaacttag tttagttgca gctcttgctg caggtgcttt ttcagcagct      60
aacgctactc cacttgaaga agcgatcaaa gatgttgatg tatcaggtgt attaagatac     120
agatacgata caggtaattt tgataaaaat ttcgttaaca actcaaattt aaacaacagc     180
aaacaagatc acaaatatag agcacaagtt aacttcagtg ctgctatagc tgataacttc     240
aaagcttttg ttcaatttga ctataatgct gctgatggtg ttatggtgc taatggaata      300 aaaaatgatc aaaaaggact ttttgttcgt caattatact taactatac aaatgaagat      360 gttgctacaa gcgtaatcgc tggtaaacaa caactaaaca ctatctggac tgacaatgga     420
gttgatggtt tagtaggaac aggtatcaaa gtagtaaaca acagcatcga tggtttaact     480
ctagctgctt tgctgtaga tagctttatg gcggaagagc aaggtgcaga tttattagga     540
aaaagtacta tatctacaac acagaacgca gttccttttc aagcagattc attaggaaat     600
ctttacggtg ctgctgctgt aggttcttat gatcttgctg gcggacaatt taatccacaa     660
ttatggttag cttactggga tcaagtagca ttcttctatg ctgtagatgc agcttatagt     720
acaactatct ttgatggaat caactggaca cttgaaggtg cttacttagg aaatagcctt     780
gatagcgaac ttgatgataa agacacgct aatggcaatt tatttgcttt aaaaggtagc     840
attgaagtaa atggttggga tgctagcctt ggtggtttat actacggtga taagaaaaa     900 gcttctacag ttgtaatcga agatcaaggt aatcttggtt ctttacttgc aggtgaggaa     960
attttctata ctactggttc aagactaaat ggtgatactg gtagaaatat cttcggttat    1020
gtaactggtg gatatacttt caacgaaaca gttcgcgttg gtgctgactt cgtatatgt     1080 ggaacaaaaa cagaagctac taatcatta ggtggtggta aaaacttga agctgttgca     1140 agagtagatt acaaatactc tccaaaactt aacttctcag cattctattc ttatgtgaac    1200
ctagatcaag gtgtaaacac taatgaaagt gctgatcata gcactgtaag acttcaagct    1260
ctttacaaat tctaa                                                    1275
```

<210> SEQ ID NO 76
<211> LENGTH: 424
<212> TYPE: PRT
<213> ORGANISM: Campylobacter jejuni

<400> SEQUENCE: 76

| | | | | | | | | | | | | | | |
|---|---|---|---|---|---|---|---|---|---|---|---|---|---|---|
| Met | Lys | Leu | Val | Lys | Leu | Ser | Leu | Val | Ala | Leu | Ala | Ala | Gly | Ala |
| 1 | | | | 5 | | | | | 10 | | | | | 15 |
| Phe | Ser | Ala | Ala | Asn | Ala | Thr | Pro | Leu | Glu | Glu | Ala | Ile | Lys | Asp | Val |
| | | | 20 | | | | | 25 | | | | | 30 | | |
| Asp | Val | Ser | Gly | Val | Leu | Arg | Tyr | Arg | Tyr | Asp | Thr | Gly | Asn | Phe | Asp |
| | | | 35 | | | | | 40 | | | | | 45 | | |
| Lys | Asn | Phe | Val | Asn | Asn | Ser | Asn | Leu | Asn | Asn | Ser | Lys | Gln | Asp | His |
| 50 | | | | | 55 | | | | | 60 | | | | | |
| Lys | Tyr | Arg | Ala | Gln | Val | Asn | Phe | Ser | Ala | Ala | Ile | Ala | Asp | Asn | Phe |
| 65 | | | | | 70 | | | | | 75 | | | | | 80 |
| Lys | Ala | Phe | Val | Gln | Phe | Asp | Tyr | Asn | Ala | Ala | Asp | Gly | Gly | Tyr | Gly |
| | | | | 85 | | | | | 90 | | | | | 95 | |
| Ala | Asn | Gly | Ile | Lys | Asn | Asp | Gln | Lys | Gly | Leu | Phe | Val | Arg | Gln | Leu |
| | | | 100 | | | | | 105 | | | | | 110 | | |
| Tyr | Leu | Thr | Tyr | Thr | Asn | Glu | Asp | Val | Ala | Thr | Ser | Val | Ile | Ala | Gly |
| | | | 115 | | | | | 120 | | | | | 125 | | |
| Lys | Gln | Gln | Leu | Asn | Thr | Ile | Trp | Thr | Asp | Asn | Gly | Val | Asp | Gly | Leu |
| 130 | | | | | 135 | | | | | 140 | | | | | |
| Val | Gly | Thr | Gly | Ile | Lys | Val | Val | Asn | Asn | Ser | Ile | Asp | Gly | Leu | Thr |
| 145 | | | | | 150 | | | | | 155 | | | | | 160 |
| Leu | Ala | Ala | Phe | Ala | Val | Asp | Ser | Phe | Met | Ala | Glu | Glu | Gln | Gly | Ala |
| | | | | 165 | | | | | 170 | | | | | 175 | |
| Asp | Leu | Leu | Gly | Lys | Ser | Thr | Ile | Ser | Thr | Thr | Gln | Asn | Ala | Val | Pro |
| | | | 180 | | | | | 185 | | | | | 190 | | |
| Phe | Gln | Ala | Asp | Ser | Leu | Gly | Asn | Leu | Tyr | Gly | Ala | Ala | Ala | Val | Gly |
| | | | 195 | | | | | 200 | | | | | 205 | | |
| Ser | Tyr | Asp | Leu | Ala | Gly | Gly | Gln | Phe | Asn | Pro | Gln | Leu | Trp | Leu | Ala |
| 210 | | | | | 215 | | | | | 220 | | | | | |
| Tyr | Trp | Asp | Gln | Val | Ala | Phe | Phe | Tyr | Ala | Val | Asp | Ala | Ala | Tyr | Ser |
| 225 | | | | | 230 | | | | | 235 | | | | | 240 |
| Thr | Thr | Ile | Phe | Asp | Gly | Ile | Asn | Trp | Thr | Leu | Glu | Gly | Ala | Tyr | Leu |
| | | | | 245 | | | | | 250 | | | | | 255 | |
| Gly | Asn | Ser | Leu | Asp | Ser | Glu | Leu | Asp | Asp | Lys | Arg | His | Ala | Asn | Gly |
| | | | 260 | | | | | 265 | | | | | 270 | | |
| Asn | Leu | Phe | Ala | Leu | Lys | Gly | Ser | Ile | Glu | Val | Asn | Gly | Trp | Asp | Ala |
| | | | 275 | | | | | 280 | | | | | 285 | | |
| Ser | Leu | Gly | Gly | Leu | Tyr | Tyr | Gly | Asp | Lys | Glu | Lys | Ala | Ser | Thr | Val |
| 290 | | | | | 295 | | | | | 300 | | | | | |
| Val | Ile | Glu | Asp | Gln | Gly | Asn | Leu | Gly | Ser | Leu | Leu | Ala | Gly | Glu | Glu |
| 305 | | | | | 310 | | | | | 315 | | | | | 320 |
| Ile | Phe | Tyr | Thr | Thr | Gly | Ser | Arg | Leu | Asn | Gly | Asp | Thr | Gly | Arg | Asn |
| | | | | 325 | | | | | 330 | | | | | 335 | |
| Ile | Phe | Gly | Tyr | Val | Thr | Gly | Tyr | Thr | Phe | Asn | Glu | Thr | Val | Arg |
| | | | 340 | | | | | 345 | | | | | 350 | | |
| Val | Gly | Ala | Asp | Phe | Val | Tyr | Gly | Gly | Thr | Lys | Thr | Glu | Ala | Thr | Asn |
| | | | 355 | | | | | 360 | | | | | 365 | | |
| His | Leu | Gly | Gly | Gly | Lys | Lys | Leu | Glu | Ala | Val | Ala | Arg | Val | Asp | Tyr |

```
                370              375              380
Lys Tyr Ser Pro Lys Leu Asn Phe Ser Ala Phe Tyr Ser Tyr Val Asn
385              390              395              400

Leu Asp Gln Gly Val Asn Thr Asn Glu Ser Ala Asp His Ser Thr Val
            405              410              415

Arg Leu Gln Ala Leu Tyr Lys Phe
            420

<210> SEQ ID NO 77
<211> LENGTH: 645
<212> TYPE: DNA
<213> ORGANISM: Campylobacter jejuni

<400> SEQUENCE: 77
atgtttaaaa aatttttgat ttttatagtg cctattttat ttttgagtgc ttgtgcaact      60
aaacaagata cttttgctca agttaatcaa atttctaaaa attctcaatg cagttcttgt     120
gaaagtcctg gtggttttga agcaaagatt aaagggcttt tatacattag cgatgttgga     180
attcaatgtt gtgccaataa cgcacttta gacactggta ttgctttgaa aaggtttat      240 ttacatagat tttatgattt aaagaaggg caaaaggttt taaatgctaa agggaaaaag     300
ttatttgtcg atgtgaattt taatgcggta ttttatactt atttaaaaca gaacttgaa      360 gctagaggaa tagttgtgct tgacaataac gatcaaaatt caccttatgt gagtaagatt     420
gatttagaat ttatatctta tggagcaact caagatgcta taggattaca ttcaaaacta     480
gtaggagttt tacaagttag tgatataaat aaaaataaga aatttacaat ccgcaccaag     540
caagatgtac aaggttttga tgatttaaaa gaaacaactt tttatactca tttgttaata     600
aaacaaatgg caaataaagc agctagttta atctctgaac tttga                    645

<210> SEQ ID NO 78
<211> LENGTH: 214
<212> TYPE: PRT
<213> ORGANISM: Campylobacter jejuni

<400> SEQUENCE: 78

Met Phe Lys Lys Phe Leu Ile Phe Ile Val Pro Ile Leu Phe Leu Ser
1               5                   10                  15

Ala Cys Ala Thr Lys Gln Asp Thr Phe Ala Gln Val Asn Gln Ile Ser
            20                  25                  30

Lys Asn Ser Gln Cys Ser Ser Cys Glu Ser Pro Gly Gly Phe Glu Ala
        35                  40                  45

Lys Ile Lys Gly Leu Leu Tyr Ile Ser Asp Val Gly Ile Gln Cys Cys
    50                  55                  60

Ala Asn Lys Arg Thr Leu Asp Thr Gly Ile Ala Leu Lys Lys Val Tyr
65                  70                  75                  80

Leu His Arg Phe Tyr Asp Leu Lys Glu Gly Gln Lys Val Leu Asn Ala
                85                  90                  95

Lys Gly Lys Lys Leu Phe Val Asp Val Asn Phe Asn Ala Val Phe Tyr
            100                 105                 110

Thr Tyr Leu Lys Gln Glu Leu Glu Ala Arg Gly Ile Val Val Leu Asp
        115                 120                 125

Asn Asn Asp Gln Asn Ser Pro Tyr Val Ser Lys Ile Asp Leu Glu Phe
    130                 135                 140

Ile Ser Tyr Gly Ala Thr Gln Asp Ala Ile Gly Leu His Ser Lys Leu
145                 150                 155                 160
```

Val Gly Val Leu Gln Val Ser Asp Ile Asn Lys Asn Lys Lys Phe Thr
                165                 170                 175

Ile Arg Thr Lys Gln Asp Val Gln Gly Phe Asp Asp Leu Lys Glu Thr
            180                 185                 190

Thr Phe Tyr Thr His Leu Leu Ile Lys Gln Met Ala Asn Lys Ala Ala
        195                 200                 205

Ser Leu Ile Ser Glu Leu
        210

<210> SEQ ID NO 79
<211> LENGTH: 645
<212> TYPE: DNA
<213> ORGANISM: Campylobacter jejuni

<400> SEQUENCE: 79

```
atgtttaaaa aattttgat ttttatagtg cctatttat ttttgagtgc ttgtgcaact     60
aaacaagata cttttgctca agttaatcaa atttctaaaa attctcaatg cagttcttgt    120
gaaagtcctg gtggttttga agcaaagatt aaagggcttt tatacattag cgatgttgga    180
attcaatgtt gtgccaataa acgcacttta gacactggta ttgctttgaa aaaggtttat    240
ttacatagat tttatgattt aaaagaagag caaaaggtt taaatgctaa agggaaaaag    300
ttatttgttg atgtgaattt taatgcggta ttttatactt atttaaaaca gaacttgaa    360
gctagaggaa tagttgtgct tgacaataac gatcaaaatt caccttatgt gagtaagatt    420
gatttagaat ttatatctta tggagcaact caagatgcta taggattaca ttcaaaacta    480
gtaggagttt tacaagttag tgatataaat aaaaataaga aatttacaat ccgcaccaag    540
caagatgtac aaggttttga tgatttaaaa gaacaacttt tttatactca tttgttaata    600
aaacaaatgg caaataaagc agctagttta atctctgaac tttga                    645
```

<210> SEQ ID NO 80
<211> LENGTH: 214
<212> TYPE: PRT
<213> ORGANISM: Campylobacter jejuni

<400> SEQUENCE: 80

Met Phe Lys Lys Phe Leu Ile Phe Ile Val Pro Ile Leu Phe Leu Ser
1               5                   10                  15

Ala Cys Ala Thr Lys Gln Asp Thr Phe Ala Gln Val Asn Gln Ile Ser
            20                  25                  30

Lys Asn Ser Gln Cys Ser Ser Cys Glu Ser Pro Gly Gly Phe Glu Ala
        35                  40                  45

Lys Ile Lys Gly Leu Leu Tyr Ile Ser Asp Val Gly Ile Gln Cys Cys
    50                  55                  60

Ala Asn Lys Arg Thr Leu Asp Thr Gly Ile Ala Leu Lys Lys Val Tyr
65                  70                  75                  80

Leu His Arg Phe Tyr Asp Leu Lys Glu Gln Lys Val Leu Asn Ala
                85                  90                  95

Lys Gly Lys Lys Leu Phe Val Asp Val Asn Phe Asn Ala Val Phe Tyr
            100                 105                 110

Thr Tyr Leu Lys Gln Glu Leu Glu Ala Arg Gly Ile Val Val Leu Asp
        115                 120                 125

Asn Asn Asp Gln Asn Ser Pro Tyr Val Ser Lys Ile Asp Leu Glu Phe
    130                 135                 140

Ile Ser Tyr Gly Ala Thr Gln Asp Ala Ile Gly Leu His Ser Lys Leu
145                 150                 155                 160

Val Gly Val Leu Gln Val Ser Asp Ile Asn Lys Asn Lys Lys Phe Thr
            165                 170                 175

Ile Arg Thr Lys Gln Asp Val Gln Gly Phe Asp Asp Leu Lys Glu Thr
        180                 185                 190

Thr Phe Tyr Thr His Leu Leu Ile Lys Gln Met Ala Asn Lys Ala Ala
    195                 200                 205

Ser Leu Ile Ser Glu Leu
    210

<210> SEQ ID NO 81
<211> LENGTH: 966
<212> TYPE: DNA
<213> ORGANISM: Campylobacter jejuni

<400> SEQUENCE: 81

| | |
|---|---|
| atgaaaatta tcatagatcg ttttaatggc aaggaaaaat atgaacaaag ttatgatatt | 60 |
| gatgataagg atacaagg aaaaactctg ctctctcttt tgcttttat caaaaaaaca | 120 |
| aaagatatta ctttaaattt taccgcctct tgtcaatctg caatttgtgg ggcttgtgca | 180 |
| gttcgtgtga atgggcattc ttatcttgct tgtgatacta aaatgcaaga tttgttaaaa | 240 |
| gaatatgata atccttcaag tatacgcatt tctccgcttg gaaattttag agtaatttct | 300 |
| gatttaattg tggattggga accttctata gaaaattaa gaaaaattcg tcctgccatg | 360 |
| gtggcaaaaa atgaatttc agcggaaaag ggctgtaaac aaagtcaaga gaatttgat | 420 |
| cgtattagca gcaatggga ttgtatttta tgtggtagct gtgcttcaga gtgtaataaa | 480 |
| ttagaagcag atagtagcga ttatatgcaa ccttttgttt ttactcatgt ttggcgtgca | 540 |
| gcggcggact ctcgaggtaa ggatcctatg ttgcatgtaa aacccagcgt aatgaatgga | 600 |
| ctttggcttt gtgttcattg tcaagagtgc gctgatcgtt gtccaaaggg tataagttca | 660 |
| gtaagtgata tagcaaattt aagagtgatg gcgattaaaa aaggtttaaa tgaaggctta | 720 |
| gggcctgatc atgctgaagc ttttataaaa gatttagttg aaggttcagg acgcttgaat | 780 |
| gaaattatc ttgctttgcg ttctgagggt gttataggtt ctatgggtaa aacagatata | 840 |
| gcttttaaac ttatgcgtgc aggaaaaatg aatcctatgc atgttttgg cgagggtgaa | 900 |
| atagaagggt ataagatttt ggttaaaatg ataaaggcgg cacaagaagc tgctgttaag | 960 |
| gagtaa | 966 |

<210> SEQ ID NO 82
<211> LENGTH: 321
<212> TYPE: PRT
<213> ORGANISM: Campylobacter jejuni

<400> SEQUENCE: 82

Met Lys Ile Ile Ile Asp Arg Phe Asn Gly Lys Glu Lys Tyr Glu Gln
1               5                   10                  15

Ser Tyr Asp Ile Asp Asp Lys Ile Gln Gly Lys Thr Leu Leu Ser
            20                  25                  30

Leu Leu Leu Phe Ile Lys Lys Thr Lys Asp Ile Thr Leu Asn Phe Thr
        35                  40                  45

Ala Ser Cys Gln Ser Ala Ile Cys Gly Ala Cys Ala Val Arg Val Asn
    50                  55                  60

Gly His Ser Tyr Leu Ala Cys Asp Thr Lys Met Gln Asp Leu Leu Lys
65                  70                  75                  80

Glu Tyr Asp Asn Pro Ser Ser Ile Arg Ile Ser Pro Leu Gly Asn Phe

```
                    85                  90                  95
Arg Val Ile Ser Asp Leu Ile Val Asp Trp Glu Pro Ser Ile Glu Asn
                100                 105                 110

Leu Arg Lys Ile Arg Pro Ala Met Val Ala Lys Asn Glu Phe Ser Ala
            115                 120                 125

Glu Lys Gly Cys Lys Gln Ser Gln Glu Glu Phe Asp Arg Ile Ser Lys
        130                 135                 140

Gln Trp Asp Cys Ile Leu Cys Gly Ser Cys Ala Ser Glu Cys Asn Lys
145                 150                 155                 160

Leu Glu Ala Asp Ser Ser Asp Tyr Met Gln Pro Phe Val Phe Thr His
                165                 170                 175

Val Trp Arg Ala Ala Ala Asp Ser Arg Gly Lys Asp Pro Met Leu His
            180                 185                 190

Val Lys Pro Ser Val Met Asn Gly Leu Trp Leu Cys Val His Cys Gln
        195                 200                 205

Glu Cys Ala Asp Arg Cys Pro Lys Gly Ile Ser Ser Val Ser Asp Ile
210                 215                 220

Ala Asn Leu Arg Val Met Ala Ile Lys Lys Gly Leu Asn Glu Gly Leu
225                 230                 235                 240

Gly Pro Asp His Ala Glu Ala Phe Tyr Lys Asp Leu Val Glu Gly Ser
                245                 250                 255

Gly Arg Leu Asn Glu Ile Tyr Leu Ala Leu Arg Ser Glu Gly Val Ile
            260                 265                 270

Gly Ser Met Gly Lys Thr Asp Ile Ala Phe Lys Leu Met Arg Ala Gly
        275                 280                 285

Lys Met Asn Pro Met His Val Phe Gly Glu Gly Glu Ile Glu Gly Tyr
    290                 295                 300

Lys Asp Leu Val Lys Met Ile Lys Ala Ala Gln Glu Ala Ala Val Lys
305                 310                 315                 320

Glu

<210> SEQ ID NO 83
<211> LENGTH: 966
<212> TYPE: DNA
<213> ORGANISM: Campylobacter jejuni

<400> SEQUENCE: 83
atgaaaatca tcatagatcg ttttaatggc aaggaaaaat atgaacaaag ttatgatatt      60
gatgataagg atatacaagg aaaaactctg ctctctcttt tgcttttat taaaaaaaca     120 aaagatatta ctttgaattt taccgcctct tgtcaatctg cgatttgtgg ggcttgtgca     180
gttcgtgtga atgggcattc ttatcttgct tgtgatacta aaatgcaaga tttgttaaaa     240
gaatatgata atccttcaag tatacgcatt tctccgcttg gaaattttag agtaatttct     300
gatttaattg tggattggga gccttctata gaaatttaa gaaaaattcg tcctgccatg     360
gtggcaaaaa atgaatttc agcggaaaag ggctgtaaac aaagtcaaga gaatttgat     420 cgtattagca agcaatggga ttgtatttta tgtggtagct gtgcttcaga gtgtaataaa     480
ttagaagcag atagtagcga ttatatgcaa ccttttgttt ttactcatgc ttggcgtgca     540
gcggcagact ctcgaggtaa ggatcctatg ttgcatgtaa aacccagcgt aatgaatgga     600
ctttggcttt gtgttcattg tcaagagtgc gctgatcgtt gtccaaaggg tataagttca     660
gtaagtgata tagcaaattt aagagtgatg gcgattaaaa aaggtttaaa tgaaggctta     720
gggcctgatc atgctgaagc ttttataaa gatttagttg aaggttcagg acgcttgaat     780
```

```
gaaatttatc ttgctttacg ttctgagggt gttataggtt ctatgggtaa aacagatata    840
gcttttaaac ttatgcgtgc aggaaagatg aatcctatgc atgtttttgg cgaggatgaa    900
atagaagggc ataagatttt ggttaaaatg ataaaggcgg cacaagaagc tgctgttaag    960
gagtaa                                                               966
```

<210> SEQ ID NO 84
<211> LENGTH: 321
<212> TYPE: PRT
<213> ORGANISM: Campylobacter jejuni

<400> SEQUENCE: 84

```
Met Lys Ile Ile Ile Asp Arg Phe Asn Gly Lys Glu Lys Tyr Glu Gln
1               5                   10                  15

Ser Tyr Asp Ile Asp Lys Asp Ile Gln Gly Lys Thr Leu Leu Ser
            20                  25                  30

Leu Leu Leu Phe Ile Lys Lys Thr Lys Asp Ile Thr Leu Asn Phe Thr
            35                  40                  45

Ala Ser Cys Gln Ser Ala Ile Cys Gly Ala Cys Ala Val Arg Val Asn
        50                  55                  60

Gly His Ser Tyr Leu Ala Cys Asp Thr Lys Met Gln Asp Leu Leu Lys
65                  70                  75                  80

Glu Tyr Asp Asn Pro Ser Ser Ile Arg Ile Ser Pro Leu Gly Asn Phe
                85                  90                  95

Arg Val Ile Ser Asp Leu Ile Val Asp Trp Glu Pro Ser Ile Glu Asn
            100                 105                 110

Leu Arg Lys Ile Arg Pro Ala Met Val Ala Lys Asn Glu Phe Ser Ala
        115                 120                 125

Glu Lys Gly Cys Lys Gln Ser Gln Glu Glu Phe Asp Arg Ile Ser Lys
    130                 135                 140

Gln Trp Asp Cys Ile Leu Cys Gly Ser Cys Ala Ser Glu Cys Asn Lys
145                 150                 155                 160

Leu Glu Ala Asp Ser Ser Asp Tyr Met Gln Pro Phe Val Phe Thr His
                165                 170                 175

Ala Trp Arg Ala Ala Ala Asp Ser Arg Gly Lys Asp Pro Met Leu His
            180                 185                 190

Val Lys Pro Ser Val Met Asn Gly Leu Trp Leu Cys Val His Cys Gln
        195                 200                 205

Glu Cys Ala Asp Arg Cys Pro Lys Gly Ile Ser Ser Val Ser Asp Ile
    210                 215                 220

Ala Asn Leu Arg Val Met Ala Ile Lys Lys Gly Leu Asn Glu Gly Leu
225                 230                 235                 240

Gly Pro Asp His Ala Glu Ala Phe Tyr Lys Asp Leu Val Glu Gly Ser
                245                 250                 255

Gly Arg Leu Asn Glu Ile Tyr Leu Ala Leu Arg Ser Glu Gly Val Ile
            260                 265                 270

Gly Ser Met Gly Lys Thr Asp Ile Ala Phe Lys Leu Met Arg Ala Gly
        275                 280                 285

Lys Met Asn Pro Met His Val Phe Gly Glu Asp Glu Ile Glu Gly His
    290                 295                 300

Lys Asp Leu Val Lys Met Ile Lys Ala Ala Gln Glu Ala Ala Val Lys
305                 310                 315                 320

Glu
```

<210> SEQ ID NO 85
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 85
tatttctatg gtttagcagg tggag                                25

<210> SEQ ID NO 86
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 86
gctctacctt ctttagtgtc attgc                                25

<210> SEQ ID NO 87
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 87
tgaatcgaag tggaaaaata gaag                                 24

<210> SEQ ID NO 88
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 88
cccatttttg tatcttcata acct                                 24

<210> SEQ ID NO 89
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 89
atgagctcaa agttgttcct aagggtaaag c                         31

<210> SEQ ID NO 90
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 90
ataccgcgga gttttattca taaatattcc ctttcc                    36

<210> SEQ ID NO 91
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 91
ataccgcggg ctcagtttaa ttatctttgg taatc                              35

<210> SEQ ID NO 92
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 92
atactcgagc attttacaag ccctataaga agg                                33

<210> SEQ ID NO 93
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 93
tctcaggact ctggaataaa gattg                                         25

<210> SEQ ID NO 94
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 94
gtgtgctata gtcactaaca gggatg                                        26

<210> SEQ ID NO 95
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 95
tctaggtgct tgtgttgcat ttag                                          24

<210> SEQ ID NO 96
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 96
tgtctacaga aaacgcatca actc                                          24

<210> SEQ ID NO 97
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 97
tcagaagatg gcaaggttat agaag                                         25

<210> SEQ ID NO 98

```
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 98
gttattgcta ttgattcagc tggac                                          25

<210> SEQ ID NO 99
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 99
tatttttgat cttactcgtg caatg                                          25

<210> SEQ ID NO 100
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 100
ttaaggtata atcgacccaa tacga                                          25

<210> SEQ ID NO 101
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 101
atataggatc cgtatcgttc tagtgatgaa aatcc                               35

<210> SEQ ID NO 102
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 102
atataccgcg gttttaaaat ttggcactac tgagc                               35

<210> SEQ ID NO 103
<211> LENGTH: 43
<212> TYPE: DNA
<213> ORGANISM: Artificial Sequence
<220> FEATURE:
<223> OTHER INFORMATION: Synthetic oligonucleotide primer

<400> SEQUENCE: 103
atataccgcg ggtttaaaat ataattttc ttgaaaatta agc                       43

<210> SEQ ID NO 104
<211> LENGTH: 37
<212> TYPE: DNA
<213> ORGANISM: Artificial Sequence
<220> FEATURE:
<223> OTHER INFORMATION: Synthetic oligonucleotide primer

<400> SEQUENCE: 104
```

-continued

```
atataggatc cttttcagaa acatcatttt tcaaacg                              37

<210> SEQ ID NO 105
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 105
taatgcgttc gccttctaat gc                                              22

<210> SEQ ID NO 106
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 106
agctgtgctc acttctataa cc                                              22

<210> SEQ ID NO 107
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 107
tgccaaaaga tggtgtagaa gg                                              22

<210> SEQ ID NO 108
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 108
tagccacttg agttaaagct gg                                              22

<210> SEQ ID NO 109
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 109
acaagatgag aatttgcttt taaagg                                          26

<210> SEQ ID NO 110
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 110
aagttcctaa aagctctcta gc                                              22

<210> SEQ ID NO 111
<211> LENGTH: 21
<212> TYPE: DNA
```

```
<213> ORGANISM: Artificial Sequence
<220> FEATURE:
<223> OTHER INFORMATION: Synthetic oligonucleotide primer

<400> SEQUENCE: 111
atgagccaac gggaaatttg g                                           21

<210> SEQ ID NO 112
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 112
acaacaagca aataaacaaa gtagc                                       25

<210> SEQ ID NO 113
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 113
ttatttgctt gttgtgtgta aatacg                                      26

<210> SEQ ID NO 114
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 114
attctaccca ctacggcacc                                             20

<210> SEQ ID NO 115
<211> LENGTH: 39
<212> TYPE: DNA
<213> ORGANISM: Artificial Sequence
<220> FEATURE:
<223> OTHER INFORMATION: Synthetic oligonucleotide primer

<400> SEQUENCE: 115
atataggatc caactttttt agtagatgaa aattcaagg                        39

<210> SEQ ID NO 116
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 116 ataccgcg gcgaaatctt ttcatcattc tctcc                              35

<210> SEQ ID NO 117
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 117 ataccgcg gagaaccttc aagcaaagtt aagg                               34
```

```
<210> SEQ ID NO 118
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 118
atataggatc cgttctgctc tatttttttc aaatcc                              36

<210> SEQ ID NO 119
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 119
atatacatat gatgatgaaa agatttcgct tgag                                34

<210> SEQ ID NO 120
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 120 ataggtac cttttaaaat ttggcactac tgagc                                 35

<210> SEQ ID NO 121
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 121 ataggatc cccttgtgct cctgttgtgc                                       30

<210> SEQ ID NO 122
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 122
atatacatat gtcctttcat ttaaaatgaa ccac                                34

<210> SEQ ID NO 123
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 123 ataggatc ctgtaaatga aagcttgcca aagg                                  34

<210> SEQ ID NO 124
<211> LENGTH: 32
<212> TYPE: DNA
<213> ORGANISM: Artificial Sequence
<220> FEATURE:
```

<223> OTHER INFORMATION: Synthetic oligonucleotide primer

<400> SEQUENCE: 124
atatactcga gtttgcttga aggttctgaa cg                      32

<210> SEQ ID NO 125
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 125 ataticcatg gtgaaaagat ttcgcttgag                         30

<210> SEQ ID NO 126
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 126
atataggtac cttactactg agccgcctta ac                      32

<210> SEQ ID NO 127
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 127
atataggatc caagcttcaa gtaaagagcc tgc                     33

<210> SEQ ID NO 128
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 128
atatactcga gctgagccgc cttaactttg c                       31

<210> SEQ ID NO 129
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 129
cccggatccc cggtttagca ggtggaggat at                      32

<210> SEQ ID NO 130
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 130
cccgaattct tattttactt gtggagttgc acgagt                  36

```
<210> SEQ ID NO 131
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 131
atataggatc ctgtaaatga aagcttgcca aagg                              34

<210> SEQ ID NO 132
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 132
atatactcga gtttgcttga aggttctgaa cg                                32

<210> SEQ ID NO 133
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 133
atataggatc caagcttcaa gtaaagagcc tgc                               33

<210> SEQ ID NO 134
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 134
atatactcga gctgagccgc cttaactttg c                                 31

<210> SEQ ID NO 135
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 135
atatactcga gtgtgctcac ttctataacc ttgc                              34

<210> SEQ ID NO 136
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 136
atataggatc cacacagctc caagacttga agc                               33

<210> SEQ ID NO 137
<211> LENGTH: 34
<212> TYPE: DNA
<213> ORGANISM: Artificial Sequence
<220> FEATURE:
<223> OTHER INFORMATION: Synthetic oligonucleotide primer
```

-continued

<400> SEQUENCE: 137
atatactcga gagaacttac aacttgactt gacc                          34

<210> SEQ ID NO 138
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 138
atataggatc gtcaagttgt aagttctaca agc                           33

<210> SEQ ID NO 139
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 139
cccggatccc cggtttagca ggtggaggat at                            32

<210> SEQ ID NO 140
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 140
cccgaattct tattttactt gtggagttgc acgagt                        36

<210> SEQ ID NO 141
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 141
agagtttgat cctggctcag                                          20

<210> SEQ ID NO 142
<211> LENGTH: 17
<212> TYPE: DNA
<213> ORGANISM: Artificial Sequence
<220> FEATURE:
<223> OTHER INFORMATION: Synthetic oligonucleotide primer

<400> SEQUENCE: 142
accgcttgtg cgggccc                                             17

<210> SEQ ID NO 143
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 143
tacggytacc ttgttacgac tt                                       22

<210> SEQ ID NO 144
<211> LENGTH: 20

<212> TYPE: DNA
<213> ORGANISM: Artificial Sequence
<220> FEATURE:
<223> OTHER INFORMATION: Synthetic oligonucleotide primer
<220> FEATURE:
<221> NAME/KEY: misc_feature
<222> LOCATION: (15)..(15)
<223> OTHER INFORMATION: n is a, c, g, or t

<400> SEQUENCE: 144
aaggaggtga tccanccrca                                          20

<210> SEQ ID NO 145
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 145
atactgctaa caacactcca gc                                       22

<210> SEQ ID NO 146
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 146
gcaaagtatt ttgaattaat tgctgc                                   26

<210> SEQ ID NO 147
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 147
tgaacacttc agcatacgaa gg                                       22

<210> SEQ ID NO 148
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 148
caacataatt ctttcttgct tctgc                                    25

<210> SEQ ID NO 149
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 149
ttaaatactg ctgtaggtaa cagc                                     24

<210> SEQ ID NO 150
<211> LENGTH: 23
<212> TYPE: DNA
<213> ORGANISM: Artificial Sequence
<220> FEATURE:

<223> OTHER INFORMATION: Synthetic oligonucleotide primer

<400> SEQUENCE: 150
ccgttaccct tgttttctaa tgg                                              23

<210> SEQ ID NO 151
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 151
gttattggta ctggtattac tatcc                                            25

<210> SEQ ID NO 152
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 152
tgtgctgcaa agtacttaga gg                                               22

<210> SEQ ID NO 153
<211> LENGTH: 30
<212> TYPE: PRT
<213> ORGANISM: Artificial Sequence
<220> FEATURE:
<223> OTHER INFORMATION: Synthetic peptide

<400> SEQUENCE: 153

Tyr Gly Ala Ala Ala Val Gly Ser Tyr Asp Leu Ala Gly Gly Gln Phe
1               5                   10                  15

Asn Pro Gln Leu Trp Leu Ala Tyr Trp Asp Gln Val Ala Phe
            20                  25                  30

<210> SEQ ID NO 154
<211> LENGTH: 115
<212> TYPE: DNA
<213> ORGANISM: Artificial Sequence
<220> FEATURE:
<223> OTHER INFORMATION: Synthetic sequence from plasmid

<400> SEQUENCE: 154
agatctacta gtcactacgg cgccggcgtc aagttccgcc tgtcggactc gctggccctg      60
cgcctggaga cccgcgacca gatcaacttc aaccacgcca acgctagcgc tgcag          115

<210> SEQ ID NO 155
<211> LENGTH: 115
<212> TYPE: DNA
<213> ORGANISM: Artificial Sequence
<220> FEATURE:
<223> OTHER INFORMATION: Synthetic sequence from plasmid

<400> SEQUENCE: 155
agatctacta gtatcaacgc cgtgaaggac accaccggcg tcgaggcgtc gatcgacgcc      60
aacggccagc tggtcctgac gtcggccgac ggccggggta tcgctagcgc tgcag          115

<210> SEQ ID NO 156
<211> LENGTH: 115
<212> TYPE: DNA
<213> ORGANISM: Artificial Sequence

```
<220> FEATURE:
<223> OTHER INFORMATION: Synthetic sequence from plasmid

<400> SEQUENCE: 156
agatctacta gttatggcgc cgccgccgtc ggctcgtatg acctggccgg cggccagttc     60
aacccgcagc tgtggctggc ctactgggac caggtcgcct tcgctagcgc tgcag         115

<210> SEQ ID NO 157
<211> LENGTH: 582
<212> TYPE: PRT
<213> ORGANISM: Artificial Sequence
<220> FEATURE:
<223> OTHER INFORMATION: Synthetic consensus sequence
<220> FEATURE:
<221> NAME/KEY: misc_feature
<222> LOCATION: (390)..(392)
<223> OTHER INFORMATION: Xaa can be any naturally occurring amino acid
<220> FEATURE:
<221> NAME/KEY: misc_feature
<222> LOCATION: (432)..(432)
<223> OTHER INFORMATION: Xaa can be any naturally occurring amino acid
<220> FEATURE:
<221> NAME/KEY: misc_feature
<222> LOCATION: (439)..(440)
<223> OTHER INFORMATION: Xaa can be any naturally occurring amino acid
<220> FEATURE:
<221> NAME/KEY: misc_feature
<222> LOCATION: (474)..(476)
<223> OTHER INFORMATION: Xaa can be any naturally occurring amino acid

<400> SEQUENCE: 157
```

Met Gly Phe Arg Ile Asn Thr Asn Val Ala Ala Leu Asn Ala Lys Ala
1               5                  10                  15

Asn Ala Asp Leu Asn Ala Lys Ser Leu Asp Ala Ser Leu Ser Arg Leu
            20                  25                  30

Ser Ser Gly Leu Arg Ile Asn Ser Ala Ala Asp Asp Ala Ser Gly Met
        35                  40                  45

Ala Ile Ala Asp Ser Leu Arg Ser Gln Ala Asn Thr Leu Gly Gln Ala
    50                  55                  60

Ile Ser Asn Gly Asn Asp Ala Leu Gly Ile Leu Gln Thr Ala Asp Lys
65                  70                  75                  80

Ala Met Asp Glu Gln Leu Lys Ile Leu Asp Thr Ile Lys Thr Lys Ala
                85                  90                  95

Thr Gln Ala Ala Gln Asp Gly Gln Ser Leu Lys Thr Arg Thr Met Leu
            100                 105                 110

Gln Ala Asp Ile Asn Arg Leu Met Glu Glu Leu Asp Asn Ile Ala Asn
        115                 120                 125

Thr Thr Ser Phe Asn Gly Lys Gln Leu Leu Ser Gly Asn Phe Ile Asn
    130                 135                 140

Gln Glu Phe Gln Ile Gly Ala Ser Ser Asn Gln Thr Val Lys Ala Thr
145                 150                 155                 160

Ile Gly Ala Thr Gln Ser Ser Lys Ile Gly Val Thr Arg Phe Glu Thr
                165                 170                 175

Gly Gly Gln Ile Ser Thr Ser Gly Val Val Gly Leu Thr Leu Lys Asn
            180                 185                 190

Tyr Asn Gly Ile Asp Asp Phe Gln Phe Gln Lys Val Val Ile Ser Thr
        195                 200                 205

Ser Val Gly Thr Gly Leu Gly Ala Leu Ala Asp Glu Ile Asn Lys Asn
    210                 215                 220

Ala Asp Lys Thr Gly Val Arg Ala Thr Phe Thr Val Glu Thr Arg Gly
225                 230                 235                 240

```
Ile Ala Ala Val Lys Ala Gly Thr Thr Ser Asp Asp Phe Ala Ile Asn
            245                 250                 255

Gly Val Thr Ile Gly Lys Val Asp Tyr Lys Asp Gly Asp Gly Asn Gly
            260                 265                 270

Ala Leu Val Ala Ala Ile Asn Ala Val Lys Asp Thr Thr Gly Val Glu
            275                 280                 285

Ala Ser Ile Asp Ala Asn Gly Gln Leu Val Leu Thr Ser Ala Asp Gly
            290                 295                 300

Arg Gly Ile Lys Ile Asp Gly Asn Ile Gly Gly Ala Gly Ile Leu
305                 310                 315                 320

Ala Asp Met Lys Glu Asn Tyr Gly Arg Leu Ser Leu Val Lys Asn Asp
            325                 330                 335

Gly Lys Asp Ile Leu Ile Ser Gly Thr Asn Leu Ser Ala Ala Gly Phe
            340                 345                 350

Gly Ala Thr Asp Phe Ile Ser Gln Ala Ser Val Ser Leu Arg Glu Ser
            355                 360                 365

Lys Gly Gln Ile Asp Ala Asn Ile Ala Asp Ala Met Gly Phe Gly Ser
            370                 375                 380

Tyr Asn Gly Gly Gly Xaa Xaa Xaa Val Val Leu Gly Gly Tyr Ser Ser
385                 390                 395                 400

Val Ser Ala Tyr Met Ser Ser Ala Gly Ser Gly Phe Ser Ser Gly Ser
            405                 410                 415

Gly Phe Ser Val Gly Ser Gly Lys Asn Tyr Ser Thr Gly Leu Ala Xaa
            420                 425                 430

Asn Ala Ile Ile Ile Ser Xaa Xaa Ala Ala Ala Ser Leu Ser Thr Val
            435                 440                 445

Tyr Asn Val Ser Ala Gly Ser Gly Phe Ser Ser Gly Ser Gly Leu Ser
            450                 455                 460

Gln Phe Ala Thr Leu Lys Thr Thr Ala Xaa Xaa Xaa Phe Gly Val Lys
465                 470                 475                 480

Asp Glu Thr Ala Gly Val Thr Thr Leu Lys Gly Ala Met Ala Val Met
            485                 490                 495

Asp Ile Ala Glu Thr Ala Ile Thr Asn Leu Asp Gln Ile Arg Ala Asp
            500                 505                 510

Ile Gly Ser Val Gln Asn Gln Val Thr Ser Thr Ile Asn Asn Ile Thr
            515                 520                 525

Val Thr Gln Val Asn Val Lys Ala Ala Glu Ser Gln Ile Arg Asp Val
            530                 535                 540

Asp Phe Ala Ala Glu Ser Ala Asn Tyr Ser Lys Ala Asn Ile Leu Ala
545                 550                 555                 560

Gln Ser Gly Ser Tyr Ala Met Ala Gln Ala Asn Ser Val Gln Gln Asn
            565                 570                 575

Val Leu Arg Leu Leu Gln
            580

<210> SEQ ID NO 158
<211> LENGTH: 576
<212> TYPE: PRT
<213> ORGANISM: Campylobacter jejuni

<400> SEQUENCE: 158

Met Gly Phe Arg Ile Asn Thr Asn Val Ala Ala Leu Asn Ala Lys Ala
1               5                   10                  15

Asn Ser Asp Leu Asn Ala Lys Ser Leu Asp Ala Ser Leu Ser Arg Leu
```

```
              20                  25                  30
Ser Ser Gly Leu Arg Ile Asn Ser Ala Ala Asp Asp Ala Ser Gly Met
            35                  40                  45
Ala Ile Ala Asp Ser Leu Arg Ser Gln Ala Asn Thr Leu Gly Gln Ala
        50                  55                  60
Ile Ser Asn Gly Asn Asp Ala Leu Gly Ile Leu Gln Thr Ala Asp Lys
65                  70                  75                  80
Ala Met Asp Glu Gln Leu Lys Ile Leu Asp Thr Ile Lys Thr Lys Ala
                85                  90                  95
Thr Gln Ala Ala Gln Asp Gly Gln Ser Leu Lys Thr Arg Thr Met Leu
            100                 105                 110
Gln Ala Asp Ile Asn Lys Leu Met Glu Glu Leu Asp Asn Ile Ala Asn
        115                 120                 125
Thr Thr Ser Phe Asn Gly Lys Gln Leu Leu Ser Gly Asn Phe Thr Asn
    130                 135                 140
Gln Glu Phe Gln Ile Gly Ala Ser Ser Asn Gln Thr Val Lys Ala Thr
145                 150                 155                 160
Ile Gly Ala Thr Gln Ser Ser Lys Ile Gly Val Thr Arg Phe Glu Thr
                165                 170                 175
Gly Ala Gln Ser Phe Thr Ser Gly Val Val Gly Leu Thr Ile Lys Asn
            180                 185                 190
Tyr Asn Gly Ile Glu Asp Phe Lys Phe Asp Asn Val Val Ile Ser Thr
        195                 200                 205
Ser Val Gly Thr Gly Leu Gly Ala Leu Ala Glu Glu Ile Asn Lys Ser
    210                 215                 220
Ala Asp Lys Thr Gly Val Arg Ala Thr Tyr Asp Val Lys Thr Thr Gly
225                 230                 235                 240
Val Tyr Ala Ile Lys Glu Gly Thr Thr Ser Gln Glu Phe Ala Ile Asn
                245                 250                 255
Gly Val Thr Ile Gly Lys Ile Glu Tyr Lys Asp Gly Asp Gly Asn Gly
            260                 265                 270
Ser Leu Ile Ser Ala Ile Asn Ala Val Lys Asp Thr Thr Gly Val Gln
        275                 280                 285
Ala Ser Lys Asp Glu Asn Gly Lys Leu Val Leu Thr Ser Ala Asp Gly
    290                 295                 300
Arg Gly Ile Lys Ile Thr Gly Asp Ile Gly Val Gly Ser Gly Ile Leu
305                 310                 315                 320
Ala Asn Gln Lys Glu Asn Tyr Gly Arg Leu Ser Leu Val Lys Asn Asp
                325                 330                 335
Gly Arg Asp Ile Asn Ile Ser Gly Thr Asn Leu Ser Ala Ile Gly Met
            340                 345                 350
Gly Thr Thr Asp Met Ile Ser Gln Ser Ser Val Ser Leu Arg Glu Ser
        355                 360                 365
Lys Gly Gln Ile Ser Ala Thr Asn Ala Asp Ala Met Gly Phe Asn Ser
    370                 375                 380
Tyr Lys Gly Gly Gly Lys Phe Val Phe Thr Gln Asn Val Ser Ser Ile
385                 390                 395                 400
Ser Ala Phe Met Ser Ala Gln Gly Ser Gly Phe Ser Arg Gly Ser Gly
                405                 410                 415
Phe Ser Val Gly Ser Gly Lys Asn Leu Ser Val Gly Leu Ser Gln Gly
            420                 425                 430
Ile Gln Ile Ile Ser Ser Ala Ala Ser Met Ser Asn Thr Tyr Val Val
        435                 440                 445
```

Ser Ala Gly Ser Gly Phe Ser Gly Ser Gly Asn Ser Gln Phe Ala
            450                 455                 460

Ala Leu Lys Thr Thr Ala Ala Asn Thr Thr Asp Glu Thr Ala Gly Val
465                 470                 475                 480

Thr Thr Leu Lys Gly Ala Met Ala Val Met Asp Ile Ala Glu Thr Ala
            485                 490                 495

Ile Thr Asn Leu Asp Gln Ile Arg Ala Asp Ile Gly Ser Ile Gln Asn
            500                 505                 510

Gln Val Thr Ser Thr Ile Asn Asn Ile Thr Val Thr Gln Val Asn Val
            515                 520                 525

Lys Ala Ala Glu Ser Gln Ile Arg Asp Val Asp Phe Ala Ser Glu Ser
530                 535                 540

Ala Asn Tyr Ser Lys Ala Asn Ile Leu Ala Gln Ser Gly Ser Tyr Ala
545                 550                 555                 560

Met Ala Gln Ala Asn Ser Ser Gln Gln Asn Val Leu Arg Leu Leu Gln
            565                 570                 575

<210> SEQ ID NO 159
<211> LENGTH: 576
<212> TYPE: PRT
<213> ORGANISM: Campylobacter jejuni

<400> SEQUENCE: 159

Met Gly Phe Arg Ile Asn Thr Asn Val Ala Ala Leu Asn Ala Lys Ala
1                   5                   10                  15

Asn Ser Asp Leu Asn Ala Lys Ser Leu Asp Ala Ser Leu Ser Arg Leu
            20                  25                  30

Ser Ser Gly Leu Arg Ile Asn Ser Ala Ala Asp Asp Ala Ser Gly Met
        35                  40                  45

Ala Ile Ala Asp Ser Leu Arg Ser Gln Ala Asn Thr Leu Gly Gln Ala
    50                  55                  60

Ile Ser Asn Gly Asn Asp Ala Leu Gly Ile Leu Gln Thr Ala Asp Lys
65                  70                  75                  80

Ala Met Asp Glu Gln Leu Lys Ile Leu Asp Thr Ile Lys Thr Lys Ala
                85                  90                  95

Thr Gln Ala Ala Gln Asp Gly Gln Ser Leu Lys Thr Arg Thr Met Leu
            100                 105                 110

Gln Ala Asp Ile Asn Lys Leu Met Glu Glu Leu Asp Asn Ile Ala Asn
        115                 120                 125

Thr Thr Ser Phe Asn Gly Lys Gln Leu Leu Ser Gly Asn Phe Thr Asn
    130                 135                 140

Gln Glu Phe Gln Ile Gly Ala Ser Ser Asn Gln Thr Val Lys Ala Thr
145                 150                 155                 160

Ile Gly Ala Thr Gln Ser Ser Lys Ile Gly Val Thr Arg Phe Glu Thr
                165                 170                 175

Gly Ala Gln Ser Phe Thr Ser Gly Val Val Gly Leu Thr Ile Lys Asn
            180                 185                 190

Tyr Asn Gly Ile Glu Asp Phe Lys Phe Asp Asn Val Val Ile Ser Thr
        195                 200                 205

Ser Val Gly Thr Gly Leu Gly Ala Leu Ala Glu Ile Asn Lys Ser
    210                 215                 220

Ala Asp Lys Thr Gly Val Arg Ala Thr Tyr Asp Val Lys Thr Thr Gly
225                 230                 235                 240

Val Tyr Ala Ile Lys Glu Gly Thr Thr Ser Gln Asp Phe Ala Ile Asn 245                 250                 255
Gly Val Thr Ile Gly Lys Ile Glu Tyr Lys Asp Gly Asp Asn Gly
            260                 265                 270

Ser Leu Ile Ser Ala Ile Asn Ala Val Lys Asp Thr Thr Gly Val Gln
        275                 280                 285

Ala Ser Lys Asp Glu Asn Gly Lys Leu Val Leu Thr Ser Ala Asp Gly
    290                 295                 300

Arg Gly Ile Lys Ile Thr Gly Asp Ile Val Gly Ser Gly Ile Leu
305                 310                 315                 320

Ala Asn Gln Lys Glu Asn Tyr Gly Arg Leu Ser Leu Val Lys Asn Asp
                325                 330                 335

Gly Arg Asp Ile Asn Ile Ser Gly Thr Asn Leu Ser Ala Ile Gly Met
            340                 345                 350

Gly Thr Thr Asp Met Ile Ser Gln Ser Ser Val Ser Leu Arg Glu Ser
        355                 360                 365

Lys Gly Gln Ile Ser Ala Thr Asn Ala Asp Ala Met Gly Phe Asn Ser
    370                 375                 380

Tyr Lys Gly Gly Gly Lys Phe Val Phe Thr Gln Asn Val Ser Ser Ile
385                 390                 395                 400

Ser Ala Phe Met Ser Ala Gln Gly Ser Gly Phe Ser Arg Gly Ser Gly
                405                 410                 415

Phe Ser Val Gly Ser Gly Lys Asn Leu Ser Val Gly Leu Ser Gln Gly
            420                 425                 430

Ile Gln Ile Ile Ser Ser Ala Ala Ser Met Ser Asn Thr Tyr Val Val
        435                 440                 445

Ser Ala Gly Ser Gly Phe Ser Ser Gly Ser Gly Asn Ser Gln Phe Ala
    450                 455                 460

Ala Leu Lys Thr Thr Ala Ala Asn Thr Thr Asp Glu Thr Ala Gly Val
465                 470                 475                 480

Thr Thr Leu Lys Gly Ala Met Ala Val Met Asp Ile Ala Glu Thr Ala
                485                 490                 495

Ile Thr Asn Leu Asp Gln Ile Arg Ala Asp Ile Gly Ser Ile Gln Asn
            500                 505                 510

Gln Val Thr Ser Thr Ile Asn Asn Ile Thr Val Thr Gln Val Asn Val
        515                 520                 525

Lys Ala Ala Glu Ser Gln Ile Arg Asp Val Asp Phe Ala Ser Glu Ser
    530                 535                 540

Ala Asn Tyr Ser Lys Ala Asn Ile Leu Ala Gln Ser Gly Ser Tyr Ala
545                 550                 555                 560

Met Ala Gln Ala Asn Ser Ser Gln Gln Asn Val Leu Arg Leu Leu Gln
                565                 570                 575

<210> SEQ ID NO 160
<211> LENGTH: 580
<212> TYPE: PRT
<213> ORGANISM: Campylobacter jejuni

<400> SEQUENCE: 160

Met Gly Phe Arg Ile Asn Thr Asn Val Ala Ala Leu Asn Ala Lys Ala
1               5                   10                  15

Asn Ser Asp Leu Asn Ala Lys Ser Leu Asp Ser Ser Leu Ala Arg Leu
            20                  25                  30

Ser Ser Gly Leu Arg Ile Asn Ser Ala Ala Asp Ala Ser Gly Met
        35                  40                  45

```
Ala Ile Ala Asp Thr Leu Arg Ser Gln Ala Asn Thr Leu Gly Gln Ala
     50                  55                  60

Ile Ser Asn Gly Asn Asp Ala Leu Gly Ile Leu Gln Thr Ala Asp Lys
 65                  70                  75                  80

Ala Met Asp Glu Gln Leu Lys Ile Leu Asp Thr Ile Lys Thr Lys Ala
                 85                  90                  95

Thr Gln Ala Ala Gln Asp Gly Gln Ser Leu Lys Thr Arg Thr Met Leu
            100                 105                 110

Gln Ala Asp Ile Asn Arg Leu Met Glu Glu Leu Asp Asn Ile Ala Asn
            115                 120                 125

Thr Thr Ser Phe Asn Gly Lys Gln Leu Leu Ser Gly Gly Phe Thr Asn
130                 135                 140

Gln Glu Phe Gln Ile Gly Ser Ser Ser Asn Gln Thr Val Lys Ala Thr
145                 150                 155                 160

Ile Gly Ala Thr Gln Ser Ser Lys Ile Gly Val Thr Arg Phe Glu Thr
                165                 170                 175

Gly Thr Gln Ser Val Thr Ser Gly Val Val Gly Leu Thr Ile Lys Asn
            180                 185                 190

Tyr Asn Gly Ile Glu Asp Phe Lys Phe Gln Asp Val Val Ile Ser Thr
            195                 200                 205

Ser Val Gly Thr Gly Leu Gly Ala Leu Ala Glu Glu Ile Asn Lys Asn
210                 215                 220

Ala Asp Lys Thr Gly Val Arg Ala Ser Tyr Asp Val Arg Thr Val Gly
225                 230                 235                 240

Ala Tyr Ala Ile Lys Ala Gly Ser Thr Ser Ser Asp Phe Ala Ile Asn
                245                 250                 255

Gly Val Thr Ile Gly Lys Val Asp Tyr Lys Asp Gly Asp Glu Asn Gly
            260                 265                 270

Ser Leu Val Ser Ala Ile Asn Ala Val Lys Asp Thr Thr Gly Val Gln
            275                 280                 285

Ala Ser Gln Asp Glu Asn Gly Arg Leu Val Leu Thr Ser Ala Asp Gly
290                 295                 300

Arg Gly Ile Lys Ile Glu Gly Asn Ile Gly Gly Ala Gly Ile Leu
305                 310                 315                 320

Gln Lys Glu Asn Tyr Gly Arg Leu Ser Leu Val Lys Asn Asp Gly Arg
                325                 330                 335

Asp Ile Asn Ile Ser Gly Thr Asn Leu Ser Ala Ile Gly Met Gly Ala
            340                 345                 350

Ala Asp Ile Ile Ser Gln Thr Ser Val Ser Leu Arg Glu Ser Lys Gly
            355                 360                 365

Gln Ile Asp Ala Asn Thr Ala Asp Ala Met Gly Phe Asn Ala Tyr Gly
370                 375                 380

Gly Gly Gly Lys Gln Val Ile Ile Asn Asn Ser Ile Ser Ser Val Ser
385                 390                 395                 400

Gly Leu Met Ser Ala Gly Ser Gly Phe Ser Lys Gly Ser Gly Phe
                405                 410                 415

Ser Ile Gly Ser Gly Lys Asn Met Ser Thr Met Leu Asp Asn Ser Ile
            420                 425                 430

Ile Ile Ala Ser Ser Met Thr Thr Ala Asn Ala Met Ser Ala Tyr Asn
            435                 440                 445

Val Ser Ala Gly Ser Gly Phe Ser Ser Gly Ser Gly Asn Ser Gln Phe
450                 455                 460

Ala Thr Leu Lys Thr Ser Ala Gly Asn Ala Val Gly Ala Ala Asn Glu
```

```
            465                 470                 475                 480
        Thr Ser Gly Val Thr Thr Leu Lys Gly Ala Met Ala Val Met Asp Ile
                        485                 490                 495

Ala Glu Thr Ala Ile Asn Asn Leu Asp Gln Ile Arg Ala Asp Ile Gly
                    500                 505                 510

Ser Val Gln Asn Gln Ile Thr Ser Thr Ile Asn Asn Ile Thr Val Thr
                    515                 520                 525

Gln Val Asn Val Lys Ala Ala Glu Ser Thr Ile Arg Asp Val Asp Phe
                530                 535                 540

Ala Ser Glu Ser Ala Asn Tyr Ser Lys Ala Asn Ile Leu Ala Gln Ser
        545                 550                 555                 560

Gly Ser Tyr Ala Met Ala Gln Ala Asn Ser Ser Gln Gln Asn Val Leu
                        565                 570                 575

Arg Leu Leu Gln
                    580

<210> SEQ ID NO 161
<211> LENGTH: 572
<212> TYPE: PRT
<213> ORGANISM: Campylobacter jejuni

<400> SEQUENCE: 161

Met Gly Phe Arg Ile Asn Thr Asn Val Ala Ala Leu Asn Ala Lys Ala
        1               5                   10                  15

Asn Ala Asp Leu Asn Ser Lys Ser Leu Asp Ala Ser Leu Ser Arg Leu
                    20                  25                  30

Ser Ser Gly Leu Arg Ile Asn Ser Ala Ala Asp Asp Ala Ser Gly Met
                    35                  40                  45

Ala Ile Ala Asp Ser Leu Arg Ser Gln Ala Asn Thr Leu Gly Gln Ala
            50                  55                  60

Ile Ser Asn Gly Asn Asp Ala Leu Gly Ile Leu Gln Thr Ala Asp Lys
        65                  70                  75                  80

Ala Met Asp Glu Gln Leu Lys Ile Leu Asp Thr Ile Lys Thr Lys Ala
                        85                  90                  95

Thr Gln Ala Ala Gln Asp Gly Gln Ser Leu Lys Thr Arg Thr Met Leu
                    100                 105                 110

Gln Ala Asp Ile Asn Arg Leu Met Glu Glu Leu Asp Asn Ile Ala Asn
                    115                 120                 125

Thr Thr Ser Phe Asn Gly Lys Gln Leu Leu Ser Gly Asn Phe Ile Asn
            130                 135                 140

Gln Glu Phe Gln Ile Gly Ala Ser Ser Asn Gln Thr Val Lys Ala Thr
        145                 150                 155                 160

Ile Gly Ala Thr Gln Ser Ser Lys Ile Gly Leu Thr Arg Phe Glu Thr
                        165                 170                 175

Gly Gly Arg Ile Ser Thr Ser Gly Glu Val Gln Phe Thr Leu Lys Asn
                    180                 185                 190

Tyr Asn Gly Ile Asp Asp Phe Gln Phe Gln Lys Val Val Ile Ser Thr
                    195                 200                 205

Ser Val Gly Thr Gly Leu Gly Ala Leu Ala Asp Glu Ile Asn Lys Asn
            210                 215                 220

Ala Asp Lys Thr Gly Val Arg Ala Thr Phe Thr Val Glu Thr Arg Gly
        225                 230                 235                 240

Ile Ala Ala Val Arg Ala Gly Ala Thr Ser Asp Thr Phe Ala Ile Asn
                        245                 250                 255
```

Gly Val Lys Ile Gly Lys Val Asp Tyr Lys Asp Gly Asp Ala Asn Gly
            260                 265                 270

Ala Leu Val Ala Ala Ile Asn Ser Val Lys Asp Thr Thr Gly Val Glu
            275                 280                 285

Ala Ser Ile Asp Ala Asn Gly Gln Leu Leu Leu Thr Ser Arg Glu Gly
            290                 295                 300

Arg Gly Ile Lys Ile Asp Gly Asn Ile Gly Gly Ala Phe Ile Asn
305                 310                 315                 320

Ala Asp Met Lys Glu Asn Tyr Gly Arg Leu Ser Leu Val Lys Asn Asp
                325                 330                 335

Gly Lys Asp Ile Leu Ile Ser Gly Ser Asn Leu Ser Ser Ala Gly Phe
            340                 345                 350

Gly Ala Thr Gln Phe Ile Ser Gln Ala Ser Val Ser Leu Arg Glu Ser
            355                 360                 365

Lys Gly Gln Ile Asp Ala Asn Ile Ala Asp Ala Met Gly Phe Gly Ser
            370                 375                 380

Ala Asn Lys Gly Val Val Leu Gly Gly Tyr Ser Ser Val Ser Ala Tyr
385                 390                 395                 400

Met Ser Ser Ala Gly Ser Gly Phe Ser Ser Gly Ser Gly Tyr Ser Val
                405                 410                 415

Gly Ser Gly Lys Asn Tyr Ser Thr Ser Phe Ala Asn Ala Ile Ala Ile
            420                 425                 430

Ser Ala Ala Ser Gln Leu Ser Thr Val Tyr Asn Val Ser Ala Gly Ser
            435                 440                 445

Gly Phe Ser Ser Gly Ser Thr Leu Ser Gln Phe Ala Thr Met Lys Thr
            450                 455                 460

Thr Ala Phe Gly Val Lys Asp Glu Thr Ala Gly Val Thr Thr Leu Lys
465                 470                 475                 480

Gly Ala Met Ala Val Met Asp Ile Ala Glu Thr Ala Ile Thr Asn Leu
                485                 490                 495

Asp Gln Ile Arg Ala Asp Ile Gly Ser Val Gln Asn Gln Val Thr Ser
            500                 505                 510

Thr Ile Asn Asn Ile Thr Val Thr Gln Val Asn Val Lys Ala Ala Glu
            515                 520                 525

Ser Gln Ile Arg Asp Val Asp Phe Ala Ala Glu Ser Ala Asn Tyr Ser
            530                 535                 540

Lys Ala Asn Ile Leu Ala Gln Ser Gly Ser Tyr Ala Met Ala Gln Ala
545                 550                 555                 560

Asn Ser Val Gln Gln Asn Val Leu Arg Leu Leu Gln
                565                 570

<210> SEQ ID NO 162
<211> LENGTH: 577
<212> TYPE: PRT
<213> ORGANISM: Campylobacter jejuni

<400> SEQUENCE: 162

Met Gly Phe Arg Ile Asn Thr Asn Val Ala Ala Leu Asn Ala Lys Ala
1               5                   10                  15

Asn Ser Asp Leu Asn Ala Lys Ser Leu Asp Ser Ser Leu Ala Arg Leu
            20                  25                  30

Ser Ser Gly Leu Arg Ile Asn Ser Ala Ala Asp Asp Ala Ser Gly Met
        35                  40                  45

Ala Ile Ala Asp Ser Leu Arg Ser Gln Ala Asn Thr Leu Gly Gln Ala
    50                  55                  60

```
Ile Ser Asn Gly Asn Asp Ala Leu Gly Ile Leu Gln Thr Ala Asp Lys
 65                  70                  75                  80

Ala Met Asp Glu Gln Leu Lys Ile Leu Asp Thr Ile Lys Thr Lys Ala
                 85                  90                  95

Thr Gln Ala Ala Gln Asp Gly Gln Ser Leu Lys Thr Arg Thr Met Leu
            100                 105                 110

Gln Ala Asp Ile Asn Lys Leu Met Glu Glu Leu Asp Asn Ile Ala Asn
        115                 120                 125

Thr Thr Ser Phe Asn Gly Lys Gln Leu Leu Ser Gly Phe Thr Asn
130                 135                 140

Gln Glu Phe Gln Ile Gly Ser Ser Ser Asn Gln Thr Val Lys Ala Thr
145                 150                 155                 160

Ile Gly Ala Thr Gln Ser Ser Lys Ile Gly Val Thr Arg Phe Glu Thr
                165                 170                 175

Gly Ser Gln Ser Phe Thr Ser Gly Val Val Gly Leu Thr Ile Lys Asn
            180                 185                 190

Tyr Asn Gly Ile Glu Asp Phe Lys Phe Asp Asn Val Val Ile Ser Thr
        195                 200                 205

Ser Val Gly Thr Gly Leu Gly Ala Leu Ala Glu Glu Ile Asn Lys Asn
210                 215                 220

Ala Asp Lys Thr Gly Val Arg Ala Thr Tyr Asp Val Lys Thr Thr Gly
225                 230                 235                 240

Ala Tyr Ala Ile Lys Ala Gly Thr Thr Ser Gln Asp Phe Ala Ile Asn
                245                 250                 255

Gly Val Ile Ile Gly Lys Val Asp Tyr Lys Asp Gly Asn Asn Gly
            260                 265                 270

Ser Leu Ile Ser Ala Ile Asn Ala Val Lys Asp Thr Thr Gly Val Gln
        275                 280                 285

Ala Ser Lys Asp Glu Asn Gly Lys Leu Val Leu Thr Ser Ala Asp Gly
290                 295                 300

Arg Gly Ile Lys Ile Thr Gly Asp Ile Gly Val Gly Ser Gly Ile Leu
305                 310                 315                 320

Ser Ala Gln Lys Glu Asn Tyr Gly Arg Leu Ser Leu Val Lys Asn Asp
                325                 330                 335

Gly Arg Asp Ile Asn Val Ser Gly Thr Gly Leu Ser Ala Ile Gly Met
            340                 345                 350

Gly Ala Ala Asp Met Ile Ser Gln Ala Ser Val Ser Leu Arg Glu Ser
        355                 360                 365

Lys Gly Gln Ile Ser Ala Ala Asn Ala Asp Ala Met Gly Phe Asn Ser
370                 375                 380

Tyr Asn Gly Gly Ala Lys Gln Ile Leu Gln Val Gln Ala Ser Ser
385                 390                 395                 400

Ile Ser Ala Phe Met Ser Gln Ala Gly Ser Gly Phe Ser Ala Gly Ser
                405                 410                 415

Gly Phe Ser Ala Gly Ser Gly Lys Gly Tyr Ser Thr Ile Leu Ser Gly
            420                 425                 430

Ser Val Gln Ile Val Ser Ser Thr Ala Ser Met Ser Ser Thr Tyr Val
        435                 440                 445

Ile Ser Ala Gly Ser Gly Phe Ser Val Gly Ser Gly Asn Ser Gln Phe
450                 455                 460

Ala Ala Leu Lys Thr Ser Thr Val Ser Ala His Glu Ala Thr Ala Gly
465                 470                 475                 480
```

-continued

```
Val Thr Thr Leu Lys Gly Ala Met Ala Val Met Asp Ile Ala Glu Thr
                485                 490                 495

Ala Ile Thr Asn Leu Asp Gln Ile Arg Ala Asp Ile Gly Ser Ile Gln
            500                 505                 510

Asn Gln Val Thr Ser Thr Ile Asn Asn Ile Thr Val Thr Gln Val Asn
        515                 520                 525

Val Lys Ser Ala Glu Ser Gln Ile Arg Asp Val Asp Phe Ala Ser Glu
    530                 535                 540

Ser Ala Asn Tyr Ser Lys Ala Asn Ile Leu Ala Gln Ser Gly Ser Tyr
545                 550                 555                 560

Ala Met Ala Gln Ala Asn Ser Ser Gln Gln Asn Val Leu Arg Leu Leu
                565                 570                 575

Gln

<210> SEQ ID NO 163
<211> LENGTH: 572
<212> TYPE: PRT
<213> ORGANISM: Campylobacter jejuni

<400> SEQUENCE: 163

Met Gly Phe Arg Ile Asn Thr Asn Val Ala Ala Leu Asn Ala Lys Ala
1               5                   10                  15

Asn Ala Asp Leu Asn Ser Lys Ser Leu Asp Ala Ser Leu Ser Arg Leu
                20                  25                  30

Ser Ser Gly Leu Arg Ile Asn Ser Ala Ala Asp Asp Ala Ser Gly Met
            35                  40                  45

Ala Ile Ala Asp Ser Leu Arg Ser Gln Ala Asn Thr Leu Gly Gln Ala
50                  55                  60

Ile Ser Asn Gly Asn Asp Ala Leu Gly Ile Leu Gln Thr Ala Asp Lys
65                  70                  75                  80

Ala Met Asp Glu Gln Leu Lys Ile Leu Asp Thr Ile Lys Thr Lys Ala
                85                  90                  95

Thr Gln Ala Ala Gln Asp Gly Gln Ser Leu Lys Thr Arg Thr Met Leu
            100                 105                 110

Gln Ala Asp Ile Asn Arg Leu Met Glu Glu Leu Asp Asn Ile Ala Asn
        115                 120                 125

Thr Thr Ser Phe Asn Gly Lys Gln Leu Leu Ser Gly Asn Phe Ile Asn
130                 135                 140

Gln Glu Phe Gln Ile Gly Ala Ser Ser Asn Gln Thr Val Lys Ala Thr
145                 150                 155                 160

Ile Gly Ala Thr Gln Ser Ser Lys Ile Gly Leu Thr Arg Phe Glu Thr
                165                 170                 175

Gly Gly Arg Ile Ser Thr Ser Gly Glu Val Gln Phe Thr Leu Lys Asn
            180                 185                 190

Tyr Asn Gly Ile Asp Asp Phe Gln Phe Gln Lys Val Val Ile Ser Thr
        195                 200                 205

Ser Val Gly Thr Gly Leu Gly Ala Leu Ala Asp Glu Ile Asn Lys Asn
210                 215                 220

Ala Asp Lys Thr Gly Val Arg Ala Thr Phe Thr Val Glu Thr Arg Gly
225                 230                 235                 240

Ile Ala Ala Val Arg Ala Gly Ala Thr Ser Asp Thr Phe Ala Ile Asn
                245                 250                 255

Gly Val Lys Ile Gly Lys Val Asp Tyr Lys Asp Gly Asp Ala Asn Gly
            260                 265                 270
```

Ala Leu Val Ala Ala Ile Asn Ser Val Lys Asp Thr Thr Gly Val Glu
            275                 280                 285

Ala Ser Ile Asp Ala Asn Gly Gln Leu Leu Thr Ser Arg Glu Gly
        290                 295                 300

Arg Gly Ile Lys Ile Asp Gly Asn Ile Gly Gly Ala Phe Ile Asn
305                 310                 315                 320

Ala Asp Met Lys Glu Asn Tyr Gly Arg Leu Ser Leu Val Lys Asn Asp
            325                 330                 335

Gly Lys Asp Ile Leu Ile Ser Gly Ser Asn Leu Ser Ser Ala Gly Phe
            340                 345                 350

Gly Ala Thr Gln Phe Ile Ser Gln Ala Ser Val Ser Leu Arg Glu Ser
            355                 360                 365

Lys Gly Gln Ile Asp Ala Asn Ile Ala Asp Ala Met Gly Phe Gly Ser
            370                 375                 380

Ala Asn Lys Gly Val Val Leu Gly Gly Tyr Ser Ser Val Ser Ala Tyr
385                 390                 395                 400

Met Ser Ser Ala Glu Ser Gly Phe Ser Ser Gly Ser Tyr Ser Val
            405                 410                 415

Gly Ser Gly Lys Asn Tyr Ser Thr Gly Phe Ala Asn Ala Ile Ala Ile
            420                 425                 430

Ser Ala Ala Ser Gln Leu Ser Thr Val Tyr Asn Val Ser Ala Gly Ser
            435                 440                 445

Gly Phe Ser Ser Gly Ser Thr Leu Ser Gln Phe Ala Thr Met Lys Thr
            450                 455                 460

Thr Ala Phe Gly Val Lys Asp Glu Thr Ala Gly Val Thr Thr Leu Lys
465                 470                 475                 480

Gly Ala Met Ala Val Met Asp Ile Ala Glu Thr Ala Ile Thr Asn Leu
            485                 490                 495

Asp Gln Ile Arg Ala Asp Ile Gly Ser Val Gln Asn Gln Val Thr Ser
            500                 505                 510

Thr Ile Asn Asn Ile Thr Val Thr Gln Val Asn Val Lys Ala Ala Glu
            515                 520                 525

Ser Gln Ile Arg Asp Val Asp Phe Ala Ala Glu Ser Ala Asn Tyr Ser
            530                 535                 540

Lys Ala Asn Ile Leu Ala Gln Ser Gly Ser Tyr Ala Met Ala Gln Ala
545                 550                 555                 560

Asn Ser Val Gln Gln Asn Val Leu Arg Leu Leu Gln
            565                 570

<210> SEQ ID NO 164
<211> LENGTH: 572
<212> TYPE: PRT
<213> ORGANISM: Campylobacter jejuni

<400> SEQUENCE: 164

Met Gly Phe Arg Ile Asn Thr Asn Val Ala Ala Leu Asn Ala Lys Ala
1               5                   10                  15

Asn Ala Asp Leu Asn Ser Lys Ser Leu Asp Ala Ser Leu Ser Arg Leu
            20                  25                  30

Ser Ser Gly Leu Arg Ile Asn Ser Ala Ala Asp Asp Ala Ser Gly Met
        35                  40                  45

Ala Ile Ala Asp Ser Leu Arg Ser Gln Ala Asn Thr Leu Gly Gln Ala
    50                  55                  60

Ile Ser Asn Gly Asn Asp Ala Leu Gly Ile Leu Gln Thr Ala Asp Lys
65                  70                  75                  80

```
Ala Met Asp Glu Gln Leu Lys Ile Leu Asp Thr Ile Lys Thr Lys Ala
                85                  90                  95

Thr Gln Ala Ala Gln Asp Gly Gln Ser Leu Lys Thr Arg Thr Met Leu
            100                 105                 110

Gln Ala Asp Ile Asn Arg Leu Met Glu Glu Leu Asp Asn Ile Ala Asn
        115                 120                 125

Thr Thr Ser Phe Asn Gly Lys Gln Leu Leu Ser Gly Asn Phe Ile Asn
    130                 135                 140

Gln Glu Phe Gln Ile Gly Ala Ser Ser Asn Gln Thr Val Lys Ala Thr
145                 150                 155                 160

Ile Gly Ala Thr Gln Ser Ser Lys Ile Gly Leu Thr Arg Phe Glu Thr
                165                 170                 175

Gly Gly Arg Ile Ser Thr Ser Gly Glu Val Gln Phe Thr Leu Lys Asn
            180                 185                 190

Tyr Asn Gly Ile Asp Asp Phe Gln Phe Gln Lys Val Val Ile Ser Thr
        195                 200                 205

Ser Val Gly Thr Gly Leu Gly Ala Leu Ala Asp Glu Ile Asn Lys Asn
    210                 215                 220

Ala Asp Lys Thr Gly Val Arg Ala Thr Phe Thr Val Glu Thr Arg Gly
225                 230                 235                 240

Ile Ala Ala Val Arg Ala Gly Ala Thr Ser Asp Thr Phe Ala Ile Asn
                245                 250                 255

Gly Val Lys Ile Gly Lys Val Asp Tyr Lys Asp Gly Asp Ala Asn Gly
            260                 265                 270

Ala Leu Val Ala Ala Ile Asn Ser Val Lys Asp Thr Thr Gly Val Glu
        275                 280                 285

Ala Ser Ile Asp Ala Asn Gly Gln Leu Leu Leu Thr Ser Arg Glu Gly
    290                 295                 300

Arg Gly Ile Lys Ile Asp Gly Asn Ile Gly Gly Ala Phe Ile Asn
305                 310                 315                 320

Ala Asp Met Lys Glu Asn Tyr Gly Arg Leu Ser Leu Val Lys Asn Asp
                325                 330                 335

Gly Lys Asp Ile Leu Ile Ser Gly Ser Asn Leu Ser Ser Ala Gly Phe
            340                 345                 350

Gly Ala Thr Gln Phe Ile Ser Gln Ala Ser Val Ser Leu Arg Glu Ser
        355                 360                 365

Lys Gly Gln Ile Asp Ala Asn Ile Ala Asp Ala Met Gly Phe Gly Ser
    370                 375                 380

Ala Asn Lys Gly Val Val Leu Gly Gly Tyr Ser Ser Val Ser Ala Tyr
385                 390                 395                 400

Met Ser Ser Ala Gly Ser Gly Phe Ser Ser Gly Ser Gly Tyr Ser Val
                405                 410                 415

Gly Ser Gly Lys Asn Tyr Ser Thr Gly Phe Ala Asn Ala Ile Ala Ile
            420                 425                 430

Ser Ala Ala Ser Gln Leu Ser Thr Val Tyr Asn Val Ser Ala Gly Ser
        435                 440                 445

Gly Phe Ser Ser Gly Ser Thr Leu Ser Gln Phe Ala Thr Met Lys Thr
    450                 455                 460

Thr Ala Phe Gly Val Lys Asp Glu Thr Ala Gly Val Thr Thr Leu Lys
465                 470                 475                 480

Gly Ala Met Ala Val Met Asp Ile Ala Glu Thr Ala Ile Thr Asn Leu
                485                 490                 495
```

```
Asp Gln Ile Arg Ala Asp Ile Gly Ser Val Gln Asn Gln Val Thr Ser
                500                 505                 510

Thr Ile Asn Asn Ile Thr Val Thr Gln Val Asn Val Lys Ala Ala Glu
            515                 520                 525

Ser Gln Ile Arg Asp Val Asp Phe Ala Ala Glu Ser Ala Asn Tyr Ser
        530                 535                 540

Lys Ala Asn Ile Leu Ala Gln Ser Gly Ser Tyr Ala Met Ala Gln Ala
545                 550                 555                 560

Asn Ser Val Gln Gln Asn Val Leu Arg Leu Leu Gln
                565                 570
```

<210> SEQ ID NO 165
<211> LENGTH: 573
<212> TYPE: PRT
<213> ORGANISM: Campylobacter jejuni

<400> SEQUENCE: 165

```
Met Gly Phe Arg Ile Asn Thr Asn Val Ala Ala Leu Asn Ala Lys Ala
1               5                   10                  15

Asn Ala Asp Leu Asn Ser Lys Ser Leu Asp Ala Ser Leu Ser Arg Leu
                20                  25                  30

Ser Ser Gly Leu Arg Ile Asn Ser Ala Ala Asp Asp Ala Ser Gly Met
            35                  40                  45

Ala Ile Ala Asp Ser Leu Arg Ser Gln Ala Asn Thr Leu Gly Gln Ala
        50                  55                  60

Ile Ser Asn Gly Asn Asp Ala Leu Gly Ile Leu Gln Thr Ala Asp Lys
65                  70                  75                  80

Ala Met Asp Glu Gln Leu Lys Ile Leu Asp Thr Ile Lys Thr Lys Ala
                85                  90                  95

Thr Gln Ala Ala Gln Asp Gly Gln Ser Leu Lys Thr Arg Thr Met Leu
            100                 105                 110

Gln Ala Asp Ile Asn Arg Leu Met Glu Glu Leu Asp Asn Ile Ala Asn
        115                 120                 125

Thr Thr Ser Phe Asn Gly Lys Gln Leu Leu Ser Gly Asn Phe Ile Asn
130                 135                 140

Gln Glu Phe Gln Ile Gly Ala Ser Ser Asn Gln Thr Val Lys Ala Thr
145                 150                 155                 160

Ile Gly Ala Thr Gln Ser Ser Lys Ile Gly Leu Thr Arg Phe Glu Thr
                165                 170                 175

Gly Gly Arg Ile Thr Ser Gly Gly Glu Val Gln Phe Thr Leu Lys Asn
            180                 185                 190

Tyr Asn Gly Ile Asp Asp Phe Gln Phe Gln Lys Val Val Ile Ser Thr
        195                 200                 205

Ser Val Gly Thr Gly Leu Gly Ala Leu Ala Asp Glu Ile Asn Lys Asn
210                 215                 220

Ala Asp Lys Thr Gly Val Arg Ala Thr Phe Thr Val Glu Thr Arg Gly
225                 230                 235                 240

Met Ala Ala Val Arg Ala Gly Thr Thr Ser Asn Asp Phe Ala Ile Asn
                245                 250                 255

Gly Val Thr Ile Gly Gln Val Ala Tyr Glu Asp Gly Asp Gly Asn Gly
            260                 265                 270

Ala Leu Val Ala Ala Ile Asn Ser Val Lys Asp Thr Thr Gly Val Glu
        275                 280                 285

Ala Ser Ile Asp Ala Asn Gly Gln Leu Leu Leu Thr Ser Arg Glu Gly
        290                 295                 300
```

Arg Gly Ile Lys Ile Asp Gly Asn Ile Gly Gly Ala Phe Ile Asn
305                 310                 315                 320

Ala Asn Met Lys Glu Asn Tyr Gly Arg Leu Ser Leu Val Lys Asn Asp
            325                 330                 335

Gly Lys Asp Ile Leu Val Ser Gly Thr Gly Leu Ser Phe Ala Gly Phe
        340                 345                 350

Gly Ala Asn Ser Phe Ile Ser Gln Ala Ser Ile Ser Leu Arg Glu Ser
            355                 360                 365

Lys Gly Gln Leu Asp Ala Asn Ile Ala Asp Ala Met Gly Phe Gly Ser
    370                 375                 380

Val Asn Lys Gly Val Val Ile Gly Gly Phe Ser Thr Val Ser Ala Tyr
385                 390                 395                 400

Met Ser Ser Glu Gly Ser Gly Phe Ser Ala Gly Ser Gly Tyr Ser Ile
            405                 410                 415

Gly Ser Gly Lys Gly Tyr Ser Ala Thr Leu Thr Gly Asn Ala Thr Phe
        420                 425                 430

Ile Ser Thr Ala Ser Ala Ala Ser Arg Val Tyr Asn Val Ser Ser Gly
            435                 440                 445

Ser Gly Phe Ser Thr Gly Ser Asn Leu Ser Gln Phe Ala Thr Met Lys
    450                 455                 460

Thr Ser Val Leu Gly Val Lys Asp Glu Thr Ala Gly Val Thr Thr Leu
465                 470                 475                 480

Lys Gly Ala Met Ala Val Met Asp Ile Ala Glu Thr Ala Ile Thr Asn
            485                 490                 495

Leu Asp Gln Ile Arg Ala Asp Ile Gly Ser Val Gln Asn Gln Val Thr
        500                 505                 510

Ser Thr Ile Asn Asn Ile Thr Val Thr Gln Val Asn Val Lys Ala Ala
            515                 520                 525

Glu Ser Gln Ile Arg Asp Val Asp Phe Ala Ala Glu Ser Ala Asn Tyr
    530                 535                 540

Ser Lys Ala Asn Ile Leu Ala Gln Ser Gly Ser Tyr Ala Met Ala Gln
545                 550                 555                 560

Ala Asn Ser Val Gln Gln Asn Val Leu Arg Leu Leu Gln
            565                 570

<210> SEQ ID NO 166
<211> LENGTH: 12
<212> TYPE: PRT
<213> ORGANISM: Artificial Sequence
<220> FEATURE:
<223> OTHER INFORMATION: Synthetic peptide

<400> SEQUENCE: 166

Ala Gly Val Lys Phe Arg Leu Ser Asp Ser Leu Ala
1               5                   10

<210> SEQ ID NO 167
<211> LENGTH: 36
<212> TYPE: DNA
<213> ORGANISM: Artificial Sequence
<220> FEATURE:
<223> OTHER INFORMATION: Syntheic oligonucleotide

<400> SEQUENCE: 167
gctggtgtta agtttcgttt atcagattca cttgct                                36

<210> SEQ ID NO 168

<211> LENGTH: 466
<212> TYPE: PRT
<213> ORGANISM: Lactobacillus crispatus

<400> SEQUENCE: 168

```
Met Lys Lys Asn Leu Arg Ile Val Ser Ala Ala Ala Ala Leu Leu
1               5                   10                  15

Ala Val Ala Pro Val Ala Ala Ser Ala Val Ser Thr Val Ser Ala Asp
            20                  25                  30

Ala Ala Ala Thr Thr Thr Ala Thr Asn Ser Asn Val Thr Leu Asn
            35                  40                  45

Leu Asn Gly Ala Gly Ser Thr Ala Thr Asp Ala Ala Asn Thr Val Asn
50                  55                  60

Val Ser Ser Asn Phe Ser Leu Asn Ala Pro Val Lys Ala Asn Asn Ala
65                  70                  75                  80

Val Thr Ala Asp Ala Thr Leu Gly Gly Glu Leu Thr Ala Thr Leu Asn
                85                  90                  95

Gly Thr Ser Val Ser Ser Leu Ala Asp Ala Ala Gln Asp Val Thr
                100                 105                 110

Val Ser Asp Gly Lys Thr Asn Leu Tyr Ser Tyr Asn Lys Glu Thr Lys
            115                 120                 125

Lys Val Glu Asn Asn Leu Asn Asn Val Val Ala Gly Gln Ser Tyr Thr
130                 135                 140

Leu Thr Leu Thr Asn Val Gly Phe Ser Phe Gly Ser Ala Met Lys Asn
145                 150                 155                 160

Lys Thr Val Thr Val Lys Leu Ala Asn Gly Glu Leu Ser Gly Lys Asn
                165                 170                 175

Val Thr Lys Asn Thr Asp Gly Ser Tyr Lys Leu Thr Leu Asp Gln Tyr
            180                 185                 190

Gly Asn Ala Thr Glu Leu Thr Tyr Thr Gln Ser Leu Lys Ala Tyr Asn
            195                 200                 205

Gln Gly Asn Thr Asn Ser Val Phe Phe Ile Asn Gln Asn Ser Gly Thr
210                 215                 220

Thr Glu Thr Lys Gly Leu Tyr Leu Thr Leu Ala Asn Gly Asn Gly Glu
225                 230                 235                 240

Leu Asn Val Ala Asp Val Leu Ala Asn Ile Glu Lys Gln Tyr Thr Ala
                245                 250                 255

Val Gln Tyr Asn Asp Ser Lys Phe Met Ser Ser Thr Glu Lys Asp Ser
            260                 265                 270

Pro Val Thr Ile Thr Thr Asn Lys Asp Ala Val Ile Ala Glu Leu Lys
            275                 280                 285

Lys Gln Asn Ile Pro Val Asn Ala Ala Gly Asn Phe Thr Ala Pro Asp
290                 295                 300

Thr Phe Thr Val Thr Leu Asn Ala Lys Ser Ser Ile Asn Gly Lys Thr
305                 310                 315                 320

Gly Gln Leu Val Val Thr Val Ser Val Pro Asn Gly Lys Lys Thr Thr
                325                 330                 335

Val Ala Ser Gln Glu Lys Thr Ile Met His Asn Ala Tyr Tyr Tyr Asp
            340                 345                 350

Lys Asp Ala Lys Arg Val Gly Thr Asp Lys Val Thr Arg Tyr Asn Lys
            355                 360                 365

Val Thr Val Ala Thr Ser Thr Thr Lys Ile Gly Asp Lys Thr Tyr Tyr
370                 375                 380

Glu Val Ile Glu Asn Gly Lys Ala Thr Gly Lys Tyr Ile Asn Ala Asp
```

| | | | | | | | | 385 | | | | | 390 | | | | | 395 | | | | | 400 |
|---|---|---|---|---|---|---|---|---|---|---|---|---|---|---|---|---|---|---|---|---|---|---|---|

Asn Ile Asp Gly Thr Lys Arg Thr Leu Lys His Asn Ala Tyr Val Tyr
             405                 410                 415

Ala Thr Ser Lys Lys Arg Ala Asn Lys Phe Val Leu Lys Lys Gly Glu
             420                 425                 430

Glu Val Thr Thr Tyr Gly Gly Thr Tyr Thr Phe Lys Asn Gly Lys Gln
             435                 440                 445

Tyr Tyr Lys Ile Gly Asn Asp Thr Lys Lys Thr Tyr Val Lys Ala Ser
        450                 455                 460

Asn Phe
465

<210> SEQ ID NO 169
<211> LENGTH: 2220
<212> TYPE: DNA
<213> ORGANISM: Lactobacillus crispatus
<220> FEATURE:
<221> NAME/KEY: misc_feature
<222> LOCATION: (115)..(115)
<223> OTHER INFORMATION: n is a, c, g, or t

<400> SEQUENCE: 169

```
attagctggt caaaaggctc aggagaaaat atcgcaagat gtagagttca cacttagacc      60
tttaacagaa atcgtatagt aatattactt tttcaattga ttttgttaca tcgtngtaaa     120
atttaagaaa aagtaaagaa acagtaaagc gggcgtatgc tcgctttttta ttgttgtgtc     180
taggattacg gcattttgtt attttagatt tgtgtgaatg gtattgggat agggaatagg     240
tgaattatta caaaagcaag attgtagtca atttaacttg ctatttttc aagaggttag     300
tacaatatga atcgtggtaa gtaataggac gtgcttcagg cgtgtcgcct gtacgcatgc     360
tgatccttca gcaatgacta ctacctcatg agagttataa actcatggat cttgctttga     420
agaattttgt acattatagg ctccctacat gctgaaccta tggcctatta catttttttat     480
atttcaagga ggaaaagacc acatgaagaa aaatttaaga attgttagcg ctgctgctgc     540
tgctttatta gctgttgctc ctgtcgctgc ttctgctgta tctactgttt cagctgatgc     600
tgctgcaact actactgcaa ctactaacag caatgttact cttaacttaa acggtgcagg     660
tagtactgca accgatgctg ctaacactgt taatgtatca tcaaacttta gcttaaacgc     720
accagttaag gctaataacg ctgtaactgc tgatgctact cttggtggtg aattaactgc     780
tactcttaac ggtactagtg tatcatcaag cttagctgac gctgctcaag acgtgactgt     840
ttctgatggt aagactaacc tttatagcta caacaaggaa actaagaaag ttgaaaataa     900
cttgaacaac gttgttgctg tcaatcata cactcttact cttactaacg ttggcttcag     960
ctttggctca gcaatgaaga acaagactgt tactgttaag cttgctaatg gtgaactttc    1020
aggtaagaat gtgactaaga atactgatgg ttcttacaag ttaactttgg accaatatgg    1080
taacgctact gaattgactt acactcaatc acttaaggct tacaaccaag gtaacactaa    1140
ttctgtattc tttattaacc aaaacagtgg tactactgaa accaaaggtt tataccttac    1200
ccttgctaat ggcaatggtg aattaaatgt tgctgatgtt ttagctaata ttgaaaagca    1260
atacactgct gttcaataca atgattcaaa attcatgagt agtactgaaa aggatagccc    1320
agtaactatt actactaaca aggatgctgt aattgctgaa cttaagaagc aaaacatccc    1380
tgttaatgct gctggtaact tcactgctcc tgacaccttc actgtgactt tgaacgctaa    1440
gtcaagcatc aacggcaaga ctggtcaatt agtagtaact gtttcagttc caaacggtaa    1500
```

-continued

```
gaagactact gttgctagcc aagaaaagac tattatgcac aacgcatatt actacgacaa   1560
ggatgctaag cgtgttggta ctgacaaggt aactcgttac aacaaggtaa ctgttgcaac   1620
ttcaactact aagatcggtg acaagactta ctacgaagta atcgaaaacg gcaaggctac   1680
tggcaagtac atcaacgccg acaacatcga cggtactaag cgtactttga agcacaacgc   1740
atacgtttac gcaacttcaa agaagcgtgc taacaagttt gttcttaaga agggtgaaga   1800
agtaactact tacggtggta cttacacatt caagaacggc aagcaatact acaagatcgg   1860
caacgatact aagaagactt acgtaaaggc ttcaaacttt taattaagtc tatgtagtag   1920
ataaagataa aacgaggcat tcgcctcgtt tttcttttgc tctagttttc attattctta   1980
cacttcattt gtagtcacac atattagtta aggcgaacag taagtagcta atctactgga   2040
ttttccatga tataattaag caagtatata atacgaggaa gtgtattaat gaaactagat   2100
gacattaaaa atatggaagc tacttatctt gattacaagg aatcattaga aactactaaa   2160
cctgtaagct ggcttaaatc tgttgtagct tttgcaaata caaaggcgg acacattatc   2220
```

<210> SEQ ID NO 170
<211> LENGTH: 442
<212> TYPE: PRT
<213> ORGANISM: Lactobacillus crispatus

<400> SEQUENCE: 170

```
Met Lys Lys Asn Leu Arg Ile Val Ser Ala Ala Ala Ala Leu Leu
1               5                   10                  15

Ala Val Ala Pro Val Ala Ala Ser Ala Val Ser Val Asn Ala Ser
                20                  25                  30

Ser Ser Ala Val Gln Thr Ala Thr Asn Ile Gly Thr Val Leu Pro Leu
            35                  40                  45

Thr Asp Gly Ser Thr Val Asn Val Lys Pro Asn Ile Ser Leu Asn Thr
        50                  55                  60

Ser Ala Tyr Glu Gly Val Lys Ala Asn Ile Ser Val Ser Phe Ser Ala
65                  70                  75                  80

Thr Val Asp Gly Thr Thr Ala Thr Ser Asn Phe Thr Pro Asn Ala Ser
                85                  90                  95

Thr Ile Glu Leu Trp Lys Asn Glu Lys Asp Lys Val Thr Gln Val Thr
            100                 105                 110

Asp Leu Gln Gln Val Thr Ser Ser Asn Ala Gly Ala Thr Tyr Gln Val
        115                 120                 125

Lys Met Thr Gln Val Gly Leu Asn Phe Gly Ser Gln Asn Ala Asn Lys
    130                 135                 140

Lys Val Thr Leu Thr Phe Pro Glu Gly Asp Met Phe Lys Thr Ala Asp
145                 150                 155                 160

Thr Ser Leu Ala Gln Ser His Glu Val Lys Leu Asp Gln Asn Gly Thr
                165                 170                 175

Ile Thr Leu Pro Glu Val Val Met Asn Val Thr Ala Lys Asp Phe Ala
            180                 185                 190

Asn Pro Ala Val Val Asn Trp Tyr Asn Thr Ala Thr Asn Ala Val Val
        195                 200                 205

Ser Thr Gly Asn Ile Glu Leu Phe Ala Gly Ser Asp Ala Gly Lys Met
    210                 215                 220

Asn Val Ala Gln Val Val Ser Ala Thr Glu Lys Lys Tyr His Ala Ser
225                 230                 235                 240

Asn Tyr Gly Thr Lys Ala Asn Gln Glu Ser Ser Thr Ile Ser Tyr Thr
                245                 250                 255
```

```
Asn Asn Leu Lys Asp Ala Leu Lys Ala Met Asn Val Asp Val Asp Ala
            260                 265                 270

Gln Gly Trp Phe Val Ala Pro Lys Ser Phe Thr Phe Asn Met Thr Ala
        275                 280                 285

Lys Ala Asn Asn Asn Asp Ala Ser Ser Thr Leu Ala Val Thr Val Ser
    290                 295                 300

Val Pro Asn Gly Lys Asp Met Thr Val Pro Ser Gln Ser Lys Thr Val
305                 310                 315                 320

Met His Asn Ala Phe Phe Tyr Asp Lys Asn Gly Lys Arg Val Gly Ser
                325                 330                 335

Asp Lys Val Thr Arg Tyr Asn Ser Ala Thr Val Ala Met Asn Thr Thr
            340                 345                 350

Thr Ile Asn Gly Lys Ala Tyr Tyr Glu Val Ile Glu Asn Gly Lys Ala
        355                 360                 365

Thr Gly Lys Phe Ile Asn Ala Ala Asn Ile Asp Gly Thr Lys Arg Thr
    370                 375                 380

Leu Lys His Asn Ala Tyr Val Tyr Lys Ser Ser Lys Lys Arg Ala Asn
385                 390                 395                 400

Lys Val Val Leu Lys Lys Gly Thr Glu Val Val Thr Tyr Gly Gly Ala
                405                 410                 415

Tyr Thr Phe Lys Asn Gly Lys Gln Tyr Tyr Lys Ile Gly Asn Asn Thr
            420                 425                 430

Asp Lys Thr Tyr Val Lys Ala Ser Asn Phe
        435                 440

<210> SEQ ID NO 171
<211> LENGTH: 1500
<212> TYPE: DNA
<213> ORGANISM: Lactobacillus crispatus

<400> SEQUENCE: 171
ggatcttgct ttgaagaatt tgtacatta taggctccct acatgctgaa cctatggcct      60
attacatttt ttatatttca aggaggaaaa gaccacatga agaaaaattt aagaattgtt     120
agcgctgctg ctgctgcttt attagctgtt gctcctgtcg ctgcttctgc tgtttctgtt     180
aacgctgcaa gctcaagtgc tgttcaaact gctaccaaca ttggtactgt tttaccatta     240
actgatggtt ctactgttaa cgttaagcca acatttcat tgaacactttc agcatacgaa     300 ggtgttaagg caaacatttc agtatcattc tcagcaactg ttgacggtac tactgctacc     360
tctaacttca ctccaaatgc ttcaactatt gaactttgga agaatgaaaa ggataaggtt     420
acccaagtaa ctgatttaca acaagtaact tcatcaaacg ctggtgctac ttaccaagtt     480
aagatgactc aagttggctt gaacttcggt tcacaaaacg ctaacaagaa ggttactttg     540
actttccctg agggtgacat gttcaagacc gctgatactt ctttagcaca atcacacgaa     600
gtaaaattag accaaaacgg tactattact ttgccagaag tagttatgaa cgtaactgct     660
aaggacttcg ctaacccagc agtagttaac tggtacaaca ctgctactaa cgcagttgta     720
agtactggta acattgaact tttcgcaggt tcagatgctg gtaagatgaa cgttgctcaa     780
gttgtttcag caactgaaaa gaagtaccac gcaagcaact acggtactaa agctaaccaa     840
gaatcaagca ctatttcata caccaacaac cttaaggatg ctttaaaggc tatgaacgtt     900
gatgttgatg ctcaaggctg gttcgttgct cctaagtcat tcactttcaa catgactgct     960
aaagctaaca caatgatgc ttcaagtacc ttagctgtaa ctgtttcagt tccaaacggt    1020
```

-continued

```
aaggacatga ctgtaccaag ccaaagcaag actgttatgc acaacgcatt cttctatgac   1080
aagaacggca agcgtgttgg ttctgacaag gtaactcgtt acaactcagc aactgttgct   1140
atgaatacta ctactatcaa cggcaaggct tactacgaag taatcgaaaa cggtaaggct   1200
actggtaagt tcatcaacgc tgccaacatt gatggtacta agcgtacttt gaagcataac   1260
gcatacgttt acaagtcttc aaagaagcgt gctaacaagg ttgttcttaa gaagggtact   1320
gaagtagtta cctacggtgg tgcttacacc ttcaagaacg gcaagcaata ctacaagatc   1380
ggtaacaata ctgacaagac ttacgtaaag gcttcaaact tttaattaag tcgatgtagt   1440
agataaggaa aacgaggcaa ttgcctcgtt tttctttttac tctaaaaaaa taagtacgat   1500
```

<210> SEQ ID NO 172
<211> LENGTH: 444
<212> TYPE: PRT
<213> ORGANISM: Lactobacillus acidophilus

<400> SEQUENCE: 172

```
Met Lys Lys Asn Leu Arg Ile Val Ser Ala Ala Ala Ala Leu Leu
1               5                   10                  15

Ala Val Ala Pro Val Ala Ala Ser Ala Val Ser Thr Val Ser Ala Ala
                20                  25                  30

Thr Thr Ile Asn Ala Ser Ser Ser Ala Ile Asn Thr Asn Thr Asn Ala
            35                  40                  45

Lys Tyr Asp Val Asp Val Thr Pro Ser Val Ser Ala Val Ala Ala Asn
    50                  55                  60

Thr Ala Asn Asn Thr Pro Ala Ile Ala Gly Asn Leu Thr Gly Thr Ile
65                  70                  75                  80

Ser Ala Ser Tyr Asn Gly Lys Thr Tyr Thr Ala Asn Leu Lys Ala Asp
                85                  90                  95

Thr Glu Asn Ala Thr Ile Thr Ala Ala Gly Ser Thr Ala Val Lys
            100                 105                 110

Pro Ala Glu Leu Ala Ala Gly Val Ala Tyr Thr Val Thr Val Asn Asp
    115                 120                 125

Val Ser Phe Asn Phe Gly Ser Glu Asn Ala Gly Lys Thr Val Thr Leu
130                 135                 140

Gly Ser Ala Asn Ser Asn Val Lys Phe Thr Gly Thr Asn Ser Asp Asn
145                 150                 155                 160

Gln Thr Glu Thr Asn Val Ser Thr Leu Lys Val Lys Leu Asp Gln Asn
                165                 170                 175

Gly Val Ala Ser Leu Thr Asn Val Ser Ile Ala Asn Val Tyr Ala Ile
            180                 185                 190

Asn Thr Thr Asp Asn Ser Asn Val Asn Phe Tyr Asp Val Thr Ser Gly
    195                 200                 205

Ala Thr Val Thr Asn Gly Ala Val Ser Val Asn Ala Asp Asn Gln Gly
    210                 215                 220

Gln Val Asn Val Ala Asn Val Val Ala Ala Ile Asn Ser Lys Tyr Phe
225                 230                 235                 240

Ala Ala Gln Tyr Ala Asp Lys Lys Leu Asn Thr Arg Thr Ala Asn Thr
                245                 250                 255

Glu Asp Ala Ile Lys Ala Ala Leu Lys Asp Gln Lys Ile Asp Val Asn
            260                 265                 270

Ser Val Gly Tyr Phe Lys Ala Pro His Thr Phe Thr Val Asn Val Lys
    275                 280                 285

Ala Thr Ser Asn Thr Asn Gly Lys Ser Ala Thr Leu Pro Val Val Val
```

```
                290                 295                 300
Thr Val Pro Asn Val Ala Glu Pro Thr Val Ala Ser Val Ser Lys Arg
305                 310                 315                 320

Ile Met His Asn Ala Tyr Tyr Asp Lys Asp Ala Lys Arg Val Gly
            325                 330                 335

Thr Asp Ser Val Lys Arg Tyr Asn Ser Val Val Leu Pro Asn Thr
            340                 345                 350

Thr Thr Ile Asn Gly Lys Thr Tyr Tyr Gln Val Val Glu Asn Gly Lys
        355                 360                 365

Ala Val Asp Lys Tyr Ile Asn Ala Ala Asn Ile Asp Gly Thr Lys Arg
370                 375                 380

Thr Leu Lys His Asn Ala Tyr Val Tyr Ala Ser Ser Lys Lys Arg Ala
385                 390                 395                 400

Asn Lys Val Val Leu Lys Lys Gly Glu Val Val Thr Thr Tyr Gly Ala
            405                 410                 415

Ser Tyr Thr Phe Lys Asn Gly Gln Lys Tyr Tyr Lys Ile Gly Asp Asn
            420                 425                 430

Thr Asp Lys Thr Tyr Val Lys Val Ala Asn Phe Arg
        435                 440

<210> SEQ ID NO 173
<211> LENGTH: 1335
<212> TYPE: DNA
<213> ORGANISM: Lactobacillus acidophilus

<400> SEQUENCE: 173
atgaagaaaa aatttaagaat cgttagcgct gctgctgctg ctttacttgc tgttgctcca      60
gttgctgctt ctgctgtatc tactgttagc gctgctacta ctattaacgc aagttcatca    120
gcaatcaata ccaacactaa tgctaagtac gatgttgatg taactcctag tgtttctgca    180
gttgctgcaa atactgctaa caacactcca gctattgccg gtaaccttac tggtactatt    240
tcagcaagtt acaatggtaa gacttatact gctaacttaa aggcagatac tgaaaatgcc    300
actattactg ctgctggtag cactactgcc gttaaacctg ctgaattagc tgcaggtgtg    360
gcttacactg taactgttaa cgatgtttca tttaacttcg gttcagaaaa tgcaggtaag    420
actgttaccc ttggttcagc taactcaaat gtaaaattca ccggtacaaa cagtgataat    480
caaactgaaa ctaatgtttc tactttgaaa gttaagttag accaaaacgg tgttgcttca    540
cttactaatg tttcaattgc aaacgtatac gcaattaaca ctactgataa cagtaacgta    600
aacttctacg acgtaactag tggtgctact gtaactaacg gtgccgtttc agttaatgct    660
gataaccaag gtcaagttaa tgttgcaaac gtagttgcag caattaattc aaaatacttt    720
gcagcacaat acgcagataa gaagttaaat actcgtactg ctaatactga agatgctatt    780
aaggcagcct taaaggacca aaagattgat gtaaactcag taggttactt caaagcacct    840
catactttca ctgttaacgt taaagcaact tcaaatacta atggtaagtc agctactttg    900
ccagtagttg ttactgttcc taatgttgct gagccaactg tagccagcgt aagcaagaga    960
attatgcaca acgcatacta ctacgacaag gacgctaagc gtgttggtac tgacagcgtt   1020
aagcgttaca actcagtaag cgtattgcca aacactacta ctatcaacgg taagacttac   1080
taccaagtag ttgaaaacgg taaggctgtt gacaagtaca tcaacgctgc aaacatcgat   1140
ggtactaagc gtactttgaa gcacaacgct tacgtttacg catcatcaaa gaagcgtgct   1200
aacaaggttg tattgaagaa gggtgaagtt gtaactactt acggtgcttc atacacattc   1260
```

```
aagaacggcc aaaagtacta caagatcggt gacaacactg acaagactta cgttaaggtt    1320
gcaaacttta gataa                                                     1335
```

<210> SEQ ID NO 174
<211> LENGTH: 457
<212> TYPE: PRT
<213> ORGANISM: Lactobacillus acidophilus

<400> SEQUENCE: 174

```
Met Lys Lys Asn Leu Arg Ile Val Ser Ala Ala Ala Ala Leu Leu
1               5                   10                  15

Ala Val Ala Pro Val Ala Ala Ser Ala Val Ser Thr Val Asn Ala Ala
            20                  25                  30

Ala Val Asn Ala Ile Ala Val Gly Gly Ser Ala Thr Pro Leu Pro Asn
        35                  40                  45

Asn Ser Asp Val Gln Ile Ser Ser Val Ala Gly Val Thr Thr Lys
    50                  55                  60

Asn Gly Ser Ser Tyr Thr Asn Gly Arg Ile Ser Gly Ser Ile Asn Ala
65                  70                  75                  80

Ser Tyr Asn Gly Thr Ser Tyr Ser Ala Asn Phe Ser Ser Ser Asn Ala
                85                  90                  95

Gly Val Val Ser Thr Pro Gly His Thr Glu Leu Ser Gly Glu Gln
            100                 105                 110

Ile Asn Gly Leu Glu Pro Gly Ser Ala Val Thr Val Thr Leu Arg Asp
        115                 120                 125

Gly Val Ser Phe Asn Phe Gly Ser Thr Asn Ala Asn Lys Thr Ile Thr
130                 135                 140

Leu Ala Phe Pro Lys Asn Val Ser Ala Ala Gly Leu Ala Asp Ala Asn
145                 150                 155                 160

Lys Val Ser Ala Thr Ser Glu Thr Ser Val Asp Ala Gly Lys Thr Ile
                165                 170                 175

Gln Val Lys Thr Asp Lys Asn Gly Val Val Ser Phe Gly Ser Ala Gln
            180                 185                 190

Val Leu Asn Val Lys Val Val Glu Thr Ser Asp Val Arg Ala Val Ser
        195                 200                 205

Phe Tyr Asp Ile Gln Thr Gly Lys Thr Val Glu Asn Gly Thr Leu Ser
    210                 215                 220

Ile Val Ala Gly Ser Asn Ala Arg Ala Asn Val Gln Glu Ile Val Asn
225                 230                 235                 240

Ala Phe Asn Ala Lys Tyr Gln Ala Ser Gln Leu Asn Asn Ala Asn Ser
                245                 250                 255

Asn Ala Asn Val Arg Leu Thr Asp Asn Asn Ala Gln Ala Val Ala Thr
            260                 265                 270

Met Leu Arg Ala Gln Asn Ile Asp Val Asp Ala Gln Gly Tyr Phe Thr
        275                 280                 285

Ala Pro Ala Ser Leu Ser Leu Thr Phe His Ala Glu Ser Thr Gln Asn
    290                 295                 300

Asn Glu Thr Ala Gln Leu Pro Val Thr Val Ser Val Thr Asn Gly Lys
305                 310                 315                 320

Glu Val Thr Pro Ser Thr Val Asp Ser Val Ser Lys Arg Ile Met His
                325                 330                 335

Asn Ala Tyr Tyr Tyr Asp Lys Asp Ala Lys Arg Val Gly Thr Asp Ser
            340                 345                 350

Val Lys Arg Tyr Asn Ser Val Ser Val Leu Pro Asn Thr Thr Thr Ile
```

Asn Gly Lys Ala Tyr Tyr Gln Val Val Glu Asn Gly Lys Ala Val Asp
                355                 360                 365
Lys Tyr Ile Asn Ala Ala Asn Ile Asp Gly Thr Lys Arg Thr Leu Lys
370                 375                 380
His Asn Ala Tyr Val Tyr Ala Ser Ser Lys Arg Ala Asn Lys Val
385                 390                 395                 400
Val Leu Lys Lys Gly Glu Val Val Thr Thr Tyr Gly Ala Ser Tyr Thr
        405                 410                 415
Phe Lys Asn Gly Gln Lys Tyr Tyr Lys Ile Gly Asp Asn Thr Asp Lys
            420                 425                 430
Thr Tyr Val Lys Val Ala Asn Phe Arg
    435                 440                 445

450                 455

<210> SEQ ID NO 175
<211> LENGTH: 1374
<212> TYPE: DNA
<213> ORGANISM: Lactobacillus acidophilus

<400> SEQUENCE: 175
atgaagaaaa atttaagaat cgttagcgct gctgctgctg ctttacttgc tgttgctcca      60
gttgctgctt ctgctgtatc tactgttaac gctgccgctg ttaatgctat tgctgttggc     120
ggttcagcta ccccattacc aaacaactca gatgtacaaa ttagttcatc agttgctggt     180
gtaactacta agaatggctc aagctacact aacggtagaa tttctggttc tatcaacgct     240
tcttacaacg gtacaagcta ttcagcaaac tttagttcat caaatgcagg tgttgttgtt     300
tcaactccag ccatactga acttagtggt gaacaaatta acggtcttga accaggtagt     360
gctgtaactg ttactttaag agatggtgtt tcatttaact ttggttcaac taatgctaac     420
aagactatta ctttagcatt ccaaagaac gtatcagctg ctggtttagc tgatgctaac     480
aaggtttcag ctacttcaga aacttcagtt gatgcaggca agactatcca agttaagact     540
gacaagaacg gtgttgtaag cttcggttca gcacaagttc ttaacgttaa ggttgttgaa     600
actagcgacg ttagagctgt ttcattctac gacatccaaa ctggtaagac tgtagaaaac     660
ggtactcttt caatcgttgc tggttctaac gcacgtgcta acgtacaaga aatcgttaac     720
gcatttaacg ctaagtacca agcttctcaa ttgaacaacg ctaacagcaa tgctaacgtt     780
cgtttgactg acaacaacgc tcaagctgtt gctactatgt taagagctca aaacattgat     840
gttgatgcac aaggttactt cactgcacca gcttcattga gcttaacttt ccacgcagaa     900
tcaactcaaa acaatgaaac tgcacaatta ccagtaactg tttcagtaac taacggtaag     960
gaagttactc cttcaactgt agacagcgta agcaagagaa ttatgcacaa tgcatactac    1020
tacgacaagg acgctaagcg tgttggtact gacagcgtta agcgttacaa ctcagtaagc    1080
gtattgccaa acactactac tatcaacggt aaggcttact accaagtagt tgaaaacggc    1140
aaggcagttg acaagtacat caacgctgca acatcgatg gtactaagcg tactttgaag    1200
cacaacgctt acgtttacgc atcatcaaag aaacgtgcta acaaggttgt attgaagaag    1260
ggtgaagttg taactactta cggtgcttca tacacattca gaacggcca aaagtactac    1320 aagatcggtg acaacactga caagacttac gttaaggttg caaactttag ataa         1374

<210> SEQ ID NO 176
<211> LENGTH: 437
<212> TYPE: PRT
<213> ORGANISM: Lactobacillus helveticus

<400> SEQUENCE: 176

Met Lys Lys Asn Leu Arg Ile Val Ser Ala Ala Ala Ala Leu Leu
1               5                   10                  15

Ala Val Ala Pro Ile Ala Ala Thr Ala Met Pro Val Asn Ala Ala Thr
            20                  25                  30

Thr Ile Asn Ala Asp Ser Ala Ile Asn Thr Asn Thr Asn Ala Lys Tyr
        35                  40                  45

Asp Val Asp Val Thr Pro Ser Ile Ser Ala Ile Ala Lys Val Ile Gly
50                  55                  60

Thr Gly Ile Thr Ile Pro Gly Ser Leu Thr Gly Ser Ile Ser Ala Ser
65                  70                  75                  80

Tyr Asn Gly Lys Ser Tyr Thr Ala Asn Leu Pro Lys Asp Ser Glu Asn
                85                  90                  95

Ala Thr Ile Thr Asn Ser Asn Asn Glu Thr Val Lys Pro Ala Asp Leu
            100                 105                 110

Glu Tyr Gly Lys Pro Tyr Lys Val Thr Val Pro Asp Val Ser Phe Asn
            115                 120                 125

Phe Gly Ser Glu Asn Ala Gly Lys Glu Ile Thr Ile Gly Ser Ala Asn
130                 135                 140

Gln Asn Val Thr Phe Thr Asn Asn Gly Gln Thr Gly Ser Thr Val Lys
145                 150                 155                 160

Val Lys Leu Asp Gln Asn Gly Val Ala Thr Leu Ser Ser Val Gln Ile
                165                 170                 175

Lys Asn Val Tyr Ala Val Asn Thr Thr Asp Asn Arg Asp Val Asn Phe
            180                 185                 190

Tyr Asp Val Thr Thr Gly Ala Thr Val Lys Thr Gly Ala Val Ser Leu
        195                 200                 205

Asp Ala Asp Asn Gln Gly Gln Leu Asn Thr Ala Ser Val Val Ala Ala
210                 215                 220

Ile Thr Ser Lys Tyr Phe Ala Ala Gln Tyr Ala Asn Lys Gln Leu Ser
225                 230                 235                 240

Gln Asp Asn Val Val Asn Thr Glu Thr Ala Val Lys Asp Ala Leu
                245                 250                 255

Lys Ala Gln Lys Ile Glu Val Asn Ser Val Gly Tyr Phe Lys Ala Pro
            260                 265                 270

His Thr Phe Thr Val Asn Val Lys Ala Thr Ser Asn Val Asn Ser Lys
        275                 280                 285

Ser Ala Thr Leu Pro Val Thr Val Thr Val Pro Asn Val Ala Glu Pro
290                 295                 300

Thr Val Pro Ser Val Ser Lys Thr Val Met His Asn Ala Tyr Phe Tyr
305                 310                 315                 320

Asp Lys Asn Ala Lys Arg Val Gly Thr Asp Lys Val Thr Arg Tyr Asp
                325                 330                 335

Thr Val Thr Val Ala Met Asn Thr Thr Lys Leu Ala Asn Gly Ile Ser
            340                 345                 350

Tyr Tyr Glu Val Ile Glu Asn Gly Lys Ala Thr Gly Lys Tyr Ile Asn
        355                 360                 365

Ala Asp Asn Ile Asp Gly Thr Lys Arg Thr Leu Lys His Asn Ala Tyr
370                 375                 380

Val Tyr Lys Thr Ser Lys Lys Arg Ala Asn Lys Val Val Leu Lys Lys
385                 390                 395                 400

Gly Thr Glu Val Thr Thr Tyr Gly Gly Ser Tyr Lys Phe Lys Asn Gly

|       |       |       | 405   |       |       |       |       | 410   |       |       |       |       | 415   |       |
|-------|-------|-------|-------|-------|-------|-------|-------|-------|-------|-------|-------|-------|-------|-------|
Gln Arg Tyr Tyr Lys Ile Gly Ala Asp Thr Lys Lys Thr Tyr Val Lys
                420                     425                     430

Val Ala Asn Phe Asp
        435

<210> SEQ ID NO 177
<211> LENGTH: 1314
<212> TYPE: DNA
<213> ORGANISM: Lactobacillus helveticus

<400> SEQUENCE: 177

```
atgaagaaaa atttaagaat tgttagcgct gctgctgctg ctttattagc tgttgcacct      60
attgctgcaa ctgctatgcc tgttaatgct gcaactacta ttaacgctga ttcagctatc     120
aatactaata ctaatgctaa gtacgatgtt gacgtaactc caagcatatc agctattgct     180
aaagttattg gtactggtat tactatccca ggtagcctta ctggtagtat ttcagcaagt     240
tacaatggta agtcatacac tgctaactta ccaaaggatt cagaaaatgc tactattacc     300
aatagtaata atgagactgt taagccagct gatttagaat atggcaagcc ttacaaagta     360
actgttcctg atgtttcatt taactttggt tcagaaaatg caggtaagga aattactatt     420
ggttcagcta accaaaatgt aacctttact aacaatggcc aaactggttc aactgtaaag     480
gttaagttag accaaaatgg tgttgctact ctttcaagtg tacaaattaa gaatgtttac     540
gcagttaaca ctactgacaa cagagatgta aacttctacg atgtaacaac tggtgctact     600
gtaaaaactg gtgctgtttc tcttgacgct gacaaccaag gtcaacttaa cactgcatct     660
gttgtagctg caattaccct caagtacttt gcagcacaat atgctaataa gcaattgtct     720
caagacaatg ttgtagttaa cactgaaact gctgtcaagg atgctttaaa ggctcaaaag     780
attgaagtaa actcagtagg ttacttcaag gctccacata ctttcactgt taatgttaag     840
gcaacttcaa acgttaacag taagtcagct actttaccag taactgtaac tgttcctaac     900
gttgcagaac caactgtacc aagtgtatca aagactgtta tgcacaacgc atacttctac     960
gacaagaacg ctaagcgtgt tggtactgac aaggtaactc gttacgacac tgtaactgtt    1020
gctatgaaca ctactaagct tgctaacggt atttcatact acgaagtaat cgaaaacggc    1080
aaggcaactg gcaagtacat caacgctgac aacatcgatg gtactaagcg tactttgaag    1140
cacaacgcat acgtttacaa gacttcaaag aagcgtgcta caaggttgt tcttaagaag    1200
ggtactgaag taactactta cggtggttca tacaagttca agaacggtca acgttactac    1260
aagatcggtg ctgacactaa gaagacttac gttaaggttg caaactttga ctaa          1314
```